(12) United States Patent
Perry et al.

(10) Patent No.: US 9,896,659 B2
(45) Date of Patent: Feb. 20, 2018

(54) METHODS, KITS, AND COMPOSITIONS FOR STEM CELL SELF-RENEWAL

(71) Applicant: STOWERS INSTITUTE FOR MEDICAL RESEARCH, Kansas City, MO (US)

(72) Inventors: John M Perry, Olathe, KS (US); Linheng Li, Leawood, KS (US); Aparna Venkatraman, Prairie Village, KS (US); Xi He, Leawood, KS (US)

(73) Assignee: STOWERS INSTITUTE FOR MEDICAL RESEARCH, Kansas City, MO (US)

( * ) Notice: Subject to any disclaimer, the term of this patent is extended or adjusted under 35 U.S.C. 154(b) by 464 days.

(21) Appl. No.: 14/352,410

(22) PCT Filed: Oct. 17, 2012

(86) PCT No.: PCT/US2012/060663
§ 371 (c)(1),
(2) Date: Apr. 17, 2014

(87) PCT Pub. No.: WO2013/059357
PCT Pub. Date: Apr. 25, 2013

(65) Prior Publication Data
US 2014/0255359 A1    Sep. 11, 2014

Related U.S. Application Data

(60) Provisional application No. 61/548,833, filed on Oct. 19, 2011.

(51) Int. Cl.
| | |
|---|---|
| C12N 5/00 | (2006.01) |
| C12N 5/02 | (2006.01) |
| C12N 5/18 | (2006.01) |
| C12N 5/0789 | (2010.01) |
| A61K 35/28 | (2015.01) |

(52) U.S. Cl.
CPC ............ *C12N 5/0647* (2013.01); *A61K 35/28* (2013.01); *C12N 2501/06* (2013.01); *C12N 2501/415* (2013.01)

(58) Field of Classification Search
None
See application file for complete search history.

(56) References Cited

U.S. PATENT DOCUMENTS

| | | | | |
|---|---|---|---|---|
| 8,263,403 B2 * | 9/2012 | Perry | ............... | C12N 5/0647 435/325 |
| 9,050,315 B2 * | 6/2015 | Klein | .................. | A61K 35/28 |
| 2005/0276793 A1 | 12/2005 | Milhem et al. | | |
| 2009/0226536 A1 | 9/2009 | Arenas | | |
| 2009/0252711 A1* | 10/2009 | Boquest | ............ | C12N 5/0696 424/93.7 |

OTHER PUBLICATIONS

Dolnikov et al., Blood, 2006, v.108 :340.*
Akashi, K., et al., A clonogenic common myeloid progenitor that gives rise to all myeloid lineages. Nature 2000. 404(6774): p. 193-7.
Al Yacoub, N., et al. Optimized production and concentration of lentiviral vectors containing large inserts. J Gene Med. Jul. 2007;9(7):579-84.
Antonchuk et al., HOXB4-induced expansion of adult hematopoietic stem cells ex vivo. Cell 109, 39-45 (2002).
Arai, F. et al. Tie2/angiopoietin-1 signaling regulates hematopoietic stem cell quiescence in the bone marrow niche. Cell. Jul. 23, 2004;118(2):149-61.
Borowitz, M. J., et al. Immunophenotyping of acute leukemia by flow cytometric analysis. Am. J. Clin. Pathol. 100, 534-540 (1993).
Burgering, B. M. T. & Medema, R. H. Decisions on life and death: FOXO Forkhead transcription factors are in command when PKB/Akt is off duty. J Leukoc Biol. Jun. 2003;73(6):689-701.
Butler, J. M. et al. Endothelial cells are essential for the self-renewal and repopulation of Notch-dependent hematopoietic stem cells. Cell stem cell 6, 251-264 (2010).
Calvi, L. M. et al. Osteoblastic cells regulate the haematopoietic stem cell niche. Nature. Oct. 23, 2003;425(6960):841-6.
Cardone, M. H., et al. Regulation of cell death protease caspase-9 by phosphorylation. Science. Nov. 13, 1998;282(5392):1318-21.
Christensen, J. L. & Weissman, I. L. Flk-2 is a marker in hematopoietic stem cell differentiation: a simple method to isolate long-term stem cells. Proc Natl Acad Sci U S A. Dec. 4, 2001;98(25):14541-6.
Cobas, M. et al. Beta-catenin is dispensable for hematopoiesis and lymphopoiesis. The Journal of experimental medicine 199, 221-229 (2004).
Cross D. A., et al. Inhibition of glycogen synthase kinase-3 by insulin mediated by protein kinase B. Nature. Dec. 21-28, 1995;378(6559):785-9.
Cully, M. et al. Beyond PTEN mutations: the PI3K pathway as an integrator of multiple inputs during tumorigenesis. Nat Rev Cancer. Mar. 2006;6(3):184-92.
Datta, S. R., et al. Akt phosphorylation of BAD couples survival signals to the cell-intrinsic death machinery. Cell. Oct. 17, 1997;91(2):231-41.
Datta, S. R., et al. Cellular survival: a play in three Akts. Genes Dev. Nov. 15, 1999;13(22):2905-27.
Delaney, C. et al. Notch-mediated expansion of human cord blood progenitor cells capable of rapid myeloid reconstitution. Nat Med vol. 16, pp. 232-236 (2010).
Donepudi, M. & Grutter, M. G. Structure and zymogen activation of caspases. Biophys Chem. Dec. 10, 2002;101-102:145-53.
El-Deiry, W. S., et al. WAF1, a potential mediator of p53 tumor suppression. Cell. Nov. 19, 1993;75(4):817-25.
Fujita, N., et al. Akt-dependent phosphorylation of p27Kip1 promotes binding to 14-3-3 and cytoplasmic localization. J Biol Chem. Aug. 9, 2002;277(32):28706-13.

(Continued)

*Primary Examiner* — Michail Belyavskyi
(74) *Attorney, Agent, or Firm* — Bryan Cave LLP

(57) ABSTRACT

Methods and kits for expanding a stem cell population, particularly a hematopoietic stem cell population, in the presence of a DNA methyltransferase modulator and a Wnt pathway modulator are disclosed.

18 Claims, 79 Drawing Sheets

(56) References Cited

OTHER PUBLICATIONS

Gothert, J. R., et al. In vivo fate-tracing studies using the Scl stem cell enhancer: embryonic hematopoietic stem cells significantly contribute to adult hematopoiesis. Blood. Apr. 1, 2005;105(7):2724-32.

Gottlieb, T. M. et al. Cross-talk between Akt, p53 and Mdm2: possible implications for the regulation of apoptosis. Oncogene. Feb. 14, 2002;21(8):1299-303.

Gray, H. R. & Helwig, E. B. Trichofolliculoma. Arch Dermatol. 86, 99-105 (1962).

Groszer, M. et al. Negative regulation of neural stem/progenitor cell proliferation by the Pten tumor suppressor gene in vivo. Science. Dec. 7, 2001;294(5549):2186-9.

Guo, W. et al. Multi-genetic events collaboratively contribute to Pten-null leukaemia stem-cell formation. Nature 453, 529-533 (2008).

Hagen, T. et al. Expression and characterization of GSK-3 mutants and their effect on beta-catenin phosphorylation in intact cells. J Biol Chem. Jun. 28, 2002;277(26):23330-5.

Harada, N., et al. Intestinal polyposis in mice with a dominant stable mutation of the beta-catenin gene. Embo J. Nov. 1, 1999;18(21):5931-42.

Haupt, Y. et al. Mdm2 promotes the rapid degradation of p53. Nature. May 15, 1997;387(6630):296-9.

He, X. C. et al. PTEN-deficient intestinal stem cells initiate intestinal polyposis. Nat Genet 39, 189-198 (2007).

Heissig, B. et al. Recruitment of stem and progenitor cells from the bone marrow niche requires MMP-9 mediated release of kit-ligand. Cell. May 31, 2002;109(5):625-37.

Himburg, H. A. et al. Pleiotrophin regulates the expansion and regeneration of hematopoietic stem cells. Nat Med vol. 16, pp. 475-482 (2010).

International Search Report, dated Feb. 27, 2013, for PCT/US2012/060663.

Katoh, M & Katoh, M. Cross-talk of WNT and FGF signaling pathways at GSK3beta to regulate beta-catenin and SNAIL signaling cascades. Cancer Biol Ther. Sep. 2006;5(9):1059-64.

Kiel, M. J., et al. SLAM family receptors distinguish hematopoietic stem and progenitor cells and reveal endothelial niches for stem cells. Cell. Jul. 1, 2005;121(7):1109-21.

Kim, L. & Kimmel, A. R. GSK3 at the edge: regulation of developmental specification and cell polarization. Curr Drug Targets. Nov. 2006;7(11):1411-9.

Kimura, T. et al. Conditional loss of PTEN leads to testicular teratoma and enhances embryonic germ cell production. Development. Apr. 2003;130(8):1691-700.

Kirstetter, P., et al. Activation of the canonical Wnt pathway leads to loss of hematopoietic stem cell repopulation and multilineage differentiation block. Nat Immunol 7, 1048-1056 (2006).

Kobayashi, M., et al. Thrombopoietin supports proliferation of human primitive hematopoietic cells in synergy with steel factor and/or interleukin-3. Blood 88, 429-436 (1996).

Kondo, M., et al. Identification of clonogenic common lymphoid progenitors in mouse bone marrow. Cell 91, 661-672 (1997).

Li, A. et al. Mechanistic insights into maintenance of high p53 acetylation by PTEN. Mol Cell. Aug. 2006;23(4):575-87.

Li, L. and Xie, T. Stem cell niche: structure and function. Annu Rev Cell Dev Biol. 2005;21:605-31.

Lopiccolo, J., et al. Targeting Akt in cancer therapy. Anticancer Drugs. Sep. 2007;18(8):861-74.

Maehama, T & Dixon, J. E. The tumor suppressor, PTEN/MMAC1, dephosphorylates the lipid second messenger, phosphatidylinositol 3,4,5-trisphosphate. J Biol Chem. May 29, 1998;273(22):13375-8.

Maira, S. M. et al. Identification and characterization of NVP-BEZ235, a new orally available dual phosphatidylinositol 3-kinase/mammalian target of rapamycin inhibitor with potent in vivo antitumor activity. Molecular cancer therapeutics 7, 1851-1863 (2008).

Matsuoka, S. et al. Fbxw7 acts as a critical fail-safe against premature loss of hematopoietic stem cells and development of T-ALL. Genes Dev 22, 986-991 (2008).

Mayo L. D., Donner D. B. A phosphatidylinositol 3-kinase/Akt pathway promotes translocation of Mdm2 from the cytoplasm to the nucleus. Proc Natl Acad Sci U S A. Sep. 25, 2001;98(20):11598-603.

Miller, C. L. & Eaves, C. J. Expansion in vitro of adult murine hematopoietic stem cells with transplantable lympho-myeloid reconstituting ability. Proc Natl Acad Sci U S A. Dec. 9, 1997;94(25):13648-53.

Mimeault, M., et al., Stem Cells: A Revolution in Therapeutics—Recent Advances in Stem Cell Biology and Their Therapeutic Applications in Regenerative Medicine and Cancer Therapies. Clin Pharmacol Ther., 82(3):252-64 (2007).

Mise-Omata S et al. Transient strong reduction of PTEN expression by specific RNAi induces loss of adhesion of the cells. Biochem Biophys Res Commun. 328(4):1034-42 2005.

Momand, J. et al. The mdm-2 oncogene product forms a complex with the p53 protein and inhibits p53-mediated transactivation. Cell. Jun. 26, 1992;69(7):1237-45.

Moon, R. T. et al. The promise and perils of Wnt signaling through beta-catenin. Science. May 31, 2002;296(5573):1644-6.

Mutter, G. L. Pten, a protean tumor suppressor. Am J Pathol. Jun. 2001;158(6):1895-8.

Nakorn et al. Myeloerythroid-restricted progenitors are sufficient to confer radioprotection and provide the majority of day 8 CFU-S. J Clin Invest. Jun. 2002;109(12):1579-85.

Nicholson, K. M., et al. The protein kinase B/Akt signalling pathway in human malignancy. Cell Signal. May 2002;14(5):381-95.

North, T. E. et al. Prostaglandin E2 regulates vertebrate haematopoietic stem cell homeostasis. Nature 447, 1007-1011 (2007).

Novak, A., et al. Z/EG, a double reporter mouse line that expresses enhanced green fluorescent protein upon Cre-mediated excision. Genesis 28, 147-155 (2000).

Oren M. Decision making by p53: life, death and cancer. Cell Death Differ. Apr. 2003;10(4):431-42.

Paquette, R. & Dorshkind, K. Optimizing hematopoietic recovery following bone marrow transplantation. The Journal of clinical investigation 109, 1527-1528 (2002).

Park, I. K. et al. Bmi-1 is required for maintenance of adult self-renewing haematopoietic stem cells. Nature 423, 302-305 (2003).

Perry, J. M. & Li, L. Self-renewal versus transformation: Fbxw7 deletion leads to stem cell activation and leukemogenesis. Genes Dev. 22, 1107-1109 (2008).

Perry, J.M., et al. Cooperation between both Wnt/β-catenin and PTEN/PI3K/Akt signaling promotes primitive hematopoietic stem cell self-renewal and expansion. Genes & Development. 25: 1928-1942 (2011).

Persad, S. et al. Tumor suppressor PTEN inhibits nuclear accumulation of beta-catenin and T cell/lymphoid enhancer factor 1-mediated transcriptional activation. J Cell Biol. Jun. 11, 2001;153(6):1161-74.

Reya, T. et al. A role for Wnt signaling in self-renewal of haematopoietic stem cells. Nature 423, 409-414 (2003).

Ring, D. B. et al. Selective glycogen synthase kinase 3 inhibitors potentiate insulin activation of glucose transport and utilization in vitro and in vivo. Diabetes 52, 588-595 (2003).

Salmena, L., et al. Tenets of PTEN Tumor Suppression. Cell 133, 403-414 (2008).

Sarbassov, D. D., et al. Phosphorylation and regulation of Akt/PKB by the rictor-mTOR complex. Science. Feb. 18, 2005;307(5712):1098-101.

Sato, et al. Maintenance of pluripotency in human and mouse embryonic stem cells through activation of Wnt signaling by a pharmacological GSK-3-specific inhibitor. Nat Med vol. 10, 55-63 (2004).

Scheller, M. et al. Hematopoietic stem cell and multilineage defects generated by constitutive [beta]-catenin activation. Nature Immunology 7, 1037-1047 (2006).

(56) References Cited

OTHER PUBLICATIONS

Schmid, A. C., et al. Bisperoxovanadium compounds are potent PTEN inhibitors. FEBS Lett 566, 35-3β (2004).
Smith, L. H. & Clayton, M. L. Distribution of injected 59Fe in mice. Exp. Hematol. 20, 82-86 (1970).
Song, G. et al. The activation of Akt/PKB signaling pathway and cell survival. J Cell Mol Med. Jan.-Mar. 2005;9(1):59-71.
Stiles, B. et al. PTENless means more. Dev Biol. Sep. 15, 2004;273(2):175-84.
Suzuki, A. et al. T cell-specific loss of Pten leads to defects in central and peripheral tolerance. Immunity. May 2001;14(5):523-34.
Tang, Y. & Eng C. PTEN autoregulates its expression by stabilization of p53 in a phosphatase-independent manner. Cancer Res. Jan. 15, 2006;66(2):736-42.
Varnum-Finney, B. et al. Pluripotent, cytokine-dependent, hematopoietic stem cells are immortalized by constitutive Notch1 signaling. Nat Med 6, 1278-1281 (2000).
Written Opinion of the International Searching Authority, dated Feb. 27, 2013, for PCT/US2012/060663.
Wu, H. et al. PTEN signaling pathways in melanoma. Oncogene. May 19, 2003;22(20):3113-22.
Xie, Y. et al. Detection of functional haematopoietic stem cell niche using real-time imaging. Nature 457, 97-101 (2009).
Yilmaz, O. H., et al. Pten dependence distinguishes haematopoietic stem cells from leukaemia-initiating cells. Nature. May 25, 2006;441(7092):475-82.
Ying, Q.-L. et al. The ground state of embryonic stem cell self-renewal. Nature 453, 519-523 (2008).
Zhang, C. C. and Lodish, H. F. Murine hematopoietic stem cells change their surface phenotype during ex vivo expansion. Blood. Jun. 1, 2005;105(11):4314-20.
Zhang, C. C., et al. Angiopoietin-like proteins stimulate ex vivo expansion of hematopoietic stem cells. Nat Med. Feb. 2006;12(2):240-5.
Zhang, J. & Li, L. BMP signaling and stem cell regulation. Dev Biol 284, 1-11 (2005).
Zhang, J. et al. Identification of the haematopoietic stem cell niche and control of the niche size. Nature. Oct. 23, 2003;425(6960):836-41.
Zhang, J., et al. PTEN maintains haematopoietic stem cells and acts in lineage choice and leukaemia prevention. Nature. May 25, 2006;441(7092):518-22.
Zhu, X. et al. A versatile approach to multiple gene RNA interference using microRNA-based short hairpin RNAs. BMC molecular biology vol. 8, p. 98 (2007).

* cited by examiner

Figure 1
A
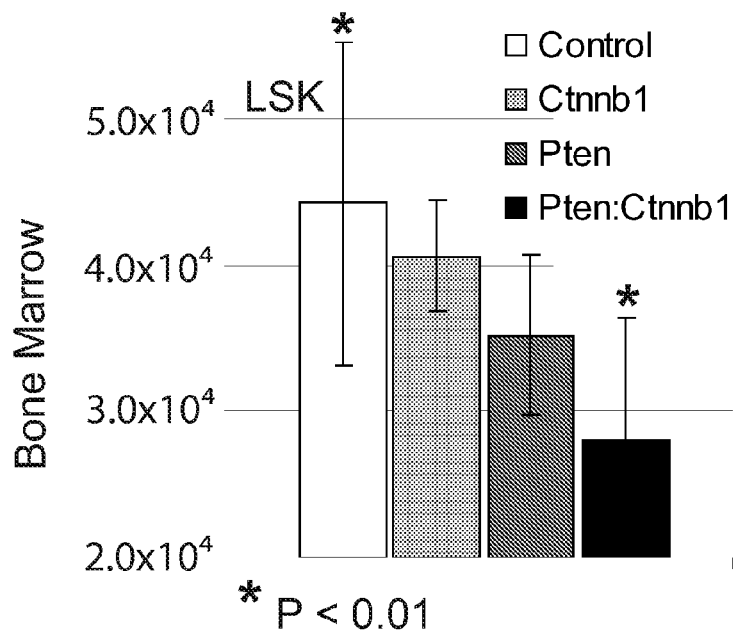
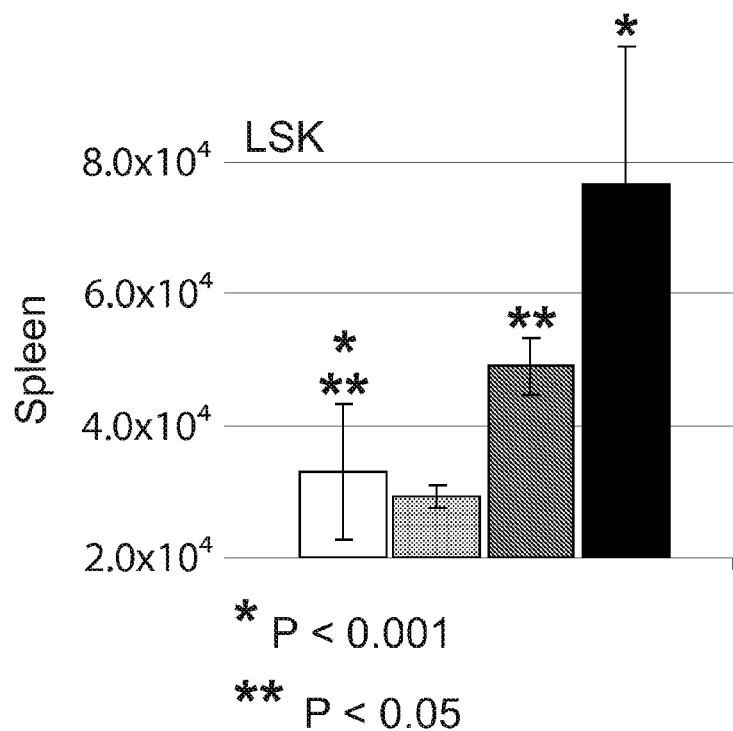

Figure 1
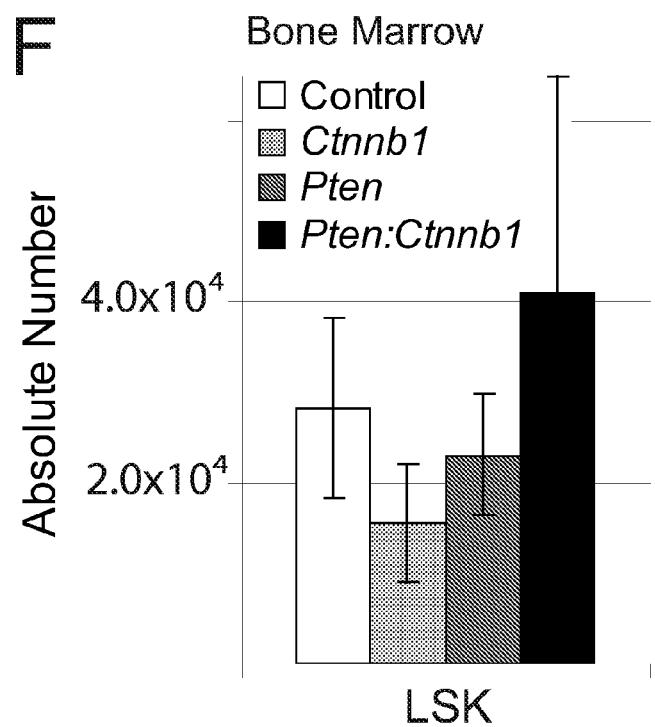
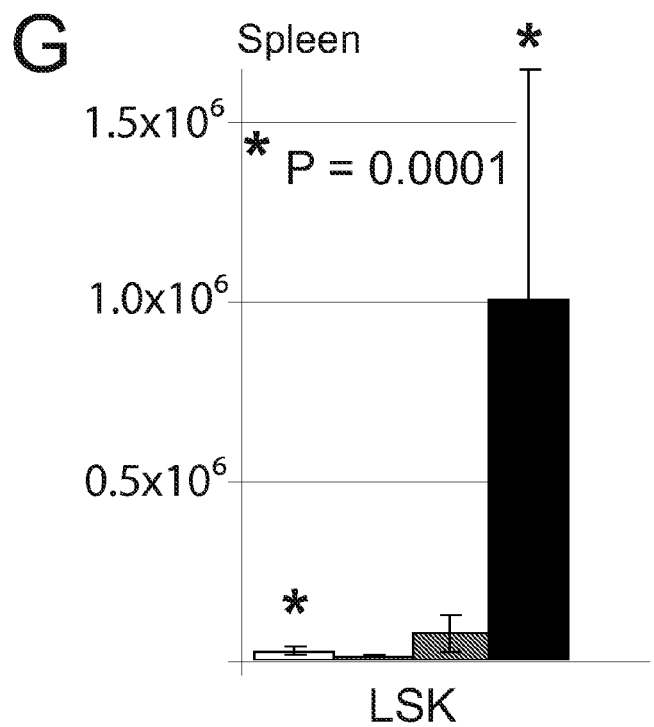

Figure 2
B
*Pten*  *Pten:Ctnnb1*
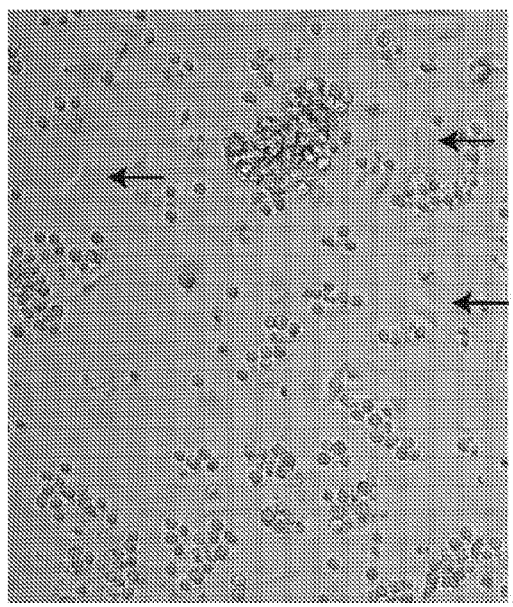 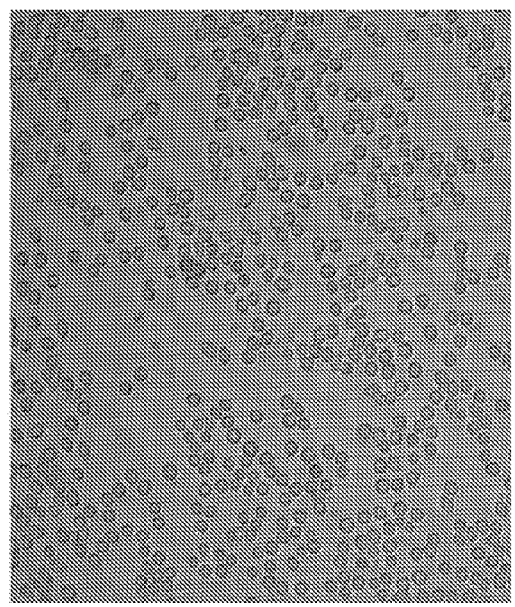

Figure 2
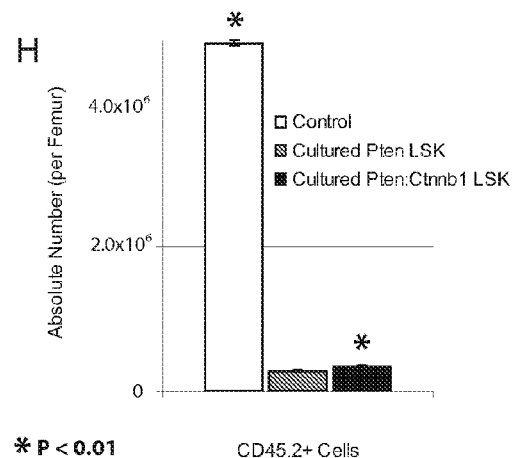
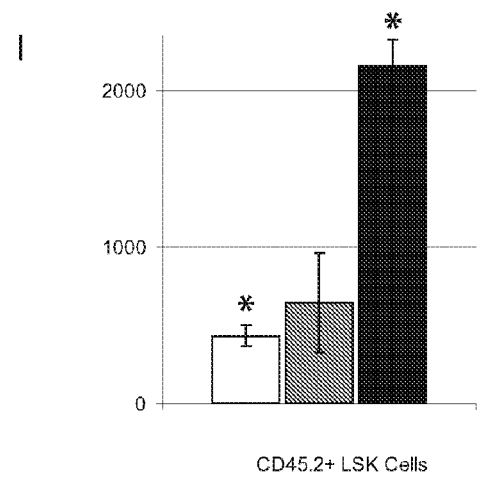
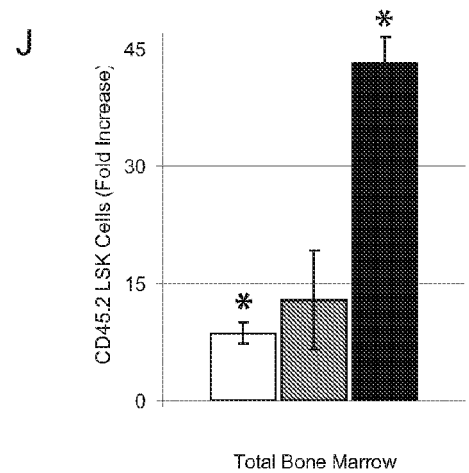

Figure 3
D
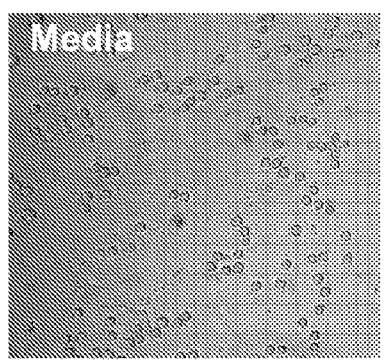
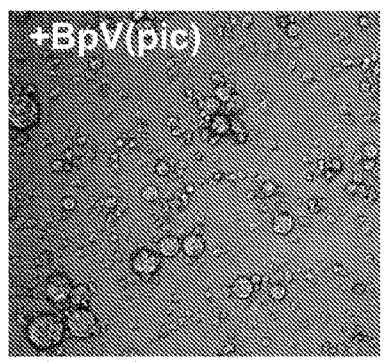
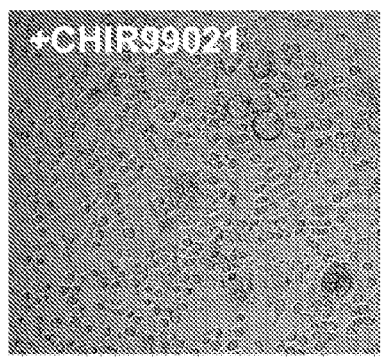
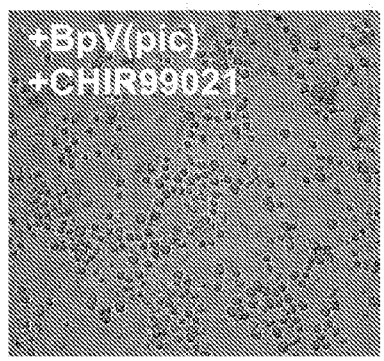

Figure 4
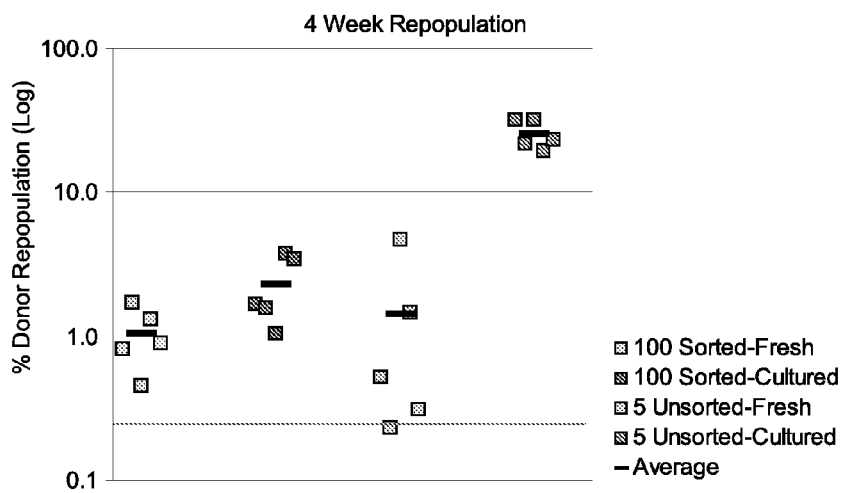
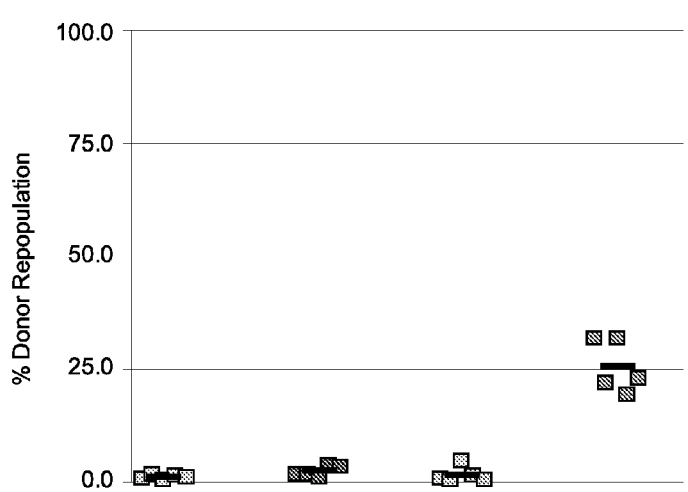
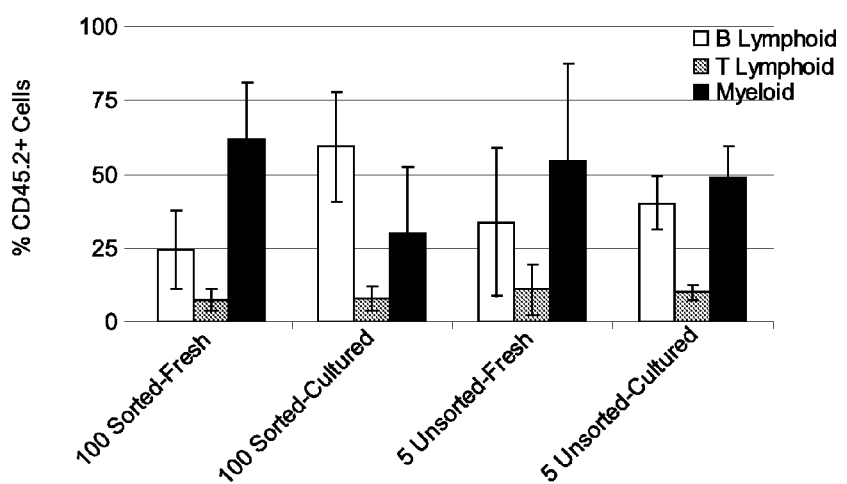

Figure 4 Continued
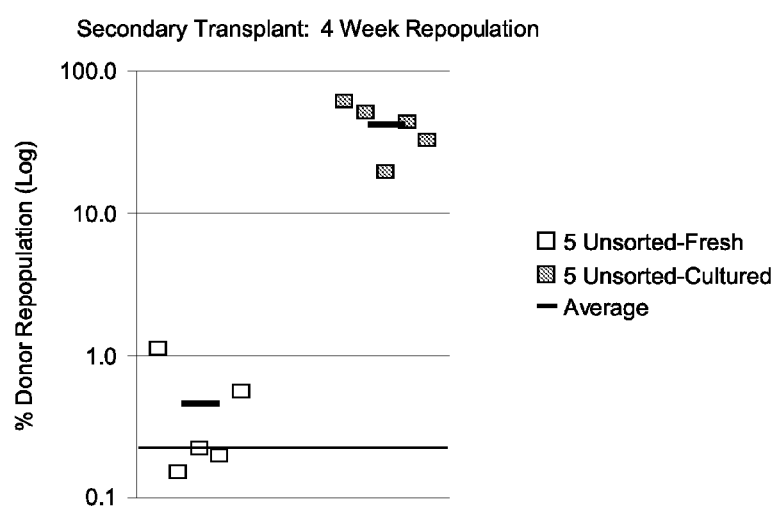
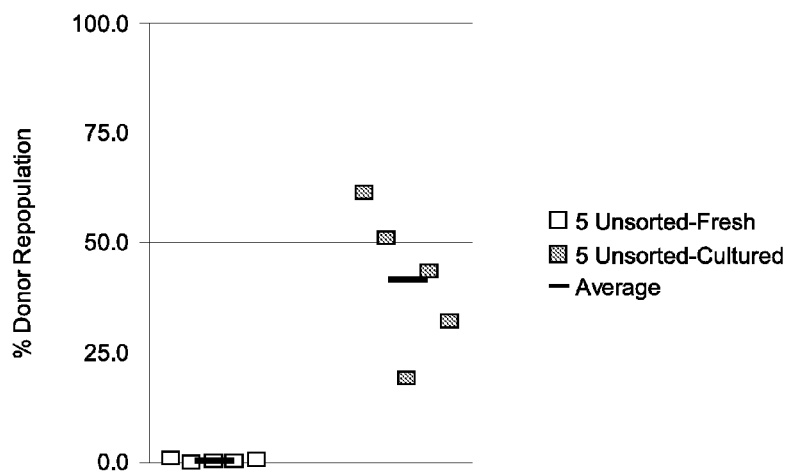

Figure 4 Continued
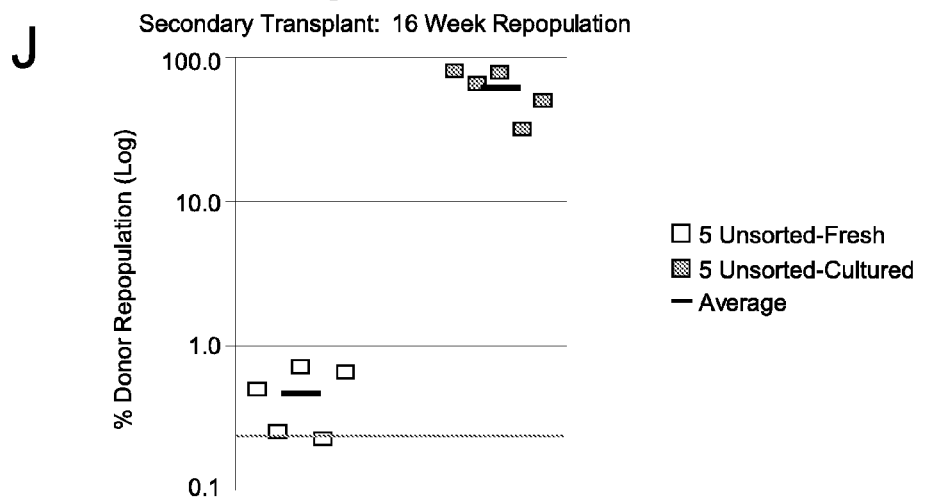
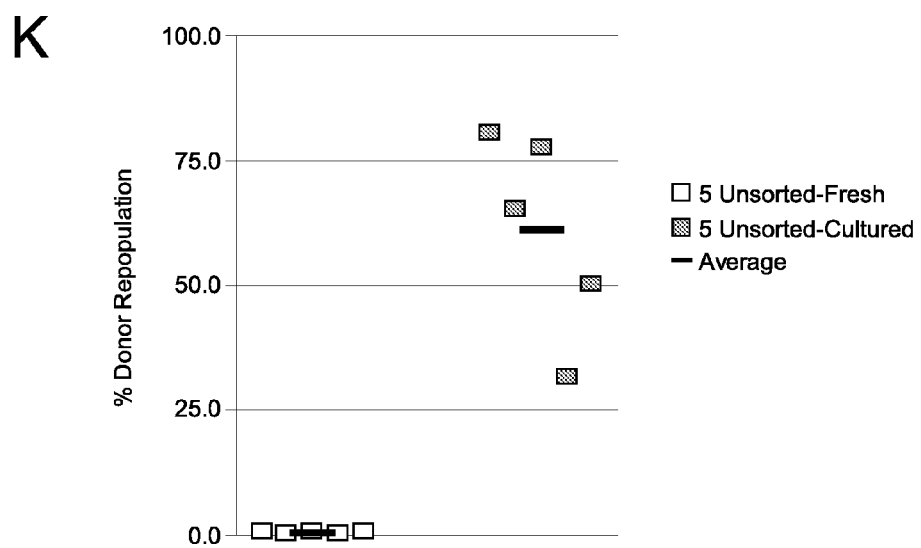
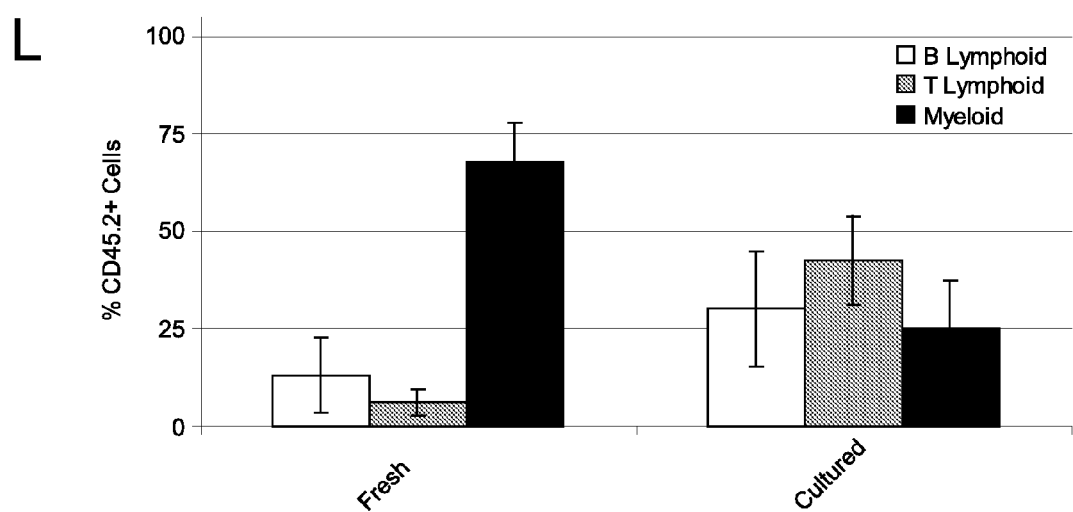

Figure 4 Continued
Secondary Transplant: 16 Week Repopulation
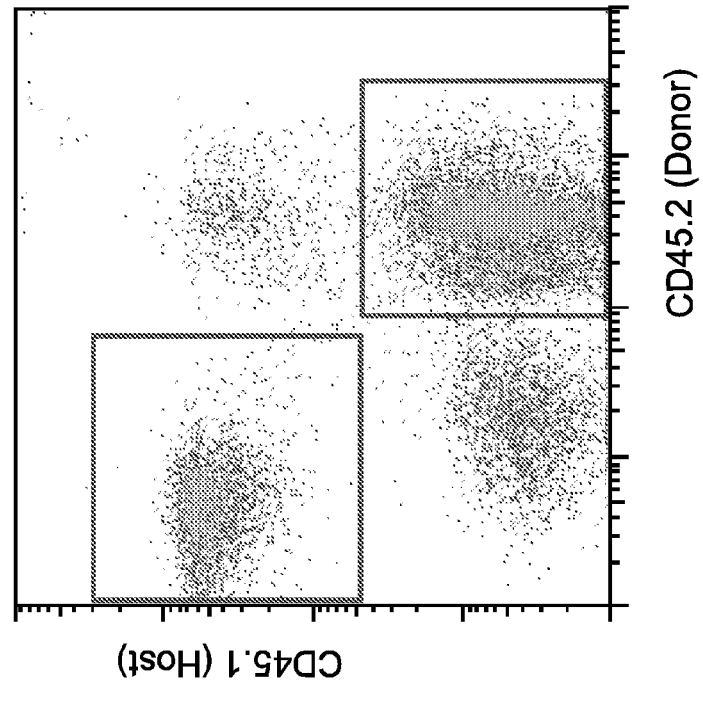
N  5 Unsorted-Cultured
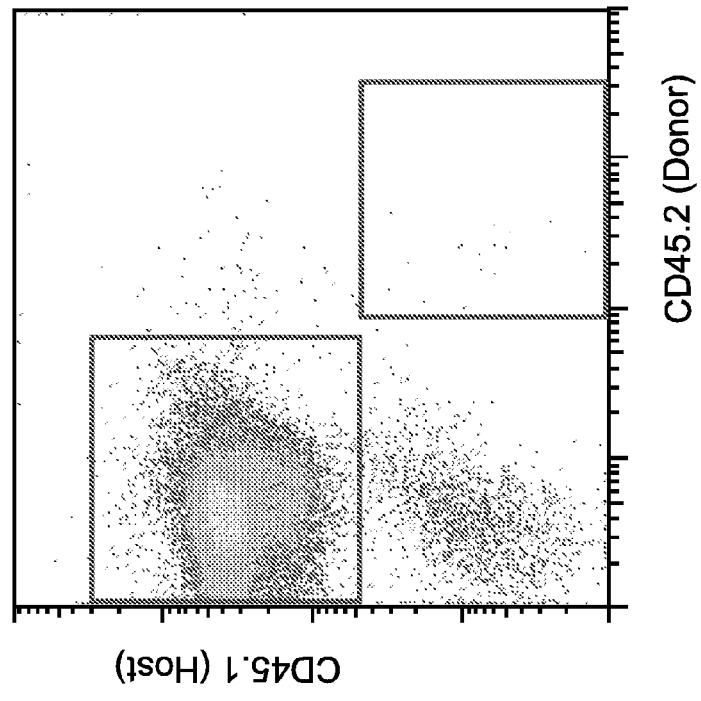
M  5 Unsorted-Fresh Figure 5
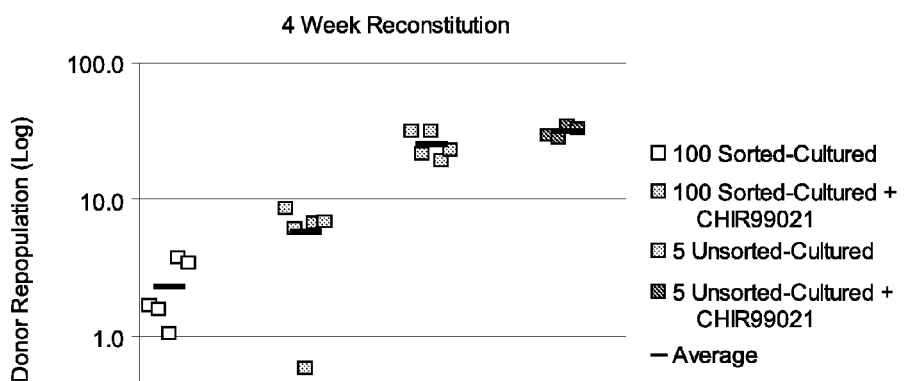
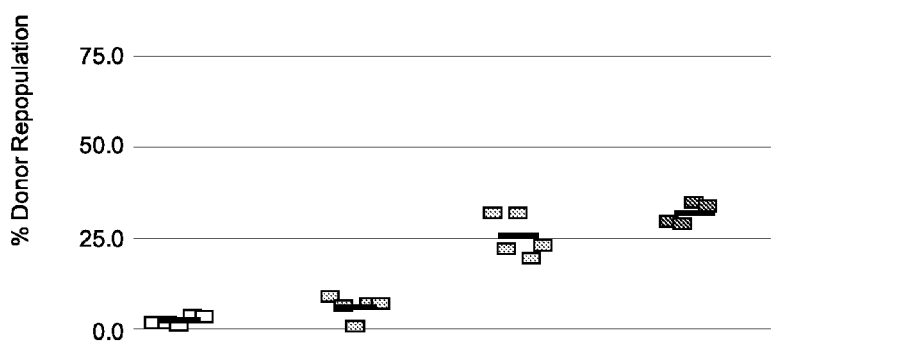
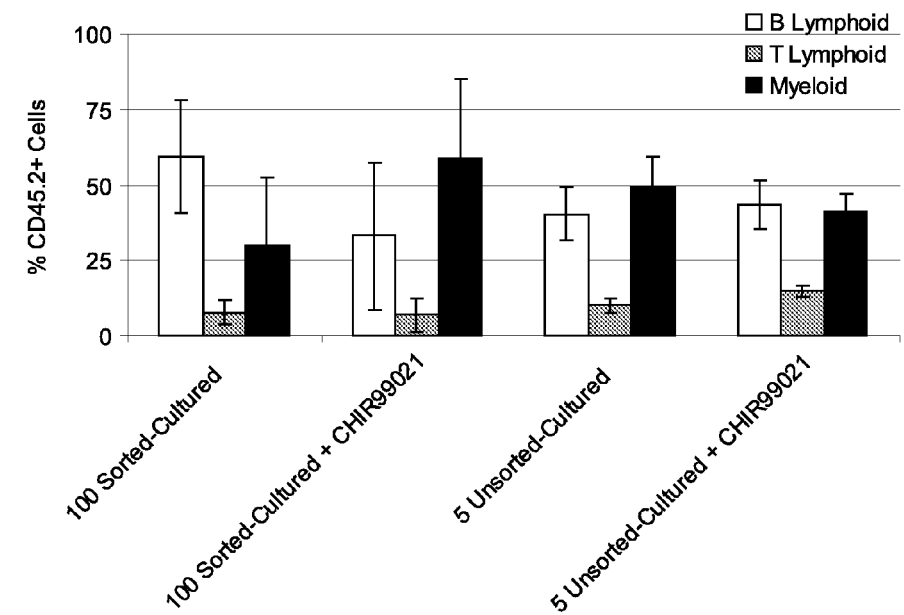

Figure 20 Continued
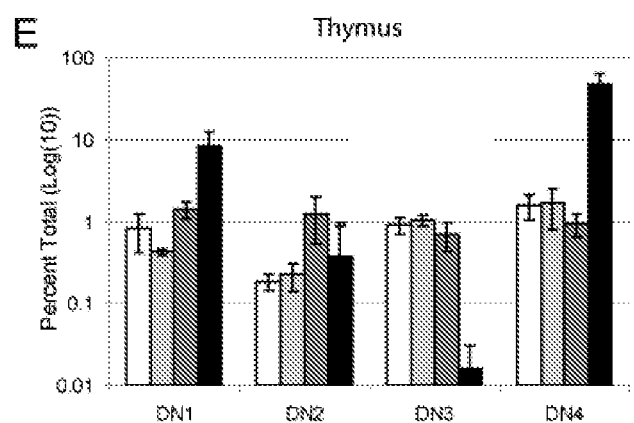
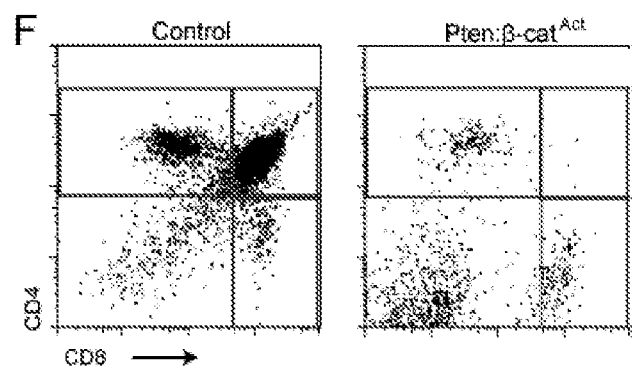
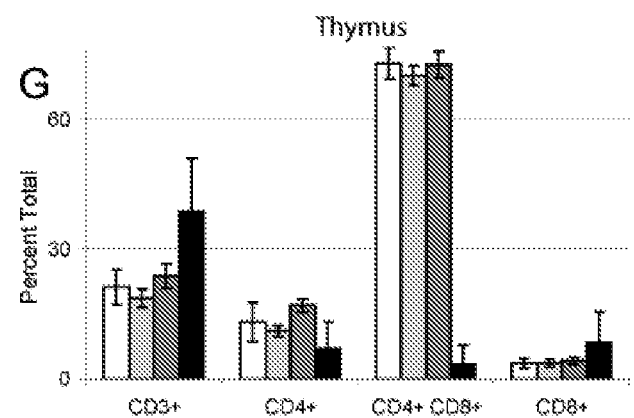

Figure 26
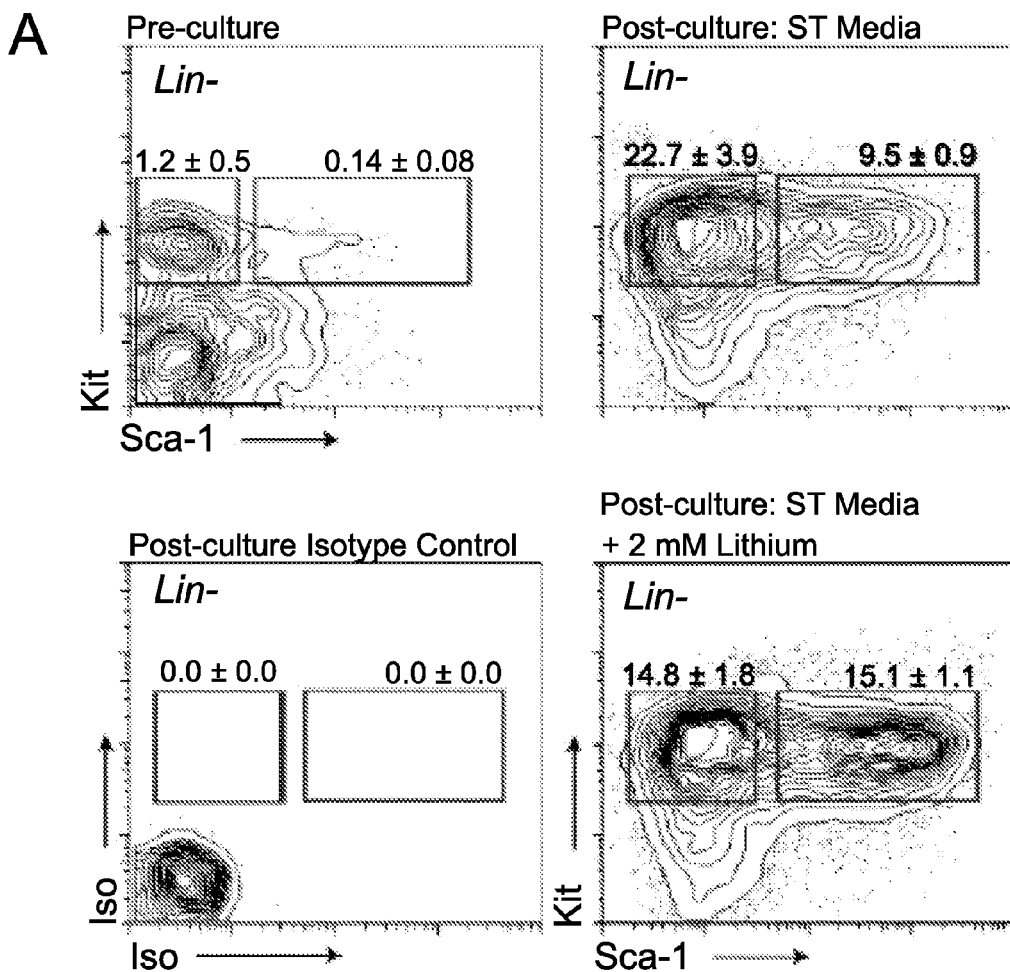
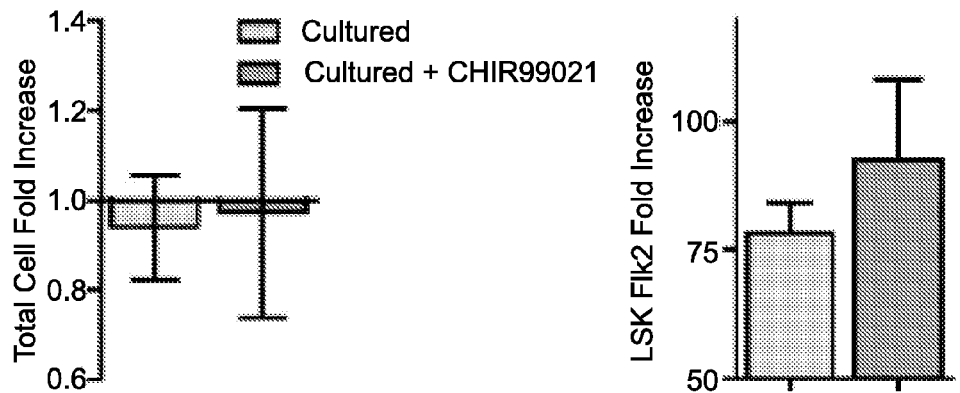

Figure 33
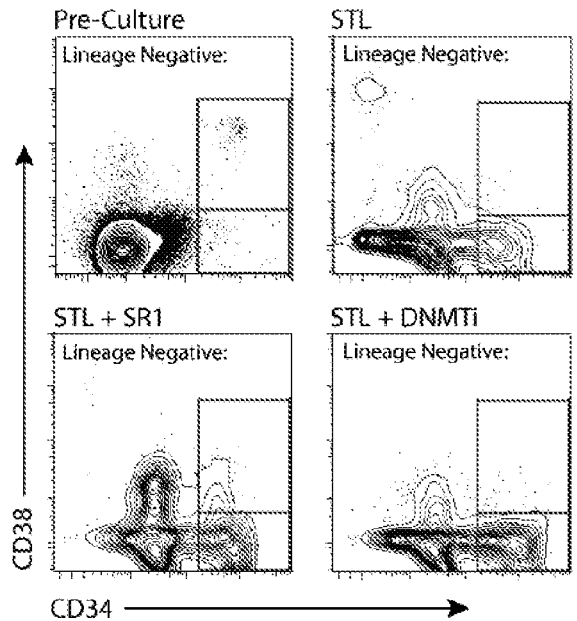
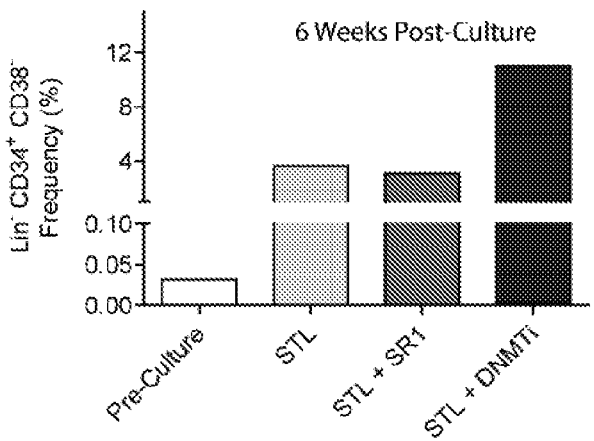
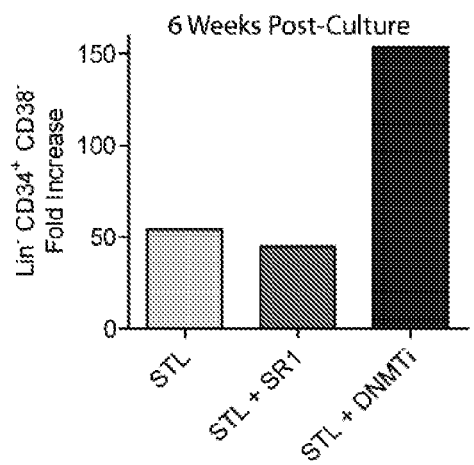

Figure 35
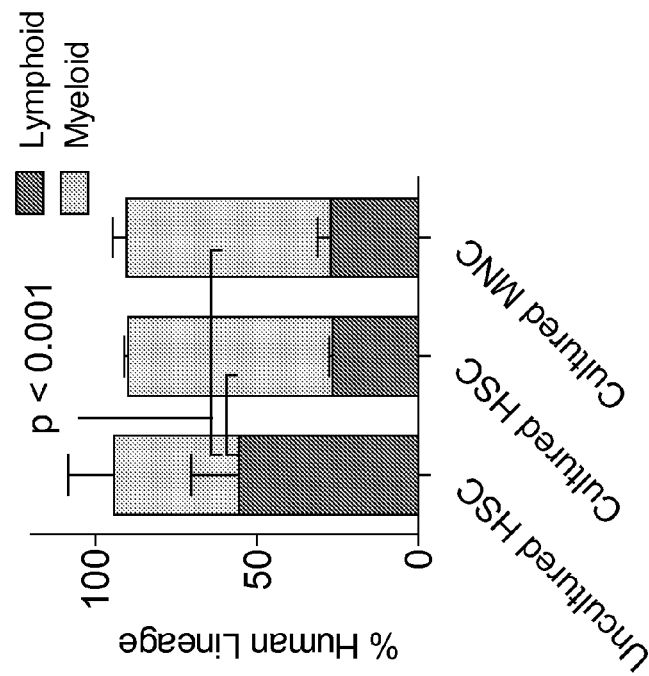
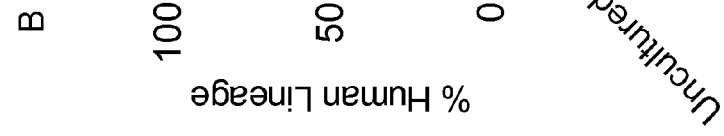
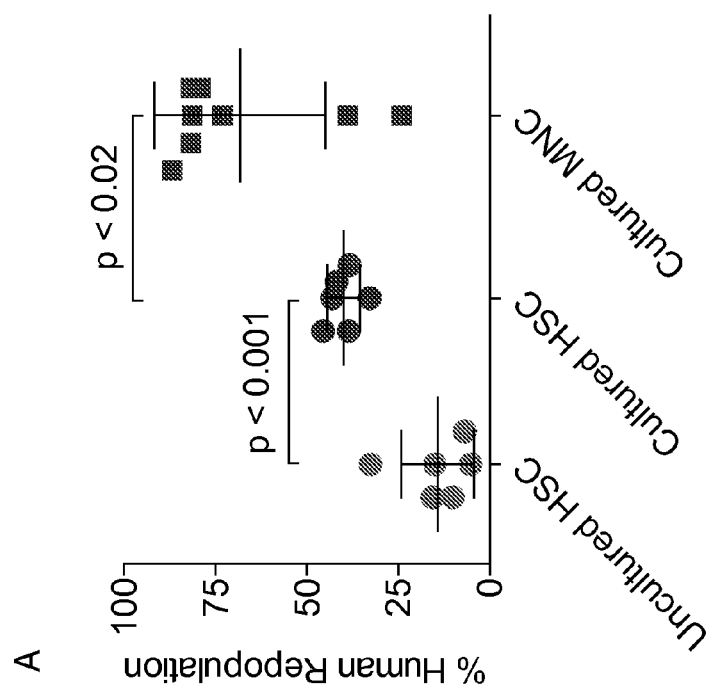

Figure 37
Pre-culture
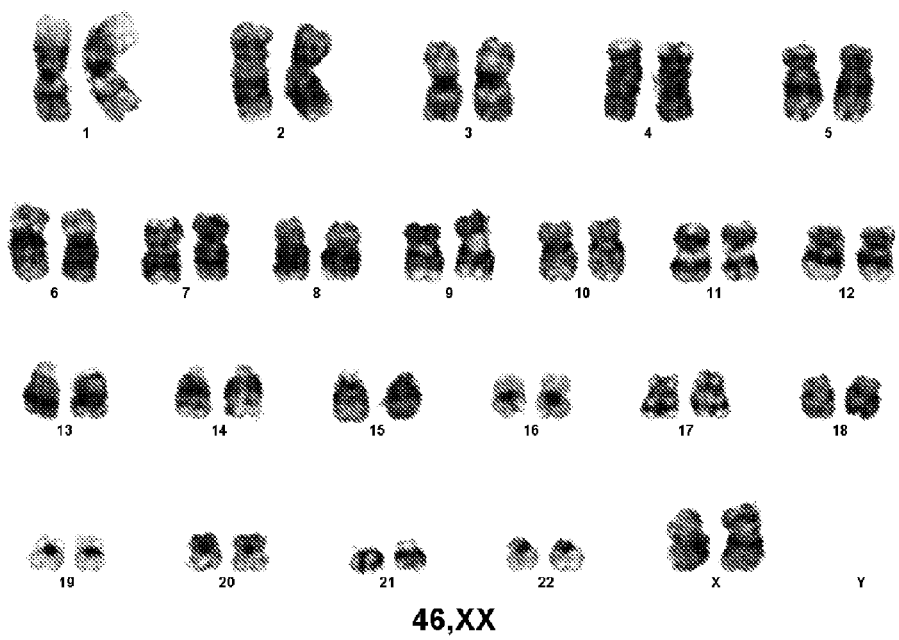
46,XX
Post-culture
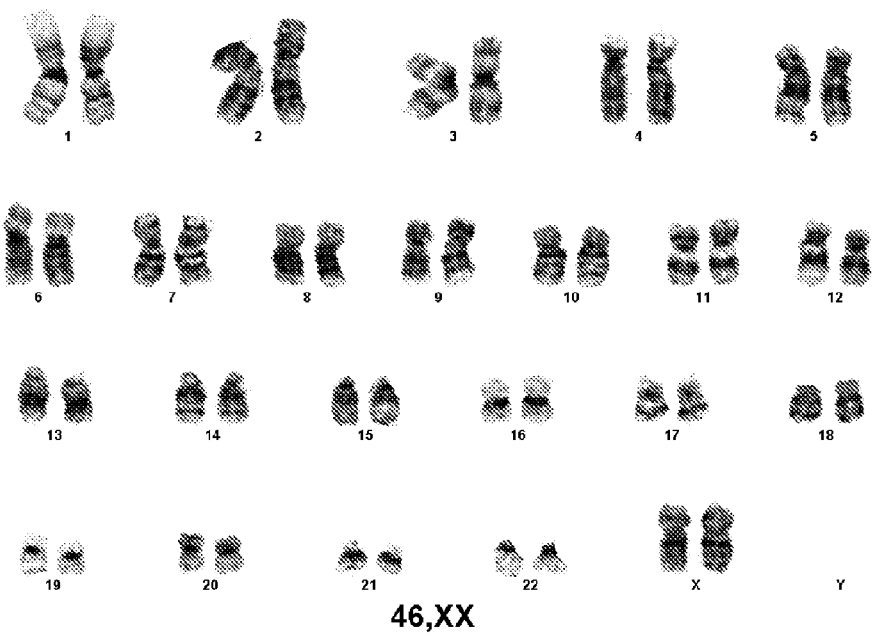
46,XX

METHODS, KITS, AND COMPOSITIONS FOR STEM CELL SELF-RENEWAL

CROSS-REFERENCE TO RELATED APPLICATIONS

The present invention is the National Stage of International Application No. PCT/US2012/060663 filed Oct. 17, 2012, which claims benefit to U.S. provisional application Ser. No. 61/548,833 filed Oct. 19, 2011. The entire contents of the above application are incorporated by reference.

FIELD OF THE INVENTION

The present invention relates to methods, kits, and compositions for expanding a stem cell population, particularly an hematopoietic stem cell population.

INCORPORATION BY REFERENCE OF SEQUENCE LISTING

This application contains references to amino acids and/or nucleic acid sequences that have been submitted as sequence listing text file "0328782pct_sequence.txt", file size of 2 KB, created on Oct. 11, 2012. The aforementioned sequence listing is hereby incorporated by reference in its entirety pursuant to 37 C.F.R. § 1.52(e)(5).

BACKGROUND OF THE INVENTION

Hematopoietic stem cells (HSGs) are clonogenic cells, which possess the properties of both self-renewal (expansion) and multilineage potential giving rise to all types of mature blood cells. HSCs are responsible for hematopoiesis and undergo proliferation and differentiation to produce mature blood cells of various lineages while still maintaining their capacity for self-renewal. The ability to self-renew maintains the HSC population for the lifespan of an animal and also allows HSCs to repopulate the bone marrow of lethally irradiated congenic hosts.

Early HSC development displays a hierarchical arrangement, starting from long-term (LT-) HSCs, which have extensive self-renewal capability, followed by the expansion state, which corresponds to short-term (ST-) HSCs (having limited self-renewal ability) and proliferative multipotent progenitors (MPPs) (having multipotent potential but no self-renewal capability). MPP is also a stage of priming or preparation for differentiation. An MPP differentiates and commits to become either a common lymphoid progenitor (CLP), which gives rise to all the lymphoid lineages, or a common myeloid progenitor (CMP), which produces all the myeloid lineages. During this process, the more primitive population gives rise to a less primitive population of cells, which is unable to give rise to a more primitive population of cells. The intrinsic genetic programs that control these processes including the multipotential, self-renewal, and activation (or transient amplification) of HSCs, and lineage commitment from MPP to CLP or CMP, remain largely unknown.

To sustain constant generation of blood cells for the lifetime of an individual, HSCs located in bone marrow niches (Zhang, J. et al. Nature 425, 836-841, 2003; Calvi, L. M. et al. Nature 425, 841-846, 2003; Kiel, M. J., et al. Cell 121, 1109-1121, 2005; Arai, F. et al. Cell 118, 149-161, 2004) must achieve a balance between quiescence and activation so that immediate demands for hematopoiesis are fulfilled, while long-term stem cell maintenance is also assured. In adults, homeostasis between the quiescent and activated states of stem cells is important to protect HSCs from losing their potential for self-renewal and, at the same time, support ongoing tissue regeneration (Li, L. and Xie, T. Annu. Rev. Cell. Dev. Biol. 21, 605-631, 2005). Overactivation and expansion of stem cells risks both eventual depletion of the stem cell population and a predisposition to tumorigenesis. Although some factors important for stem cell activation have been identified (Heissig, B. et al. Cell 109, 625-637, 2002), the molecular events governing the transition between quiescence and activation are poorly understood.

Phosphatase and tensin homolog (PTEN) functions as a negative regulator of the PI3K/Akt pathway, which plays crucial roles in cell proliferation, survival, differentiation, and migration (Stiles, B. et al. Dev. Biol. 273, 175-184, 2004). The PTEN tumor suppressor is commonly mutated in tumors, including those associated with lymphoid neoplasms, which feature deregulated hematopoiesis (Mutter, G. L. Am. J. Pathol. 158, 1895-1898, 2001; Suzuki, a. et al. Immunity 14, 523-534, 2001). PTEN-deficiency has been associated with expansion of neural and embryonic stem cell populations (Groszer, M. et al. Science 294, 2186-2189, 2001; Kimura, T. et al. Development 130, 1691-1700, 2003). But, the role of PTEN in stem cells and tumorigenesis and the recurrence of tumors heretofore has been not understood.

PTEN functions as an antagonist of phosphatidyl inositol 3-kinase (PI3K) (Maehama T & Dixon J E. J Biol Chem. 273:13375-13378. 1998). The serine kinase Akt is downstream of the PI3K signal (Cross D A, Alessi D R, Cohen P et al. Nature 378:785-789 1995). PTEN has been shown to inhibit Akt and thereby inhibit the nuclear accumulation of β-catenin (Persad S et al. J Cell Biol. 153:1161-1174 2001).

Akt has a broad range of effects. Its major function is to provide a survival signal and to block apoptosis, complementary to its regulation of β-catenin function. (Song, G. et al., J. Cell. Mol. Med., 9(1): 59-71, 2005) Akt acts through a number of proteins, including mammalian target of rapamycin (mTOR), the Forkhead family of transcription factors (FoxO), BAD, caspase 9, murine double minute 2 (Mdm2).

Akt can directly and indirectly activate the serine/threonine kinase mTOR, which activates protein translation through a signaling cascade. (LoPiccolo, J., et al., Anti-Cancer Drugs, 18:861-874, 2007). Indirect activation occurs through tuberous sclerosis complex-2 (TSC2), which, when in the unphosphorylated state, forms a complex with tuberous sclerosis complex-1 (TSC1, also known as hamartin). This complex promotes the GTPase activity of Ras homolog enriched in brain (RHEB), which in turn, acts to downregulate mTOR activity. Upon phosphorylation by Akt, however, the ability of the TSC1-TSC2 complex to promote RHEB's GTPase activity is inhibited, and therefore, mTOR's activity is promoted. (Cully, M. et al., Nat. Rev. Cancer, 6:184-192, 2006). mTOR can also form a complex with Rictor, and this complex can provide positive feedback on the Akt signaling cascade by phosphorylating and activating Akt. (Sarbassov, D. D., et al., Science, 307: 1098-1101, 2005).

Akt also regulates cell survival through transcriptional factors, including FoxO. Akt's phosphorylation of FoxO inhibits FoxO, resulting in inhibition of transcription of several proapoptotic genes, such as Fas-L, IGFBP1 and Bim. (Datta, S. R., et al., Cell, 91:231-241, 1997; Nicholson, K. M., et al., Cell Signal, 14:381-395, 2002).

One of the down-stream targets of FoxO is p27 (Kip1), a potent inhibitor of cyclin E/cdk2 complexes. (Wu, H. et al., Oncogene, 22: 3113-3122, 2003). FoxO factors induce expression of p27, which can bind to cyclin E/cdk2 complexes and inhibit their activity, resulting in a block in cellular proliferation. (Burgering, B. M. T. & Medema, R. H., J. Leukocyte Biol., 73:689-701, 2003). In addition, Akt itself can also directly phosphorylate p27 on T157, resulting in the redistribution of p27 from the nucleus to the cytoplasm, away from cyclin E/cdk2 complexes. (Id.) Phosphorylation of p27 on T198 was critical for the binding of p27 to 14-3-3 proteins, and through this pathway, Akt may directly promote p27's degradation. (Fujita, N., et al., J. Biol. Chem., 277(32): 28706-28713, 2002).

Another one of the targets of Akt in promoting cell survival is BAD, a member of the Bcl-2 family of proteins. In the absence of Akt phosphorylation, BAD forms a complex with Bcl-2 or Bcl-X on the mitochondrial membrane and inhibits the anti-apoptotic potential of Bcl-2 and Bcl-X. (Song, G. et al., J. Cell. Mol. Med., 9(1): 59-71, 2005) Akt phosphorylates BAD on Serine 136, thus releasing BAD from the Bcl-2/Bcl-X complex. (Song, G. et al., J. Cell. Mol. Med., 9(1): 59-71, 2005; Datta, S. R., et al., Genes Dev., 13:2905-2927, 1999). Therefore, Akt suppresses BAD-mediated apoptosis and promotes cell survival.

Furthermore, by phosphorylation of pro-caspase-9 at Serine 196, Akt inhibits proteolytic processing of pro-caspase-9 to the active form, caspase-9, which is an initiator and an effecter of apoptosis (Cardone et al., 1998, Science, 282: 1318-1320, Donepudi, M. & Grutter, M. G., Biophys. Chem., 145-152, 2002).

Additionally, Akt regulates cell survival via the Mdm2/p53 pathway. Akt can activate Mdm2 by direct phosphorylation, thereby inducing the nuclear import of Mdm2 or the up-regulation of Mdm2's ubiquitin ligase activity. (Mayo L. D., Donner D. B., 2001, Proc. Natl., Acad. Sci. USA 98:11598-11603; Gottlieb T. M. et al, Ocogene, 21: 1299-1303, 2002). Mdm2 negatively regulates the p53 protein, which may induce cell death in response to stresses (Oren M., Cell Death Differ., 10:431-442, 2003), by targeting p53 for ubiquitin-mediated proteolysis (Haupt, Y. et al., 1997, Nature 387: 296-299) or by binding to the transactivation domain of p53, thereby inhibiting p53-mediated gene regulation. (Momand, J. et al., Cell, 69: 1237-1245, 1992) One of the down-stream targets of p53 is the p21 (CIP1/WAF1) gene. The p53 gene product binds to a site located 2.4 kb upstream of the p21 coding sequence, and this binding site confers p53-dependent transcriptional regulation. (El-Deiry, W. S., et al., Cell, 75: 817-825, 1993) Thus, down-regulation of p53 also down-regulates the transcription of p21.

PTEN not only regulates p53 protein through antagonizing the Akt-Mdm2 pathway, it can also directly regulate p53. First, PTEN can enhance p53 transactivation in a phosphatase-independent manner (Tang, Y. & Eng C., Cancer Research, 66: 736-742, 2006). Second, PTEN forms a complex with p300 in the nucleus and plays a role in maintenance of high p53 acetylation, which is the activated form of p53. (Li A. et al., Molecular Cell, 23 (4): 575-587, 2006). In turn, p53 may also activate the transcription of PTEN. (Cully, M. et al., Nat. Rev. Cancer, 6:184-192, 2006).

Canonical signals in the Wnt pathway are involved in stem cell proliferation. (Kim, L. & Kimmel, A. R. Current Drug Targets 7:1411-1419, 2006). Glycogen synthase kinase 3 beta (GSK-3β) is a part of the Wnt signaling pathway, and its primary substrate is β-catenin. (Hagen, T et al., J. Biochem. 277(26):23330-23335). In the absence of canonical Wnt signaling, GSK-3β binds to β-catenin and phosphorylates β-catenin, thereby targeting β-catenin for ubiquitination and followed by proteosome-mediated degradation, which is mediated by Adenomatous Polyposis Coli (APC). (Id., Moon, R. T. et al., Science 296:1644-1646. 2002). Canonical Wnt signals induce the release of β-catenin from GSK-3β, thereby activating β-catenin. (Katoh, M & Katoh, M. Cancer Biol Ther. 5(9):1059-64, 2006). β-catenin then localizes to the nucleus, where it activates gene transcription. (Id.).

In view of the foregoing, it would be advantageous to elucidate the interaction between Wnt and PTEN signaling pathways and to provide new insights into molecular regulation of stem cell proliferation and differentiation. It would also be advantageous to use such insights to provide new methods, kits, and compositions for expanding stem cells in vivo and ex vivo, which stem cells would be of the kind and quantity sufficient to transplant into a suitable recipient.

SUMMARY OF THE INVENTION

Thus, one embodiment of the present invention is an ex vivo method for expanding the number of hematopoietic stem cells (HSC) in a population of mononuclear cells (MNC). This method comprises culturing the population of MNCs comprising at least one HSC in an HSC expansion media for a period of time sufficient to expand the number of HSCs in the MNC population, wherein the HSC expansion media comprises a modulator of DNA methyltransferase (DNMT) and a modulator of the Wnt pathway.

An additional embodiment of the present invention is an expanded, substantially undifferentiated HSC population made by any method disclosed herein.

Another embodiment of the present invention is a kit for expanding, ex vivo, the number of hematopoietic stem cells (HSC) in a population of mononuclear cells (MNC). The kit comprises a DNA methyltransferase inhibitor (DNMTi) and a GSK-3β inhibitor, and instructions for the use of the inhibitors, wherein, when used, the kit provides expanded number of HSCs.

Yet another embodiment of the present invention is a media for carrying out ex vivo expansion of HSCs in a population of MNCs. This media comprises a fluid media suitable for maintaining viable stem cells, a DNMTi, and a GSK-3β inhibitor present in the media at concentrations sufficient to enable expansion of the HSC.

An additional embodiment of the present invention is an ex vivo method for expanding the number of HSCs in a population of MNCs. This method comprises contacting the HSCs with (i) 5-aza-2'-deoxycytidine, a prodrug thereof, pharmaceutically acceptable salts thereof, or combinations thereof; and (ii) lithium, pharmaceutically acceptable salts thereof, or combinations thereof to expand the number of HSCs.

A further embodiment of the present invention is an ex vivo method for expanding the number of hematopoietic stem cell (HSC) in a population of mononuclear cells (MNCs). This method comprises culturing the population of MNCs comprising at least one HSC in an HSC expansion media for a period of time sufficient to expand the number of HSCs in the MNC population, wherein the population of MNCs is enriched for CD34$^+$ cells, and wherein the wherein the HSC expansion media comprises of a modulator of the Wnt pathway.

Another embodiment of the present invention is a method for administering an hematopoietic stem cell (HSC) population to a patient in need thereof. This method comprises:
(a) culturing an HSC population in a population of mononuclear cells (MNCs) in an HSC expansion media for a period of time sufficient to expand the number of HSCs to a number sufficient to transplant into the patient, wherein the MNC population is enriched for CD34+ cells, and wherein the HSC expansion media comprises of a modulator of the Wnt pathway; and (b) administering the cultured HSC population to the patient.

An additional embodiment of the present invention is a method for providing HSCs, which, when transplanted into a patient, reduce the likelihood of the patient developing a complication from the transplant. This method comprises culturing a population of HSCs in an HSC expansion media for a period of time sufficient to expand the number of HSCs prior to administering the HSCs to the patient, wherein the HSC expansion media comprises an activator of the Wnt pathway, an activator of the PI3K/Akt pathway, and a DNMTi.

Another embodiment of the present invention is an ex vivo method for expanding the number of hematopoietic stem cells (HSC) in a population of mononuclear cells (MNC). This method comprises culturing the population of MNCs comprising at least one HSC in an HSC expansion media for a period of time sufficient to expand the number of HSCs in the MNC population, wherein the expanded HSCs are functional with long term, multi-lineage, repopulating potential.

An additional embodiment of the present invention is a kit for expanding, ex vivo, the number of hematopoietic stem cells (HSC) in a population of mononuclear cells (MNC). The kit comprises a GSK-3β inhibitor, and instructions for the use of the inhibitor, wherein, when used, the kit provides expanded HSCs that are functional with long term, multi-lineage, repopulating potential.

A further embodiment of the present invention is a media for carrying out ex vivo expansion of a stem cell in a population of MNCs. This media comprises a fluid media suitable for maintaining viable stem cells and a GSK-3β inhibitor present in the media at a concentration sufficient to enable expansion of the stem cell population while maintaining a long term, multi-lineage, repopulating potential in the stem cells, wherein the stem cells, when transplanted into a recipient, exhibit greater than 5% donor repopulation.

Yet another embodiment of the invention is an ex vivo method for expanding the number of cells capable of supporting multi-lineage repopulation in a population of mononuclear cells (MNC). This method comprises culturing a population of MNCs comprising at least one hematopoietic stem cell (HSC) and at least one hematopoietic progenitor cell in an HSC expansion media for a period of time sufficient to expand the number of cells capable of supporting multi-lineage repopulation in the MNC population.

Another embodiment of the invention is a method for expanding a population of stem cells obtained from a tissue selected from the group consisting of peripheral blood, cord blood, and bone marrow. This method comprises modulating a PTEN pathway and a Wnt pathway in the population of stem cells to expand the number of stem cells.

Another embodiment of the invention is a method for ex vivo expansion of a substantially undifferentiated stem cell population. This method comprises modulating a PTEN pathway and a Wnt pathway in the undifferentiated stem cell population to expand the number of undifferentiated stem cells without significant differentiation of the stem cell population.

Yet another embodiment of the invention is a method for ex vivo expansion of an hematopoietic stem cell (HSC) population obtained from a tissue selected from the group consisting of peripheral blood, cord blood, and bone marrow. This method comprises modulating a PTEN pathway and a Wnt pathway in the HSC population to expand the HSC population to a sufficient quantity while maintaining a multilineage differentiation potential in the HSC population, which is sufficient for subsequent transplantation into a patient in need thereof.

Another embodiment of the invention is an expanded, substantially undifferentiated stem cell population made by a method of the present invention. In a related embodiment, the invention is an expanded HSC population made by a method of the present invention.

An additional embodiment is a method for ex vivo expansion of hematopoietic stem cells (HSCs) by at least 40-fold, the expanded HSCs being competent to reconstitute an HSC lineage upon transplantation into a mammalian patient in need thereof. This method comprises culturing a population of HSCs in a suitable culture medium comprising a PTEN inhibitor and a GSK-3β inhibitor.

A further embodiment of the invention is a kit for expanding an hematopoietic stem cell (HSC) population for subsequent transplantation into a patient in need thereof. The kit comprises a PTEN inhibitor, a GSK-3β inhibitor, and instructions for the use of the inhibitors.

An additional embodiment is a media for carrying out ex vivo expansion of a stem cell population. The media comprises a fluid media suitable for maintaining viable stem cells and PTEN and GSK-3β inhibitors present in the media at concentrations sufficient to enable expansion of the stem cell population while maintaining a multilineage differentiation potential in the stem cells.

A further embodiment is a method for administering an hematopoietic stem cell (HSC) to a patient in need thereof. This method comprises (a) culturing, in a suitable culture media, a sample containing an HSC population in the presence of a modulator of a molecule in the PTEN pathway and a modulator of a molecule in the Wnt pathway for a period of time sufficient to expand the number of HSCs in the sample to a number sufficient to transplant into the patient; (b) removing from the culture the PTEN and Wnt pathway modulators; and (c) administering the HSCs to the patient.

A further embodiment of the invention is a method for reconstituting bone marrow in a patient in need thereof. This method comprises: (a) culturing, in a suitable culture media, a sample containing an HSC population in the presence of a modulator of a molecule in the PTEN pathway and a modulator of a molecule in the Wnt pathway for a period of time sufficient to expand the number of HSCs in the sample to a number sufficient to transplant into the patient; (b) removing from the culture the PTEN and Wnt pathway modulators; and (c) administering the HSCs to the patient.

Another embodiment is a method for expanding a population of hematopoietic stem cells (HSCs). This method comprises culturing a population of HSCs under conditions sufficient to result in an expansion of the HSC population by at least 40-fold, wherein the expanded population of HSCs is suitable for transplantation into a mammal in need thereof.

Yet another embodiment is a method for treating a patient in need of a transplant selected from the group consisting of a bone marrow transplant, a peripheral blood transplant, and an umbilical cord blood transplant. This method comprises administering to the patient a population of HSCs obtained by a method of the present invention.

A further embodiment is a method for expanding a population of hematopoietic stem cells (HSCs) comprising: (a) obtaining from a mammal a tissue sample comprising an HSC population; (b) expanding, in vitro, the HSC population from the sample, wherein: (i) the HSC population expands by at least 40-fold; and (ii) the expanded HSC population has the ability to reconstitute an hematopoietic lineage for at least 4-weeks after transplantation into a recipient.

An additional embodiment is a method for reconstituting an hematopoietic stem cell lineage in a recipient in need thereof. This method comprises: (a) obtaining from a mammal a tissue sample comprising an HSC population; (b) expanding, in vitro, the HSC population from the sample, wherein: (i) the HSC population expands by at least 40-fold; and (ii) the expanded HSC population has the ability to reconstitute an hematopoietic lineage for at least 4-weeks after transplantation into a recipient in need thereof; and (c) transplanting the expanded HSC population into a recipient in need thereof.

A further embodiment of the invention is a method for expanding a hematopoietic stem cell population in a mammal in need of such expansion. This method comprises administering to the mammal a therapeutically effective amount of a modulator of Wnt and Akt for a period of time sufficient to expand the HSC population by at least 40-fold with HSCs that possess the ability to reconstitute an hematopoietic lineage in the mammal.

These and other aspects of the invention are further disclosed in the detailed description and examples which follow.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIG. 1A is two bar graphs showing the absolute numbers (per femur+tibia) of lineage negative, Sca-1$^+$Kit$^+$ (LSK) cells in Scl-Cre negative control and Scl-Cre$^+$ PTEN with constitutively activated β-catenin (Pten:Ctnnb1, also referred to as Pten:β-cat$^{Act}$) double mutant and each single mutant bone marrow (top) and spleen (bottom) as determined by FACS analysis. (Harada, N., et al., *Embo J*, 18(21): 5931-42 1999. Yilmaz, O. H., et al., *Nature*, 441:475-82 2006. Zhang, J., et al., *Nature*, 441(7092): 518-22 2006.) Mice are at 10 days post-induction of Tamoxifen. Reduction of LSK cells in double mutant bone marrow with expansion in the spleen is indicative of mobilization from bone marrow to spleen. Scl-Cre is an HSC-specific Tamoxifen inducible Cre-recombinase used to achieve conditional knockout of LoxP flanked (floxed) Pten and Ctnnb1 alleles. (Gothert, J. R., et al., *Blood*, 105(7): 2724-2732, 2005.)

FIGS. 1B-1C show representative results of FACS analysis (pre-gated for lineage negative (Lin$^-$) cells) of LSK cells (right blue box) and myeloid progenitors (left blue box) in control, single and double mutant bone marrow and spleen as indicated. Mean frequencies are based on total cell number±SD. Cells were collected from mice at 6 weeks post-induction (wpi) of Tamoxifen.

FIG. 1D shows the frequency of CD34$^-$ cells within the LSK population in control, single and double mutants at 6 wpi.

FIG. 1E shows the absolute number of LSK CD34$^-$ cells in control, single and double mutant bone marrow (tibia+femur) and spleen at 6 wpi.

FIGS. 1F and G are bar graphs showing the absolute number of LSK cells per femur and tibia in control, Ctnnb1, Pten, and Pten:Ctnnb1 double mutant bone marrow (F) and spleen (G) at 6 weeks post-induction. While the percentage of LSKs is increased in double mutants (see FIG. 1C), low cellularity of bone marrow from double mutants yields only moderately increased absolute numbers compared to control.

FIGS. 1H and I are bar graphs and FACS analysis, respectively, of percentage of LSK cells, which are Flk2$^-$ (indicating long-term reconstituting (LT)-HSCs) in control, single and double mutant bone marrow (as indicated) at 6 weeks post-induction. Single mutants are not significantly different from controls at this time point. Boxes in FIG. 1I indicate Flk2$^-$ (LT HSC) cells.

FIG. 1J is a set of FACS analyses of CD45 in leukemic Pten:Ctnnb1 mutant bone marrow. CD45 (high) blast crisis cells are indicated (blue box, left panel). No blast cell population is observed in control or Ctnnb1 mutants while a minor population has been observed in 1 of 1 Pten single mutant mice at 6 weeks post-induction (data not shown). The right panel shows LSK analysis of leukemic Pten:Ctnnb1 mutant mouse bone marrow. Note the conversion to blast cells (lower left) with only a remnant LSK population (compare to FIG. 1C).

FIG. 1K is a bar graph showing early hematopoietic progenitors defined by FACS analysis in control, single, and double mutant bone marrow as indicated. Common myeloid progenitor (CMP); granulocyte-monocyte progenitor (GMP); megakaryocyte-erythrocyte progenitor (MEP); and common lymphoid progenitor (CLP).

FIG. 2A is a series of photographs showing 100 LSK cells isolated from control, active β-catenin (Ctnnb1), Pten mutant, and double mutant (Pten:Ctnnb1) mice after 10 days in culture (original magnification 100×). Cell numbers are not dramatically increased from 100 seeded LSKs in control while Ctnnb1 single mutant LSKs do not survive. In contrast, Pten single mutant LSKs exhibit greater proliferation but appear more heterogeneous indicating more significant differentiation. The greatest and most homogeneous expansion occurs from Pten:Ctnnb1 double mutant LSKs.

FIG. 2B is a set of photographs showing LSK cells from Pten and Pten:Ctnnb1 mutants at 34 days culture (original magnification 200×). (Note: wild-type control cultures do not expand beyond 4 weeks; Ctnnb1 mutant cultures do not survive beyond 10 days.) Pten mutant HSC cultures appear more heterogeneous with significant cell clumping and more irregular cell morphology. Also note the spindle-shaped adherent cells (arrows) showing differentiation. In contrast, double mutant HSC cultures exhibit consistent morphology. Therefore, while Pten single mutant LSKs survive and expand, they have undergone more significant differentiation than the much more homogeneous Pten:Ctnnb1 double mutant LSKs.

FIGS. 2C and D are bar graphs showing the results of an expansion experiment. Pten and Pten:Ctnnb1 LSK seven week cultures were counted and analyzed by FACS for maintenance of the LSK phenotype (wild-type control and Ctnnb1 cultures did not survive this long in vitro). Double mutant LSKs undergo >1,200 fold expansion vs. 50 fold for Pten single mutant LSKs. LSK purity of cultures is significantly greater in Pten:Ctnnb1 cultures maintaining the LSK phenotype in about 85% of total live cells vs. about 50% for Pten single mutant cultures.

FIG. 2E is a FACS analysis of a 7 week culture of Pten:Ctnnb1 LSK cells (pre-gated on live, lineage negative cells) along with isotype control. The boxed area indicates $Kit^+Sca-1^+$ (LSK) cells.

FIGS. 2F and G are FACS analyses showing a transplant engraftment experiment. At 5 weeks culture (see FIG. 2B), Pten and Pten:Ctnnb1 LSK cultures were re-sorted and 1000 LSK cells ($CD45.2^+$) from each were transplanted into lethally irradiated (10 Gy) $CD45.1^+$ recipient mice along with $2\times10^5$ congenic whole bone marrow competitor cells. Because wild-type cells did not survive 5 weeks culture, 1000 fresh wild-type LSK cells were also transplanted as a separate control group. At 4 weeks post-transplant, there was no detectable engraftment from peripheral blood analysis of mice transplanted with either Pten or Pten:Ctnnb1 LSK cultures (data not shown). At 5 weeks post-transplant, bone marrow from recipient mice was analyzed for donor engraftment ($CD45.2^+$ cells) and donor LSK cells ($CD45.2^+$ LSKs). FIGS. 2F and G display representative donor engraftment (left, boxed areas indicate $CD45.2^+$ donor cells) and donor LSK cell engraftment (right, boxed areas indicate LSK cells) from bone marrow of mice transplanted with 1000 Fresh LSK cells (F) or 1000 cultured Pten:Ctnnb1 LSK cells (G).

FIGS. 2H-J are bar graphs showing the quantitative analysis of donor ($CD45.2^+$) cells (H), donor LSK cells (I), and fold increase in donor LSKs (J) isolated from bone marrow of recipient mice described in FIGS. 2F and 2G at 5 weeks post-transplant.

FIG. 3A is a schematic illustrating representative members of the Wnt and PTEN pathways. Inhibition of GSK-3β leads to β-catenin activation which blocks HSC differentiation. Inhibition of PTEN leads to Akt activation which promotes survival. Both pathways individually have been shown to promote HSC proliferation.

FIGS. 3B and C are photographs of HSCs. One hundred LSK Flk2⁻ cells were sorted from wild-type (C57Bl/6) mice and cultured in (1) media, (2) media+1 µM CHIR99021 (GSK-3β inhibitor), (3) media+200 nM Dipotassium Bisperoxo(picolinato)oxovanadate (BpV(pic), a PTEN inhibitor), and (4) media+1 µM CHIR99021+200 nM BpV(pic). An alternative PTEN inhibitor, Shikonin, was also utilized at 200 nM alone (5) or in combination with 1 µM CHIR99021 (6). Pictures are at 17 days culture (B, original magnification 100×) and 23 days (C, original magnification 40×). Compared to control, both inhibitors applied individually yield greater expansion of LSK cells indicating that GSK-3β inhibition is not strictly equivalent to constitutive activation of β-catenin shown in Ctnnb1 mutant LSKs while BpV(pic) yields similar results compared to Pten mutant LSKs (see FIG. 2). Similar to double mutant LSKs (FIG. 2), the greatest expansion is shown with both inhibitors present (FIG. 3B/C, panel 4).

FIG. 3D is a series of photographs showing LSK Flk2⁻ cells at 28 days culture in the indicated media conditions (original magnification 200×). Here, significant expansion relative to control is observed with both inhibitors present individually; however, significant differentiation/heterogeneity of cell morphology is observed in both single inhibitor cultures, including more variable cell size/morphology and/or differentiation to adherent, spindle-shaped cells (middle panels). In contrast, and quite surprisingly, expansion with homogeneity is achieved when both inhibitors are present (last panel).

FIG. 3E is a FACS analysis of 28 day LSK Flk2⁻ cells cultured in media containing both inhibitors (200 nM BpV (pic) and 1 µM CHIR99021). Cells were pre-gated on live, lineage negative cells. The boxed area indicates $Kit^+Sca1^+$ (LSK) cells. Greater than 90% of LSKs retain Flk2 negativity (data not shown). The LSK Flk2⁻ phenotype is maintained with high purity in cultures containing both inhibitors.

FIG. 3F is a bar graph showing fold expansion of LSK Flk2⁻ cells after 28 days culture in the indicated conditions. While both inhibitors added individually lead to significant expansion compared to media without either inhibitor, the greatest expansion (~270 fold) is observed when both inhibitors are added together.

FIGS. 3G and H are bar graphs showing the % repopulation and % $CD45.2^+$ cells from engrafted mice. Twenty-eight day cultures (FIGS. 3D-F) were re-sorted for LSK Flk2⁻ cells and 1000 LSK Flk2⁻ cells ($CD45.2^+$) from each media condition were transplanted into lethally irradiated (10 Gy) $CD45.1^+$ recipient mice along with $2\times10^5$ congenic whole bone marrow competitor cells. At 4 weeks post-transplant, peripheral blood was analyzed for donor (G) and multi-lineage (H) engraftment. In FIG. 3G, each bar represents an individual mouse; the horizontal-dashed line represents the average "engraftment" of mice transplanted with competitor cells only and thus the limit of detectability for true engraftment. Long-term (4 month) engraftment has not been observed from 28-day cultures (data not shown). 6 of 8 mice show >1% engraftment when transplanted with LSK Flk2⁻ cells cultured with both inhibitors present compared to 4/8 with only CHIR99021 present, 0/10 with only BpV(pic) present, and 2/6 with media only. One percent or greater engraftment is a standard limit for substantial engraftment. (Zhang, C. C., et al., Nat Med, 12(2): 240-5, 2006. Zhang, C. C. and H. F. Lodish, Blood, 105(11): 4314-20, 2005.) Thus, while use of both inhibitors together leads to greatest expansion in LSKs (FIG. 3F), transplantation of equivalent numbers of these cultured LSK Flk2⁻ cells also yields increased short-term engraftment/functionality when cultured with both inhibitors compared to no or either single inhibitor only.

FIG. 3I is a bar graph showing the fold expansion of LSK Flk2⁻ cells after 9 days culture in (1) media, (2) media+200 nM BpV(pic), (3) media+100 nM CHIR99021, and (4) media+200 nM BpV(pic)+100 nM CHIR99021. Because long-term engraftment was not observed from 28 day cultures (FIGS. 3D-H and data not shown), LSK Flk2⁻ cells were cultured for only 9 days to test if both expansion and long-term repopulation can be achieved. Similar trends are observed here to the 28 day cultures (compare to FIG. 3F) although the extent of expansion is substantially reduced at only 9 days compared to 28 days culture.

Figure 3:
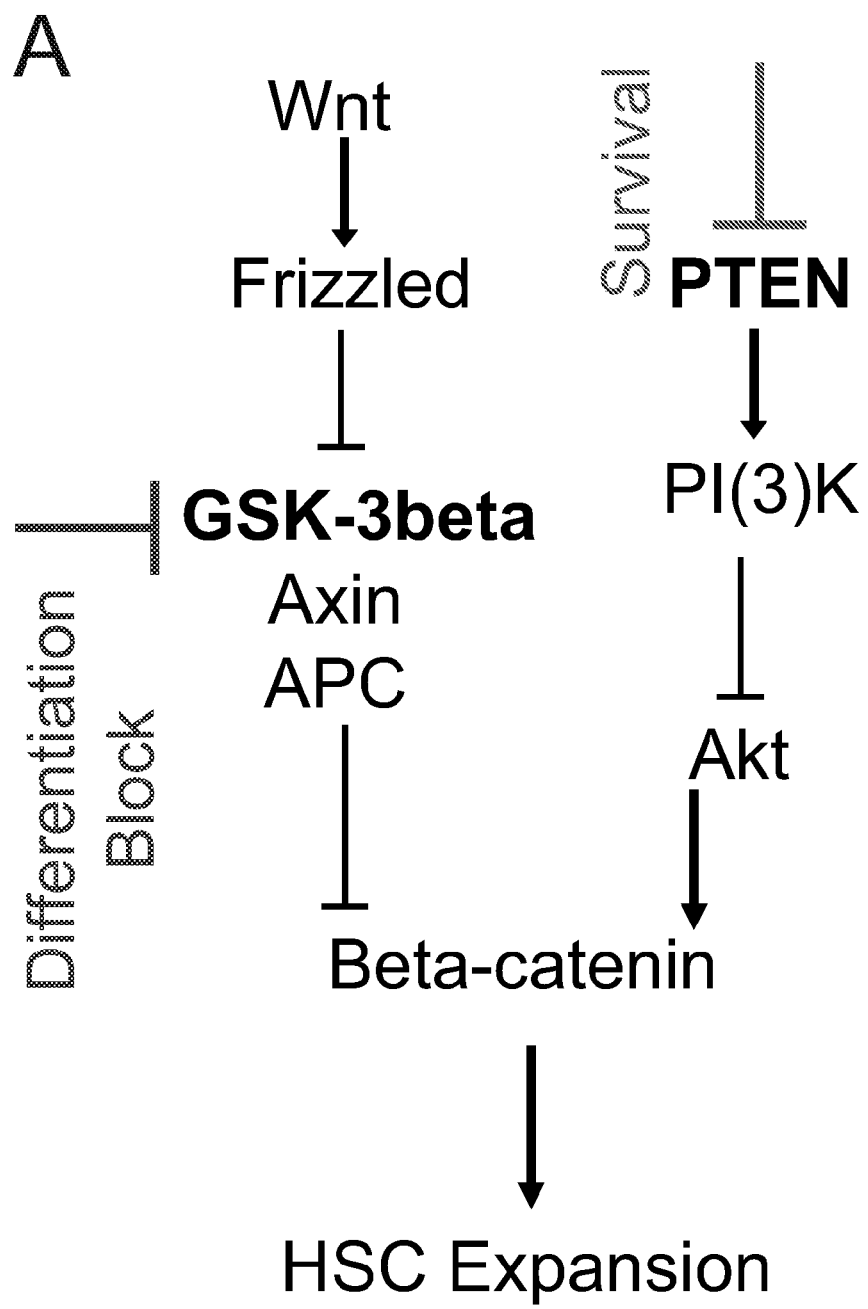
FIGS. 3A-K are schematics, photographs, bar graphs, and FACS analyses demonstrating that ex vivo pharmacological manipulation of the PTEN/Akt and Wnt/β-catenin signaling pathways cooperatively drive functional HSC expansion.
Figure 3:
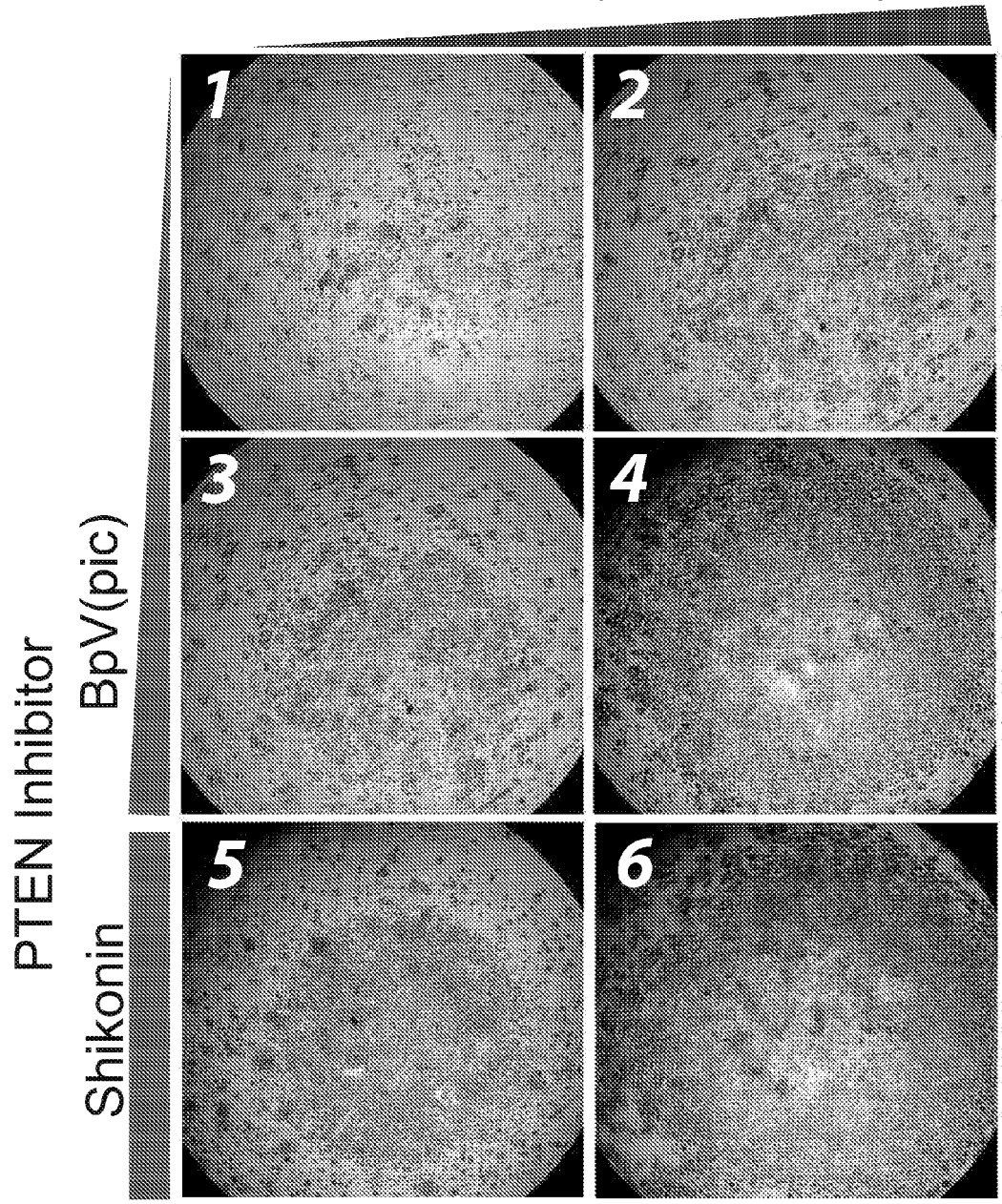
Figure 3:
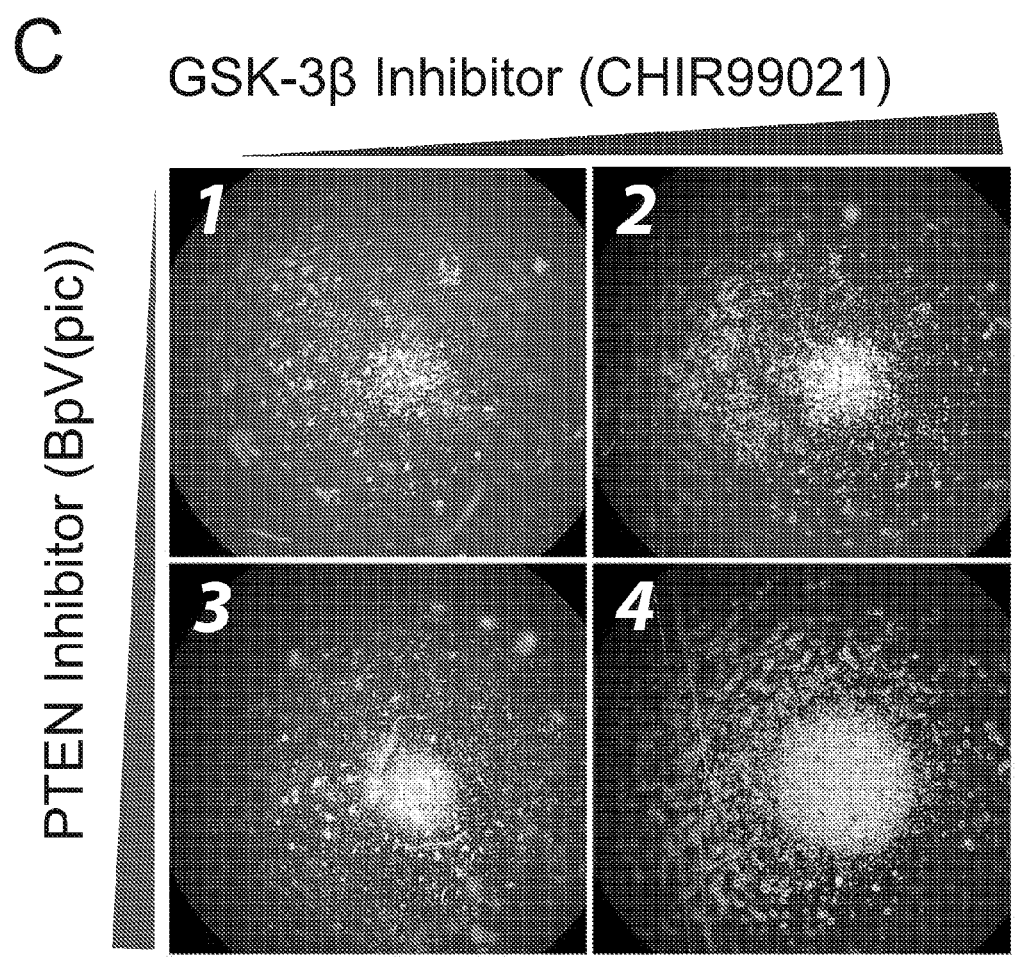
Figure 3:
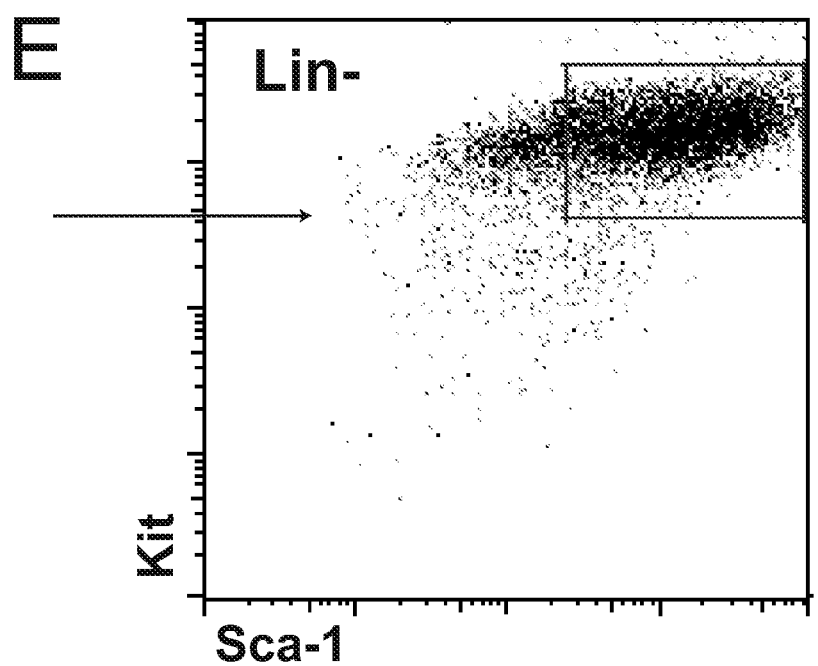
Figure 3:
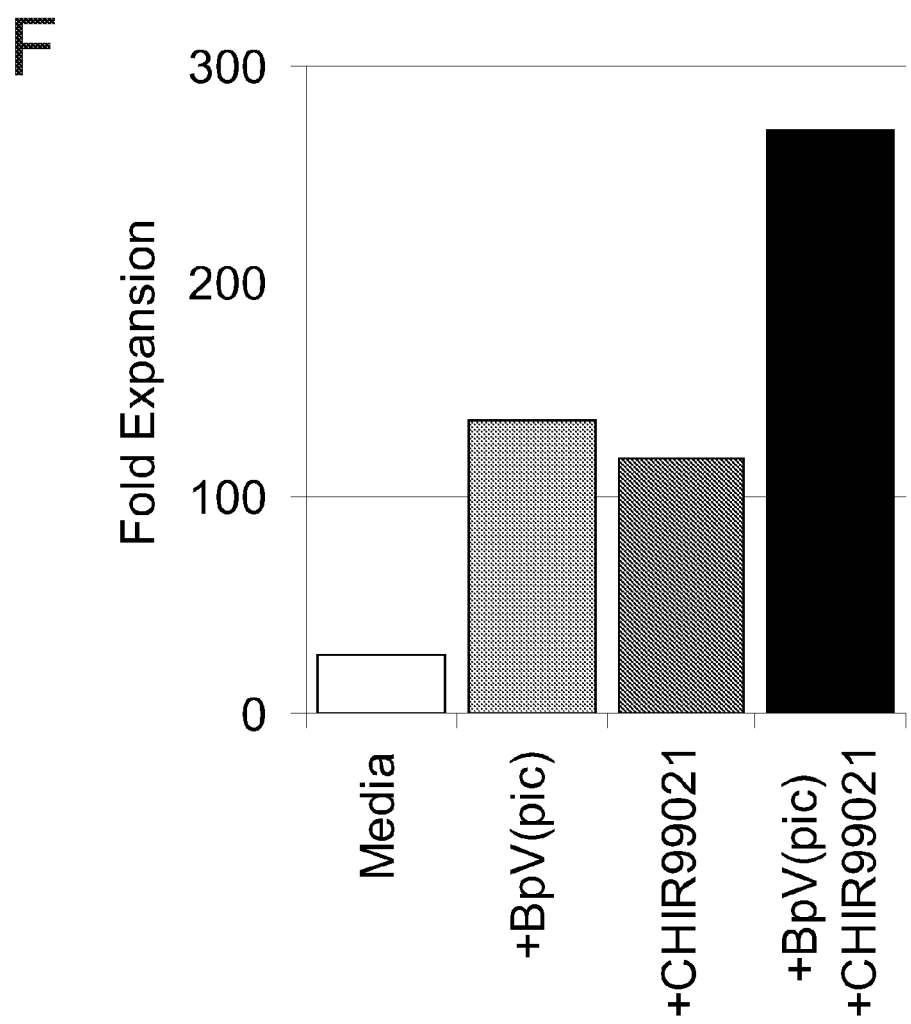
Figure 3:
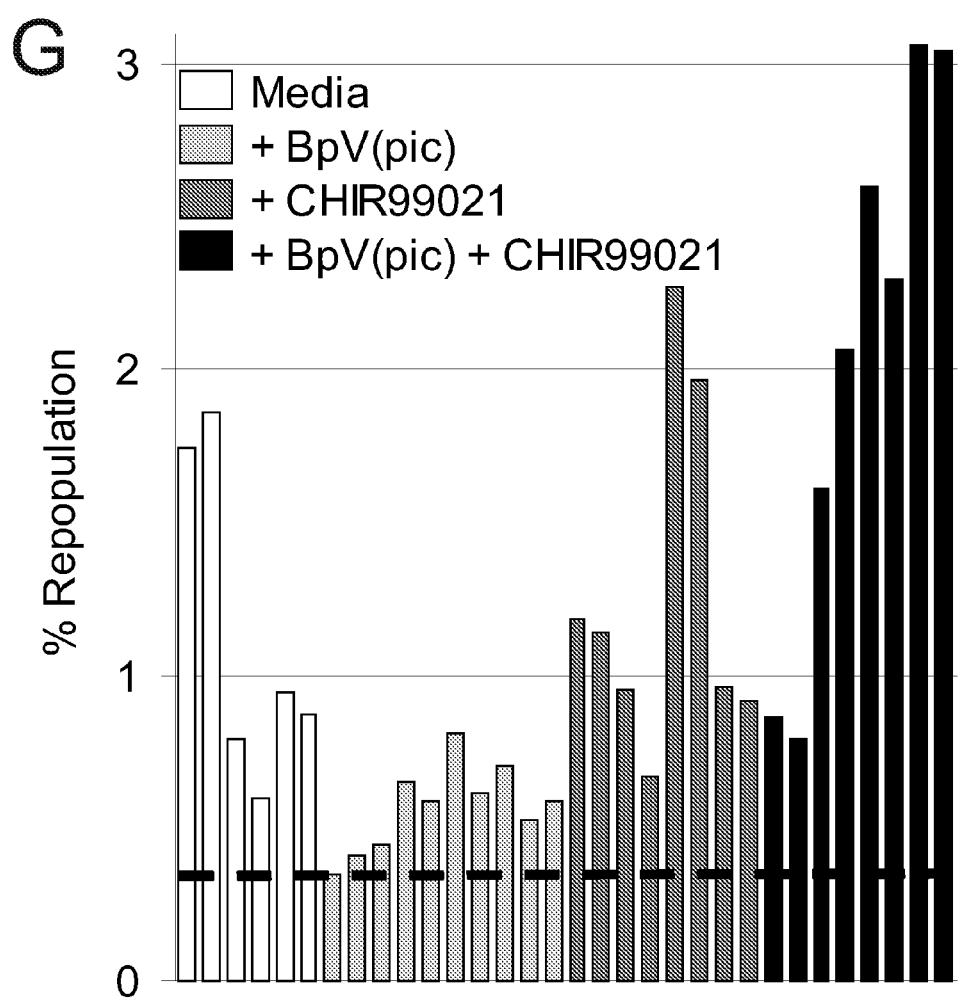
Figure 3:
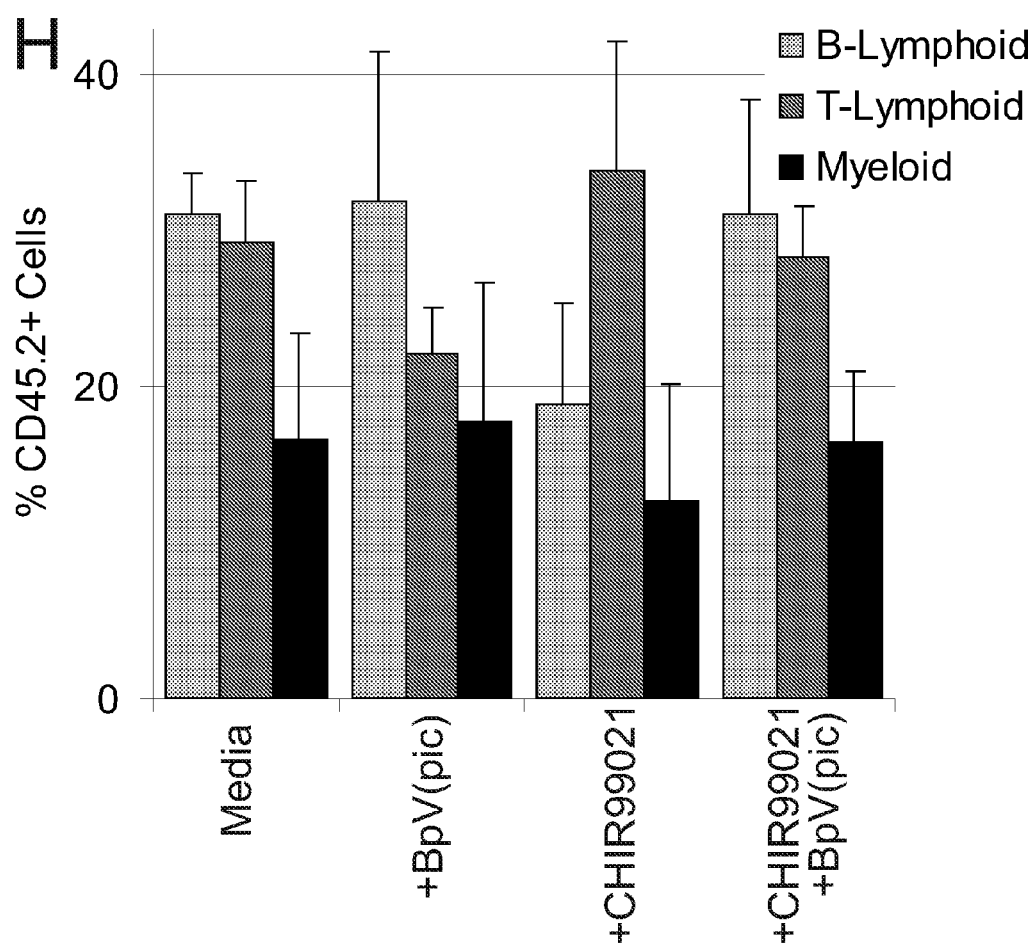
Figure 3:
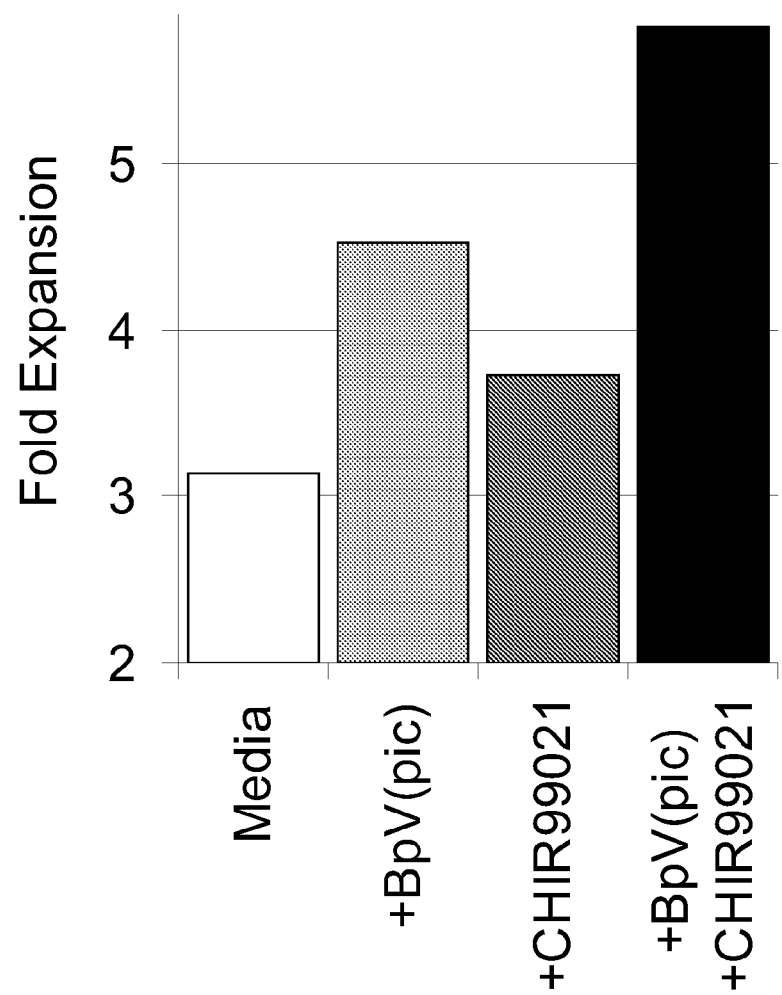
Figure 3:
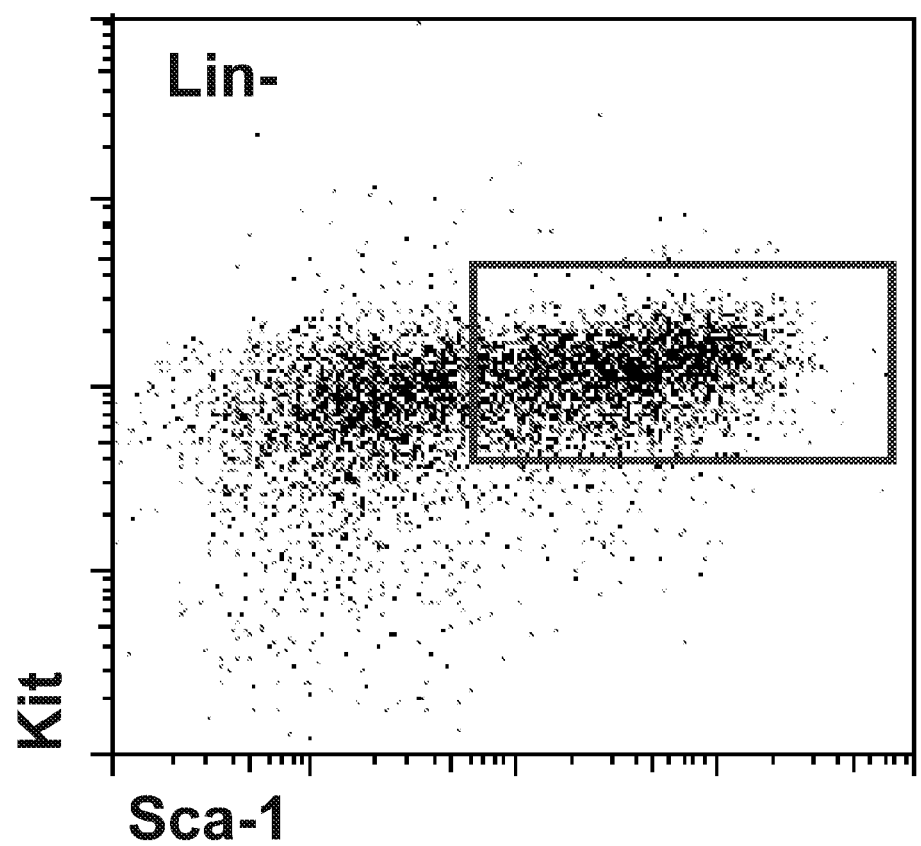
Figure 3:
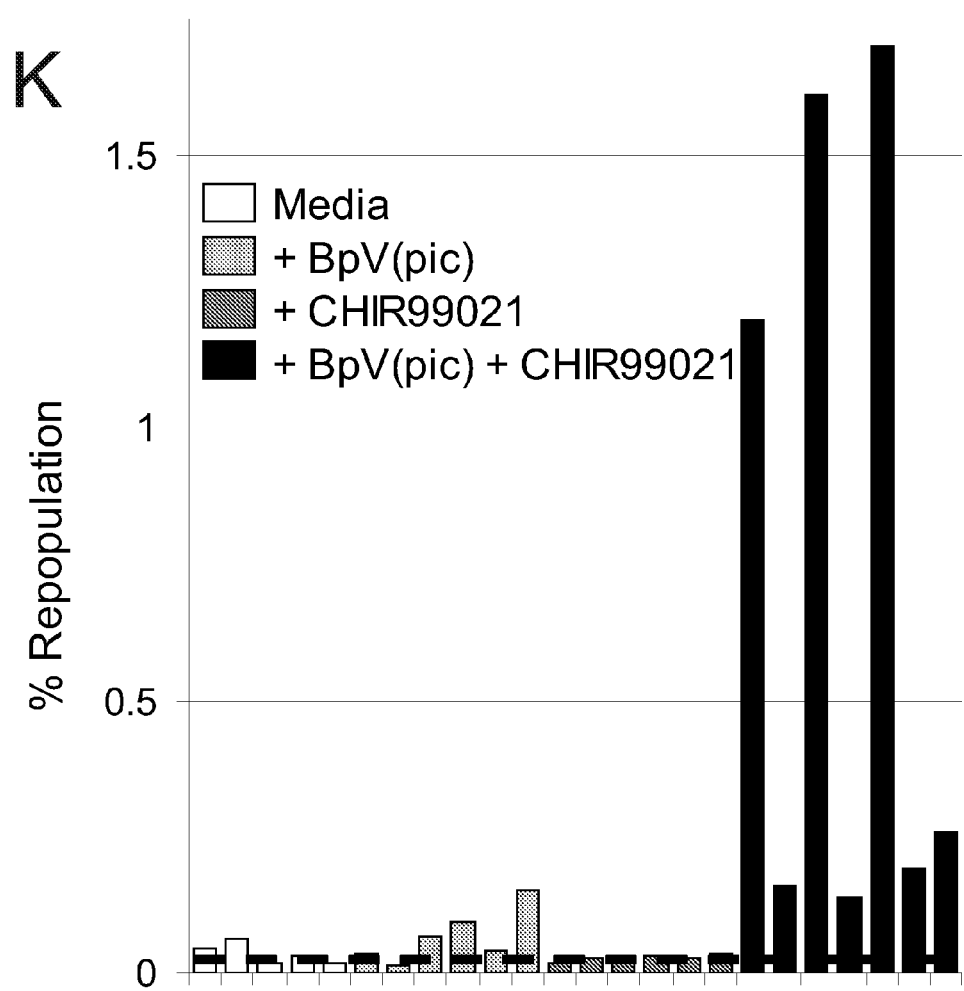

FIG. 3J is a FACS analysis of 9 day LSK Flk2⁻ cells cultured in media+200 nM BpV(pic)+100 nM CHIR99021. The boxed area indicates $Kit^+Sca-1^+$ (LSK) cells. Cells were pre-gated on live, lineage negative cells. Greater than 90% of LSKs retain Flk2 negativity (data not shown). Here, the levels of Sca-1 and Kit appear normal compared to the Sca-1$^{(high)}$Kit$^{(high)}$ population shown from 28 day cultures (FIG. 3E).

FIG. 3K is a bar graph showing % repopulation of 10-day cultured cells in mice. Ten day cultures were transplanted into lethally irradiated (10 Gy) CD45.1$^+$ recipient mice along with $2\times10^5$ congenic whole bone marrow competitor cells. The total, non-adherent cell product after 10 days culture of 100 initial LSK Flk2$^-$ cells was transplanted per mouse. At 8 weeks post-transplant, peripheral blood was analyzed for donor engraftment. As in FIG. 3H, multi-lineage reconstitution was observed from all mice exhibiting true engraftment (data not shown). Each bar represents an individual mouse; the horizontal-dashed line represents the average 'engraftment' of mice transplanted with competitor cells only and thus the limit of detectability for true engraftment. Here, 3/7 mice transplanted with LSK Flk2$^-$ cells cultured in the presence of both inhibitors exhibited 1% or greater donor engraftment vs. no mice reaching this threshold in the single or no inhibitor groups.

Figure 4:
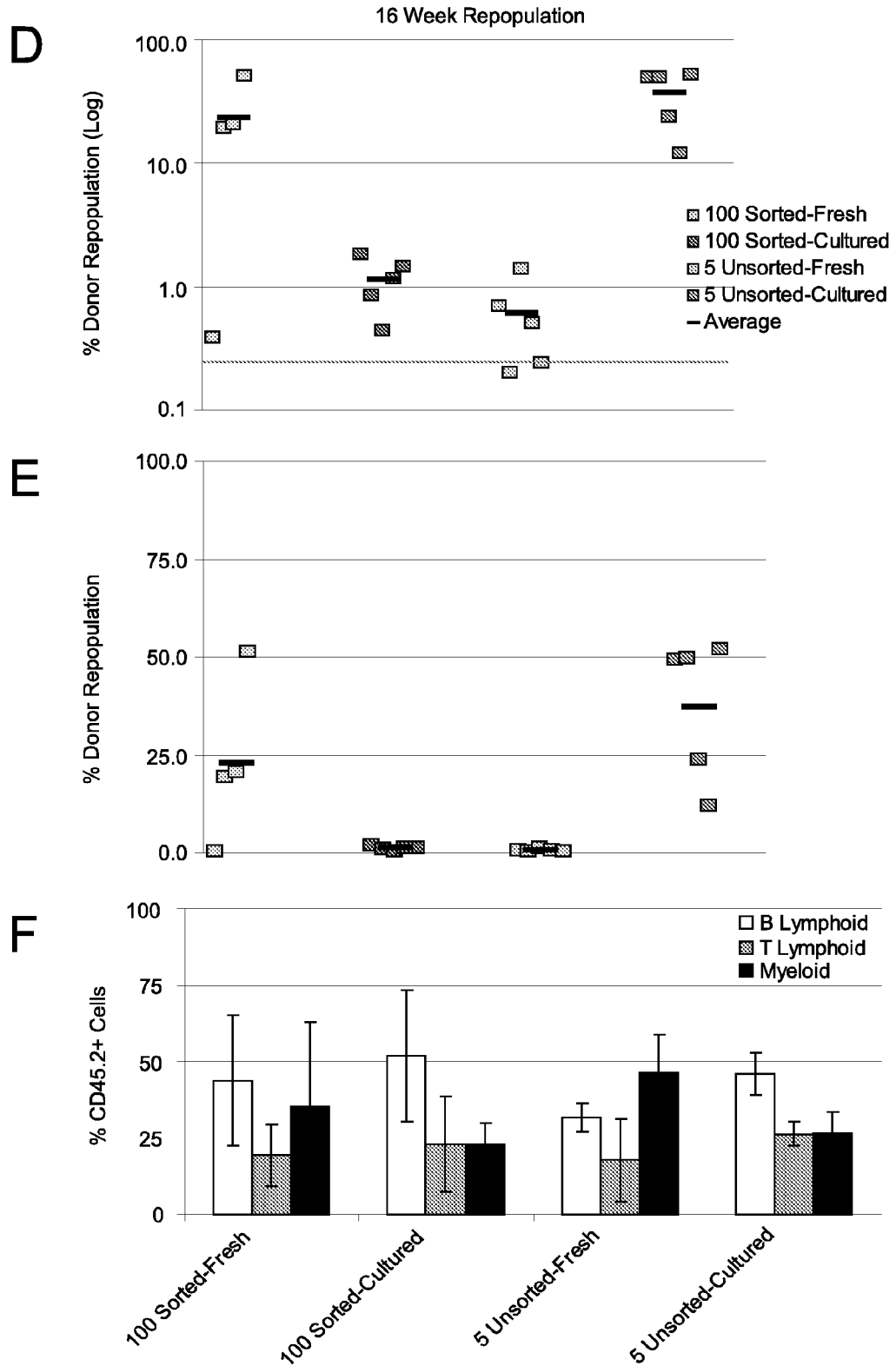

FIG. 4 shows that ex vivo expansion of unsorted bone marrow mononuclear cells enhances functional long-term hematopoietic reconstitution relative to sorted, ex vivo expanded HSCs.

FIG. 4A is a logarithmic plot of CD45.2 (donor) frequency of total CD45$^+$ cells in peripheral blood of transplant recipients. Red line denotes limit of detectable engraftment as determined by "engraftment" found in mice transplanted with competitor cells only.

FIG. 4B is a linear plot of CD45.2 (donor) frequency of total CD45$^+$ cells in peripheral blood of transplant recipients. Putative HSCs were identified by fluorescence activated cell sorting (FACS) based upon cell-surface markers, including lineage marker negative, Sca-1$^+$, c-Kit$^+$, Flk2$^-$ (LSKF$^-$), sorted and cultured for 14 days. Bone marrow mononuclear cells (MNCs) were also fractionated and the concentration of LSKF$^-$ cells was determined. MNCs containing a known quantity of LSKF$^-$ cells were cultured for 14 days. After 14 days, the cellular product of these cultures was transplanted into lethally-irradiated recipients at a dosage corresponding to an original input into culture of 100 LSKF$^-$ cells per mouse for sorted cultures and MNCs containing 5 LSKF$^-$ cells per mouse for unsorted cultures. In addition, 100 freshly isolated, sorted LSKF$^-$ cells per mouse and freshly isolated MNCs containing 5 LSKF$^-$ cells per mouse were transplanted into two additional groups. $1\times10^5$ competitor bone marrow cells congenic with the hosts (CD45.1$^+$) were included per mouse. At 4 weeks post-transplant, peripheral blood was collected from each transplant recipient, and donor vs. host derived hematopoietic cells were determined by FACS analysis.

FIG. 4C shows the percentage of donor derived peripheral blood cells (CD45.2$^+$) contributing to the main hematopoietic lineages (B lymphoid, T lymphoid, and myeloid cells) from transplant recipients described in FIGS. 4A and 4B at 4 weeks post-transplantation.

FIGS. 4D-4F show repopulation data obtained from peripheral blood samples from transplant recipients described in FIGS. 4A-4C at 16 weeks post-transplant.

FIGS. 4G-4H show the results of a secondary transplantation. At 16 weeks post-transplant, mice transplanted with MNCs containing 5 LSKF$^-$ cells cultured for 14 days described in FIG. 4A-4F were sacrificed, and bone marrow was isolated. A secondary transplantation was performed on new groups of lethally irradiated mice by transplanting $1\times10^6$ bone marrow cells from the original transplant group per mouse. At 4 weeks post-transplant, peripheral blood was collected from each transplant recipient and donor-derived repopulation was determined as in FIGS. 4A-4B.

FIG. 4I shows the percentage of donor derived peripheral blood cells (CD45.2$^+$) contributing to the main hematopoietic lineages from transplant recipients described in FIG. 4G-4H at 4 weeks post-transplant.

FIGS. 4J-4L show repopulation data obtained from peripheral blood samples from transplant recipients described in FIGS. 4G-4I at 16 weeks post-transplant.

FIGS. 4M-4N show representative FACS plots of donor (CD45.2) vs. host (CD45.1) cells obtained from peripheral blood samples from recipients described in FIGS. 4J-4K.

Figure 5:
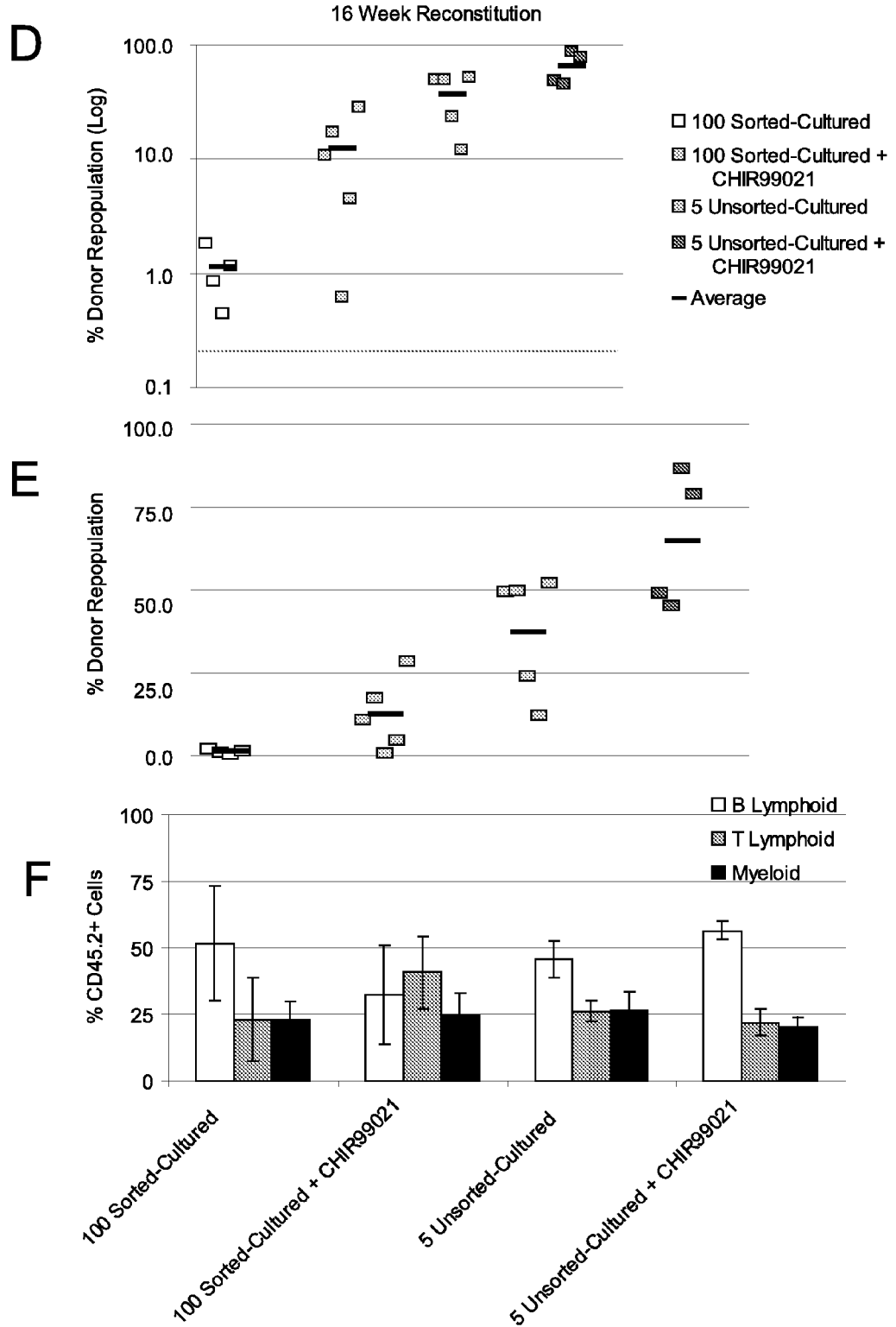

FIG. 5 shows that culturing with the small-molecule inhibitor of GSK-3β, CHIR99021, enhances long-term engraftment of ex vivo expanded HSCs.

FIG. 5A is a logarithmic plot of CD45.2 (donor) frequency of total CD45$^+$ cells in peripheral blood of transplant recipients at 4 weeks post-transplant. FIG. 5B is a linear plot of the same. Sorted LSKF$^-$ cells and MNCs with a known quantity of LSKF$^-$ cells were cultured and transplanted as described in FIG. 4A. Cultures contained media alone or media with 250 nM CHIR99021 for each group.

FIG. 5C shows the percentage of donor derived peripheral blood cells (CD45.2$^+$) contributing to the main hematopoietic lineages from transplant recipients described in FIGS. 5A-5B at 4 weeks post-transplant.

FIGS. 5D-5F show the repopulation data obtained from peripheral blood samples from transplant recipients described in FIGS. 5A-5C at 16 weeks post-transplant.

Figure 6:
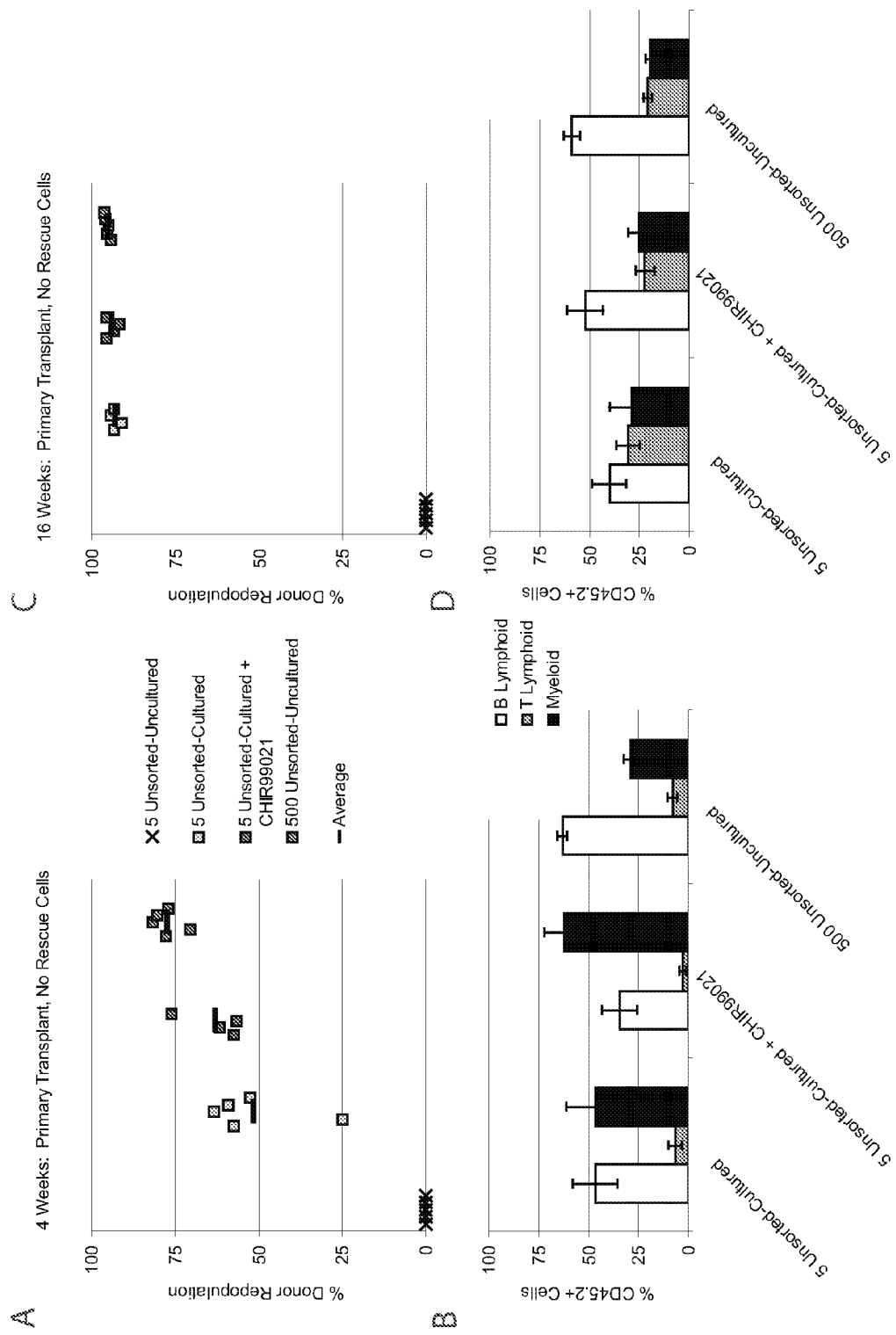
Figure 6:
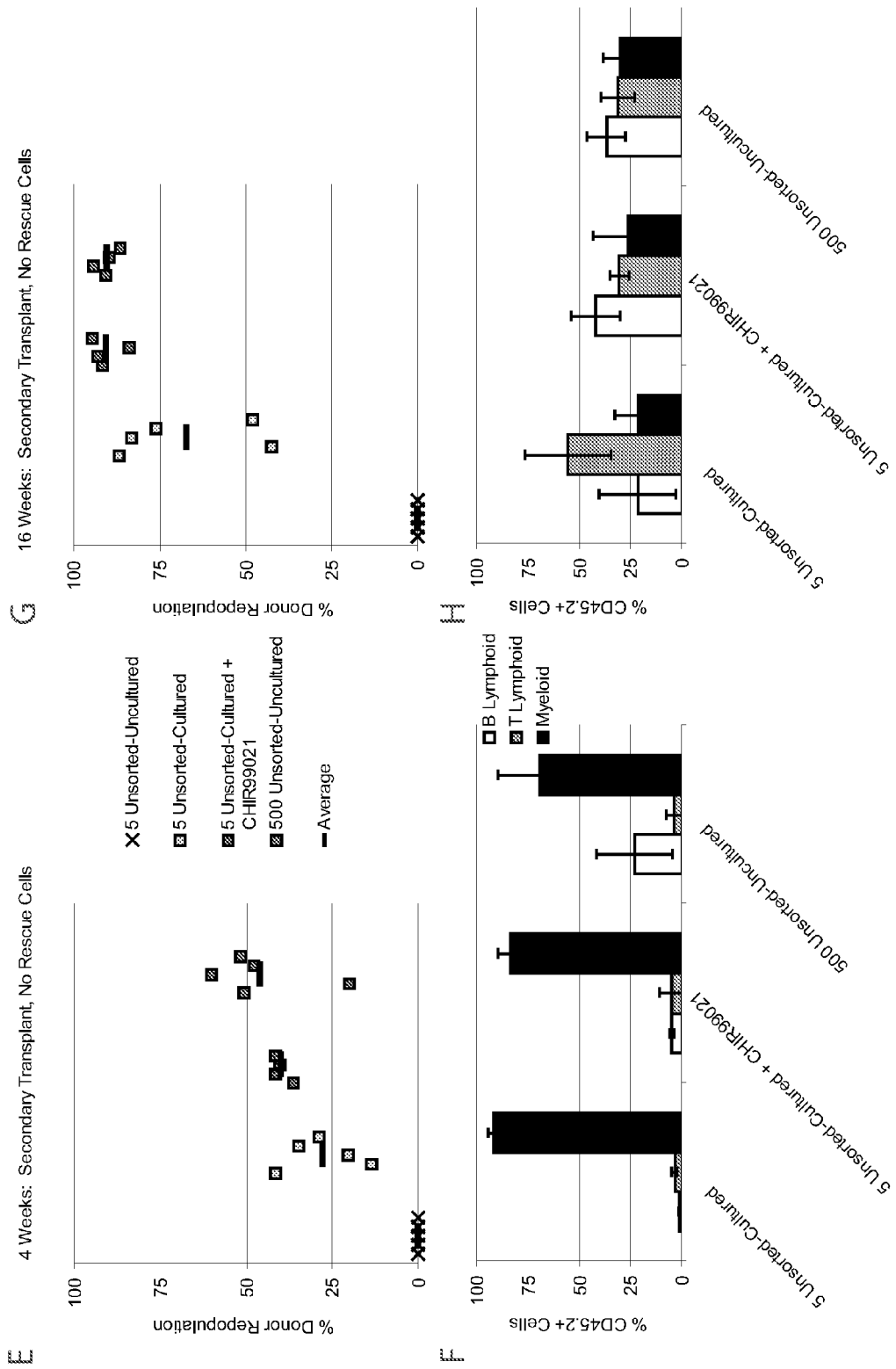

FIG. 6 shows that the ex vivo expansion protocol allows for elimination of bone marrow rescue cells and yields engraftment equivalent to a one-hundred fold greater dosage of freshly isolated cells.

FIG. 6A shows CD45.2 (donor) frequency of total CD45$^+$ cells in peripheral blood of transplant recipients at 4 weeks post-transplant. Mice transplanted with freshly isolated MNCs containing 5 LSKF$^-$ cells (indicated by "X") do not survive beyond 2-3 weeks post-transplant preventing measurement of engraftment. For this experiment, MNCs with a known quantity of putative HSCs were cultured with and without CHIR99021 for 14 days. After 14 days, the cellular product of these cultures was transplanted into lethally-irradiated recipients at a dosage corresponding to an original input into culture of MNCs containing 5 LSKF$^-$ cells per mouse. Freshly isolated MNCs containing either 5 or 500 LSKF– cells were also transplanted into 2 additional lethally irradiated groups of mice. No rescue/competitor bone marrow cells were included.

FIG. 6B shows the percentage of donor derived peripheral blood cells (CD45.2$^+$) contributing to the main hematopoietic lineages from transplant recipients described in FIG. 6A at 4 weeks post-transplant.

FIGS. 6C-6D show repopulation data obtained from peripheral blood samples from transplant recipients described in FIGS. 6A-6B at 16 weeks post-transplant.

FIG. 6E shows the results of a secondary transplant. At 16 weeks post-transplant, mice transplanted with MNCs containing 5 or 500 LSKF$^-$ cells freshly isolated or cultured for 14 days described in FIGS. 6A-6D were sacrificed and bone marrow isolated. A secondary transplantation was performed on new groups of lethally irradiated mice by transplanting $1\times10^6$ bone marrow cells from the original transplant group per mouse. At 4 weeks post-transplant, peripheral blood was collected from each transplant recipient and donor-derived repopulation was determined. Mice transplanted with freshly isolated MNCs containing 5 LSKF$^-$ cells (indicated by "X") do not survive beyond 2-3 weeks post-transplant, thus preventing secondary transplantation.

FIG. 6F shows the percentage of donor derived peripheral blood cells (CD45.2$^+$) contributing to the main hematopoietic lineages from transplant recipients described in FIG. 6E at 4 weeks post-transplant.

FIGS. 6G-6H show repopulation data obtained from peripheral blood samples from transplant recipients described in FIGS. 6E-6F at 16 weeks post-transplant.

Figure 7:
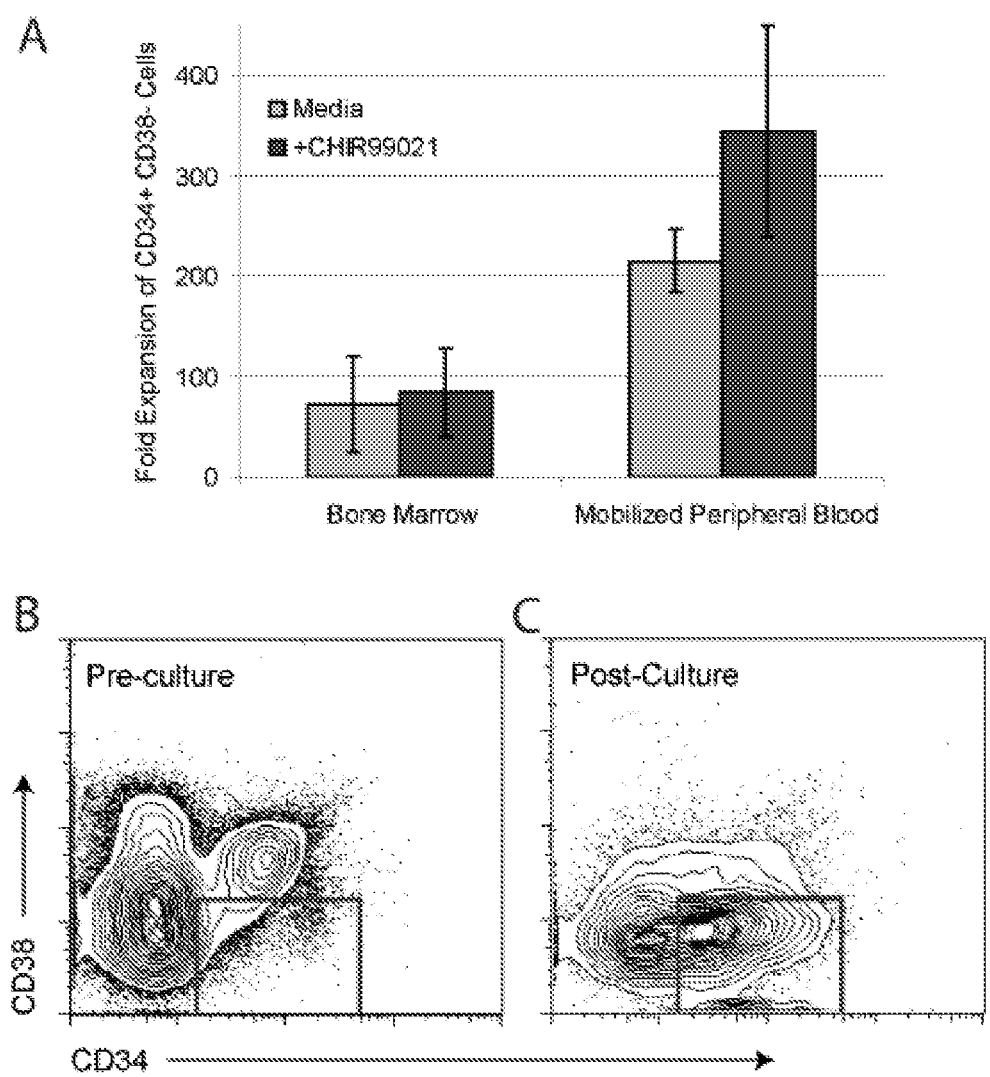

FIG. 7 shows ex vivo expansion of human HSCs. In FIG. 7A, bone marrow and mobilized peripheral blood was collected from human patients. Putative HSCs (CD34$^+$ CD38$^-$ cells) were identified by FACS analysis. Ex vivo expansion was performed with and without CHIR99021. After 14 days culture, the cellular product of these cultures was analyzed to determine the expansion of CD34$^+$ CD38$^-$ cells. FIGS. 7B-7C are representative FACS plots of CD34$^+$ CD38$^-$ cells prior to (FIG. 7B) and following (FIG. 7C) ex vivo expansion.

Figure 8:
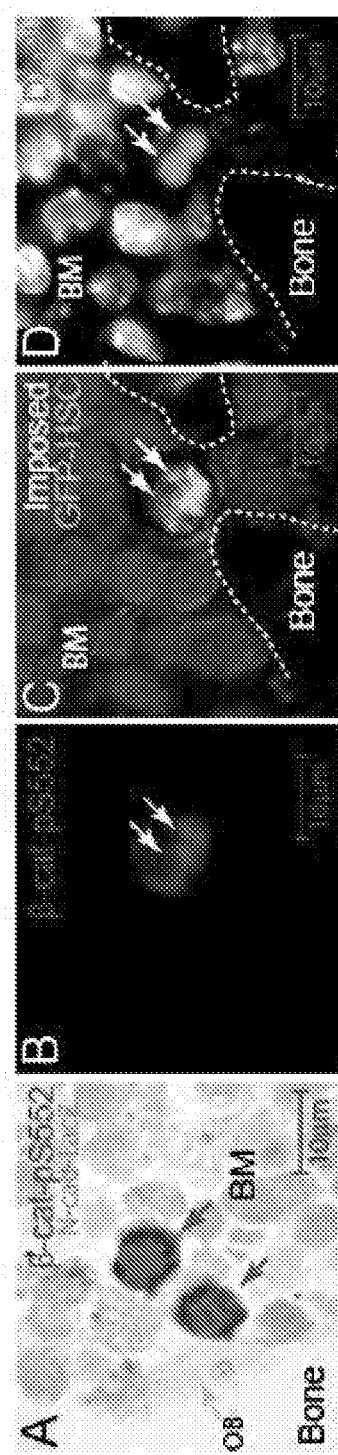

FIG. 8A shows a β-cat-pS552 immunoassaying of homed GFP-HSCs. Detection of β-cat-pS552$^+$ (red) cells adjacent or close to N-cadherin-LacZ$^+$ (blue) osteoblasts (OB) which have been identified with the HSC niche (Xie, Y. et al. Detection of functional haematopoietic stem cell niche using real-time imaging. Nature 457, 97-101 (2009); Zhang, J. et al. Identification of the haematopoietic stem cell niche and control of the niche size. Nature 425, 836-841 (2003)). "BM" indicates bone marrow. FIGS. 8B-8D show detection of dividing GFP$^+$ HSCs (white arrows). DAPI for nucleic staining, GFP for donor HSC, and red for β-cat-pS552 GFP signal was imposed on the merged image of DAPI, DIC and red.

Figure 9:
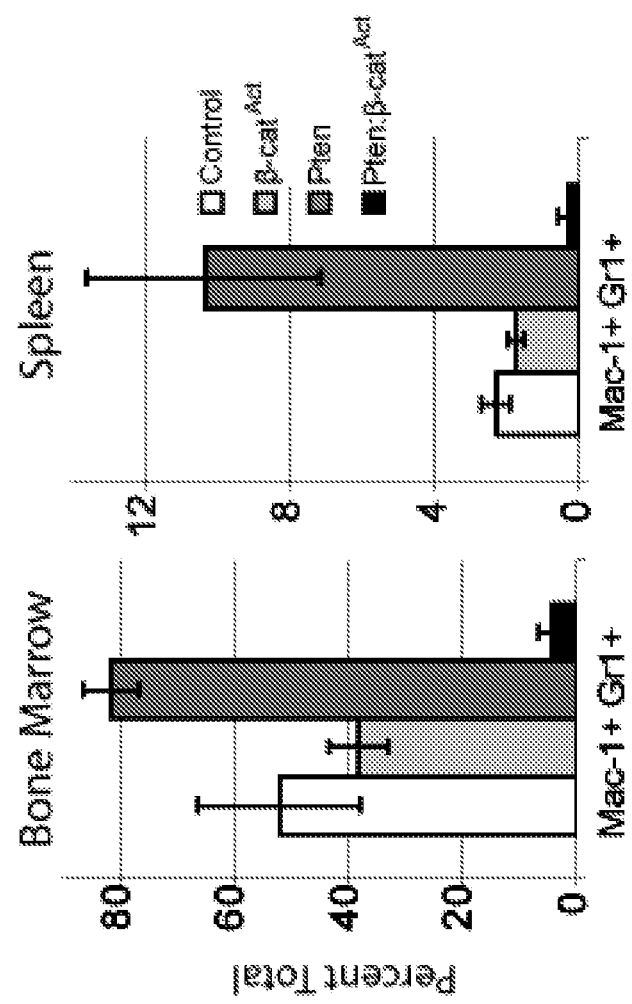

FIG. 9 shows the percent of Mac-1+ Gr1+ myeloid cells in bone marrow and spleen at 8-9 weeks post-induction (wpi) in control, single and double mutants as determined by FACS. Results are graphed as mean±SD.

Figure 10:
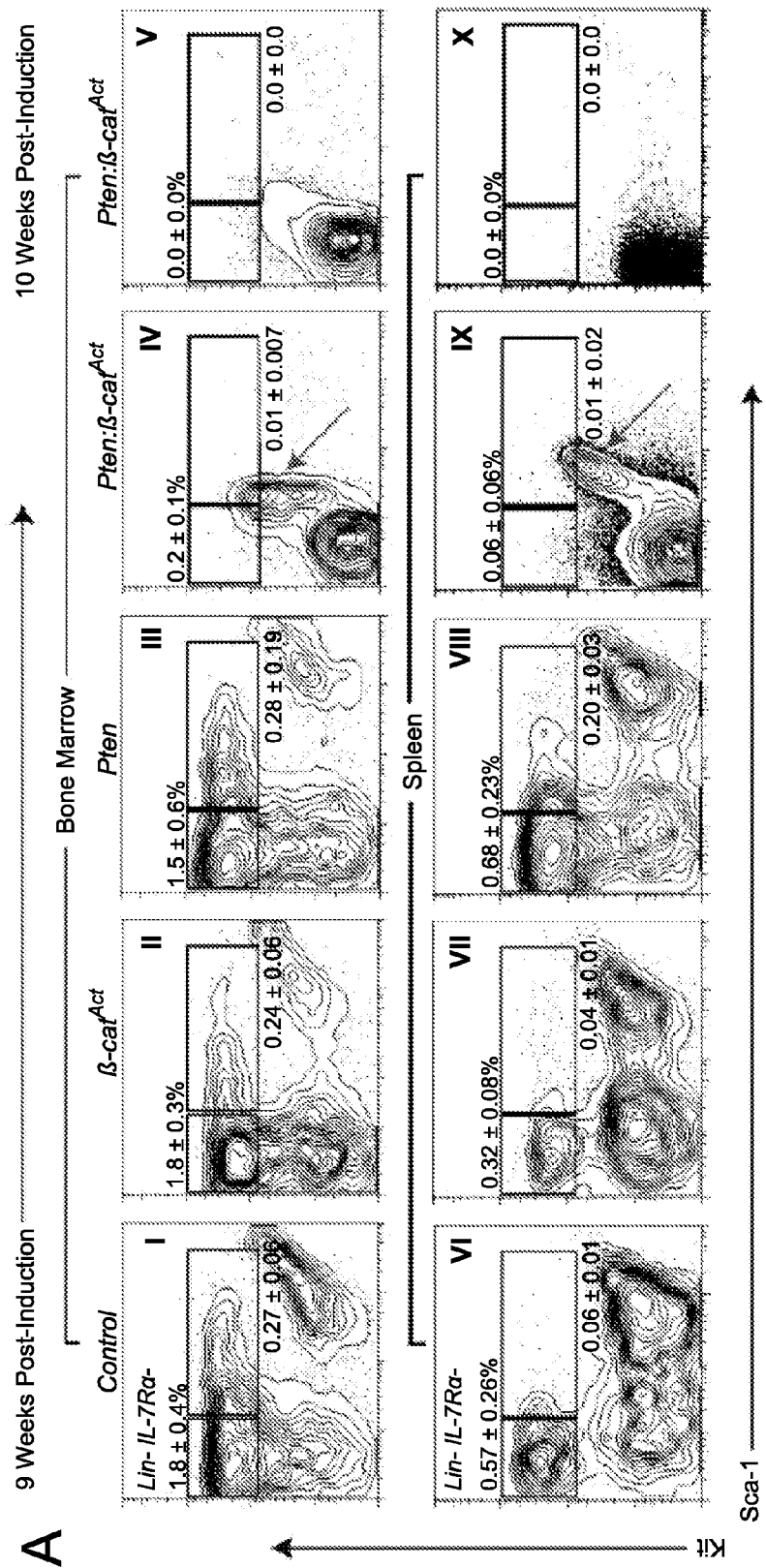
Figure 10:
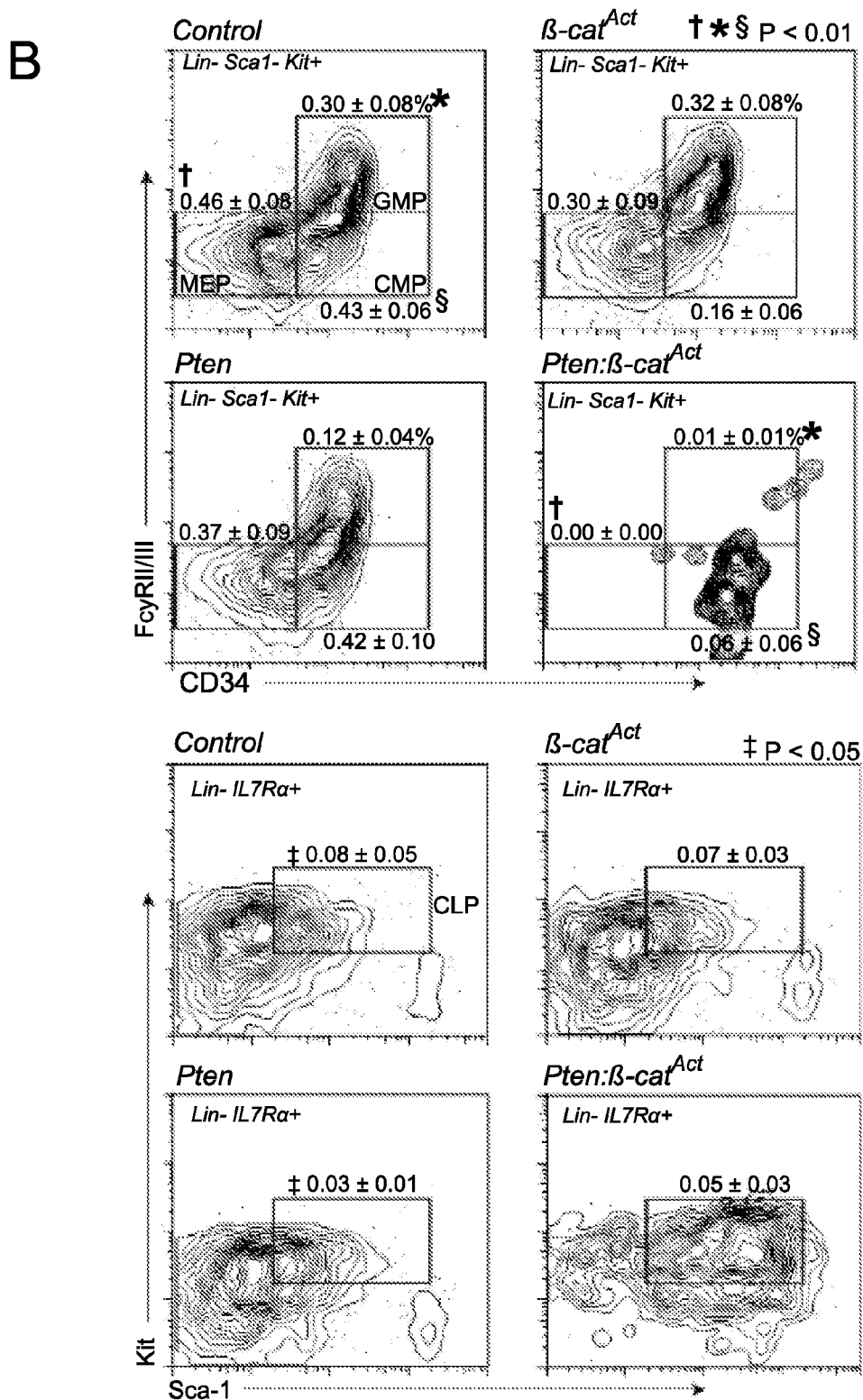
Figure 10:
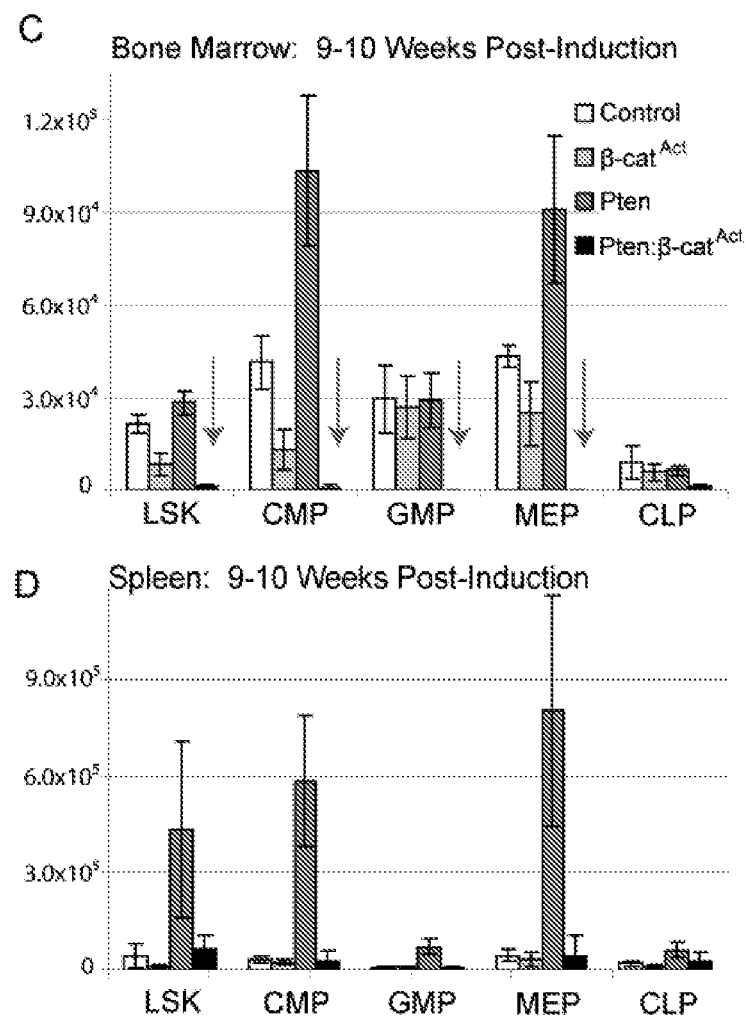
Figure 10:
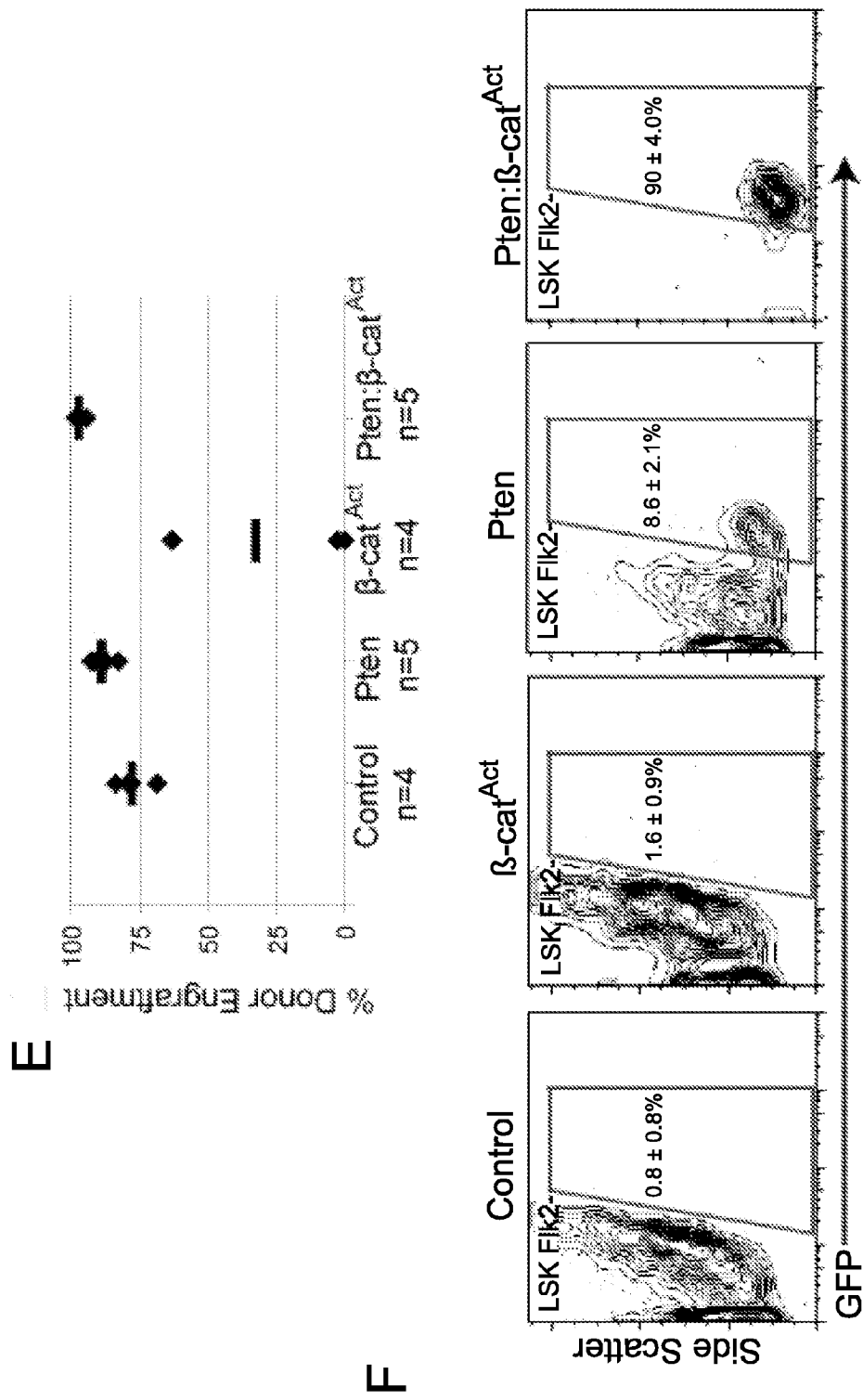

FIG. 10 shows that double mutant mice lose early myeloid progenitors as mutant HSCs predominate. Data shown relate to lethally irradiated recipient mice previously transplanted with 1,000 LSK Flk2$^-$ cells derived from control, single and double mutant donors +200,000 congenic rescue bone marrow cells. FIG. 10A shows FACS diagrams of LSK cells (right blue boxes) and myeloid progenitors (left blue boxes) in control, single and double mutant bone marrow (top panels) and spleen (bottom panels) as indicated. As used herein, β-cat$^{Act}$ is used interchangeably with Ctnnb1, and Pten:β-cat$^{Act}$ is used interchangeably with Pten:Ctnnb1. Mice were at 9 or 10 wpi as indicated. Note the LS$^{Low}$K$^{Mid}$ population in double mutants at 9 wpi (red arrows). FIG. 10B shows FACS analysis of early hematopoietic progenitors in control, single and double mutant bone marrow at 9 wpi. FIGS. 10C and 10D shows the absolute number of bone marrow (per tibia and femur) (FIG. 10C) or spleen (FIG. 10D) LSK cells and early hematopoietic progenitors in control, single, and double mutants at 9-10 wpi. Note the collapse of LSK and early progenitor populations in double mutant bone marrow (red arrows) with conversion to a dominant "blast" population (see also FIG. 12). FIG. 10E shows percent donor engraftment at 9 wpi of lethally-irradiated recipient mice previously transplanted with 1,000 LSK Flk2$^-$ cells derived from control, single and double mutant donors +200,000 congenic rescue bone marrow cells. FIG. 10F shows the EGFP-reporter expression of LSK Flk2$^-$ cells in control, single and double mutants with the Z/EG transgenic reporter construct at 9 wpi.

Figure 11:
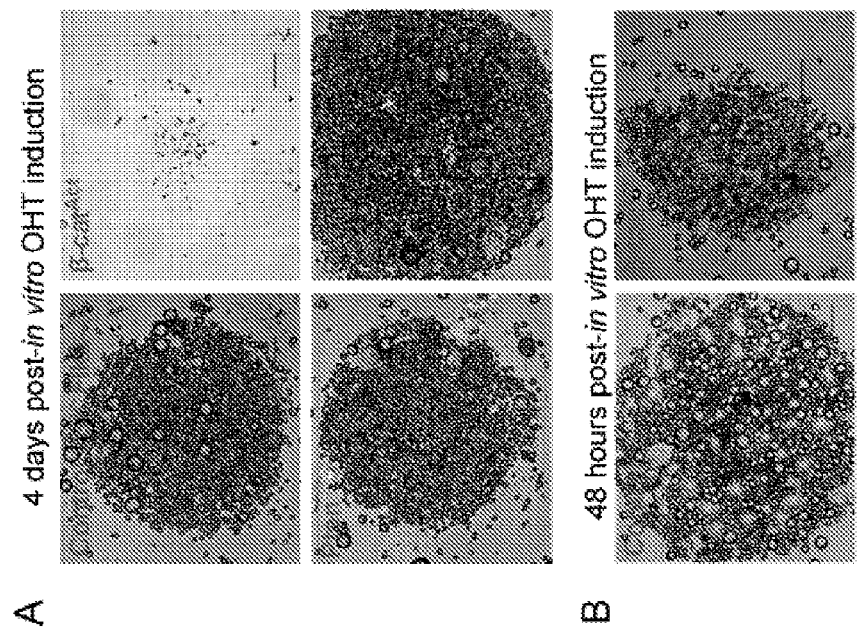
Figure 11:
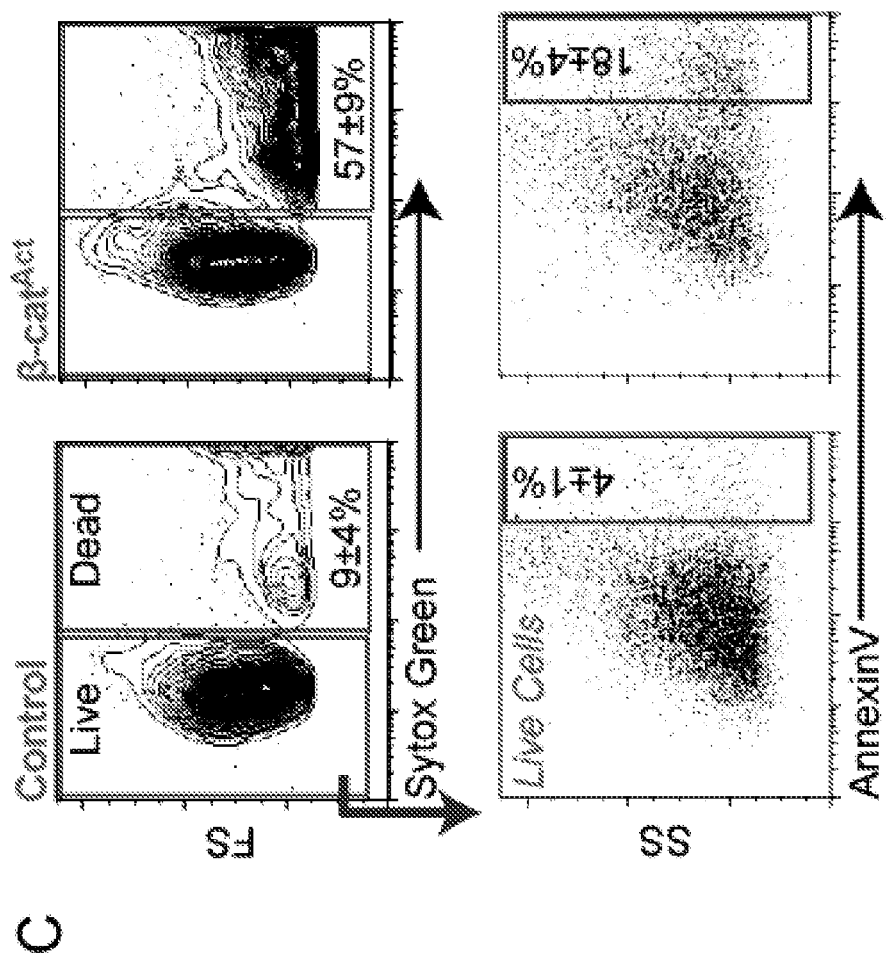
Figure 11:
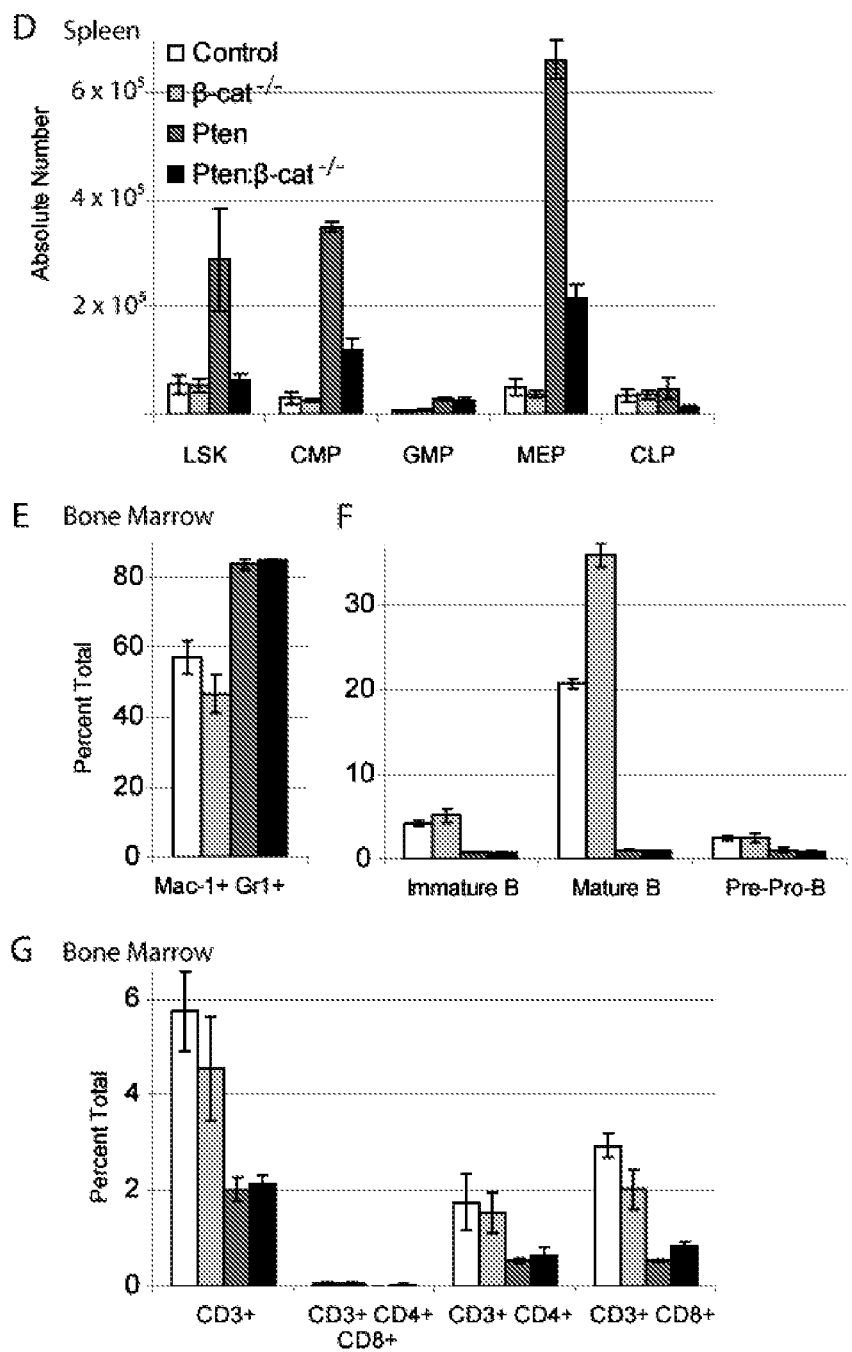

FIG. 11 shows Ctnnb1 (β-cat$^{Act}$) HSCs undergo apoptosis whereas β-catenin deletion prevents PTEN-deficiency-induced HSC expansion but not myeloproliferative disorder (MPD). To obtain the results shown in FIG. 11A, 1,000 LSK Flk2$^-$ cells per well were sorted from bone marrow isolated from uninduced control, Pten, Ctnnb1 (β-cat$^{Act}$) and Pten: Ctnnb1 (Pten:β-cat$^{Act}$) mice. Within 12 hours of sorting, OHT was added to the cultures for a final concentration of 1 μM. Cultures depicted at 4 days post-in vitro induction. FIG. 11B shows control and Ctnnb1 (β-cat$^{Act}$) cultures as described in FIG. 11A at 48 hours post-in vitro induction. FIG. 11C shows representative FACS plots distinguishing live (Sytox Green negative) from dead (Sytox Green positive) cells. Cultures from FIG. 11B were stained with Sytox Green and Annexin V according to manufacturer's instructions (Vybrant Apoptosis Kit #9, Invitrogen) and analyzed by FACS. Live cells were further gated for Annexin V positive (apoptotic) cells. Numbers within gates represent the average±standard deviation from 3 independent experiments. FIG. 11D shows the absolute number of LSK cells and early progenitors in spleen as determined by FACS analysis. Mice were transplanted with control, β-cat$^{-/-}$, Pten, and Pten:β-cat$^{-/-}$ mice bone marrow as indicated; analysis is at 10 wpi. FIGS. 11E-G show the percent of Gr1$^+$ Mac-1$^+$ cells (FIG. 11E), B-cells (FIG. 11F), and T-cells (FIG. 11G) in bone marrow of mice described in FIG. 11D as determined by FACS (see FIG. 20).

Figure 12:
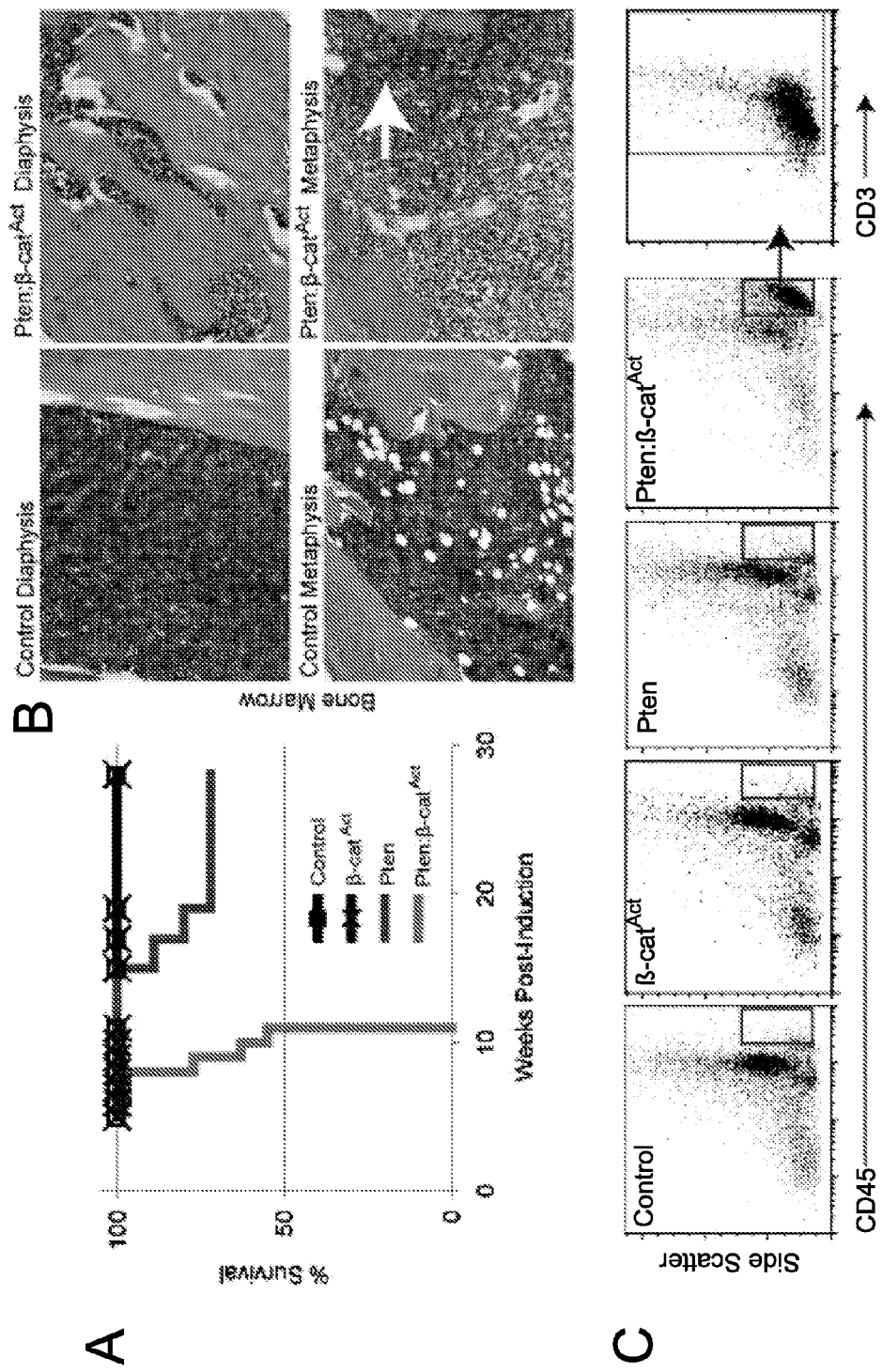

FIG. 12 shows that Leukemia development and niche disruption in double mutants. FIG. 12A shows a Kaplan-Meier survival curve for control, single and double mutants (as indicated in the figure legend) following tamoxifen induction (Scl-Cre system unless otherwise specified). FIG. 12B shows H&E stained sections of control and double mutant bone marrow at 9 wpi. White arrow indicates grossly normal cellularity in trabecular bone area. FIG. 12C shows FACS analysis of control, single and double mutant bone marrow at 10 wpi demonstrating typical CD45 expression. Note CD45$^{High}$ blast cells (blue box) only mainly appear in double mutants. Blast cells from double mutants were further analyzed for cell surface marker expression of the T-cell specific marker, CD3.

Figure 13:
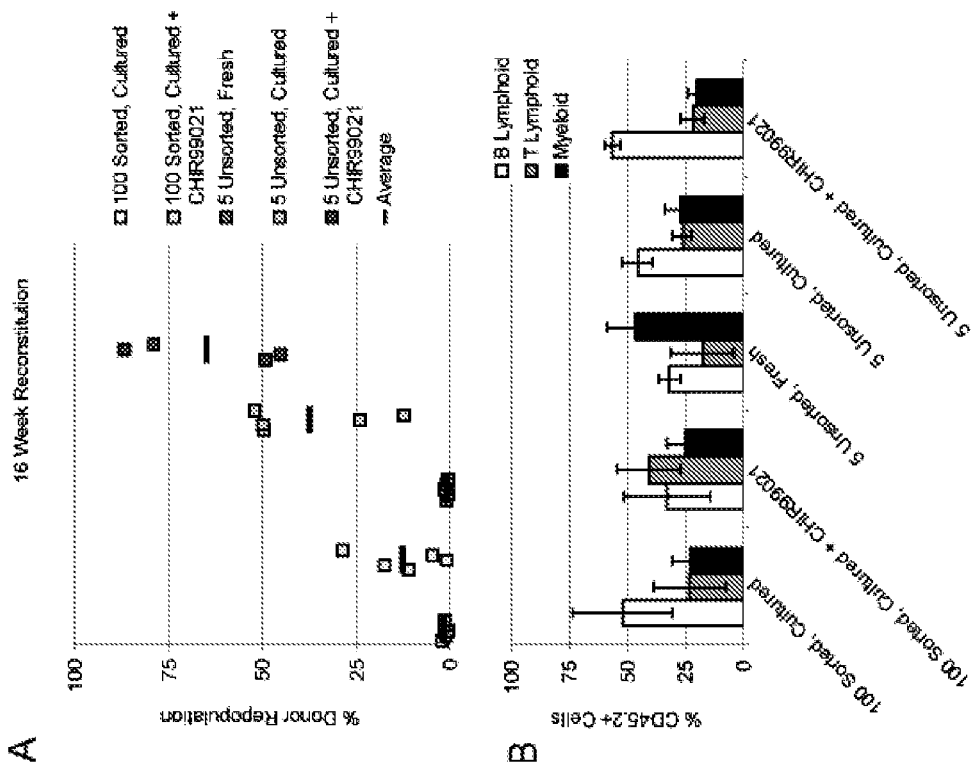
Figure 13:
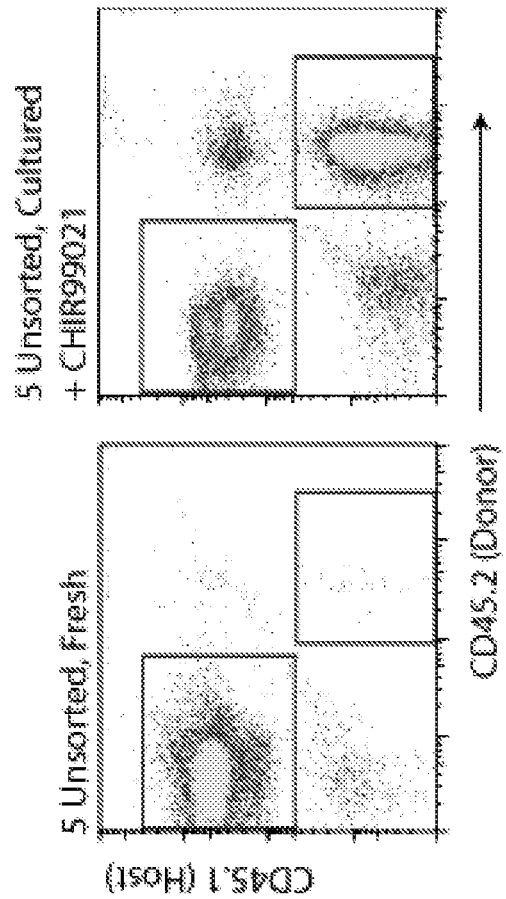

FIG. 13 shows that Ex vivo expansion of HSCs is enhanced by inhibition of GSK3β. For the experimental results shown in FIG. 13A, sorted LSK Flk2$^-$ cells and unsorted MNCs containing a known quantity of LSK Flk2$^-$ cells (CD45.2$^+$) were cultured for 14 days in ST media with and without CHIR99021. The cultured product of 100 sorted or 5 unsorted LSK Flk2$^-$ cells per mouse were transplanted into lethally irradiated recipients (CD45.1$^+$). 5 freshly isolated, unsorted LSK Flk2$^-$ cells per mouse were transplanted into a separate group. 1×10$^5$ freshly isolated CD45.1$^+$ competitor/radioprotective cells were also added per mouse. Peripheral blood analysis of recipients at 16 weeks post-transplant depicts % chimerism. FIG. 13B shows the percentage of donor-derived peripheral blood cells (CD45.2$^+$) contributing to the main hematopoietic lineages (B lymphoid, T lymphoid, and myeloid cells) from transplant recipients described in (FIG. 13A) at 16 weeks post-transplantation. FIG. 13C shows representative FACS plots of donor (CD45.2) vs. host (CD45.1) cells obtained from peripheral blood samples at 16 weeks post-transplant from recipients described in FIG. 13A.

Figure 14:
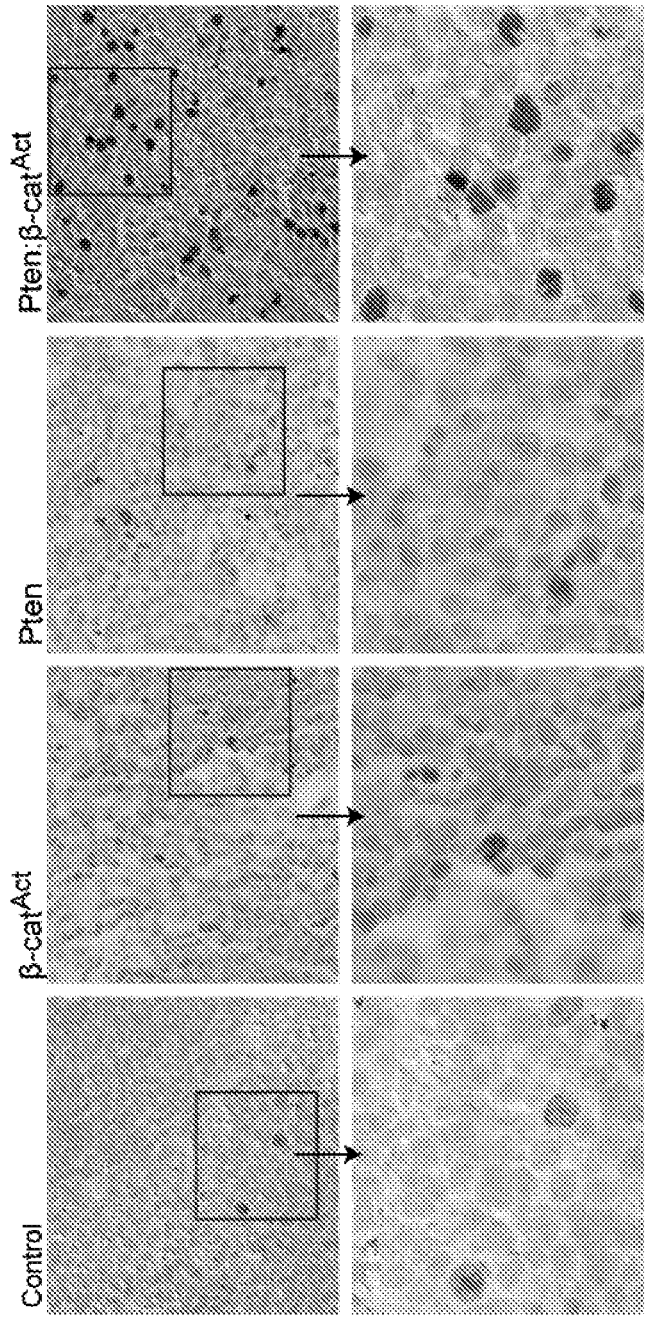

FIG. 14 shows abundant β-cat-pS552$^+$ cells in double mutant spleen. Spleen sections stained with β-cat-pS552 antibody in control, single and double mutants at 3 dpi using Mx1-Cre system. Original magnification 400× (upper panels) and 1000× (lower panels).

Figure 15:
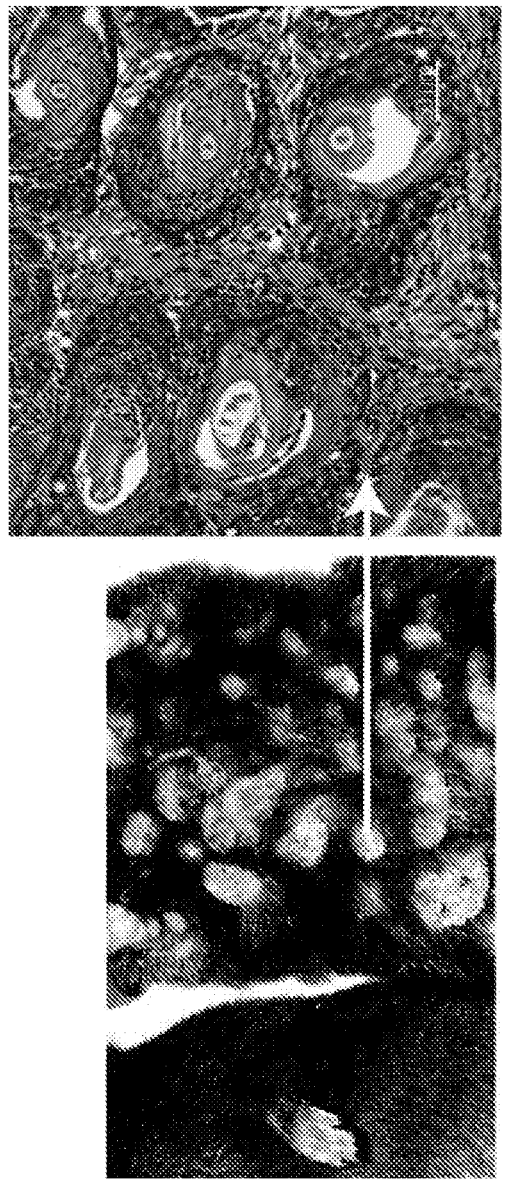

FIG. 15 shows trichofolliculoma in double mutants using Mx1-Cre mediated conditional knockout. Abdomen of Mx1-

Cre+ Pten:Ctnnb1 (Pten:β-cat$^{Act}$) mutant (left panel, control mouse at left). H&E stained section of hair follicle tumor showing multiple, well-developed but densely packed hair follicles in cross section (right panel).

Figure 16:
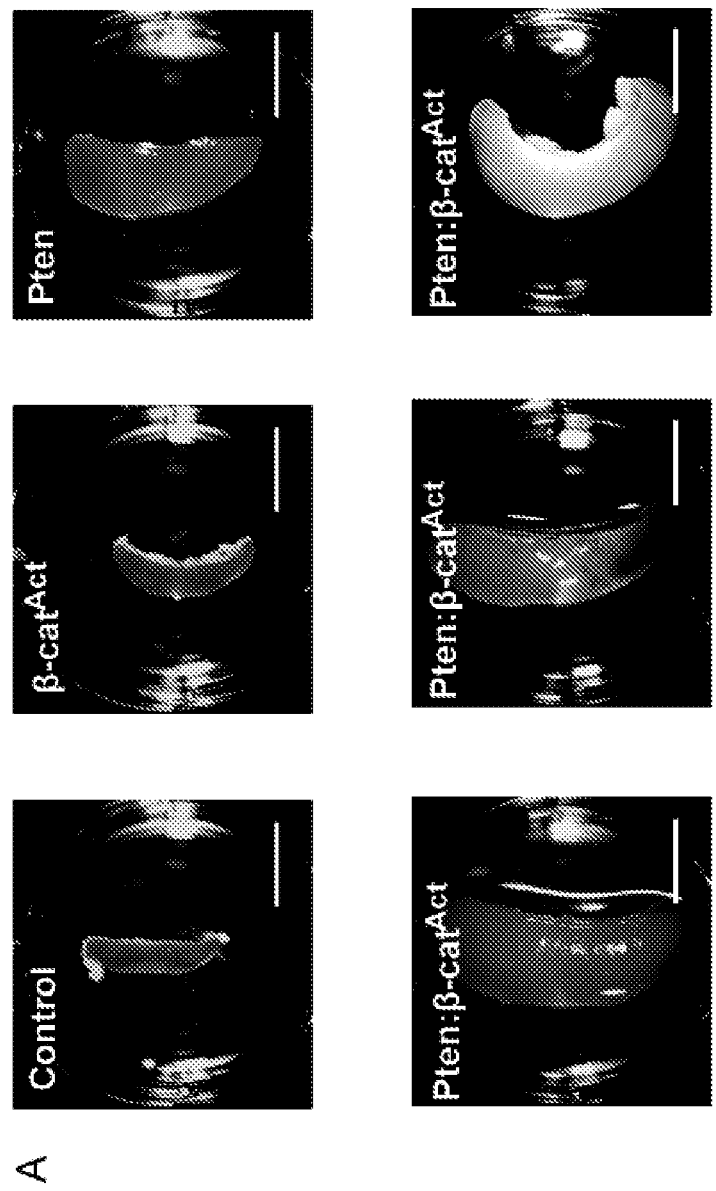
Figure 16:
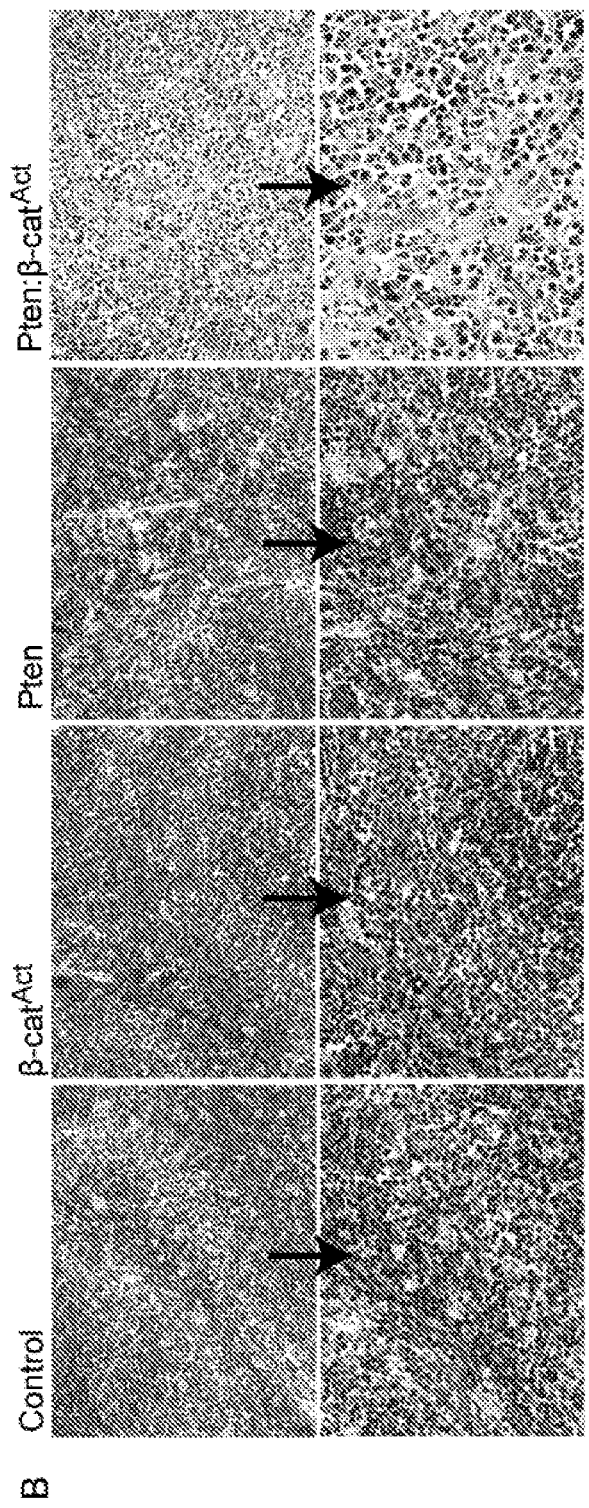

FIG. 16 shows vascular niche disruption by splenic fibrosis in double mutants. FIG. 16A shows whole spleen isolated from control, single and double mutants at 9 wpi. Three examples of double mutant spleen exhibiting mild to severe fibrosis are shown. Scale bar indicates 1 cm. FIG. 16B shows Masson's Trichrome stained sections of control, single and double mutant spleens at 9 wpi. Red arrows indicate examples of collagen fibers (light blue).

Figure 17:
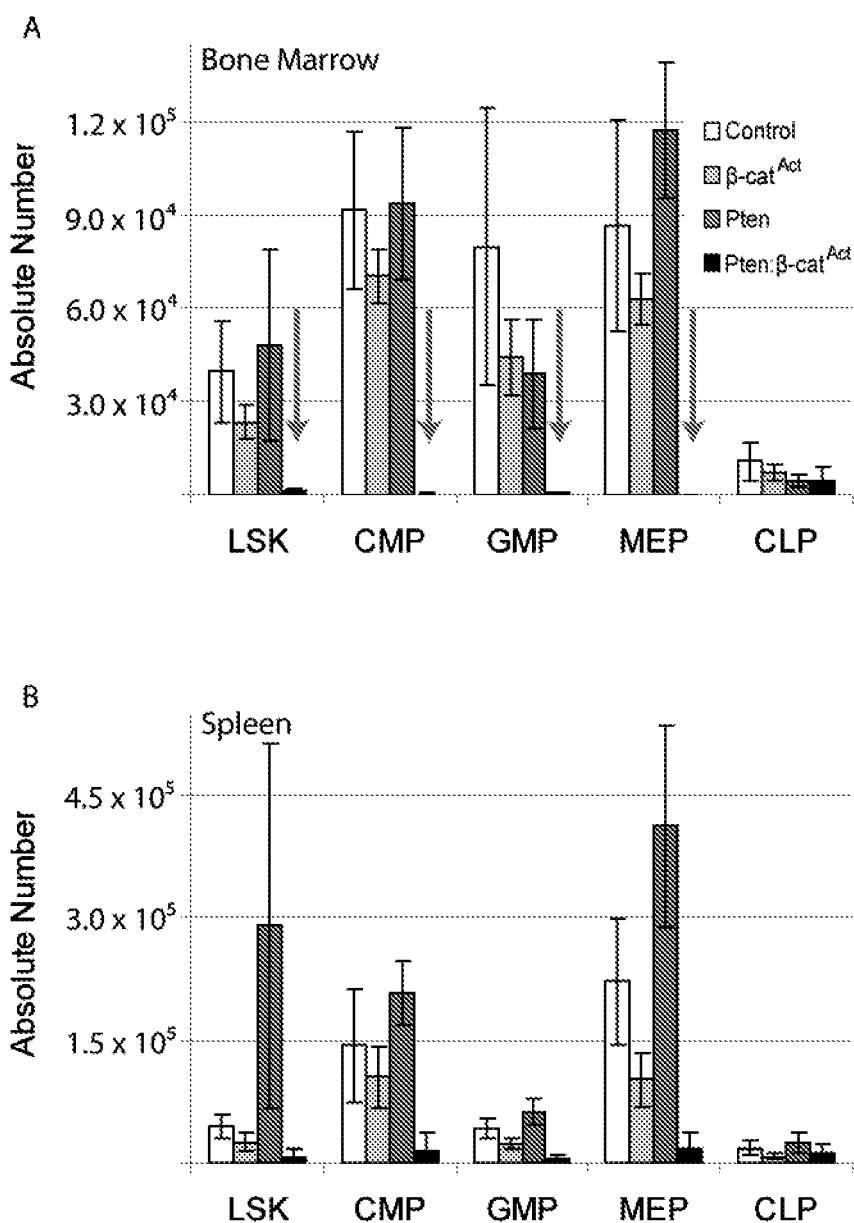

FIG. 17 shows the number of different types of LSK cells and early progenitors, as determined by FACS (see FIG. 10) except that primary mutant mice were utilized here instead of transplant recipients as in FIG. 10. Absolute number of bone marrow (per tibia and femur) (FIG. 17A) or spleen (FIG. 17B) LSK cells and early hematopoietic progenitors in control, single and double mutants at 9-10 wpi. Note the collapse of LSK and early progenitor populations in double mutant bone marrow (red arrows) with conversion to a dominant "blast" population. Compare to FIG. 10.

Figure 18:
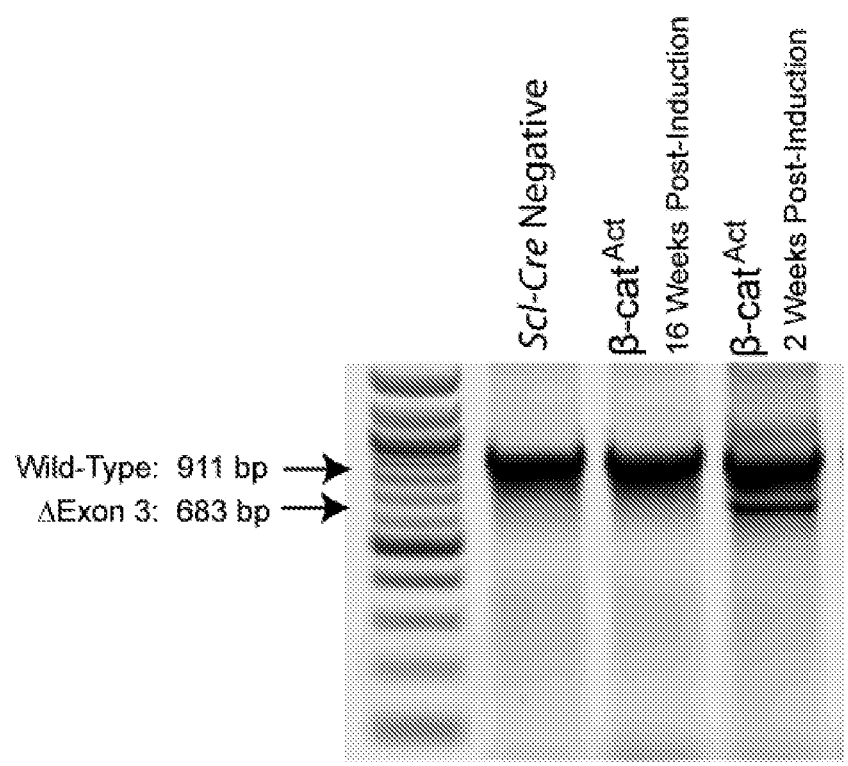

FIG. 18 shows that Ctnnb1 (β-cat$^{Act}$) mutant HSCs are not maintained in viva LSK Flk2$^-$ cells were sorted from Scl-Cre negative control and Ctnnb1 (β-cat$^{Act}$) mutants at 2 and 16 wpi and genotyped for deletion of exon 3. Primers utilized were: 5'-CGTGGACAATGGCTACTCAA-3' (forward) (SEQ ID NO: 1) and 5'-TGTCAGCTCAGGAATTG-CAC-3' (reverse) (SEQ ID NO: 2) to yield wild-type (911 bp) and ΔExon 3 alleles (683 bp). Note that mice with the dominant β-cat$^{Act}$ allele are all heterozygous for this allele.

Figure 19:
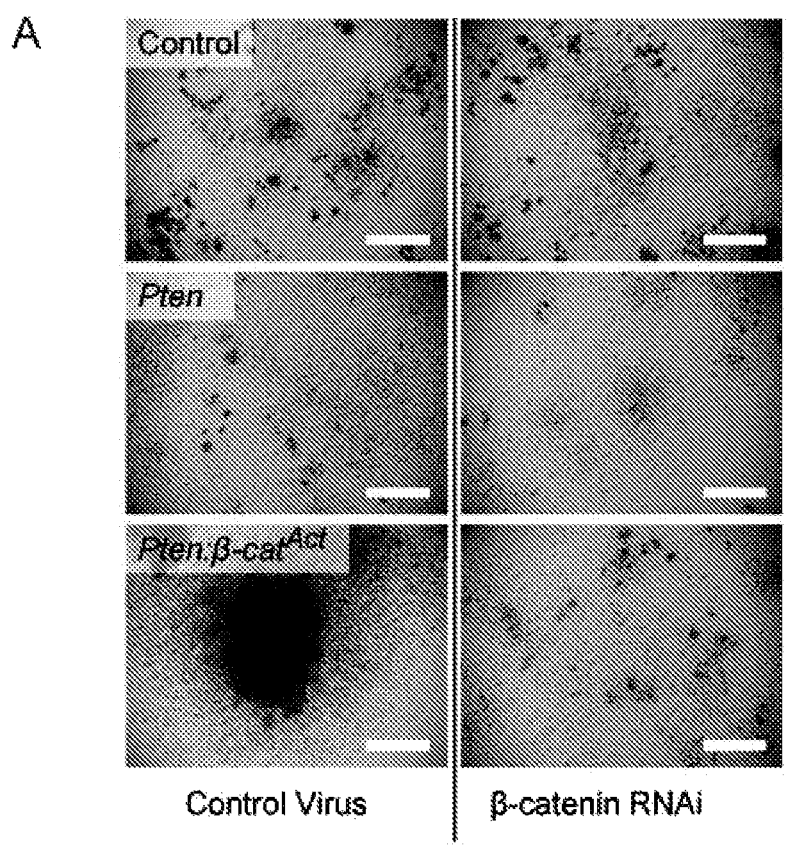
Figure 19:
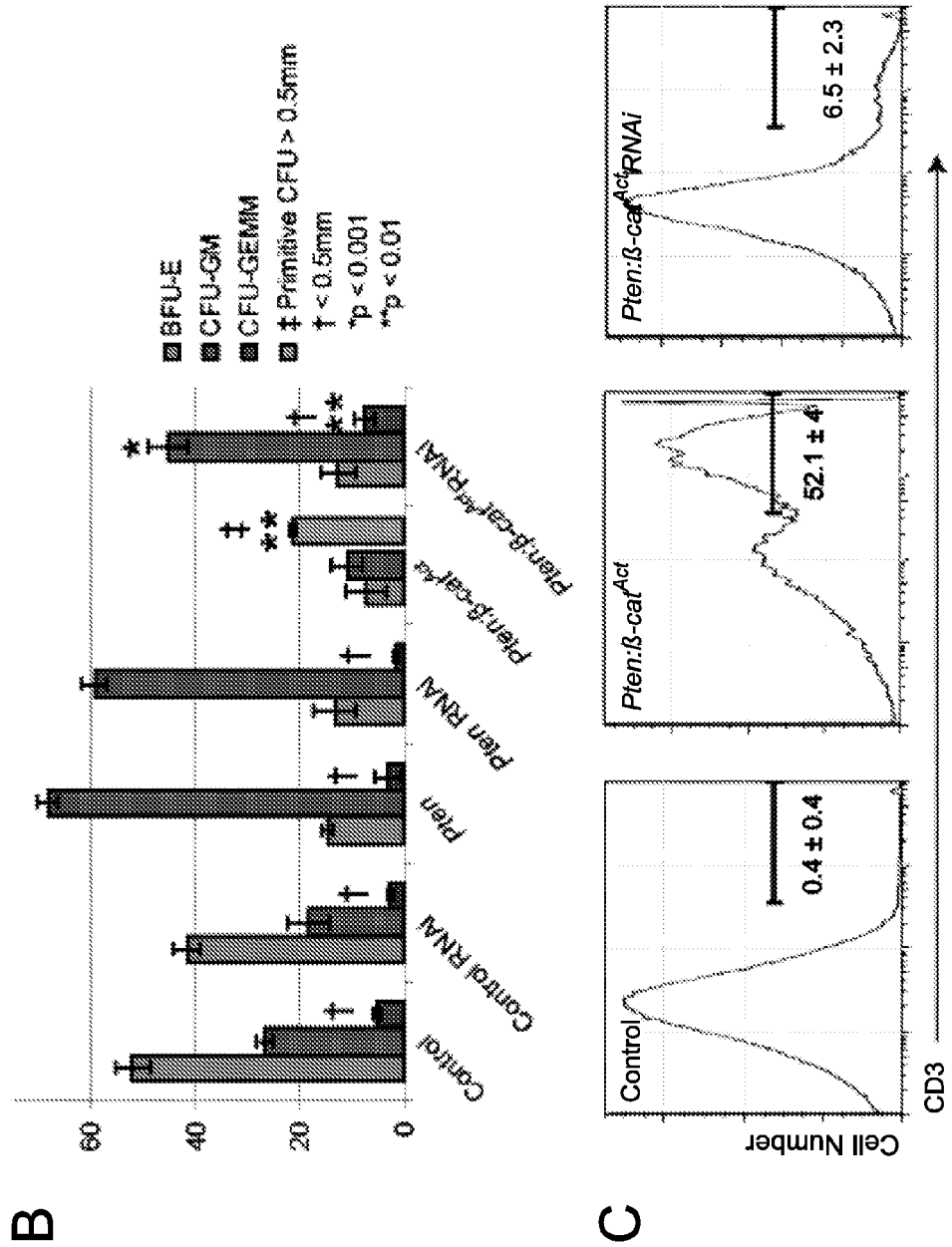

FIG. 19 shows the functional reversibility of myeloid differentiation blockage in double mutant HSCs. To obtain the experimental results shown in FIG. 19A, LSK Flk2$^-$ cells were sorted from uninduced control, Pten, and Pten:Ctnnb1 (Pten:β-cat$^{Act}$) mice into an HSC expansion media containing 0.25 µM 4-hydroxy-tamoxifen (OHT) and cultured for 3 days. Cultures were transduced with lentiviral vector control and vector expressing shRNA targeting β-catenin transcripts. Colony forming unit (CFU) assays were performed on day 6. Images depict typical colonies from control, Pten, and Pten:Ctnnb1 (Pten:β-cat$^{Act}$) cultures transduced with control vector (left panels) and vector expressing shRNA targeting β-catenin (right panels). Scale bar indicates 0.5 mm. FIG. 19B shows the quantification of colonies by type from FIG. 19A including early erythoid progenitors (BFU-E, burst-forming unit-erythroid), granulocyte-monocyte progenitors (CFU-GM, colony forming unit-granulocyte/monocyte), and mixed early myeloid progenitors (CFU-GEMM, granulocyte/erythroid/macrophage/megakaryocyte). Large CFU (>0.5 mm diameter), which are further characterized in FIG. 19C and form only from double mutant cultures transduced with control vector, are designated as primitive CFU. FIG. 19C shows panels depicting representative plots of CD3 expression in control and Pten:Ctnnb1 (Pten:β-cat$^{Act}$) cells transduced with control vector and Pten:β-cat$^{Act}$ cells transduced with vector expressing shRNA targeting β-catenin transcripts. CFU were harvested, disaggregated into single-cell suspension and subjected to FACS analysis for CD3 expression. Average percentage of CD3$^+$ cells from 3 experiments±S.D. are shown.

Figure 20:
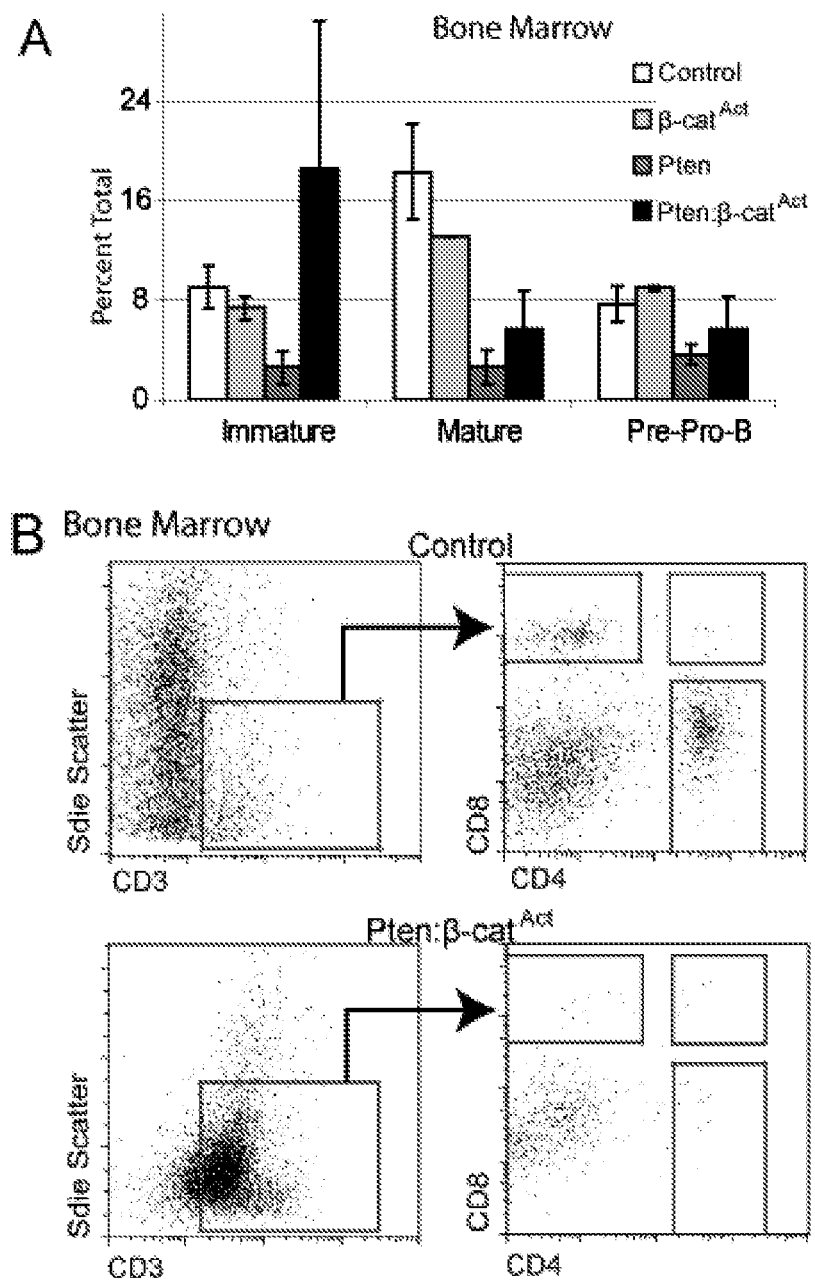
Figure 20:
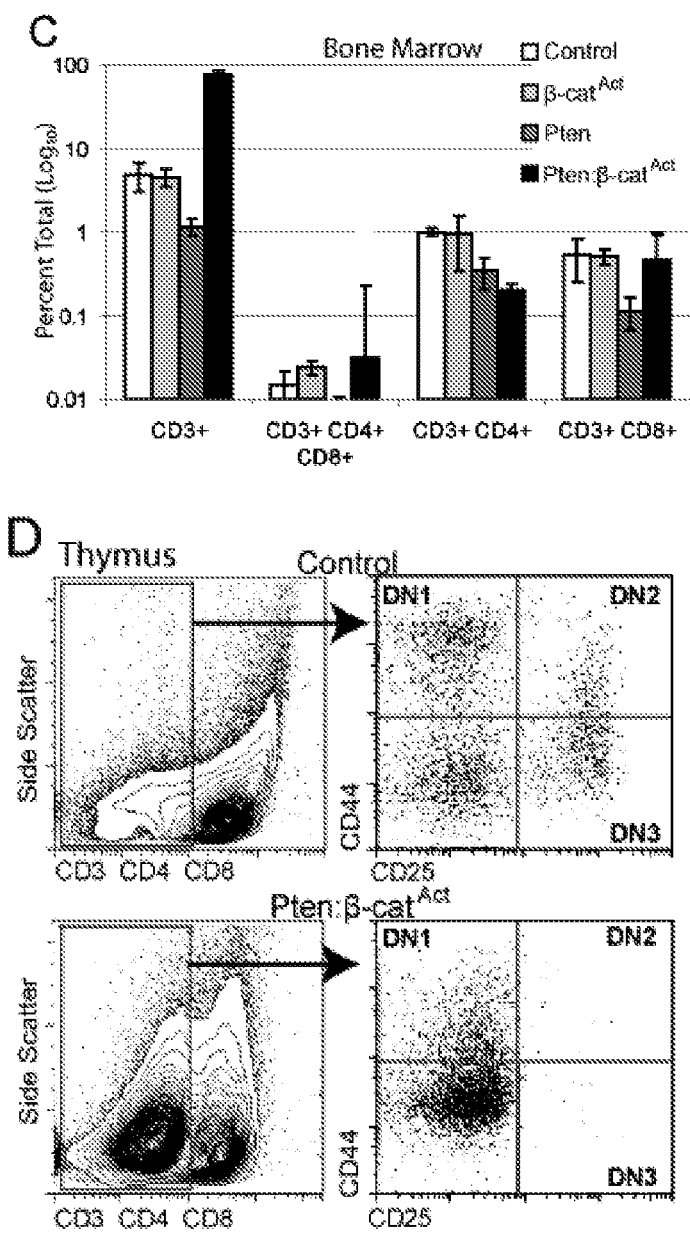

FIG. 20 shows hematopoietic lineage defects and leukemogenesis in single vs. double mutants. As in FIG. 10, mice here refer to transplant recipients of 1,000 LSK Flk2$^-$ cells derived from control, single and double mutants as indicated along with 2×10$^5$ congenic rescue bone marrow cells. FIG. 20A shows the percent of immature (B220$^{Low}$, IgM$^+$), mature (B220$^{High}$, IgM$^+$) and Pre-Pro B (B220$^{Low}$, IgM$^-$) cells in control, single and double mutant bone marrow at 8-9 wpi as determined by FACS. FIG. 20B shows FACS diagrams illustrating control and double mutant data on T-cell lineage quantified in FIG. 20C. FIG. 20C shows percent of CD3+, double and single positive T cells in control, single and double mutant bone marrow at 8-9 wpi. Note the logarithmic scale. FIGS. 20D-E show Double Negative (DN) populations in control, single and double mutant thymus at 8-9 wpi. Representative FACS plots of control (upper panel) and double mutant (lower panel) thymus are shown in FIG. 20D. Note the logarithmic scale in FIG. 20E. FIGS. 20E-G show double and single positive thymocyte populations from control, single and double mutants. Representative FACS plots of control (left panel) and double mutant (right panel) thymus (FIG. 20F). Results are graphed as mean±SD (FIG. 20G).

Figure 21:
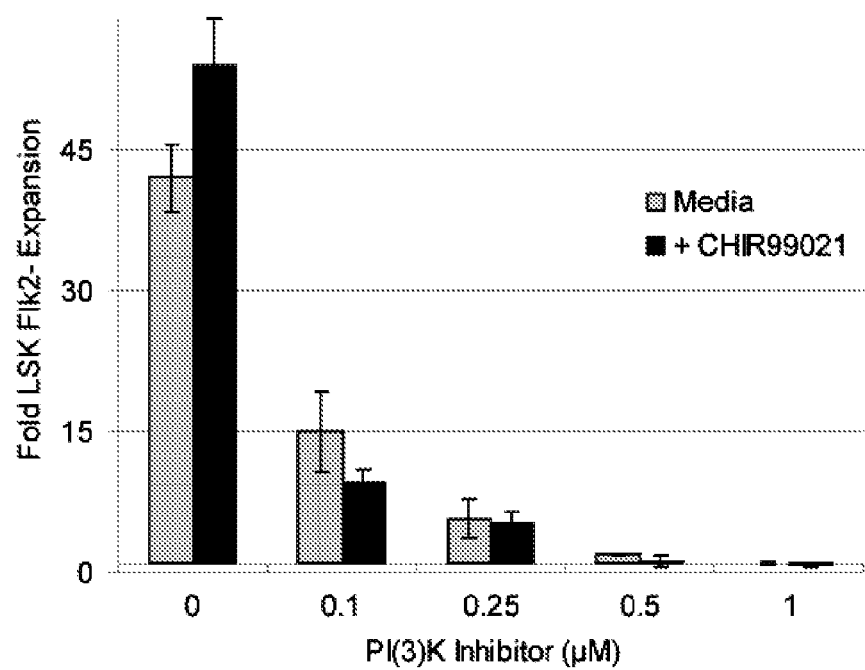

FIG. 21 shows that PI3K inhibition reverses ex vivo HSC expansion and inhibits CHIR99021's ability to enhance this expansion. Bone marrow MNCs were cultured for 10 days in an HSC expansion media with and without 250 nM CHIR99021, along with the indicated concentrations of PI3K inhibitor (NVP-BEZ235) (Maira, S. M. et al. Identification and characterization of NVP-BEZ235, a new orally available dual phosphatidylinositol 3-kinase/mammalian target of rapamycin inhibitor with potent in vivo antitumor activity. *Molecular cancer therapeutics* 7, 1851-1863 (2008)), and then subjected to FACS analysis to determine expansion of LSK Flk2$^-$ cells.

Figure 22:
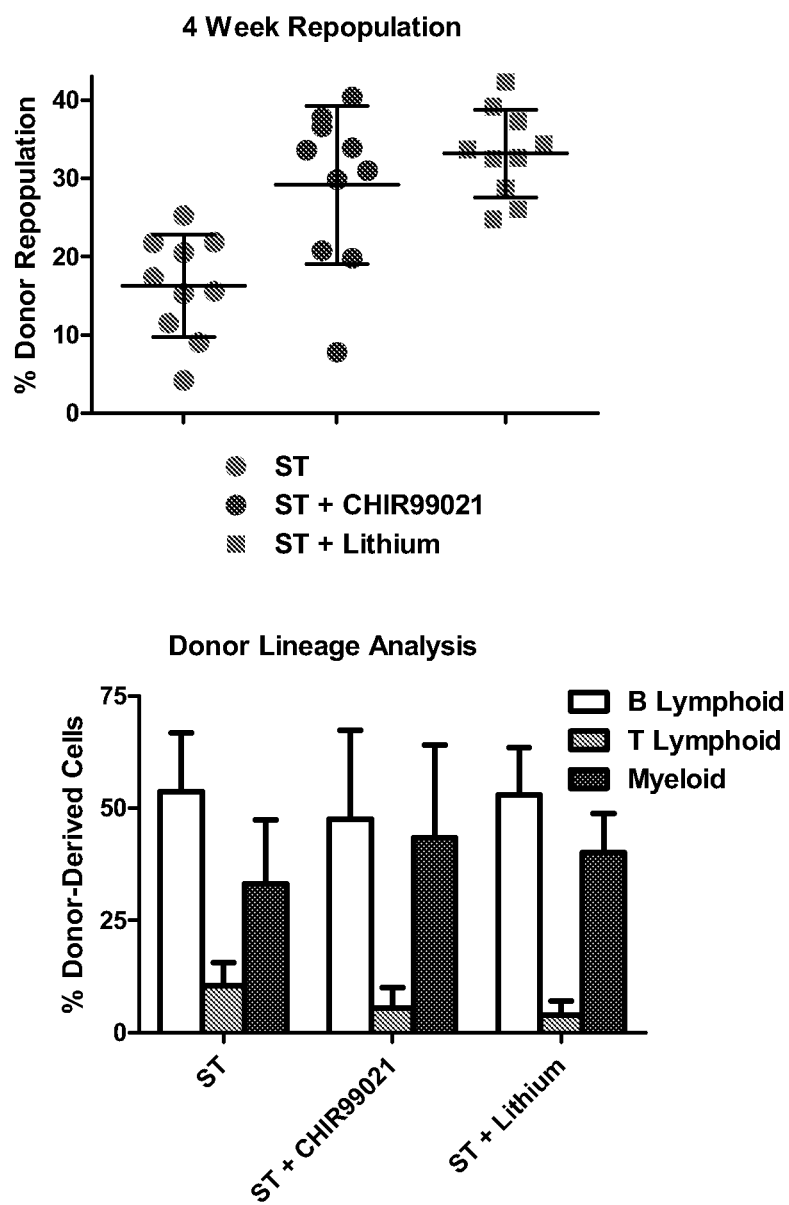

FIG. 22 shows that both CHIR99021 and lithium enhance repopulation capacity of ex vivo expanded hematopoietic stem cells. The experimental conditions of the results shown in FIG. 22 are as follows. Bone marrow mononuclear cells (MNCs) were fractionated and the concentration of lineage marker negative, Sca-1$^+$, c-Kit$^+$, Flk2$^-$ (LSKF$^-$) cells was determined. MNCs containing a known quantity of LSKF$^-$ cells were cultured for 14 days in media containing SCF and Tpo (ST), ST media with 250 nM CHIR99021 or ST media with 2 mM lithium chloride (LiCl) as indicated. After 14 days, the cellular product of these cultures was transplanted into lethally-irradiated recipients (10 Gray units) at a dosage corresponding to an original input into culture of MNCs containing 5 LSKF$^-$ cells per mouse for each group. 1×10$^5$ competitor bone marrow cells congenic with the hosts (CD45.1$^+$) were included per mouse. At 4 weeks post-transplant, peripheral blood was collected from each transplant recipient, and donor vs. host derived hematopoietic cells were determined by FACS analysis. Top panel shows a plot of CD45.2 (donor) frequency of total CD45$^+$ cells in peripheral blood of transplant recipients from each group. Bottom panel shows the percentage of donor derived peripheral blood cells (CD45.2$^+$) contributing to the main hematopoietic lineages (B lymphoid, T lymphoid, and myeloid cells) from transplant recipients as described above.

Figure 23:
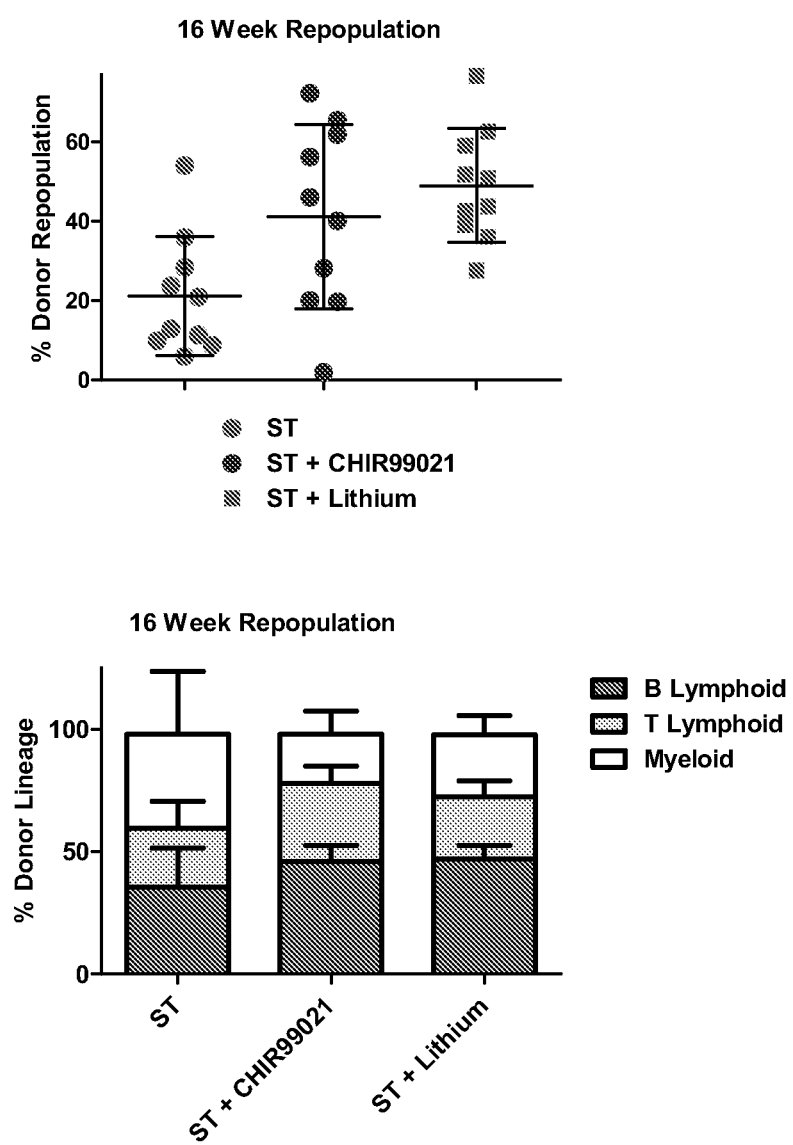

FIG. 23 shows that both CHIR99021 and lithium enhance long-term repopulation capacity of ex vivo expanded hematopoietic stem cells. The experimental conditions of the results shown in FIG. 23 are as follows. Bone marrow mononuclear cells (MNCs) were fractionated and the concentration of lineage marker negative, Sca-1$^+$, c-Kit$^+$, Flk2$^-$ (LSKF$^-$) cells was determined. MNCs containing a known quantity of LSKF$^-$ cells were cultured for 14 days in media containing SCF and Tpo (ST), ST media with 250 nM CHIR99021 or ST media with 2 mM lithium chloride (LiCl) as indicated. After 14 days, the cellular product of these cultures was transplanted into lethally-irradiated recipients (10 Gray units) at a dosage corresponding to an original input into culture of MNCs containing 5 LSKF⁻ cells per mouse for each group. 1×10⁵ competitor bone marrow cells congenic with the hosts (CD45.1$^+$) were included per mouse. At 16 weeks post-transplant, peripheral blood was collected from each transplant recipient, and donor vs. host derived hematopoietic cells were determined by FACS analysis. The top panel of FIG. 23 shows a plot of CD45.2 (donor) frequency of total CD45$^+$ cells in peripheral blood of transplant recipients from each group. The bottom panel shows the percentage of donor derived peripheral blood cells (CD45.2$^+$) contributing to the main hematopoietic lineages (B lymphoid, T lymphoid, and myeloid cells) from transplant recipients as described above.

Figure 24:
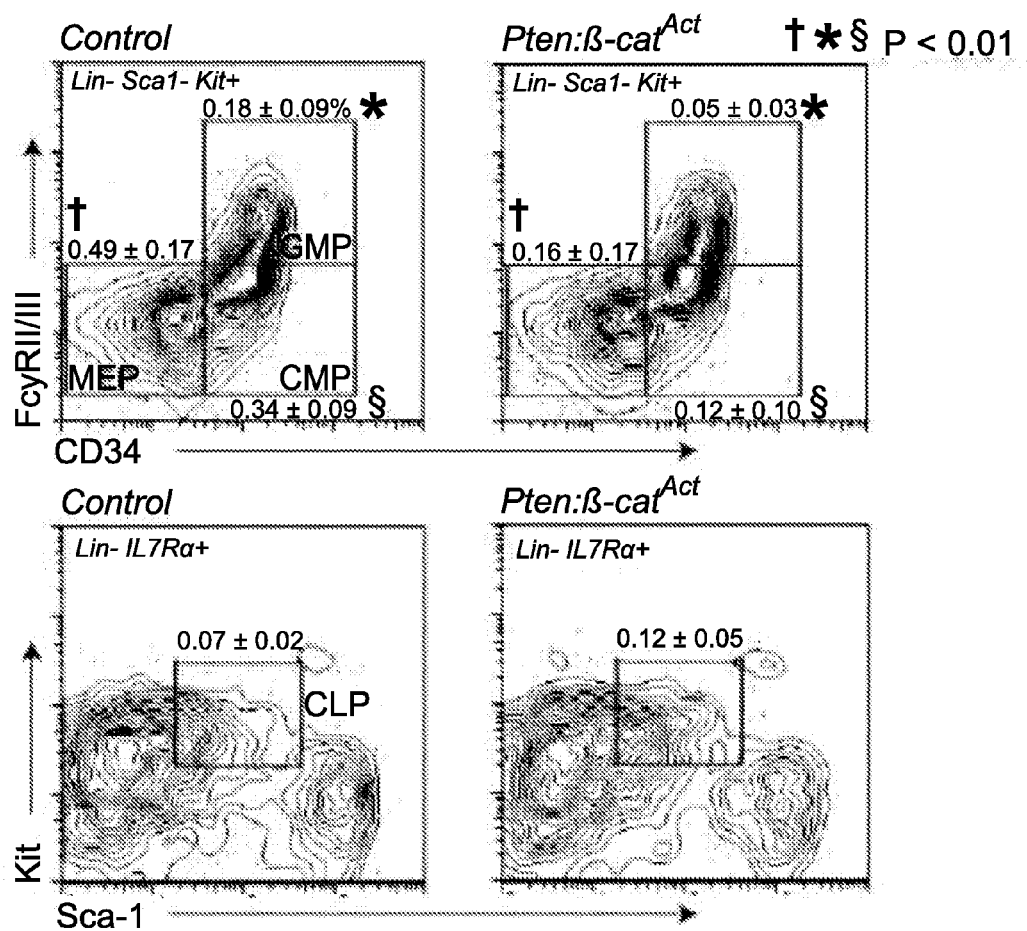

FIG. 24 shows FACS diagrams with frequencies of early progenitors in control and double mutants as indicated.

Figure 25:
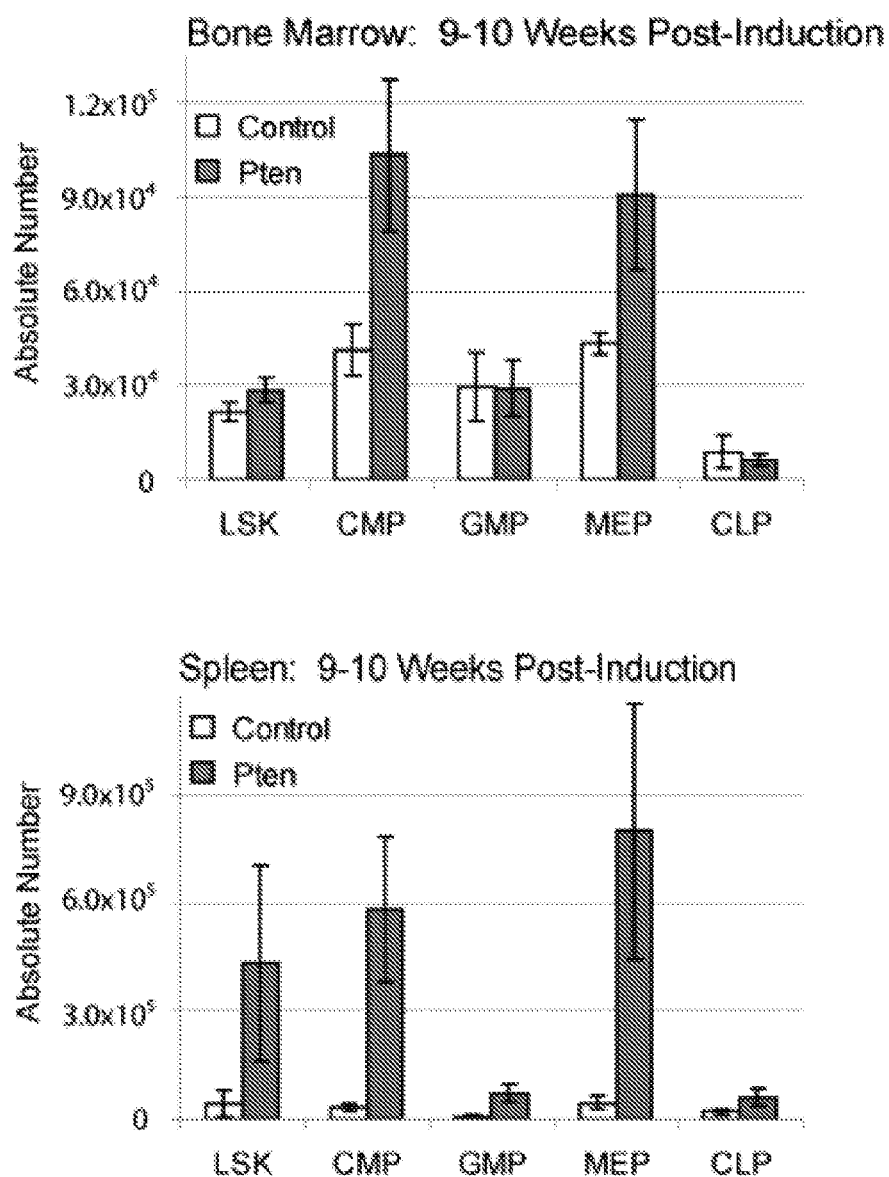

FIG. 25 shows the absolute number of LSK cells and early hematopoietic progenitors in control and Pten mutant bone marrow (tibia and femur) and spleen as determined by FACS analysis at 9-10 wpi.

FIG. 26A shows FACS diagrams (pre-gated Lin⁻ cells) demonstrating pre-culture and 14-day post-culture analysis of LSK and early progenitor cells with and without addition of lithium. Frequency of early myeloid (left, blue box) and LSK (right, blue box) per total, live cells is shown ±SD. FIG. 26B shows the quantification of total cell and LSK Flk2⁻ cell expansion after 14-day culture of MNC cells with and without 250 nM CHIR99021.

Figure 27A:
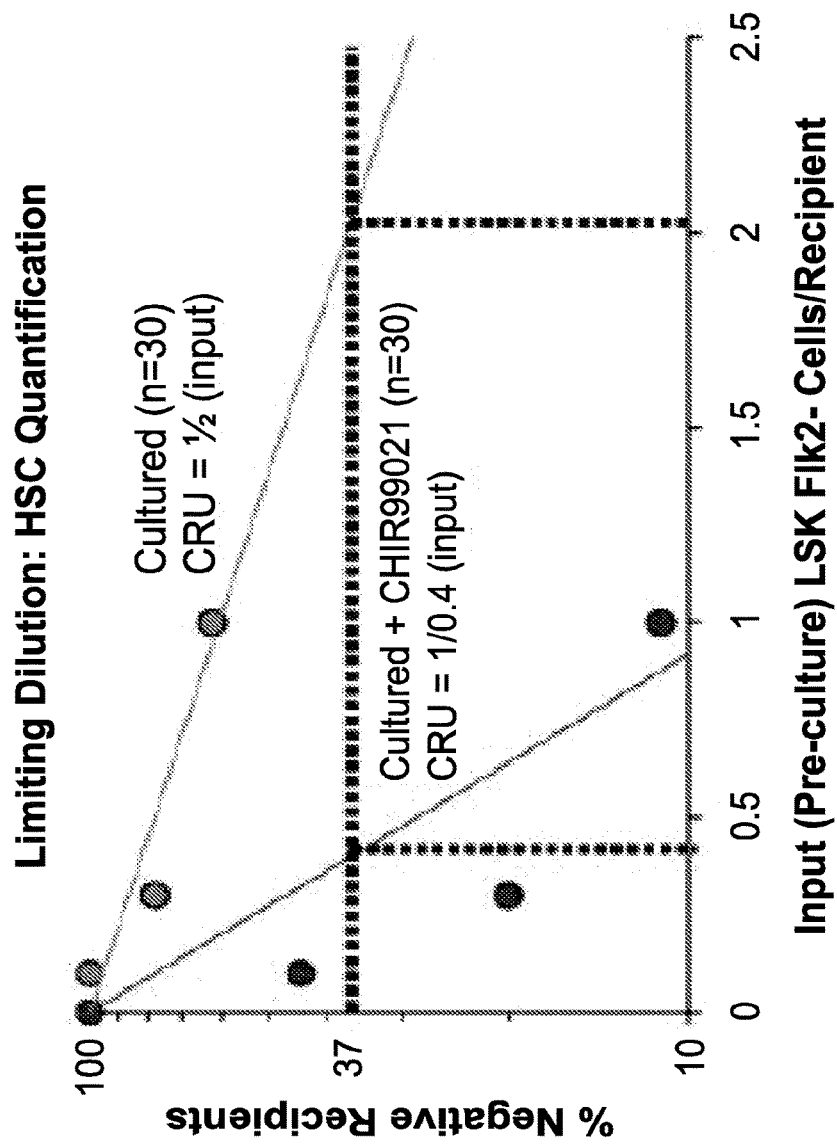
Figure 27:
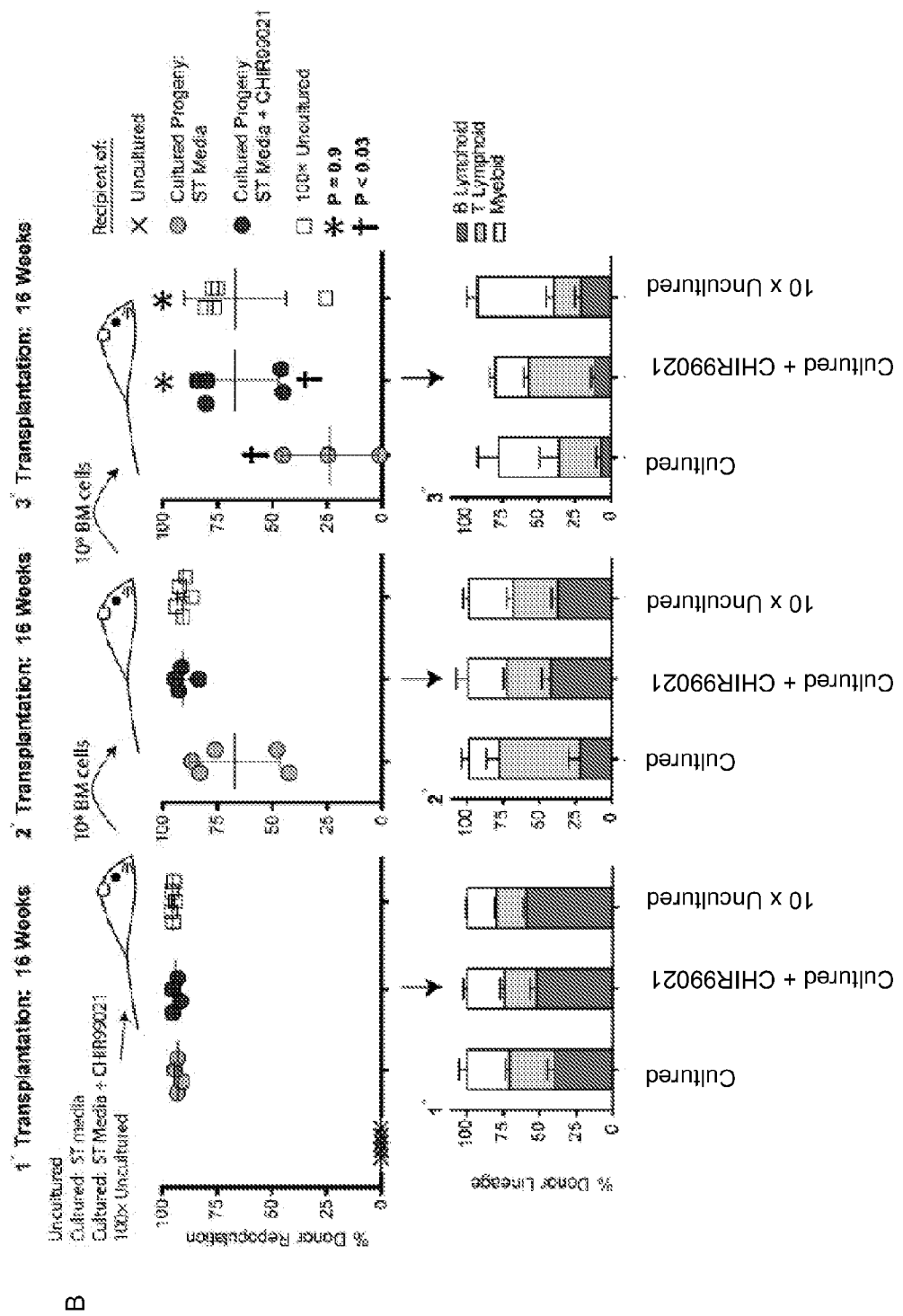
Figure 27:
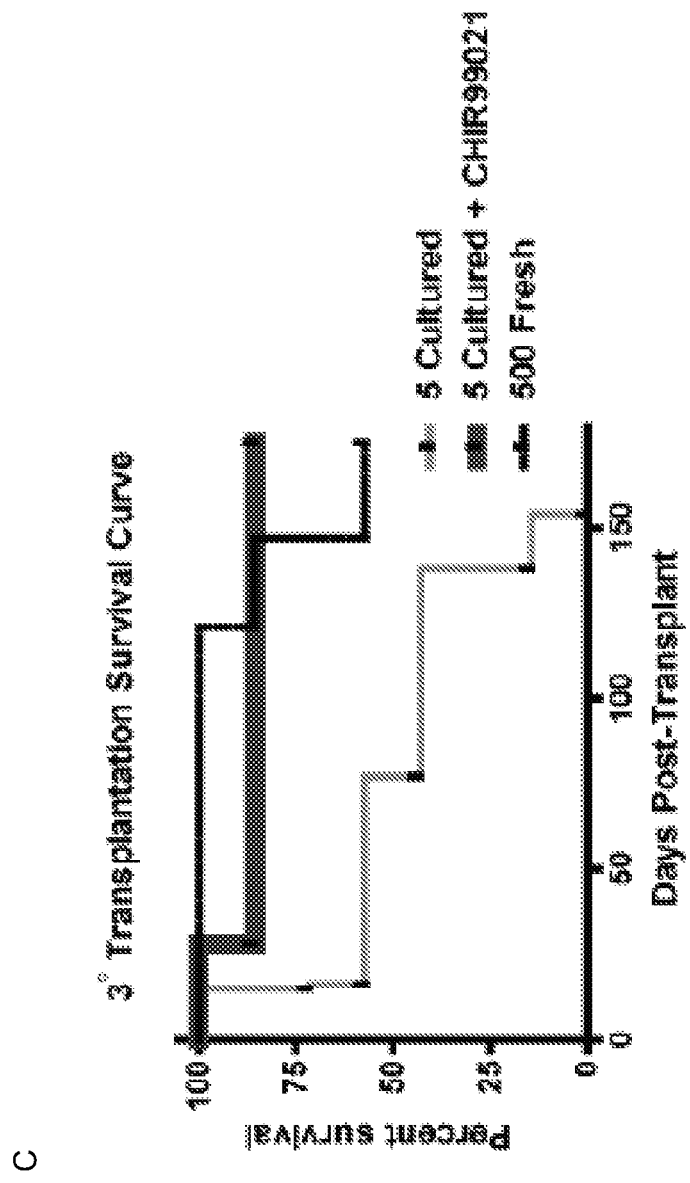

FIGS. 27A-C show ex vivo expansion of normal, long-term repopulating HSC. The experimental conditions of the results shown in FIG. 27A are as follows. MNCs containing a known quantity of LSK Flk2⁻ cells were cultured for 14 days with and without CHIR99021. The cultured progeny of MNCs containing a pre-culture dosage of 0.1, 0.3 or 1.0 LSK Flk2⁻ cells were transplanted into lethally irradiated recipients along with 1×10⁵ rescue/competitor cells (n=10 for each of 6 groups). Peripheral blood was analyzed at 16 weeks post-transplant and competitive repopulating unit (CRU) frequency was determined using L-Calc software (Stem Cell Technologies, Inc.) based on Poisson statistics (Zhang, C. C. & Lodish, H. F. Murine hematopoietic stem cells change their surface phenotype during ex vivo expansion. Blood, Vol. 105, pages 4314-4320 (2005); Miller, C. L. & Eaves, C. J. Expansion in vitro of adult murine hematopoietic stem cells with transplantable lympho-myeloid reconstituting ability. Proceedings of the National Academy of Sciences of the United States of America, Vol. 94, pages 13648-13653 (1997)). FIG. 27B shows a serial transplantation assay. The experimental conditions of the results shown in FIG. 27B are as follows. Fresh MNCs containing 5 or 500 LSK Flk2⁻ cells, or the progeny of MNCs containing 5 LSK Flk2⁻ cells cultured for 14 days with and without CHIR99021, were transplanted into lethally irradiated recipients without rescue/competitor cells. At 16-17 weeks post-transplant, bone marrow isolated from 1° recipients was transplanted into 2° recipients and, at 16-17 weeks post-secondary transplant, from 2° into 3° recipients at a dosage of 1×10⁶ cells per mouse. Peripheral blood was analyzed for percent donor repopulation at 16 weeks post-1°, 2°, and 3° transplant (upper panels) and percent mature donor-derived B, T and myeloid cells (lower panels). FIG. 27C shows Kaplan-Meier survival curve for 3° transplant recipients from FIG. 27B.

Figure 28:
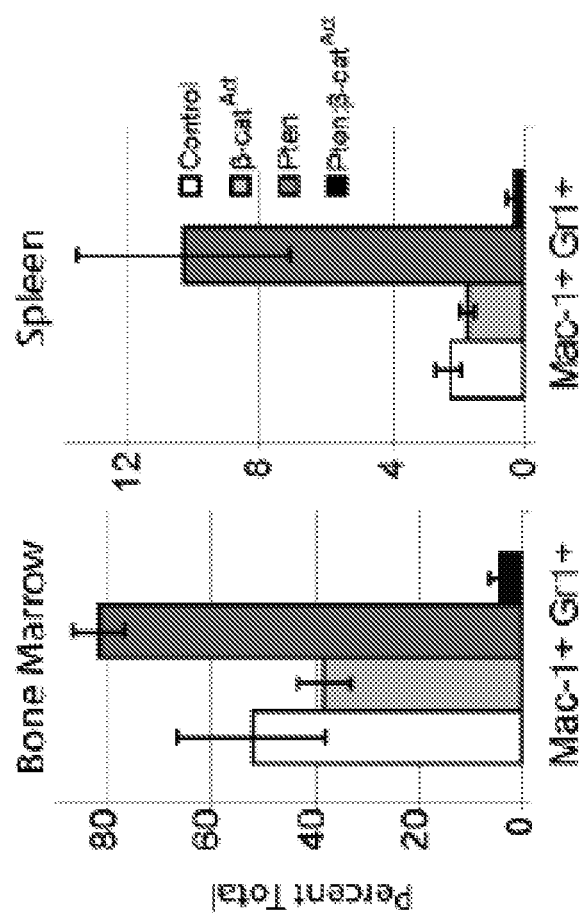

FIG. 28 shows the percent of Mac-1+ Gr1+ myeloid cells in bone marrow and spleen in control, single and double mutants as determined by FACS.

Figure 29:
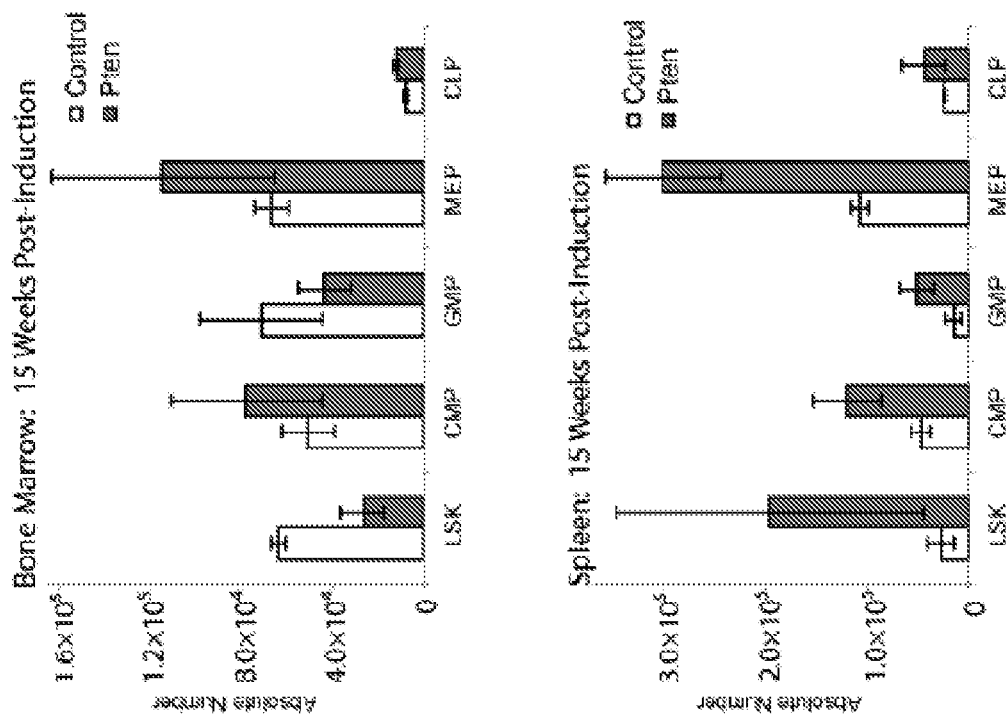

FIG. 29 shows long-term mobilization of LSK cells coupled with increased myeloid differentiation in Pten single mutants. Absolute number of LSK cells and early hematopoietic progenitors in control and Pten mutant bone marrow (tibia and femur) (top panel) and spleen (lower panel) were determined by FACS analysis at 15 wpi.

Figure 30:
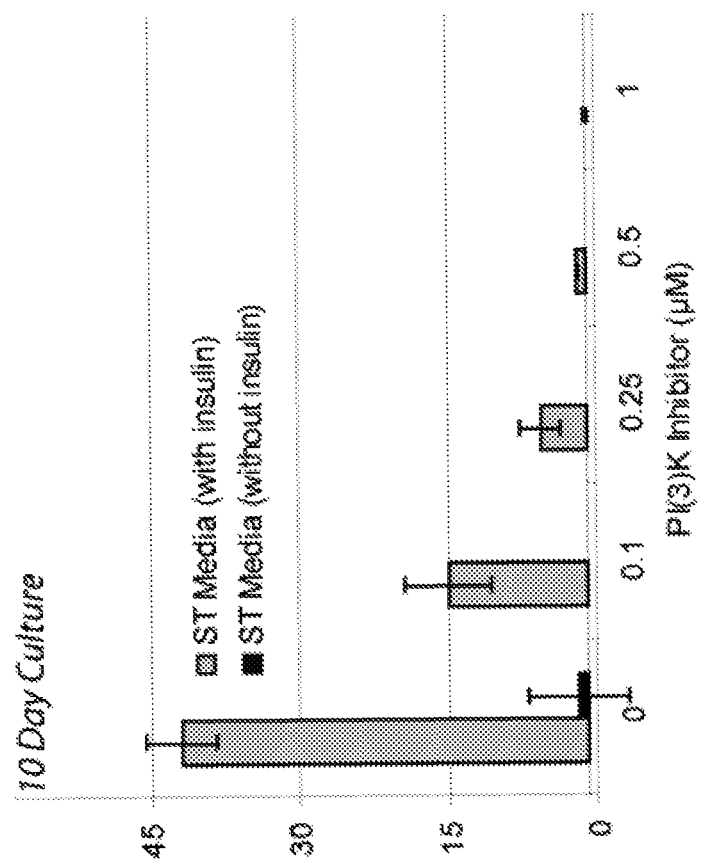

FIG. 30 shows that media without insulin was unable to substantially expand HSCs. Bone marrow MNCs from C57BL/6 mice were cultured for 10 days in ST media with or without insulin along with the indicated concentrations of PI3K inhibitor (NVP-BEZ235) (Maira, S. M. et al. Identification and characterization of NVP-BEZ235, a new orally available dual phosphatidylinositol 3-kinase/mammalian target of rapamycin inhibitor with potent in vivo antitumor activity. *Molecular cancer therapeutics* 7, 1851-1863 (2008)) and then analyzed by FACS to determine expansion of LSK Flk2⁻ cells.

Figure 31:
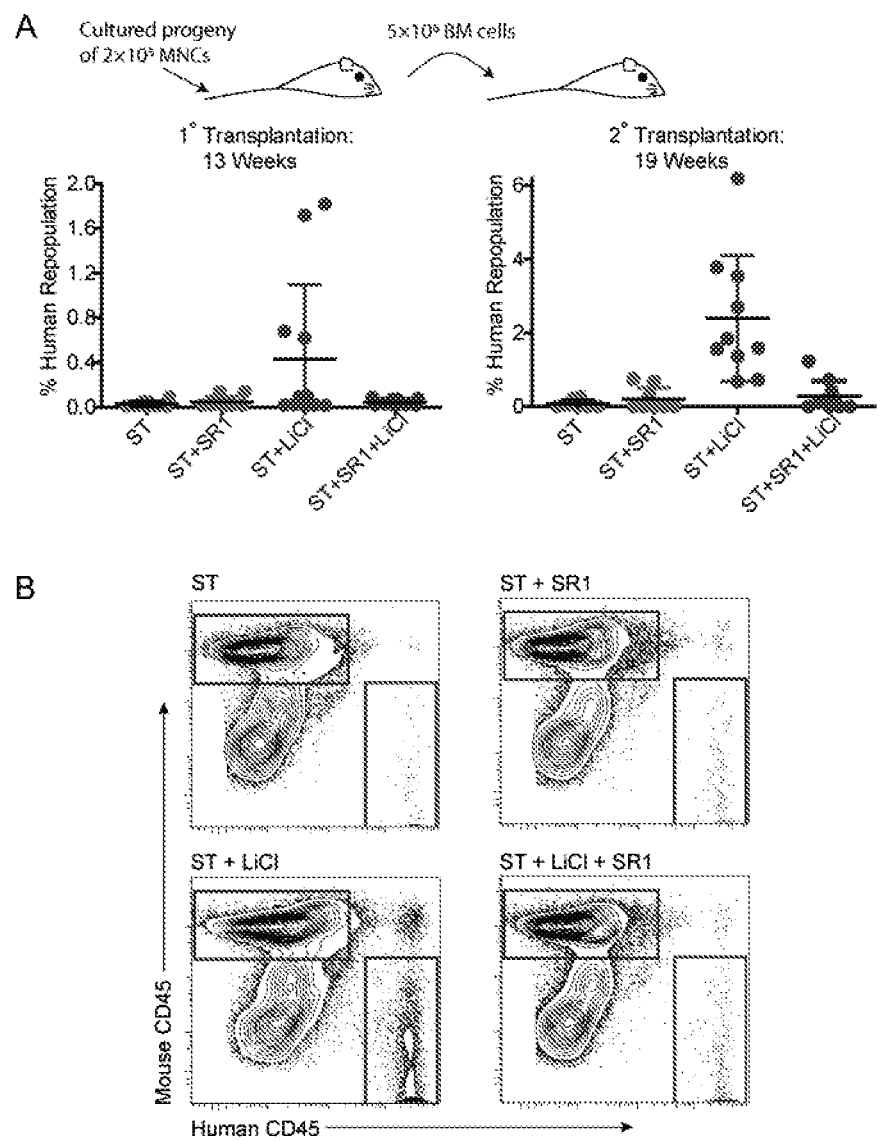

FIG. 31 shows that the activation of both Wnt/β-catenin and PI3K/Akt signaling during ex vivo expansion preferentially expands human, long-term reconstituting hematopoietic stem cells (LT-HSC). FIG. 31A shows a cartoon of the experimental setup and the results of the expansion experiment. FIG. 31B shows representative FACS plots of repopulation data quantified in FIG. 31A.

Figure 32:
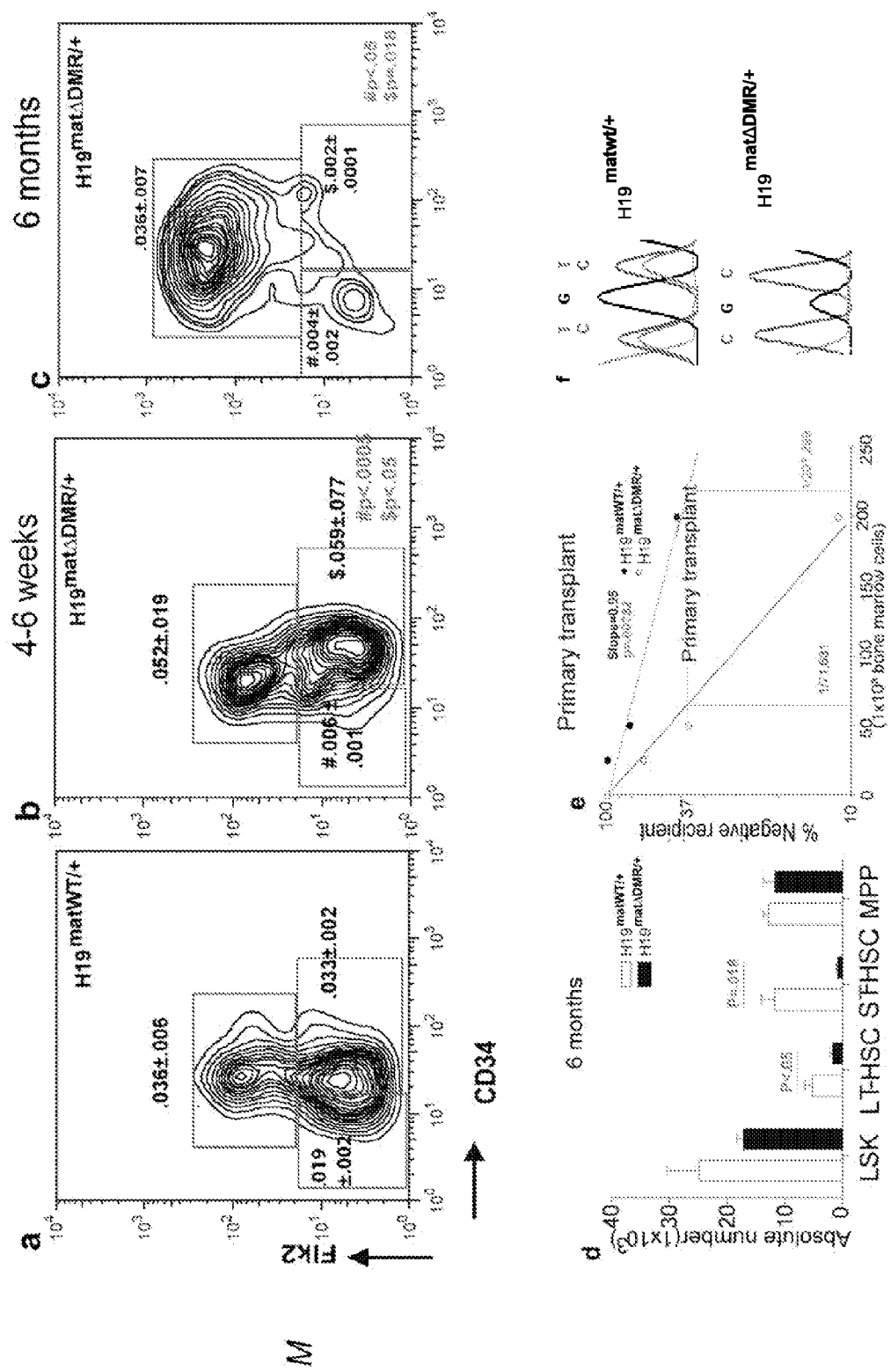
Figure 32:
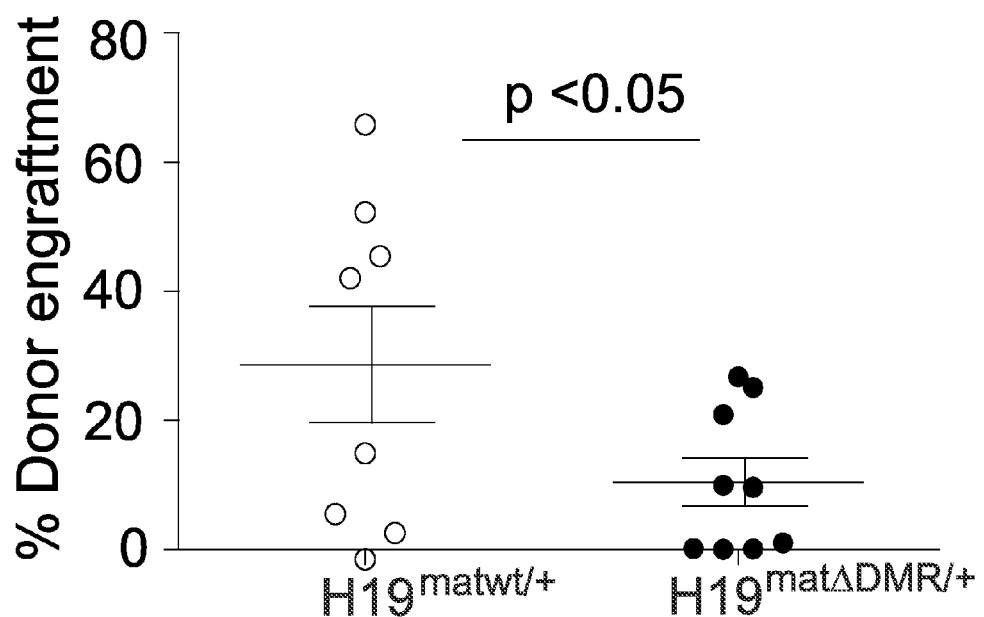

FIG. 32 shows that a hypomethylated state in the maternal DMR of the H19 gene is required for long term maintenance of quiescent, long-term hematopoietic stem cells in vivo. Bone marrow cells isolated from the maternally deleted hypomethylated region of imprinting gene H19(H19DMR) were analyzed by flow cytometry. Representative FACS analysis of gated on Lineage negative⁻Sca-1⁺, CD34 and Flk2 expression after conditional deletion of H19 DMR are indicated. FIG. 32A shows a FACS plot of a control littermate. FIGS. 32B and C show FACS plots at different time points. FIG. 32D shows the absolute number of stem cells at different time points from a mutant and its control littermate. FIG. 32E shows a competitive repopulation unit plot for different doses of bone marrow cells transplanted from mutant and its control littermate to the recipient mice. FIG. 32F shows representative DNA sequencing after bisulphite conversion in a mutant and its control littermate. FIG. 32G shows analysis of % donor engraftment 16 weeks after secondary transplant using the competitive repopulation assay.

FIG. 33 shows that the inhibition of DNA methyltransferase (DNMT) activity enhances phenotypic HSC expansion in long-term, ex vivo cultures. In this experiment, mononuclear cells (MNCs) were isolated from human umbilical cord blood (UCB) and cultured in STL media (activating both Wnt/β-catenin and PI3K/Akt signaling), STL+StemRegenin1 (SR1), or STL+DNMT inhibitor (DNMTi) and analyzed by flow cytometry. FIG. 33A shows a representative FACS analysis of Lineage negative (Lin⁻), CD34 and CD38 expression on UCB prior to culture and in the indicated culture conditions at 41 days post-culture. FIG. 33B shows the frequency of Lin⁻, CD34⁺, CD38⁻ cells before and after culture. FIG. 33C shows the fold-increase in Lin⁻, CD34⁺, CD38⁻ cells for the indicated culture conditions following 6 weeks culture.

Figure 34:
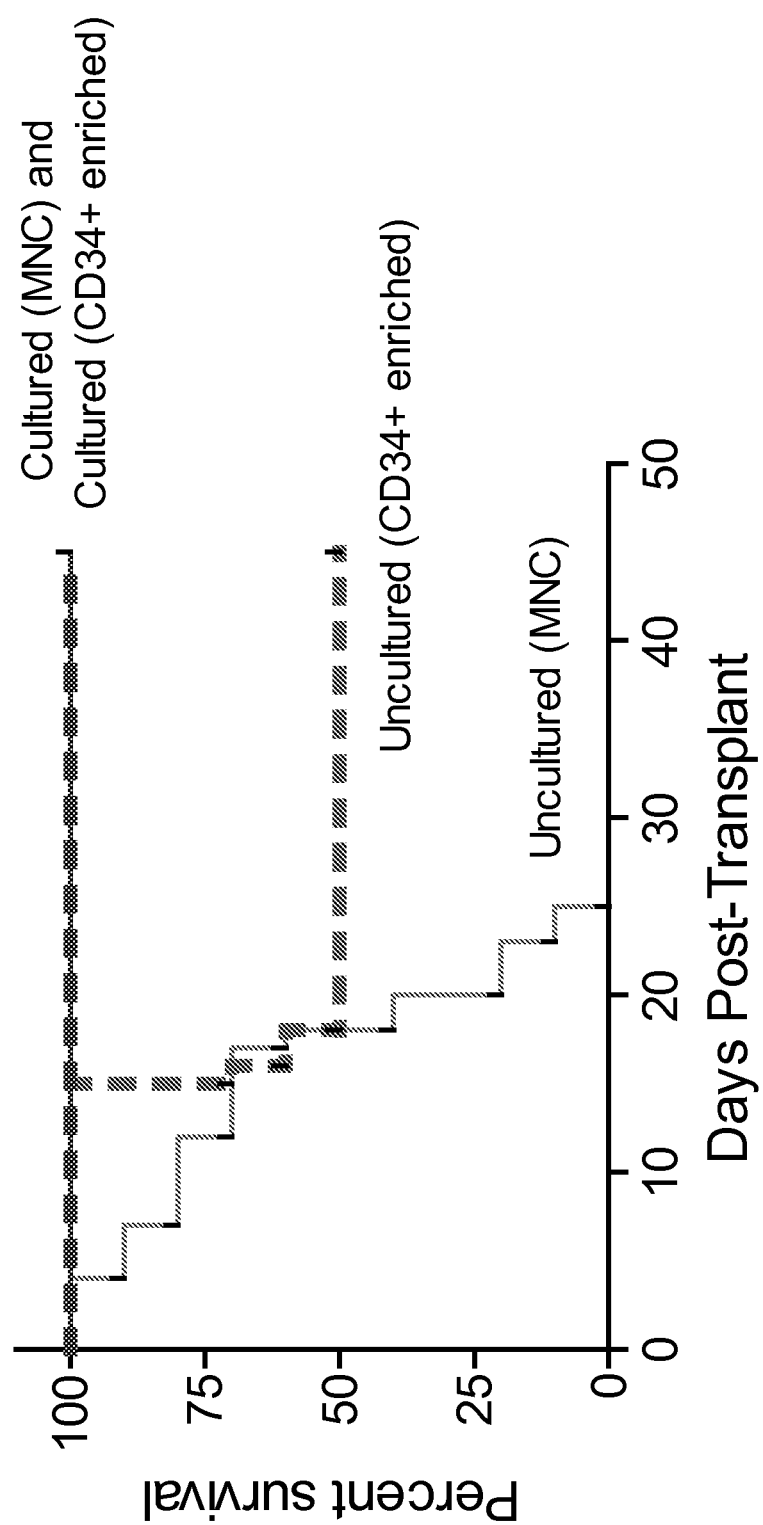

FIG. 34 shows that transplantation of cells cultured in media activating both the PI3K/Akt and Wnt/β-catenin pathways (STL media) improves survival of xenograft recipient mice.

FIG. 35 shows that ex vivo culture of cells obtained from human umbilical cord blood in media activating both the PI3K/Akt and Wnt/β-catenin pathways expands functional human HSCs. Using MNCs rather than sorted HSCs as the original culture input results in further HSC expansion. FIG. 35A shows a repopulation analysis of recipient bone marrow at 12 weeks post-transplant. FIG. 35B shows the contribution of human lymphoid and myeloid lineages to repopulation.

Figure 36:
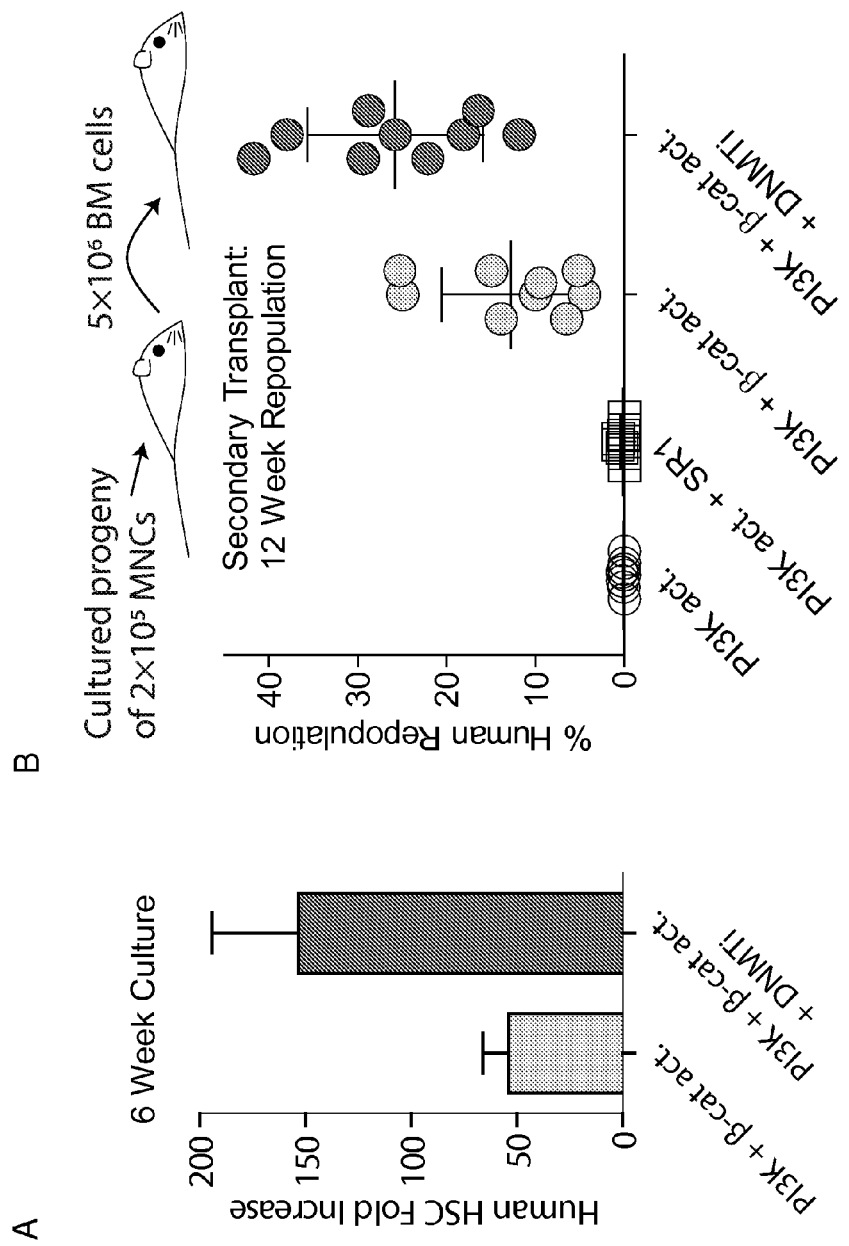

FIG. 36 shows that ex vivo culture in media activating both the PI3K/Akt and Wnt/β-catenin pathways expands functional, primitive human HSCs in serial transplant recipients. This effect is further enhanced by brief exposure to low levels of the epigenetic modulator, Decitabine. FIG. 36A shows the results of a FACS analysis of HSC expansion performed 6 weeks post-culture. FIG. 36B shows human donor cell repopulation at 12 weeks post-secondary transplant in mice. MNCs isolated from human UCB were cultured in media activating the PI3K/Akt pathway (ST media) ("PI3K act."), ST media with StemRegenin1 (SR1) ("PI3K act.+SR1"), media activating both the PI3K/Akt and Wnt/β-catenin pathways (STL media) (PI3K+β-cat act."), or STL media+DNMTi ("PI3K+β-cat act.+DNMTi") for 14 days. The cultured progeny of $2 \times 10^5$ MNCs per recipient were transplanted into sub-lethally irradiated (3.25 Gy) NSG recipients. 12 weeks post-transplant, bone marrow was harvested and transplanted into secondary recipients.

FIG. 37 shows that long-term ex vivo expansion of human $CD34^+$ cells in media activating both the PI3K/Akt and Wnt/β-catenin pathways yields normal karyotypes.

DETAILED DESCRIPTION OF THE INVENTION

In the present invention, it is demonstrated that the epigenetic memory of imprinting genes, as elaborated by the un-methylated state of H19-DMR and other regions, is critical for maintaining a quiescent HSC pool. See, e.g., Examples 15 and 16. This implies that blocking DNA methylation may maintain the stemness of HSCs and that blocking DNA methylation by the use of DNA methylation inhibitors may be used to culture and to expand HSCs.

Thus, one embodiment of the invention is an ex vivo method for expanding the number of hematopoietic stem cells (HSC) in a population of mononuclear cells (MNC). This method comprises culturing the population of MNCs comprising at least one HSC in an HSC expansion media for a period of time sufficient to expand the number of HSCs in the MNC population, wherein the HSC expansion media comprises a modulator of DNA methyltransferase (DNMT) and a modulator of the Wnt pathway.

As used herein, "expand", "expanding" and like terms means to increase the number of stem cells in the population relative to the number of stem cells in the original population in vitro, in vivo or ex vivo using any of the methods disclosed herein.

In the present invention, "stem cells" mean cells that possess the ability to give rise to many different types of cells and which have the ability to self-renew. Representative, non-limiting examples of stem cells according to the present invention include bronchioalveolar stem cells (BASCs), bulge epithelial stem cells (bESCs), corneal epithelial stem cells (CESCs), cardiac stem cells (CSCs), epidermal neural crest stem cells (eNCSCs), embryonic stem cells (ESCs), endothelial progenitor cells (EPCs), hepatic oval cells (HOCs), hematopoetic stem cells (HSCs), keratinocyte stem cells (KSCs), mesenchymal stem cells (MSCs), neuronal stem cells (NSCs), pancreatic stem cells (PSCs), retinal stem cells (RSCs), and skin-derived precursors (SKPs).

Hematopoietic stem cells or HSCs, for example, have the ability to self-renew (i.e., expand) and can give rise to all the types of progenitor cells (such as, e.g., CMP, GMP, MEP and CLP) and ultimately all the types of blood cells (such as e.g., red blood cells, B lymphocytes, T lymphocytes, natural killer cells, neutrophils, basophils, eosinophils, monocytes, macrophages, and platelets) in the hematopoietic system.

The HSC may be obtained from a mammalian tissue selected from the group consisting of cord blood, peripheral blood, and bone marrow. Preferably, the HSC is obtained from mammalian cord blood. As used herein, "obtained" from a tissue means any conventional method of harvesting or partitioning tissue from a donor. For example, the tissue may obtained from a blood sample, such as a peripheral or cord blood sample, or harvested from bone marrow. Methods for obtaining such samples are well known to the artisan. In the present invention, the samples may be fresh, i.e., obtained from the donor without freezing. Moreover, the samples may be further manipulated to remove extraneous or unwanted components prior to expansion. The samples may also be obtained from a preserved stock. For example, in the case of peripheral or cord blood, the samples may be withdrawn from a cryogenically or otherwise preserved bank of such blood. Such samples may be obtained from any suitable donor. Preferably, the donor is a mammal, for example, a primate, such as a human; or laboratory animals such as mice, rats, dogs, and pigs. Furthermore, the sample may be obtained from an autologous or allogeneic donor or source. Preferably, the sample is obtained from an autologous source.

As used herein, "mononuclear cells" or "MNC" mean blood cells that have a one-lobed nucleus. MNCs include without limitation monocytes, lymphocytes, plasma cells, macrophages, and mast cells.

As used herein, "HSC expansion media" means any media suitable for expanding the number of HSC population in a culture. It includes without limitation, the particular media disclosed in the Examples.

As used herein, "a modulator of DNA methyltransferase (DNMT)" means any agent that regulates the activity of DNMT, such as increasing or decreasing the expression or function of DNMT. As used herein, "DNMT" means any agent, such as, e.g., an enzyme that catalyzes the transfer of a methyl group to DNA. Non-limiting examples of DNMT include mammalian, such as, human DNMTs such as DNMT1, DNMT3A, and DNMT3B.

Preferably, the modulator of DNA methyltransferase is a DNA methyltransferase inhibitor (DNMTi). The DNMTi may be a small molecule, a biologic, an antisense RNA, a small interfering RNA (siRNA), and combinations thereof. For example, the DNMTi may be a small molecule such as a nucleoside analog. As used herein, a "nucleoside analog" means a molecule that resembles a naturally occurring nucleoside, but which has a chemical or physical modification on the base and/or the sugar moiety, such as a different or additional side group. Such analogs are discussed in, e.g., Scheit, Nucleotide Analogs (John Wiley & Son, 1980) and Uhlman et al., *Chemical Reviews* 90:543-584, 1990. Non-limiting examples of DNMTi nucleoside analogs include azacitidine (5-azacytidine), decitabine (5-aza-2'-deoxycytidine), 5-fluoro-2'-deoxycitidine, 5,6-dihydro-5-azacytidine (DHAC), zebularine (1-β-D-ribofuranosyl-2(1H)-pyrimidinone), fazarabine (1-β-D-arabinofuranosyl-5-azacytosine), RX-3117 (Rexahn Pharmaceuticals Inc., Rockville, Md.), SGI-110 (Astex Pharmaceuticals, Dublin, Calif.), DNA methyltransferase inhibitors (IkerChem, San Sebastian, Spain), EGX-30P (EpiGenX Pharmaceuticals, Santa Barbara, Calif.), MeTase inhibitor (MethylGene, Montreal, Canada), prodrugs thereof, pharmaceutically acceptable salts thereof, and combinations thereof. Preferably, the DNMTi is 5-aza-2'-deoxycytidine, pharmaceutically acceptable salts thereof, or combinations thereof.

As used herein, a "prodrug" means a substance that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester to facilitate transmittal across a cell membrane, but which then is metabolically hydrolyzed to the active entity once inside the cell. SGI-110 is a non-limiting example of a prodrug (in this case, a prodrug of decitabine). Conventional procedures for the selection and preparation of suitable prodrug derivatives are described, for example, in Design of Prodrugs, (ed. H. Bundgaard, Elsevier, 1985), which is incorporated herein by reference for the purpose of describing procedures and preparation of suitable prodrug derivatives.

The DNMTi may also be a non-nucleoside analog. Non-limiting examples of DNTMi non-nucleoside analogs include hydralizine, disulfiram, procaine, procainamide, epigallocatechin gallate, psammaplins, RG108 ((S)-2-(1,3-dioxo-1,3-dihydro-isoindol-2-yl)-3-(1H-indol-3-yl)-propionic acid), antineoplaston AS2-1 (Burzynski Research Institute, Houston, Tex.), prodrugs thereof, pharmaceutically acceptable salts thereof, and combinations thereof.

Furthermore, the DNMTi may be a biologic. Non-limiting examples of DNTMi biologics include CC-014 (CellCentric, Cambridge, UK), CC-034 (CellCentric), and combinations thereof.

Additionally, the DNMTi may be an antisense RNA. Non-limiting examples of DNTMi antisense RNA include MG-98 (MethylGene, Montreal, Canada).

In the present invention, "a modulator of a Wnt Pathway" (or "Wnt pathway modulator") is any agent that regulates the activity of any member of the Wnt pathway, which results in, e.g., increased β-catenin expression in a stem cell, and/or increased β-catenin function in a stem cell, and/or increased β-catenin localization to a nucleus of a stem cell. A modulator of the Wnt pathway may act upstream or downstream of Wnt. Preferably, the modulator acts at GSK-3β. Representative, non-limiting examples of members of the Wnt pathway, include Wnt, seven-transmembrane Frizzled (Fz), the single-pass, LDL receptor-related proteins (LRP) 5/6, Axin, Dishevelled, glycogen synthase kinase 3 beta (GSK-3β), adenomatous polyposis coli (APC), and β-catenin. Preferably, the modulator of the Wnt pathway down-regulates GSK-3β. As used herein, "down-regulating" GSK-3β means decreasing or inhibiting the expression or the function of GSK-3β.

In a preferred embodiment, the modulator of the Wnt pathway is a reversible GSK-3β inhibitor selected from the group consisting of a small molecule, a biologic, an antisense RNA, a small interfering RNA (siRNA), and combinations thereof. As used herein, "reversible" means that the effect of the down-regulation is not permanent.

Preferably, the reversible GSK-3β inhibitor is a small molecule. Non-limiting examples of reversible GSK-3β inhibitor include Hymenialdisine, Flavopiridol, Kenpaullone, Alsterpaullone, Azakenpaullone, Indirubin-30-oxime, 6-Bromoindirubin-30-oxime (BIO), 6-Bromoindirubin-30-acetoxime, Aloisine A, Aloisine B, TDZD8, Compound 12, CHIR98014, CHIR99021 (CT99021), CT20026, Compound 1, SU9516, ARA014418, Staurosporine, Compound 5a, Compound 29, Compound 46, GF109203x (bisindolylmaleimide I), Ro318220 (bisindolylmaleimide IX), SB216763, SB415286, 15, CGP60474, Compound 8b, TWS119, Compound 1A, Compound 17, Lithium, Beryllium, Zinc, small molecule GSK-3β inhibitors (Vertex Pharmaceuticals), NP-12 (Neuropharma), GSK-3β inhibitors (Amphora), GSK-3β inhibitors (CrystalGenomics), SAR-502250 (Sanofi-Aventis), 3544 (Hoffmann-La Roche), GSK-3β inhibitors (Lundbeck), TDZD-8 (Cancer Center, University of Rochester), pharmaceutically acceptable salts thereof, and combinations thereof. Preferably, the GSK-3β inhibitor is CHIR99021 or lithium.

In this embodiment, a "period of time sufficient" to expand the number of HSCs means the minimum time which are sufficient to increase the number of HSCs relative to the original number of HSCs in the population.

In one aspect of this embodiment, the HSC expansion is 3-fold more compared to the same method in which the HSC expansion media does not contain a DNMT modulator. It is contemplated that the HSC expansion may be more than 3-fold, including expansion to clinically relevant HSC numbers, compared to the same method in which the HSC expansion media does not contain a DNMTi modulator.

An additional embodiment of the present invention is an expanded, substantially undifferentiated HSC population made by any method disclosed herein. Preferably, the HSC is human.

Another embodiment of the present invention is kit for expanding, ex vivo, the number of hematopoietic stem cells (HSC) in a population of mononuclear cells (MNC). The kit comprises a DNMTi and a GSK-3β inhibitor, and instructions for the use of the inhibitors, wherein, when used, the kit provides expanded number of HSCs.

Suitable DNMTis, GSK-3β inhibitors, and the source of the HSCs are as disclosed herein.

In one aspect of this embodiment, the kit provides 3-fold higher HSC expansion compared to use of the kit without the DNMTi.

Yet another embodiment of the present invention is a media for carrying out ex vivo expansion of HSCs in a population of MNCs. This media comprises a fluid media suitable for maintaining viable stem cells, a DNMTi, and a GSK-3β inhibitor present in the media at concentrations sufficient to enable expansion of the HSC. Suitable media, DNMTis, GSK-3β inhibitors, and source of the HSCs are as disclosed herein.

An additional embodiment of the present invention is an ex vivo method for expanding the number of HSCs in a population of MNCs. This method comprises contacting the HSCs with (i) 5-aza-2'-deoxycytidine, a prodrug thereof, pharmaceutically acceptable salts thereof, or combinations thereof; and (ii) lithium, pharmaceutically acceptable salts thereof, or combinations thereof to expand the number of HSCs.

Another embodiment of the present invention is an ex vivo method for expanding the number of hematopoietic stem cell (HSC) in a population of mononuclear cells (MNCs). This method comprises culturing the population of MNCs comprising at least one HSC in an HSC expansion media for a period of time sufficient to expand the number of HSCs in the MNC population, wherein the population of MNCs is enriched for CD34$^+$ cells, and wherein the wherein the HSC expansion media comprises of a modulator of the Wnt pathway.

As used herein, "enriched" for CD34$^+$ cells means that the percentage of CD34$^+$ cells relative to other cells in a population is increased. Methods for the enrichment of CD34$^+$ cells are disclosed herein and are also known in the art. For example, CD34+ cells may be enriched by fluorescence-activated cell scanning (FACS), magnetic cell sorting, and centrifugation. See, e.g., U.S. Pat. Nos. 5,474,687; 5,677,136, and 6,004,743, as well as US Patent Publication No. 20010039052.

Suitable media, modulators of the Wnt pathway, and source of the HSCs are as disclosed herein.

In one aspect of this embodiment, the HSC expansion media further comprises a DNMTi. Suitable DNMTis are as disclosed herein.

A further embodiment of the present invention is a method for administering an hematopoietic stem cell (HSC) population to a patient in need thereof. This method comprises:

(a) culturing an HSC population in a population of mononuclear cells (MNCs) in an HSC expansion media for a period of time sufficient to expand the number of HSCs to a number sufficient to transplant into the patient, wherein the MNC population is enriched for CD34+ cells, and wherein the HSC expansion media comprises of a modulator of the Wnt pathway; and (b) administering the cultured HSC population to the patient.

Suitable media, modulators of the Wnt pathway, and source of the HSCs are as disclosed herein.

In one aspect of this embodiment, the HSC expansion media further comprises a DNMTi. Suitable DNMTis are as disclosed herein.

Another embodiment of the present invention is a method for providing HSCs, which, when transplanted into a patient, reduce the likelihood of the patient developing a complication from the transplant. This method comprises culturing a population of HSCs in an HSC expansion media for a period of time sufficient to expand the number of HSCs prior to administering the HSCs to the patient, wherein the HSC expansion media comprises an activator of the Wnt pathway, an activator of the PI3K/Akt pathway, and a DNMTi.

As used herein, "an activator of the Wnt pathway" means any agent that regulates the activity of any member of the Wnt pathway, which results in an effect that mimics the activation of Wnt receptor. Thus, such activators of the Wnt pathway may act upstream or downstream of Wnt, and includes without limitation, reversible GSK-3β inhibitors as set forth above.

As used herein, "an activator of PI3K/Akt pathway" is any agent that regulates the activity of any member of the PI3K/Akt pathway, which results in decreased function or expression of phosphatidylinositol 3-kinase (PI3K) and/or increased function or expression of the serine/threonine protein kinase Akt.

Representative non-limiting examples of activators of PI3K/Akt pathway include pervanadate (Maude Tessier and James R. Woodgett, J. Biol. Chem., 281(33):23978-23989 (2006)); carbachol (Cui, Q L, et al., Neurochem Int, 48:383-393 (2006)); nicotine (West, K. et al., J. Clinical Investigation, 111:81-90 (2003)); 4-(methylnitrosamino)-1-(3-pyridyl)-1-butanone (NNK) (Id.); lysophosphatidic acid; macrophage stimulating factor; sphingosine-1-phosphate; Ro-31-8220 (Wen, H. et al., Cellular signaling, 15:37-45 (2003)); 4-(methylnitrosamino)-1-(3-pyridyl)-1-butanone (NNK) (West, K. et al., J. Clinical Investigation, 111:81-90 (2003)); adrenomedullin (AM) (Nikitenko, L L et al, British J. Cancer, 94:1-7 (2006)); platelet activating factor; cAMP-elevating agents, such as forskolin, chlorophenylthio-cAMP, prostaglandin-E1, and 8-bromo-cAMP (Song et al., J. Cell. Mol. Med., 9(1):59-71 (2005)); and growth factors, including insulin and insulin growth factor-1 (Datta, S. R., et al., Cell, 91:231-241 (1997)), platelet derived growth factor (Datta, S. R., et al., Cell 91:231-241 (1997)), and stem cell factor (SCF).

Preferably, the activator of the Wnt pathway is lithium, and the activator of the PI3K/AKt pathway is selected from the group consisting of insulin, stem cell factor (SCF), and mixtures thereof.

Suitable media, DNMTis, and source of the HSCs are as disclosed herein.

As used herein, a "complication" means an unfavorable evolution of a disease or a health condition. For example, wherein the complication is related to the immune system, such as rejection of a transplant or host vs. graft disease. Acute host vs. graft disease may result in the death of a patient. Other complications may be the development of abnormal proportions of lymphocytes and myeloid cells in the patient. As used herein, "abnormal" means that the proportions of lymphocytes and myeloid cells in the patient is different from those in the population at large.

Another embodiment of the invention is an ex vivo method for expanding the number of hematopoietic stem cells (HSC) in a population of mononuclear cells (MNC). This method comprises culturing the population of MNCs comprising at least one HSC in an HSC expansion media for a period of time sufficient to expand the number of HSCs in the MNC population, wherein the expanded HSCs are functional with long term, multi-lineage, repopulating potential.

As used herein, cells with "long term, multi-lineage repopulating potential" means cells that are capable of repopulating many different types of blood cells in irradiated recipients upon transplantation and/or cells that possess high proliferative potential in vitro.

Preferably, the expansion is at least 40-fold compared to the original number of stem cells in the population. More preferably, the expansion is at least 80-fold, 100-fold, 150-fold, 200-fold, 250-fold, or 270-fold compared to the original number of stem cells.

In one aspect of this embodiment, this method provides HSCs that, upon transplant into a recipient, exhibit greater than 5% donor repopulation, such as greater than 10%, 15%, 20%, 25%, 30%, 35%, 40%, 55%, 60%, 65%, 70%, 75%, 80%, 85%, or 90% donor repopulation. Preferably, the method provides HSCs that, upon transplant into a recipient, exhibit greater than 25%, 35%, 45%, or 60% donor repopulation. Preferably, the recipient is a mammal, for example, a primate, such as a human; or laboratory animals such as mice, rats, dogs, and pigs. In the present invention, "recipient" is used interchangeably with "patient."

In another aspect of this embodiment, the HSC expansion media comprises a modulator of the Wnt pathway. Preferably, the modulator of the Wnt pathway down-regulates GSK-3β. In a preferred embodiment, the modulator of the Wnt pathway is a reversible GSK-3β inhibitor selected from the group consisting of a small molecule, a biologic, an antisense RNA, a small interfering RNA (siRNA), and combinations thereof.

Preferably, the reversible GSK-3β inhibitor is a small molecule. Examples of reversible GSK-3β inhibitors include without limitation, Hymenialdisine, Flavopiridol, Kenpaullone, Alsterpaullone, Azakenpaullone, Indirubin-30-oxime, 6-Bromoindirubin-30-oxime (BIO), 6-Bromoindirubin-30-acetoxime, Aloisine A, Aloisine B, TDZD8, Compound 12, CHIR98014, CHIR99021 (CT99021), CT20026, Compound 1, SU9516, ARA014418, Staurosporine, Compound 5a, Compound 29, Compound 46, GF109203x (bisindolylmaleimide I), Ro318220 (bisindolylmaleimide IX), SB216763, SB415286, I5, CGP60474, Compound 8b, TWS119, Compound 1A, Compound 17, Lithium, Beryllium, Zinc, small molecule GSK-3β inhibitors (Vertex Pharmaceuticals), NP-12 (Neuropharma), GSK-3β inhibitors (Amphora), GSK-3β inhibitors (CrystalGenomics), SAR-502250 (Sanofi-Aventis), 3544 (Hoffmann-La Roche), GSK-3β inhibitors (Lundbeck), TDZD-8 (Cancer Center, University of Rochester), pharmaceutically acceptable salts thereof, or combinations thereof. Preferably, the GSK-3β inhibitor is CHIR99021, or lithium, a pharmaceutically acceptable salt thereof, or combinations thereof.

In another preferred embodiment, the method comprises culturing the population of MNCs comprising at least one HSC in any of the HSC expansion media disclosed herein, and the method provides HSCs that, upon transplant into a recipient, exhibit greater than 5%, such as greater than 10%, 15%, 20%, 25%, 30%, 35%, 40%, 45%, 50%, 55%, 60%, 65%, 70%, 75%, 80%, 85%, or 90% donor repopulation, preferably, greater than 60% donor repopulation.

In another aspect of this embodiment, the HSC is obtained from a mammalian tissue selected from the group consisting of cord blood, peripheral blood, and bone marrow.

A further aspect of this embodiment is an expanded, substantially undifferentiated HSC population made by any of the methods disclosed herein. Preferably, the substantially undifferentiated HSC population is made using an HSC expansion media comprising a modulator of the Wnt pathway. More preferably, the substantially undifferentiated HSC population is made using an HSC expansion media comprising lithium, a pharmaceutically acceptable salt thereof, or combinations thereof.

A stem cell population is "substantially undifferentiated" if a sufficient number of cells in that population retain the ability to self-renew and can give rise to various differentiated cell types when transplanted into a recipient, for example, in the case of an HSC population, repopulating the HSC lineage when transplanted. As used herein, "without significant differentiation" means the expanded stem cell population has a sufficient number of cells that maintain a multi-lineage differentiation potential that the full scope of a target stem lineage may be regenerated upon transplantation of the expanded stem cell population into a recipient. Thus, e.g., in the case of an HSC population, the expanded HSC population, when transplanted into a recipient, is capable of regenerating the entire hematopoietic cell lineage.

An additional embodiment of the invention is a kit for expanding, ex vivo, the number of hematopoietic stem cells (HSC) in a population of mononuclear cells (MNC). The kit comprises a GSK-3β inhibitor, and instructions for the use of the inhibitor, wherein, when used, the kit provides expanded HSCs that are functional with long term, multi-lineage, repopulating potential. In one aspect of this embodiment, the GSK-3β inhibitor is as disclosed herein. Preferably, the GSK-3β inhibitor is CHIR99021, or lithium, a pharmaceutically acceptable salt thereof, or combinations thereof.

In another aspect of this embodiment, the kit provides HSCs that, upon transplant into a recipient, exhibit greater than 5%, such as greater than 10%, 15%, 20%, 25%, 30%, 35%, 40%, 45%, 50%, 55%, 60%, 65%, 70%, 75%, 80%, 85%, or 90% donor repopulation, preferably, greater than 60% donor repopulation. The kit may be packaged in any convenient manner and include additional reagents and/or devices for carrying out its intended purpose.

A further embodiment of the invention is a media for carrying out ex vivo expansion of a stem cell in a population of MNCs. This media comprises a fluid media suitable for maintaining viable stem cells and a GSK-3β inhibitor present in the media at a concentration sufficient to enable expansion of the stem cell population while maintaining a long term, multi-lineage, repopulating potential in the stem cells, wherein the stem cells, when transplanted into a recipient, exhibit greater than 5% donor repopulation, such as greater than 10%, 15%, 20%, 25%, 30%, 35%, 40%, 45%, 50%, 55%, 60%, 65%, 70%, 75%, 80%, 85%, or 90% donor repopulation. Preferably, the GSK-3β inhibitor is lithium, a pharmaceutically acceptable salt thereof, or combinations thereof.

Yet another embodiment of the invention is an ex vivo method for expanding the number of cells capable of supporting multi-lineage repopulation in a population of mononuclear cells (MNC). This method comprises culturing the population of MNCs comprising at least one hematopoietic stem cell (HSC) and at least one hematopoietic progenitor cell in an HSC expansion media for a period of time sufficient to expand the number of cells capable of supporting multi-lineage repopulation in the MNC population.

As used herein, "cells capable of supporting multi-lineage repopulation" means those cells that are capable of repopulating many different types of blood cells in irradiated recipients upon transplantation. Non-limiting examples of such cells include HSCs.

As used herein, an "hematopoietic progenitor cell" means a cell that has lost the capacity of self-renewal but is still able to give rise to different types of blood cells. Non-limiting examples of hematopoietic progenitor cells include CMP, GMP, MEP, and CLP.

In one aspect of this embodiment, the HSC expansion media comprises a reversible GSK-3β inhibitor. Preferably, the GSK-3β inhibitor is lithium, a pharmaceutically acceptable salt thereof, or combinations thereof.

Another embodiment of the invention is a method for expanding a population of stem cells obtained from a tissue selected from the group consisting of peripheral blood, cord blood, and bone marrow. This method comprises modulating a PTEN pathway and a Wnt pathway in the population of stem cells to expand the number of stem cells.

In the present invention, "modulating", "modulation" and like terms mean altering the signal transduction pathway, e.g., a protein in the PTEN and/or Wnt pathways, including but not limited to lowering or increasing the expression level of a protein, altering the sequence of such a protein (by mutation, pre-translational or post-translational modification or otherwise), or inhibiting or activating such a protein (whether by binding, phosphorylation, glycosylation, translocation or otherwise). Such modulation may be achieved genetically or pharmacologically.

As used herein, "a modulator of a PTEN pathway" (or "PTEN pathway modulator") is any agent that regulates the activity of any member of the PTEN pathway, which results in, e.g., increased β-catenin expression in a stem cell, and/or increased β-catenin function in a stem cell, and/or increased β-catenin localization to a nucleus of a stem cell and/or provides a survival signal complementary to β-catenin. Thus, a modulator of the PTEN pathway may act upstream or downstream of PTEN; preferably the modulator acts at or downstream from PTEN. Inhibition of PTEN leads to Akt activation which promotes survival (FIG. 3A). Representative, non-limiting examples of members of the PTEN pathway, include PTEN, phosphatidylinositol 3-kinase (PI3K), the serine/threonine protein kinase Akt, and β-catenin.

Representative non-limiting examples of PI3K modulators, particularly PI3K activators, include pervanadate (Maude Tessier and James R. Woodgett, J. Biol. Chem., 281(33):23978-23989 (2006)), insulin (Hui, L., et al., Brain Research, 1052(1):1-9 (2005)), insulin-like growth factor (Kenney, A. M., et al., Development, 131:217-228 (2004) and Datta, S. R., et al., Cell, 91:231-241 (1997)), platelet derived growth factor (Datta, S. R., et al., Cell 91:231-241 (1997)), carbachol (Cui, Q L, et al., Neurochem Int, 48:383-393 (2006)), nicotine (West, K. et al., J. Clinical Investigation, 111:81-90 (2003)), 4-(methylnitrosamino)-1-(3-pyridyl)-1-butanone (NNK) (Id.), adrenomedullin (AM) (Nikitenko, L L et al., British J. Cancer, 94:1-7 (2006)), lysophosphatidic acid, platelet activating factor, macrophage simulating factor, and sphingosine-1-phosphate.

Representative non-limiting examples of Akt modulators, particularly Akt activators, include Ro-31-8220 (Wen, H. et al., Cellular signaling, 15:37-45 (2003)); Nicotine (West, K. et al., J. Clinical Investigation, 111:81-90 (2003)); carbachol (Cui Q L, Fogle E & Almazan G Neurochem Int, 48:383-393 (2006)); 4-(methylnitrosamino)-1-(3-pyridyl)-1-butanone (NNK) (West, K. et al., J. Clinical Investigation, 111:81-90 (2003)); adrenomedullin (AM) (Nikitenko, L L et al, British J. Cancer, 94:1-7 (2006)); lysophosphatidic acid; platelet activating factor, macrophage simulating factor; sphingosine-1-phosphate; cAMP-elevating agents, such as forskolin, chlorophenylthio-cAMP, prostaglandin-E1, and 8-bromo-cAMP (Song et al., J. Cell. Mol. Med., 9(1):59-71 (2005)); and growth factors, including insulin and insulin growth factor-1 (Datta, S. R., et al., Cell, 91:231-241 (1997)), and platelet derived growth factor.

Additional preferred modulators of the present invention include those that target mTOR, RHEB, FoxO, p27, BAD, caspase-9, or p53. Representative non-limiting examples of such modulators include mTOR modulators, particularly mTOR activators, such as phosphatidic acid (PA) (see, e.g., WO/2006/027545; Foster, D. A., Cancer Res, 67(1):1-4 (2007); and Tee et al., J. Biol. Chem. 278:37288-96 (2003)); RHEB modulators, particularly RHEB-GTPase inhibitors, such as RHEB antibodies (see, e.g., WO/2004/048536); FoxO modulators, particularly FoxO inhibitors, such as FKH(DBD), which is a truncated version of FKHRL1 (see, e.g., Gilley, J., et al., J. Cell Biol. 162(4):613-622 (2003)); p27 modulators, particularly p27 inhibitors, such as p27 antisense inhibitors and triplex forming oligonucleotides, protein and peptide antagonists (see, e.g., U.S. Pat. No. 5,958,769); BAD modulators, particularly BAD inhibitors, such as 14-3-3 protein (see, e.g., S. Hsu et al., Molecular Endocrinology 11 (12):1858-1867 (1997)); caspase-9 modulators, particularly caspase-9 inhibitors, such as LB-84451 (LG Life Sciences) and Z-LEHD-FMK Caspase Inhibitor (Thornberry, N. A., and Lazebnik, Y., Science 281:1312-1316 (1998)); and p53 modulators, particularly p53 inhibitors, such as Pifithrin-α and its derivatives (see, e.g., Science, Komarov et al., 285 (5434): 1733-1737 (1999), Pietrancosta et al., Drug Dev Res 65:43-49 (2005)).

In one aspect of the present invention, modulating the PTEN pathway comprises introducing a mutation into a population of stem cells, which mutation results in modulation of a molecule in the PTEN pathway. In the present invention, modulation of the PTEN pathway also includes contacting the stem cells with a modulator of a molecule in the PTEN pathway that leads to β-catenin activation. Representative, non-limiting examples of such modulators include a small molecule, a biologic, an antisense RNA, a small interfering RNA (siRNA), and combinations thereof. This aspect of the invention further includes modulating the Wnt pathway, which comprises introducing a mutation into a population of stem cells that results in modulation of a molecule in the Wnt pathway. In the present invention modulation of the Wnt pathway also includes contacting the stem cells with a modulator of a molecule in the Wnt pathway. Representative, non-limiting examples of such a modulator include a small molecule, a biologic, an antisense RNA, a small interfering RNA (siRNA), and combinations thereof.

As used herein, "introducing a mutation" means any conventional method for producing an alteration in the genetic makeup of the stem cell population. Non-limiting examples for introducing a mutation into a stem cell population include mutagenesis via ultra-violet light irradiation, chemical mutagenesis, targeted mutagenesis such as site directed mutagenesis of a stem cell, and creation of a transgenic mouse.

In the present invention, the phrase "modulation of a molecule in the PTEN pathway" means altering the function of a member of the PTEN pathway, which altered function has an effect similar to inhibiting or decreasing the function of PTEN. Non-limiting examples of such "modulation" include constitutively activating β-catenin, constitutively activating Akt, or loss-of-function or null alleles of PTEN. The phrase "modulation of a molecule in the Wnt pathway" means blocking or decreasing the function of a member of the Wnt pathway, which has an effect similar to blocking or decreasing GSK-3β function. Non-limiting examples of such modulation include constitutively activating β-catenin and loss-of-function or null alleles of GSK-3β.

"Modulators of a molecule in the PTEN pathway" are molecules that cause, directly or indirectly, activation of β-catenin. Non-limiting examples of such molecules include those that activate β-catenin, activate Akt, activate PI3K, or inhibit PTEN. "Modulators of a molecule in the Wnt pathway" are molecules that directly or indirectly block or decrease the function of a member of the Wnt pathway. Non-limiting examples of such molecules include those that activate β-catenin or that inhibit GSK-3β, Axin, or APC.

In another aspect of the present invention, modulating the PTEN and Wnt pathways comprises contacting the stem cell population with a small molecule inhibitor of the PTEN pathway and a small molecule inhibitor of the Wnt pathway. Preferably, modulating the PTEN and Wnt pathways comprises down-regulating PTEN and GSK-3β, respectively. As used herein, "down-regulating" means inhibiting or reducing the amount of or inhibiting or decreasing the activity of PTEN and GSK-3β. Such down-regulation may be accomplished using, e.g. antisense RNA, siRNA, antibodies, or small molecules.

Preferably, down-regulating PTEN and GSK-3β comprises contacting the stem cell population with: (a) a reversible PTEN inhibitor selected from the group consisting of a small molecule, a biologic, an antisense RNA, a small interfering RNA (siRNA), and combinations thereof and (b) a reversible GSK-3β inhibitor selected from the group consisting of a small molecule, a biologic, an antisense RNA, a small interfering RNA (siRNA), and combinations thereof. In the present invention, genetic alteration of both the PTEN and the Wnt pathways leads to an increased ability to self-renew both in vitro as well as in vivo following long-term culture but a failure to differentiate and thus a failure to repopulate the hematopoietic system of transplant recipients. In contrast, use of reversible down-regulators of both pathways, such as, e.g., bpV(pic) and CHIR99021, allows for expansion of functional HSCs, but (1) once the down-regulator is withdrawn, cultured HSCs can differentiate unlike cultured HSCs from genetic mutants, and (2) if such cultured HSC are transplanted, recipient animals do not develop leukemia as genetic mutants do.

Preferably, both the reversible PTEN inhibitor and the reversible GSK-3β inhibitor are small molecules. In one aspect, the reversible PTEN inhibitor is any molecule, such as a small molecule, which is capable of inhibiting PTEN or a down-stream member of the PTEN pathway, which inhibition leads to β-catenin activation. Preferably, the PTEN inhibitor is selected from the group consisting of shikonin, a bisperoxovanadium compound, SF-1751 (Semafore Pharmaceuticals), pharmaceutical salts thereof, and combinations thereof. In this aspect, the bisperoxovanadium compound is selected from the group consisting of bpV(phen)2, bpV(pic), pharmaceutical salts thereof, and combinations thereof.

In the present invention, the reversible GSK-3β inhibitor is any molecule that is capable of reversibly inhibiting GSK-3β. Preferably, such an inhibitor is selected from the group consisting of Hymenialdisine, Flavopiridol, Kenpaullone, Alsterpaullone, Azakenpaullone, Indirubin-30-oxime, 6-Bromoindirubin-30-oxime (BIO), 6-Bromoindirubin-30-acetoxime, Aloisine A, Aloisine B, TDZD8, Compound 12, CHIR98014, CHIR99021 (CT99021), CT20026, Compound 1, SU9516, ARA014418, Staurosporine, Compound 5a, Compound 29, Compound 46, GF109203x (bisindolylmaleimide I), Ro318220 (bisindolylmaleimide IX), SB216763, SB415286, 15, CGP60474, Compound 8b, TWS119, Compound 1A, Compound 17, Lithium, Beryllium, Zinc, small molecule GSK-3β inhibitors (Vertex Pharmaceuticals), NP-12 (Neuropharma), GSK-3β inhibitors (Amphora), GSK-3β inhibitors (CrystalGenomics), SAR-502250 (Sanofi-Aventis), 3544 (Hoffmann-La Roche), GSK-3β inhibitors (Lundbeck), TDZD-8 (Cancer Center, University of Rochester), pharmaceutically acceptable salts thereof, and combinations thereof.

While the PTEN and GSK-3β inhibitors may be contacted with the stem cell population in any convenient manner that achieves the desired level of stem cell expansion, it is preferred that the inhibitors are co-administered. Moreover, multiple GSK-3β and PTEN inhibitors may be contacted with the stem cells. Furthermore, the PTEN and GSK-3β inhibitors may be contacted/administered to the stem cells in concert with other agents suitable for promoting stem cell self renewal. Preferably, the PTEN inhibitor is bpV(pic) and the GSK-3β inhibitor is CHIR99021.

In an additional aspect of the present invention, the number of stem cells is increased by a factor of at least 40-fold. Preferably, the number of stem cells is increased by a factor of at least 80-fold, such as at least 100-fold, including at least 150-fold, at least 200-fold, at least 250-fold, or at least 270-fold. Surprisingly and unexpectedly such levels of stem cell expansion are achieved using the methods of the present invention.

As noted above, the methods of the present invention may be used to expand any population of stem cells. Representative, non-limiting examples of stem cells are as set forth above. Preferably, the stem cells that may be expanded according to the methods of the present invention may selected from hematopoietic stem cells (HSGs), endothelial progenitor cells (EPCs), mesenchymal stem cells (MSCs), cardiac stem cells (CSCs), neuronal stem cells (NSCs), and combinations thereof. More preferably, the stem cells are HSCs.

Another embodiment of the invention is a method for ex vivo expansion of a substantially undifferentiated stem cell population. This method comprises modulating a PTEN pathway and a Wnt pathway in the undifferentiated stem cell population to expand the number of undifferentiated stem cells without significant differentiation of the stem cell population.

A further embodiment of the invention is a method for ex vivo expansion of an hematopoietic stem cell (HSC) population obtained from a tissue selected from the group consisting of peripheral blood, cord blood, and bone marrow. This method comprises modulating a PTEN pathway and a Wnt pathway in the HSC population to expand the HSC population to a sufficient quantity while maintaining a multilineage differentiation potential in the HSC population, which is sufficient for subsequent transplantation into a patient in need thereof.

In this method, "maintaining a multilineage differentiation potential" means that the expanded HSC population has the ability, when transplanted into a patient in need of such a transplant, to regenerate all the types of progenitor cells e.g., CMP, GMP, MEP, and CLP, and ultimately all the types of blood cells including, e.g., red blood cells, B lymphocytes, T lymphocytes, natural killer cells, neutrophils, basophils, eosinophils, monocytes, macrophages, and platelets in the hematopoietic system.

In the present invention, that quantity of expanded HSCs, which is "sufficient for subsequent transplantation" generally corresponds to that number of HSCs, which would result in greater than about 1% engraftment after transplantation. This is one accepted measure of a successful transplant. In the present invention, any conventional method may be used to determine the % engraftment, including the one set forth in the Examples. Such a measure may be carried out with or without competitor cells, typically and preferably, without competitor cells. (Zhang, C. C., et al., *Nat Med,* 12(2): 240-5, 2006. Zhang, C. C. and H. F. Lodish, *Blood,* 105(11): 4314-20, 2005).

In the above described ex vivo expansion methods, modulating the PTEN and Wnt pathways may be achieved as previously set forth. Modulating the PTEN and Wnt pathways may include contacting the stem cell population with a small molecule inhibitor of the PTEN pathway and a small molecule inhibitor of the Wnt pathway. Modulating the PTEN and Wnt pathways may include down-regulating PTEN and GSK-3β, respectively. Preferably, down-regulating the PTEN and Wnt pathways comprises contacting the stem cell population with a reversible PTEN inhibitor and a reversible GSK-3β inhibitor as previously described. Preferably, both the reversible PTEN inhibitor and the reversible GSK-3β inhibitor are small molecules.

The reversible PTEN inhibitor may be selected from the group consisting of shikonin, a bisperoxovanadium compound, SF-1751 (Semafore Pharmaceuticals), pharmaceutical salts thereof, and combinations thereof. Preferably, the bisperoxovanadium compound is selected from the group consisting of bpV(phen)2, bpV(pic), pharmaceutical salts thereof, and combinations thereof.

The reversible GSK-3β inhibitor may be selected from the group consisting of Hymenialdisine, Flavopiridol, Kenpaullone, Alsterpaullone, Azakenpaullone, Indirubin-30-oxime, 6-Bromoindirubin-30-oxime (BIO), 6-Bromoindirubin-30-acetoxime, Aloisine A, Aloisine B, TDZD8, Compound 12, CHIR98014, CHIR99021 (CT99021), CT20026, Compound 1, SU9516, ARA014418, Staurosporine, Compound 5a, Compound 29, Compound 46, GF109203x (bisindolylmaleimide I), Ro318220 (bisindolylmaleimide IX), SB216763, SB415286, 15, CGP60474, Compound 8b, TWS119, Compound 1A, Compound 17, Lithium, Beryllium, Zinc, small molecule GSK-3β inhibitors (Vertex Pharmaceuticals), NP-12 (Neuropharma), GSK-3β inhibitors (Amphora), GSK-3β inhibitors (CrystalGenomics), SAR-502250 (Sanofi-Aventis), 3544 (Hoffmann-La Roche), GSK-3β inhibitors (Lundbeck), TDZD-8 (Cancer Center, University of Rochester), pharmaceutically acceptable salts thereof, and combinations thereof.

In these ex vivo expansion methods, preferably, the PTEN inhibitor is bpV(pic), and the GSK-3β inhibitor is CHIR99021. In these methods, it is preferred that the stem cell is selected from HSCs, endothelial progenitor cells, (EPCs), mesenchymal stem cells (MSCs), cardiac stem cells (CSCs), neuronal stem cells (NSCs), and combinations thereof. Preferably the stem cell is an HSC. In these methods, the HSC is obtained from a mammalian, e.g., primate or human, tissue selected from the group consisting of cord blood, peripheral blood, and bone marrow.

In another aspect of the method for ex vivo expansion of an hematopoietic stem cell (HSC) population, the expansion of the number of stem cells is by at least 40-fold, such as e.g., by at least 80-fold, including at least 100-fold, at least 150-fold, at least 200-fold, at least 250-fold, or at least 270-fold.

Yet another embodiment of the present invention is an expanded, substantially undifferentiated stem cell population made by a method of the present invention, such as, e.g., the method for ex vivo expansion of a substantially undifferentiated stem cell population or the method for ex vivo expansion of an hematopoietic stem cell (HSC) population.

An additional embodiment of the present invention is a method for ex vivo expansion of hematopoietic stem cells (HSCs) by at least 40-fold, wherein the expanded HSCs, are competent to reconstitute an HSC lineage upon transplantation into a mammalian patient in need thereof. This method comprises culturing a population of HSCs in a suitable culture medium comprising a PTEN inhibitor and a GSK-3β inhibitor.

In this aspect of the invention, "competent to reconstitute an HSC lineage" means that the expanded HSCs, when transplanted into a suitable mammalian patient, result in greater than 1% engraftment in the recipient, which engrafted cells are able to differentiate into the cell lineages necessary to have a normal functioning hematopoietic system. In this method, a "suitable culture medium", "fluid media" and "media" which are used interchangeably herein, mean physiologically balanced salt solutions that can maintain a stem cell population for a required period of time, which solution may be supplemented with the PTEN and GSK-3β modulator/inhibitors of the present invention. Such base culture media are well known in the arts. A non-limiting example of a suitable base culture medium for HSCs is StemSpan Media (Stem Cell Technologies; Cat. No. 09600), which is supplemented with 10 ug/ml Heparin, 0.5× Penicillin/Streptomycin, 10 ng/ml recombinant mouse (rm) Stem Cell Factor, and 20 ng/ml rm-Thrombopoietin.

Typically, the culture media also includes from about 100 to about 1000 nM of the PTEN inhibitor. The culture media may further include from about 50 nM to about 500 nM of the GSK-3β inhibitor. In the present invention, when a range is recited, any value within that range, including the endpoints, is contemplated. Preferably, the culture media includes both the PTEN and the GSK-3β inhibitors at the concentrations indicated. For example, the media may contain as the PTEN inhibitor, bpV(pic), and as the GSK-3β inhibitor, CHIR99021.

In one aspect of this embodiment, the HSCs are obtained from a mammalian tissue, preferably primate or human tissue, which is selected from cord blood, peripheral blood, and bone marrow. In this embodiment, the number of HSCs is expanded by a factor of at least 80-fold, such as at least 100-fold, including at least 150-fold, at least 200-fold, at least 250-fold, or at least 270-fold.

Yet another embodiment of the present invention is a kit for expanding an hematopoietic stem cell (HSC) population for subsequent transplantation into a patient in need thereof. The kit comprises a PTEN inhibitor and a GSK-3β inhibitor as described above and instructions for the use of the inhibitors. Preferably, in the kit, the PTEN inhibitor is bpV(pic) and the GSK-3β inhibitor is CHIR99021. The kit and the components therein may be packaged in any suitable manner for distribution and/or storage.

A further embodiment of the present invention is a media for carrying out ex vivo expansion of a stem cell population. The media comprises a fluid media suitable for maintaining viable stem cells and PTEN and GSK-3β inhibitors present in the media at concentrations sufficient to enable expansion of the stem cell population while maintaining a multilineage differentiation potential in the stem cells.

In this embodiment, a "concentration sufficient to enable expansion" means the minimum concentration of the PTEN and GSK-3β inhibitors, which are sufficient to achieve the desired level of stem cell renewal, e.g., expansion sufficient for successful engraftment.

In one aspect of this embodiment, expansion of the number of stem cells is by a factor selected from the group consisting of at least 40-fold, at least 80-fold, at least 100-fold, at least 150-fold, at least 200-fold, at least 250-fold, or at least 270-fold.

A further embodiment of the present invention is a method for administering an hematopoietic stem cell (HSC) to a patient in need thereof. The method comprises (a) culturing, in a suitable culture media, a sample containing an HSC population in the presence of a modulator of a molecule in the PTEN pathway and a modulator of a molecule in the Wnt pathway for a period of time sufficient to expand the number of HSCs in the sample to a number sufficient to transplant into the patient; (b) removing from the culture the PTEN and Wnt pathway modulators; and (c) administering the HSCs to the patient. In this embodiment, the culture media, sample, and PTEN and GSK-3β modulators are previously described.

An additional embodiment of the present invention is a method for reconstituting bone marrow in a patient in need thereof. The method comprises culturing, in a suitable culture media, a sample containing an HSC population in the presence of a modulator of a molecule in the PTEN pathway and a modulator of a molecule in the Wnt pathway for a period of time sufficient to expand the number of HSCs in the sample to a number that is sufficient to transplant into the patient. Next, the PTEN and Wnt pathway modulators are removed from the culture. Then, the expanded HSCs are administered to the patient in any conventional manner.

In this method, "reconstituting bone marrow" means restoration of all or a portion of the bone marrow in a patient suffering from a disease in which normal bone marrow function has been compromised. Non-limiting examples of such diseases include aplastic anemia, myelodysplastic syndromes (MDS), paroxysmal nocturnal hemoglobinuria (PNH), and blood cancers, such as leukemia. Thus, as used herein, "reconstituted" means that the transplanted HSCs are able to successfully engraft in the host and differentiate into all the cell lineages typically found in or derived from bone marrow.

In this method, "a period of time sufficient to expand the number of HSCs" means the minimum amount of time to expand the HSCs in culture to a point where there is a sufficient number of HSCs for one or more transplantations. Typically, such a period of time may be at least about 10 days in culture. Under certain circumstances, it may be desirable to expand the stem cell, e.g., HSC, population beyond what is required for a single transplantation. For example, it may be desirable to expand the stem cell, e.g., HSC, population to a number sufficient for multiple transplantations, such as e.g., from about 2 to about 100 transplantations. In these circumstances, the excess cells may be preserved for later use by any conventional method, such as e.g., by cryo-preservation.

As indicated previously, "a number sufficient to transplant" means the minimum number of stem cells, e.g., HSCs, necessary to achieve greater than 1% engraftment in a recipient. "Administering the HSCs to the patient" means conventional methods for delivering HSCs to the patient, including but not limited to, delivering the HSCs surgically and/or intravenously. In this embodiment, the tissue the HSCs are obtained from, and the PTEN and GSK-3β inhibitors are as previously described.

An additional embodiment of the present invention is a method for expanding a population of hematopoietic stem cells (HSCs). This method comprises culturing a population of HSCs under conditions sufficient to result in an expansion of the HSC population by at least 40-fold, wherein the expanded population of HSCs is suitable for transplantation into a mammal in need thereof. In this embodiment the "conditions sufficient to result in an expansion of the HSC population" are those conditions that can result in expansion of HSCs in culture by, e.g., at least 40-fold, such as, e.g., by at least 80-fold, at least 150-fold, at least 200-fold, at least 250-fold, or at least 270-fold. "Suitable for transplantation into a mammal" means that the number and quality of HSCs is sufficient to support greater than 1% engraftment in a mammalian recipient, such as, e.g., a primate recipient, including an human recipient, in need thereof.

Yet another embodiment of the present invention is a method for treating a patient in need of a bone marrow transplant, a peripheral blood transplant, or a cord blood transplant comprising administering to the patient a population of HSCs obtained by a method disclosed herein, particularly the methods for expanding a population of hematopoietic stem cells (HSGs).

A further embodiment of the present invention is a method for expanding a population of hematopoietic stem cells (HSGs). The method comprises (a) obtaining from a mammal a tissue sample comprising an HSC population; (b) expanding, in vitro, the HSC population from the sample, wherein (i) the HSC population expands by at least 40-fold; and (ii) the expanded HSC population has the ability to reconstitute an hematopoietic lineage for at least 4-weeks, such as for example at least 8-weeks, after transplantation into a recipient. In this embodiment the "ability to reconstitute an hematopoietic lineage" means that the expanded HSC population when transplanted into a recipient will result in greater than 1% engraftment of HSC in a recipient. In one aspect of this embodiment, the HSC population expands by at least 80-fold, such as e.g., at least 100-fold, including at least 150-fold, at least 200-fold, at least 250-fold, or at least 270-fold. In another aspect of this embodiment, the mammal is a primate, including a human. Preferably, the human requires a peripheral blood transplant, a cord blood transplant, or a bone marrow transplant. In a further aspect, the tissue sample is obtained from a tissue selected from the group consisting of cord blood, peripheral blood, and bone marrow.

An additional embodiment of the present invention is a method for reconstituting an hematopoietic stem cell lineage in a recipient in need thereof. The method comprises (a) obtaining from a mammal a tissue sample comprising an HSC population; (b) expanding, in vitro, the HSC population from the sample, wherein: (i) the HSC population expands by at least 40-fold, such as for example, by at least 80-fold, including at least 100-fold, at least 150-fold, at least 200-fold, at least 250-fold, or at least 270-fold, and (ii) the expanded HSC population has the ability to reconstitute an hematopoietic lineage for at least 4-weeks, for example, at least 8-weeks, after transplantation into a recipient in need thereof; and (c) transplanting the expanded HSC population into a recipient such as a mammal, including a primate or human, in need thereof.

In this embodiment, "reconstituting an hematopoietic stem cell lineage" means that the expanded HSCs, when transplanted into a recipient result in greater than 1% engraftment of hematopoietic cells, which are able to differentiate into the normal hematopoietic lineages. In this embodiment, the human recipient requires a peripheral blood transplant, a cord blood transplant or a bone marrow transplant. Thus, in a further aspect, the tissue sample is obtained from a tissue selected from the group consisting of cord blood, peripheral blood, and bone marrow. The sample may be obtained from an autologous or allogeneic source. Preferably, the sample is obtained from an autologous source.

In the present invention, it is preferred that the expanded HSC population comprises HSCs that have a phenotype selected from the group consisting of CD34$^-$ or CD34$^+$/CD38$^{-/low}$/Thy-1$^+$/CD90$^+$/Kit$^{-/lo}$/Lin$^-$/CD133$^+$VEGFR2$^+$, which are markers for the most primitive and long-term undifferentiated human HSCs; CD150$^+$/CD48$^-$/CD244$^-$, which is a marker for human HSCs and their progenitors; and/or CD150$^-$/CD48$^-$/CD244$^+$ and CD150$^-$/CD48$^+$/CD244$^+$, which are markers for non-self-renewing multipotent hematopoietic progenitors, and combinations thereof. (See, e.g., Mimeault, M., et al., Stem Cells: A Revolution in Therapeutics—Recent Advances in Stem Cell Biology and Their Therapeutic Applications in Regenerative Medicine and Cancer Therapies. Clin Pharmacol Ther., 82(3):252-64 (2007)).

The exact proportions of HSCs having these markers in the population is not critical, so long as the expanded HSC population as a whole is sufficient to result in at least 1% engraftment in a recipient.

In another embodiment, the invention is a method for expanding a hematopoietic stem cell population in a mammal in need of such expansion. This method comprises administering to the mammal a therapeutically effective amount of a modulator of Wnt and Akt for a period of time sufficient to expand the HSC population by at least 40-fold with HSCs that possess the ability to reconstitute an hematopoietic lineage in the mammal.

In this method, the respective modulators of Wnt and Akt may be any molecule, such as a small molecule, a biologic, an antisense RNA, a siRNA, or combinations thereof, which acts directly or indirectly to activate β-catenin. Preferably, the Wnt modulator is selected from a Wnt polypeptide, QS11 (Zhang, Q. et al., PNAS, 104(18):7444-8 (2007)), 2-amino-4-[3,4-(methylenedioxy)benzyl-amino]-6-(3-methoxyphenyl)pyrimidine (Liu, J. et al., Angew Chem Int Ed Engl. 44(13):1987-90 (2005)), deoxycholic acid (R. Pai et al., Mol Biol Cell. 15(5):2156-63 (2004)), and combinations thereof. Preferably, the modulator of Akt is selected from the group consisting of Ro-31-8220 (Wen, H. et al., Cellular signaling, 15:37-45 (2003)); Nicotine (West, K. et al., J. Clinical Investigation, 111:81-90 (2003)); carbachol (Cui Q L, Fogle E & Almazan G Neurochem Int, 48:383-393 (2006)); 4-(methylnitrosamino)-1-(3-pyridyl)-1-butanone (NNK) (West, K. et al., J. Clinical Investigation, 111:81-90 (2003)); adrenomedullin (AM) (Nikitenko, L L et al, British J. Cancer, 94:1-7 (2006)); lysophosphatidic acid; platelet activating factor, macrophage simulating factor; sphingosine-1-phosphate; cAMP-elevating agents, such as forskolin, chlorophenylthio-cAMP, prostaglandin-E1, and 8-bromo-cAMP (Song et al., J. Cell. Mol. Med., 9(1):59-71 (2005)); and growth factors, including insulin and insulin growth factor-1 (Datta, S. R., et al., Cell, 91:231-241 (1997)), platelet derived growth factor, and combinations thereof.

In this method, the Wnt and Akt modulators may be administered using any regimen that effectively expands the HSC population by at least 40-fold with HSCs that possess the ability to reconstitute an hematopoietic lineage in the mammal. Preferably, the Wnt and Akt modulators are co-administered.

In the present invention, a "therapeutically effective amount" is an amount sufficient to effect beneficial or desired results. In terms of treatment of a mammal, a "therapeutically effective amount" of a modulator is an amount sufficient to treat, manage, palliate, ameliorate, or stabilize a condition, such as a bone marrow disease, in the mammal. A therapeutically effective amount can be administered in one or more doses.

The therapeutically effective amount is generally determined by a physician on a case-by-case basis and is within the skill of one in the art. Several factors are typically taken into account when determining an appropriate dosage. These factors include age, sex and weight of the patient, the condition being treated, the severity of the condition and the form of the drug being administered.

Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of animal, and like factors well known in the arts of medicine and veterinary medicine. In general, a suitable dose of a modulator according to the invention will be that amount of the modulator, which is the lowest dose effective to produce the desired effect. The effective dose of a modulator maybe administered as two, three, four, five, six or more sub-doses, administered separately at appropriate intervals throughout the day.

A modulator, particularly a Wnt or Akt modulator of the present invention, may be administered in any desired and effective manner: as pharmaceutical compositions for oral ingestion, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a modulator, particularly a Wnt or Akt modulator, of the present invention may be administered in conjunction with other treatments. A modulator, particularly a Wnt or Akt modulator, of the present invention maybe encapsulated or otherwise protected against gastric or other secretions, if desired.

While it is possible for a modulator, particularly a Wnt or Akt modulator, of the invention to be administered alone, it is preferable to administer the modulator as a pharmaceutical formulation (composition). Such pharmaceutical formulations typically comprise one or more modulators as an active ingredient in admixture with one or more pharmaceutically-acceptable carriers and, optionally, one or more other compounds, drugs, ingredients and/or materials. Regardless of the route of administration selected, the modulator, particularly a Wnt or Akt modulator, of the present invention is formulated into pharmaceutically-acceptable dosage forms by conventional methods known to those of skill in the art. See, e.g., Remington's Pharmaceutical Sciences (Mack Publishing Co., Easton, Pa.).

Pharmaceutically acceptable carriers are well known in the art (see, e.g., Remington's Pharmaceutical Sciences (Mack Publishing Co., Easton, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition comprising a modulator of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

Pharmaceutical compositions comprising a modulator of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions for rectal or vaginal administration may be presented as a suppository, which maybe prepared by mixing one or more active ingredient(s) with one or more suitable nonirritating carriers which are solid at room temperature, but liquid at body temperature and, therefore, will melt in the rectum or vaginal cavity and release the active compound. Pharmaceutical compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active compound may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more modulator in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug containing a modulator of the present invention, it is desirable to slow its absorption from subcutaneous or intramuscular injection. This may be accomplished by the use of a liquid suspension of crystalline or amorphous material having poor water solubility.

The rate of absorption of the drug then depends upon its rate of dissolution which, in turn, may depend upon crystal size and crystalline form. Alternatively, delayed absorption of a parenterally-administered drug may be accomplished by dissolving or suspending the drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Additional Definitions

In the present invention, the term "small molecule" includes any chemical or other moiety, other than polypeptides and nucleic acids, that can act to affect biological processes, particularly to modulate members of the DNMT, Wnt, and PTEN pathways. Small molecules can include any number of therapeutic agents presently known and used, or that can be synthesized in a library of such molecules for the purpose of screening for biological function(s). Small molecules are distinguished from macromolecules by size. The small molecules of the present invention usually have a molecular weight less than about 5,000 daltons (Da), preferably less than about 2,500 Da, more preferably less than 1,000 Da, most preferably less than about 500 Da.

Small molecules include without limitation organic compounds, peptidomimetics and conjugates thereof. As used herein, the term "organic compound" refers to any carbon-based compound other than macromolecules such as nucleic acids and polypeptides. In addition to carbon, organic compounds may contain calcium, chlorine, fluorine, copper, hydrogen, iron, potassium, nitrogen, oxygen, sulfur and other elements. An organic compound may be in an aromatic or aliphatic form. Non-limiting examples of organic compounds include acetones, alcohols, anilines, carbohydrates, monosaccharides, oligosaccharides, polysaccharides, amino acids, nucleosides, nucleoside analogs, nucleotides, lipids, retinoids, steroids, proteoglycans, ketones, aldehydes, saturated, unsaturated and polyunsaturated fats, oils and waxes, alkenes, esters, ethers, thiols, sulfides, cyclic compounds, heterocyclic compounds, imidizoles, and phenols. An organic compound as used herein also includes nitrated organic compounds and halogenated (e.g., chlorinated) organic compounds.

Preferred small molecules are relatively easier and less expensively manufactured, formulated or otherwise prepared. Preferred small molecules are stable under a variety of storage conditions. Preferred small molecules may be placed in tight association with macromolecules to form molecules that are biologically active and that have improved pharmaceutical properties. Improved pharmaceutical properties include changes in circulation time, distribution, metabolism, modification, excretion, secretion, elimination, and stability that are favorable to the desired biological activity. Improved pharmaceutical properties include changes in the toxicological and efficacy characteristics of the chemical entity.

As used herein, the term "biologic" means products derived from living sources as opposed to a chemical process. Non-limiting examples of a "biologic" include proteins, conditioned media, and partially purified products from tissues.

The terms "peptide," "polypeptide," and "protein" are used interchangeably herein. In the present invention, these terms mean a linked sequence of amino acids, which may be natural, synthetic, or a modification or combination of natural and synthetic. The term includes antibodies, antibody mimetics, domain antibodies, lipocalins, targeted proteases, and polypeptide mimetics. The term also includes vaccines containing a peptide or peptide fragment intended to raise antibodies against the peptide or peptide fragment.

"Antibody" as used herein includes an antibody of classes IgG, IgM, IgA, IgD, or IgE, or fragments or derivatives thereof, including Fab, F(ab')$_2$, Fd, and single chain antibodies, diabodies, bispecific antibodies, and bifunctional antibodies. The antibody may be a monoclonal antibody, polyclonal antibody, affinity purified antibody, or mixtures thereof, which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety. The antibody may be a human or humanized antibody. These and other antibodies are disclosed in U.S. Published Patent Application No. 20070065447.

Other antibody-like molecules are also within the scope of the present invention. Such antibody-like molecules include, e.g., receptor traps (such as entanercept), antibody mimetics (such as adnectins, fibronectin based "addressable" therapeutic binding molecules from, e.g., Compound Therapeutics, Inc.), domain antibodies (the smallest functional fragment of a naturally occurring single-domain antibody (such as, e.g., nanobodies; see, e.g., Cortez-Retamozo et al., Cancer Res. 2004 Apr. 15; 64(8):2853-7)).

Suitable antibody mimetics generally can be used as surrogates for the antibodies and antibody fragments described herein. Such antibody mimetics may be associated with advantageous properties (e.g., they may be water soluble, resistant to proteolysis, and/or be nonimmunogenic). For example, peptides comprising a synthetic beta-loop structure that mimics the second complementarity-determining region (CDR) of monoclonal antibodies have been proposed and generated. See, e.g., Saragovi et al., Science. Aug. 16, 1991; 253(5021):792-5. Peptide antibody mimetics also have been generated by use of peptide mapping to determine "active" antigen recognition residues, molecular modeling, and a molecular dynamics trajectory analysis, so as to design a peptide mimic containing antigen contact residues from multiple CDRs. See, e.g., Cassett et al., Biochem Biophys Res Commun. Jul. 18, 2003; 307(1): 198-205. Additional discussion of related principles, methods, etc., that may be applicable in the context of this invention are provided in, e.g., Fassina, Immunomethods. October 1994; 5(2):121-9.

Targeted proteases are polypeptides which are capable of, e.g., substrate-targeted inhibition of post-translational modification such as disclosed in, e.g., U.S. Patent Application Publication No. 20060275823.

In general, a polypeptide mimetic ("peptidomimetic") is a molecule that mimics the biological activity of a polypeptide, but that is not peptidic in chemical nature. While, in certain embodiments, a peptidomimetic is a molecule that contains no peptide bonds (that is, amide bonds between amino acids), the term peptidomimetic may include molecules that are not completely peptidic in character, such as pseudo-peptides, semi-peptides, and peptoids.

"Antisense" molecules as used herein include antisense or sense oligonucleotides comprising a single-stranded nucleic acid sequence (either RNA or DNA) capable of binding to target mRNA (sense) or DNA (antisense) sequences. The ability to derive an antisense or a sense oligonucleotide, based upon a cDNA sequence encoding a given protein is described in, for example, Stein and Cohen, Cancer Res. 48:2659, (1988) and van der Krol et al., BioTechniques 6:958, (1988).

Antisense molecules can be modified or unmodified RNA, DNA, or mixed polymer oligonucleotides. These molecules function by specifically binding to matching sequences resulting in inhibition of peptide synthesis (Wu-Pong, November 1994, BioPharm, 20-33) either by steric blocking or by activating an RNase H enzyme. Antisense molecules can also alter protein synthesis by interfering with RNA processing or transport from the nucleus into the cytoplasm (Mukhopadhyay & Roth, 1996, Crit. Rev. in Oncogenesis 7, 151-190). In addition, binding of single stranded DNA to RNA can result in nuclease-mediated degradation of the heteroduplex (Wu-Pong, supra). Backbone modified DNA chemistry, which have thus far been shown to act as substrates for RNase H are phosphorothioates, phosphorodithioates, borontrifluoridates, and 2'-arabino and 2'-fluoro arabino-containing oligonucleotides.

Antisense molecules may be introduced into a cell containing the target nucleotide sequence by formation of a conjugate with a ligand binding molecule, as described, e.g., in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described, e.g., in WO 90/10448.

The term small interfering RNA ("siRNA") refers to small inhibitory RNA duplexes that induce the RNA interference (RNAi) pathway. (Elbashir, S. M. et al. Nature 411:494-498 (2001); Caplen, N. J. et al. Proc. Natl. Acad. Sci. USA 98:9742-9747 (2001); Harborth, J. et al. J Cell Sci. 114: 4557-4565 (2001).) These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region. As used herein, siRNA molecules are not limited to RNA molecules but further encompass chemically modified nucleotides and non-nucleotides. siRNA gene-targeting may be carried out by transient siRNA transfer into cells, achieved by such classic methods as lipid-mediated transfection (such as encapsulation in liposome, complexing with cationic lipids, cholesterol, and/or condensing polymers, electroporation, or microinjection). siRNA gene-targeting may also be carried out by administration of siRNA conjugated with antibodies or siRNA complexed with a fusion protein comprising a cell-penetrating peptide conjugated to a double-stranded (ds) RNA-binding domain (DRBD) that binds to the siRNA (see, e.g., U.S. Patent Application Publication No. 2009/0093026).

The following examples are provided to further illustrate the methods and compositions of the present invention. These examples are illustrative only and are not intended to limit the scope of the invention in any way.

EXAMPLES

Example 1

Loss of PTEN with Constitutively Active β-Catenin Leads to HSC Expansion with Loss of Early Hematopoietic Progenitors Animals All mice used in this study were housed in the animal facility at Stowers Institute for Medical Research (SIMR) and handled according to Institute and NIH guidelines. All procedures were approved by the IACUC of SIMR. Pten/constitutively active β-catenin double mutant mice were induced by intra-peritoneal injection of Tamoxifen (Sigma, Cat. No. T5648) everyday for 5 days using 5 mg on day 1 and 2 mg on days 2-5 each dissolved in 0.1 ml of corn oil (Sigma, Cat. No. C8267) (complete dissolution was achieved by 42° C. water bath sonication for about 5 minutes). Mx-1 Cre induction was achieved by 250 μg injection of polyI:C every other day utilizing 1 dose (for the Mx-1 Cre Pten:β-cat$^{Act}$ model) or 5 doses (for the Mx1-Cre Pten:β-cat$^{-/-}$ transplant model). Scl-Cre, Pten, β-cat$^{Act}$, and β-cat$^{-/-}$ mice were obtained from Joachim Goethert (University of Duisburg-Essen, Germany), Hong Wu (UCLA, Los Angeles, Calif.), Makoto Taketo (Kyoto University, Japan) and the Jackson Laboratory (Bar Harbor, Me.), respectively.

Histology

Paraffin sections of spleen, tumors or decalcified femurs were stained with H&E or Masson's Trichrome as indicated.

Immunofluorescent Assays

GFP$^+$ HSCs were sorted and transplanted as previously reported (Xie, Y. et al. Detection of functional haematopoietic stem cell niche using real-time imaging. Nature 457, 97-101 (2009)). Femurs and tibias were fixed in 4% PFA or Zn$^{2+}$-Formalin and processed for paraffin and frozen sections, respectively. For immunofluorescent staining, after antigen retrieval using EZ Retriever Microwave (BioGenex, San Ramon, Calif.) for 10 minutes at 95° C. in citrate buffer, non-specific antibody binding was blocked by incubating slides with 1× Universal Block (BioGenex, # HK085-5k) at room temperature for 1 hour. pβ-cat-S552 was stained as previously reported (He, X. C. et al. PTEN-deficient intestinal stem cells initiate intestinal polyposis. Nat Genet 39, 189-198 (2007)).

Induction of PTEN/Constitutively Active β-Catenin Double Mutant Mice

The inventors have previously demonstrated that PTEN deficiency leads to excessive intestinal stem cell (ISC) proliferation resulting in intestinal polyposis, a pre-cancerous neoplasia (He, X. C. et al. PTEN-deficient intestinal stem cells initiate intestinal polyposis. Nat Genet 39, 189-198 (2007)). Akt has been shown to phosphorylate β-catenin at serine residue 552 (S552), with the resulting phosphorylated form of β-catenin being nuclear localized in ISCs. An antibody highly-specific for β-catenin phosphorylated at S552 (β-cat-pS552) reveals that cells with nuclear (activated) β-cat-pS552 initiate ISC expansion, resulting in polyposis in PTEN-deficient mice. Staining with β-cat-pS552 antibody shows simultaneous activation of the two pathways. Considering its role in ISCs, it was hypothesized that β-cat-pS552 antibody may also recognize activated HSCs. To investigate this, purified HSCs which express green fluorescent protein (GFP$^+$ HSCs) was transplanted into irradiated and non-irradiated mice. The recipients were sacrificed, and their bone sections were stained with anti- β-cat-pS552 antibody. With irradiation, a condition previously shown to result in rapid HSC expansion (Xie, Y. et al. Detection of functional haematopoietic stem cell niche using real-time imaging. *Nature* 457, 97-101 (2009)), purified GFP$^+$-HSCs were observed to be adjacent to their endosteal niche with 5 of 40 GFP$^+$ HSCs costaining as β-cat-pS552$^+$ cells, some of which were in the process of active division (FIGS. 8A-D). However, without irradiation, a condition where HSCs do not expand (Id.), 0 of 15 GFP$^+$ HSCs were found to be β-cat-pS552$^+$ (data not shown). β-cat-pS552 antibody were also used to visualize Wnt/β-catenin and PTEN/Akt signaling pathway interaction in control, single, and double mutant spleen. At 3 days post-induction (dpi), control and single mutant spleens showed only rare and lightly stained cells, while double mutants exhibited more intense and abundant β-cat-pS552 staining (FIG. 14). These results support the importance of activated Akt and β-catenin interaction in normal but proliferating HSCs and show that this pathway interaction is enhanced in double mutants compared to single mutants or control.

The consequences of combining both conditional Pten deletion with constitutive activation of β-catenin (β-cat$^{Act}$) (Ctnnb1$^{tm1Mmt}$) (Harada, N. et al. Intestinal polyposis in mice with a dominant stable mutation of the beta-catenin gene. *The EMBO journal* 18, 5931-5942 (1999)) was studied using Mx1-Cre. This interferon-inducible system results in tissue non-specific knockout of LoxP-flanked (foxed) alleles and has been used in previous studies focusing on either Pten or β-cat$^{Act}$ single mutants (Kirstetter, P., Anderson, K., Porse, B. T., Jacobsen, S. E. & Nerlov, C. Activation of the canonical Wnt pathway leads to loss of hematopoietic stem cell repopulation and multilineage differentiation block. *Nat Immunol* 7, 1048-1056 (2006); Scheller, M. et al. Hematopoietic stem cell and multilineage defects generated by constitutive [beta]-catenin activation. *Nature Immunology* 7, 1037-1047 (2006); Yilmaz, O. H. et al. Pten dependence distinguishes haematopoietic stem cells from leukaemia-initiating cells. *Nature* 441, 475-482 (2006); Zhang, J. et al. PTEN maintains haematopoietic stem cells and acts in lineage choice and leukaemia prevention. *Nature* 441, 518-522 (2006)). Mx1-Cre$^+$ Pten:β-cat$^{Act}$ double mutants exhibit severe tumors consisting of well-formed but densely packed hair follicles which rapidly cover the body (FIG. 15), suggesting a stem cell proliferation defect (Gray, H. R. & Helwig, E. B. Trichofolliculoma. *Arch Dermatol*. 86, 99-105 (1962)).

Because this severe tumor phenotype made it impossible to complete long-term studies of the hematopoietic system in these double mutants using Mx1-Cre, Pten and β-cat$^{Act}$ (Ctnnb1$^{fl/fl}$) single and double mutants were crossed with the tamoxifen-inducible HSC-SCL-Cre-ER$^T$ strain (hereafter referred to as Scl-Cre), which allowed for studying the effects in the hematopoietic system, in particular those effects which initiate primarily from HSCs (Gothert, J. R., et al., "In vivo fate-tracing studies using the Scl stem cell enhancer: embryonic hematopoietic stem cells significantly contribute to adult hematopoiesis." *Blood*, 2005. 105(7): p. 2724-2732). The cross is set forth in more detail below.

Mice with homozygous floxed (fl) alleles of Pten (Pten$^{fl/fl}$) were bred with Ctnnb1$^{fl/fl}$ mice in which exon 3 of the mouse β-catenin gene (where all phosphorylation target serine/threonine residues are located) was sandwiched by two loxP sequences. (Harada, N., et al., *Embo J*, 18(21): 5931-42 1999. Yilmaz, O. H., et al., *Nature*, 441:475-82 2006. Zhang, J., et al., *Nature*, 441(7092): 518-22 2006.) Double heterozygous mice from this cross were then crossed to generate Pten$^{fl/fl}$ Ctnnb1$^{fl/+}$ mice (since Ctnnb1 is a gain-of-function allele, only heterozygous mice for Ctnnb1 are necessary). Concurrently, Pten$^{fl/fl}$ mice were bred with Scl-Cre$^+$ transgenic mice to generate Scl-Cre$^+$ Pten$^{fl/+}$ mice. These were then crossed to generate Scl-Cre$^+$ Pten$^{fl/fl}$ mice ("Pten"). Finally, Pten$^{fl/fl}$ Ctnnb1$^{fl/+}$ mice were bred with Scl-Cre$^+$ Pten$^{fl/fl}$ mice to generate Scl-Cre$^+$ Pten$^{fl/fl}$ Ctnnb1$^{fl/+}$ mice ("Pten:Ctnnb1"). Scl-Cre mice were also bred with Ctnnb1$^{fl/fl}$ mice to generate the single mutant Scl-Cre$^+$ Ctnnb1$^{fl/+}$ mice ("Ctnnb1"). Mice lacking Scl-Cre ("Scl-Cre negative" or "Control") were used as controls.

HSC Analysis

For phenotype analysis, hematopoietic cells were harvested from bone marrow (femur and tibia), spleen, peripheral blood, and thymus. Red blood cell lysis was performed using hemolysis buffer (0.16M ammonium chloride, Sigma Cat. No. A9434). Cells were stained for lineage markers using CD3, CD4, CD8, B220, IgM, Mac-1, Gr1, and Ter119 antibodies along with Kit, and Sca-1 for LSK analysis or these markers along with IL-7Rα, CD34 and CD16/32 for progenitor analysis (Akashi, K., et al., *A clonogenic common myeloid progenitor that gives rise to all myeloid lineages*. Nature 2000. 404(6774): p. 193-7). Flk2 was added as indicated for LT-HSC analysis.

Unless otherwise indicated, all antibodies were obtained from eBiosciences (San Diego, Calif.) as indicated below: Fluorescein isothiocyanate (FITC) conjugated CD3 antibody (Cat. No. 11-0452-85), FITC conjugated CD4 antibody (Cat. No. 11-0042-85), FITC conjugated CD8 antibody (Cat. No. 11-0081-85), FITC conjugated B220 antibody (Cat. No. 11-0452-85), FITC conjugated Ter119 antibody (Cat. No. 11-5921-85), FITC conjugated Mac-1 antibody (Cat. No. 11-0112-85), FITC conjugated Gr1 antibody (Cat. No. 11-5931-85), FITC conjugated IgM antibody (Cat. No. 11-5790-85), Phycoerythrin (PE) conjugated Sca-1 antibody (Cat. No. 12-5981-83), Allophycocyanin (APC) conjugated Kit antibody (Cat. No. 17-1171-83), Biotin conjugated CD135 (Flk-2) antibody (Cat. No. 13-1351-85), PE-Cy5 conjugated CD127 (IL-7Rα) antibody (Cat. No. 15-1271-83), PE-Cy7 conjugated CD16/32 (FcγRII/III) antibody (Cat. No. 25-0161-82), Biotin conjugated CD34 antibody (Cat. No. 13-0341-85), Streptavidin conjugated PE-Cy7 antibody (Cat. No. 25-4317-82), Streptavidin conjugated APC-Cy7 antibody (Cat. No. 10-4317-82), APC conjugated Gr1 antibody (Cat. No. 17-5931-82), APC conjugated B220 antibody (Cat. No. 17-0452-83), PE conjugated Mac-1 antibody (Cat. No. 12-0112-83), and PE conjugated CD3 antibody (Cat. No. 12-0031-85).

Antibody stained cells were sorted by FACS using a MoFlo (Dako, Ft. Collins, Colo.) flow cytometer and/or a CyAn ADP (Dako, Ft. Collins, Colo.), and analyzed for lineage negative, Sca-1$^+$Kit$^+$ (LSK) cells in Scl-Cre negative control and Scl-Cre$^+$ PTEN with constitutively activated β-catenin (Pten:Ctnnb1; also referred to as Pten:β-cat$^{Act}$) double mutant bone marrow and spleen. Data analysis was performed using FlowJo software (Ashland, Oreg.).

In order to study the consequences of Pten deletion combined with β-catenin activation on stem cells in vivo, HSCs and early progenitors were analyzed from single and double mutants bred onto the Scl-Cre line. At 10 days post-induction (dpi), Pten:Ctnnb1 (hereafter mutants are Scl-Cre$^+$ unless otherwise specified as Mx1-Cre$^+$) LSK cells were slightly reduced in bone marrow but significantly increased in spleen (p<0.001), suggesting a mobilization of HSCs. Similar to previous reports (Yilmaz, O. H. et al. Pten dependence distinguishes haematopoietic stem cells from leukaemia-initiating cells. *Nature* 441, 475-482 (2006); Zhang, J. et al. PTEN maintains haematopoietic stem cells and acts in lineage choice and leukaemia prevention. *Nature* 441, 518-522 (2006)), LSK cells in Pten mutants were also significantly increased in spleen (p<0.05), though this expansion was not as great as in double mutant spleen (FIG. 1A). At 4 weeks post-induction (wpi), early myeloid progenitors including common myeloid, megakaryocyte-erythroid, and granulocyte-monocyte progenitors (CMPs, MEPs, and GMPs, respectively) (Akashi, K., Traver, D., Miyamoto, T. & Weissman, I. L. A clonogenic common myeloid progenitor that gives rise to all myeloid lineages. *Nature* 404, 193-197 (2000)) were significantly reduced in Pten:Ctnnb1 bone marrow. No other dramatic differences were observed between control, single, and double mutant bone marrow and spleen (data not shown).

By 6 wpi, the frequency of LSK cells (lineage negative, Sca-1$^+$, Kit$^+$), which are highly enriched in HSCs, significantly increased in Pten:Ctnnb1 bone marrow, although the absolute number of LSK cells was not significantly increased in bone marrow due to low cellularity (FIGS. 1B and 1F; cells were pre-gated on live, lineage negative cells.). Strikingly, LSK cells in spleen, which increased only modestly in Pten single mutants, were dramatically increased in double mutants (FIGS. 1C and 1G). However, the frequency of progenitor cells (lineage negative, Sca-1$^-$, Kit$^+$ cells) decreased in both bone marrow and spleen in double mutants, indicating a failure to differentiate (FIGS. 1B-1C).

Because LSK cells are heterogeneous, the LSK population was further examined based on Flk2 and CD34 expression, the negative fractions of which further define long-term reconstituting HSCs (Himburg, H. A. et al., "Pleiotrophin regulates the expansion and regeneration of hematopoietic stem cells" *Nat Med* Vol. 16, pages 475-482 (2010); Sato, et al., "Maintenance of pluripotency in human and mouse embryonic stem cells through activation of Wnt signaling by a pharmacological GSK-3-specific inhibitor" *Nat Med* Vol. 10, 55-63 (2004)). LSKs may be subdivided based on Flk2 expression, which allowed for further enrichment long-term reconstituting (LT) HSCs (Flk2$^-$) from short-term reconstituting (ST) HSCs (Flk2$^+$) (Christensen, J. L. & Weissman, I. L. Flk-2 is a marker in hematopoietic stem cell differentiation: a simple method to isolate long-term stem cells. *Proceedings of the National Academy of Sciences of the United States of America* 98, 14541-14546 (2001)). Double mutants exhibited a higher frequency of both Flk2$^-$ and CD34$^-$ cells within the LSK population than control or either single mutant (FIGS. 1D, 1H, and 1I). The absolute number of LSK CD34$^-$ cells was also significantly increased in both bone marrow and spleen of double mutants compared to both control and single mutants (FIG. 1E).

Despite the substantial increase in phenotypic HSCs, further characterization of early myeloid progenitors showed that both frequency and absolute numbers of common myeloid, megakaryocyte-erythroid, and granulocyte-monocyte progenitors (CMPs, MEPs, and GMPs, respectively) were significantly reduced in double mutants (FIGS. 1B-1C) (Akashi, K., Traver, D., Miyamoto, T. & Weissman, I. L. A clonogenic common myeloid progenitor that gives rise to all myeloid lineages. *Nature* 404, 193-197 (2000)). However, the frequency and absolute numbers of common lymphoid progenitors (CLP) was similar to control (FIGS. 1K and 24) (Nakorn et al., "Myeloerythroid-restricted progenitors are sufficient to confer radioprotection and provide the majority of day 8 CFU-S." *J. clinical investigation* Vol. 109, pages 1579-1585 (2002); Datta et al. "Akt phosphorylation of BAD couples survival signals to the cell-intrinsic death machinery." *Cell* Vol. 91, pages 231-241 (1997)). These data demonstrate that phenotypic HSCs are substantially expanded in double mutants compared to control and single mutants. Furthermore, this expansion is coupled with reduced differentiation of myeloid progenitors but without significant corresponding increases in early lymphoid differentiation. In contrast, Pten single mutants exhibit excessive myeloid differentiation, progressing to MPD (FIG. 9).

Figure 1:
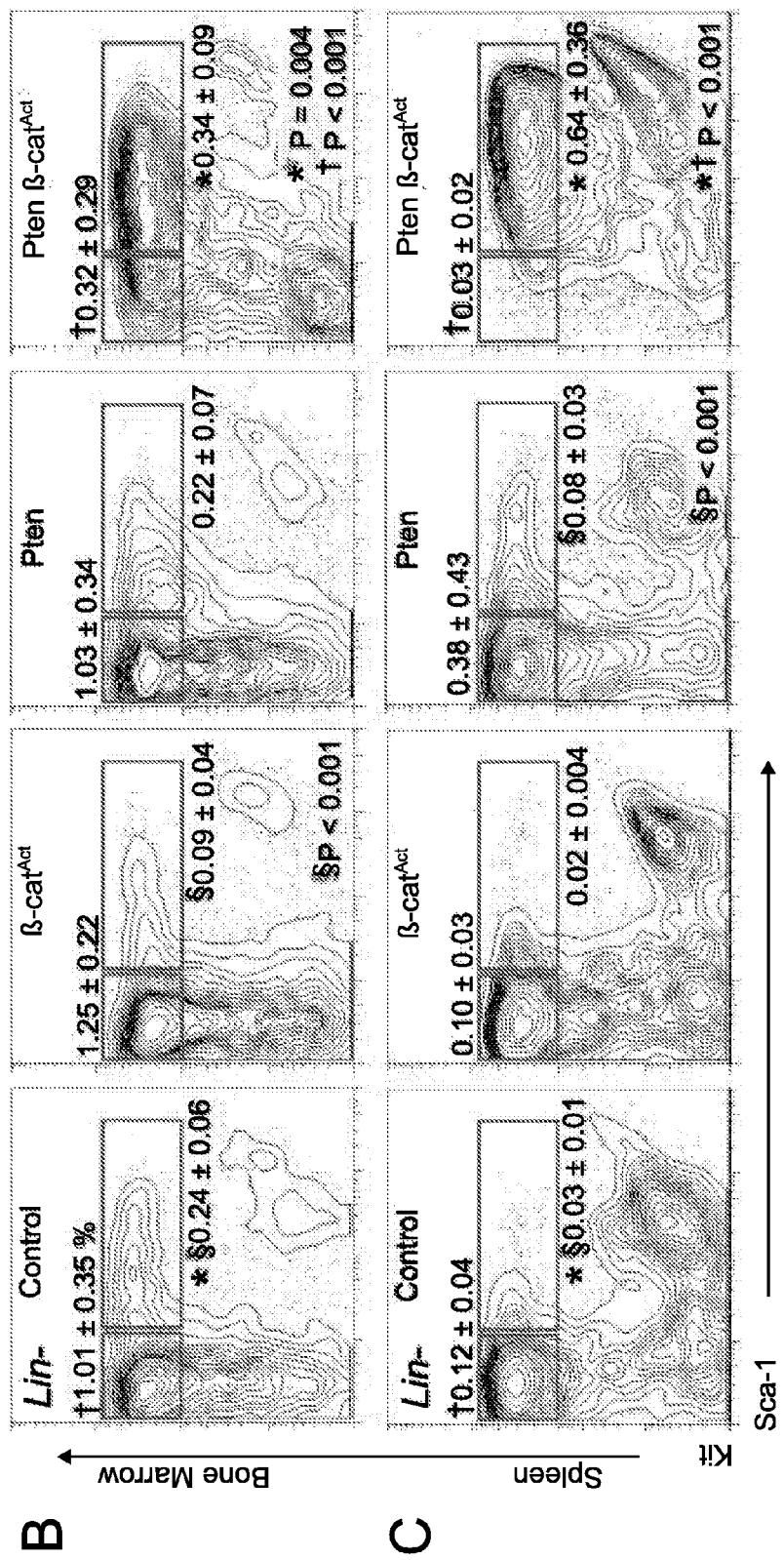
FIG. 1 is a series of bar graphs and fluorescence activated cell sorting ("FACS") analyses that collectively show that loss of PTEN with constitutively active β-catenin leads to hematopoietic stem cell (HSC) expansion with loss of early hematopoietic progenitors.
Figure 1:
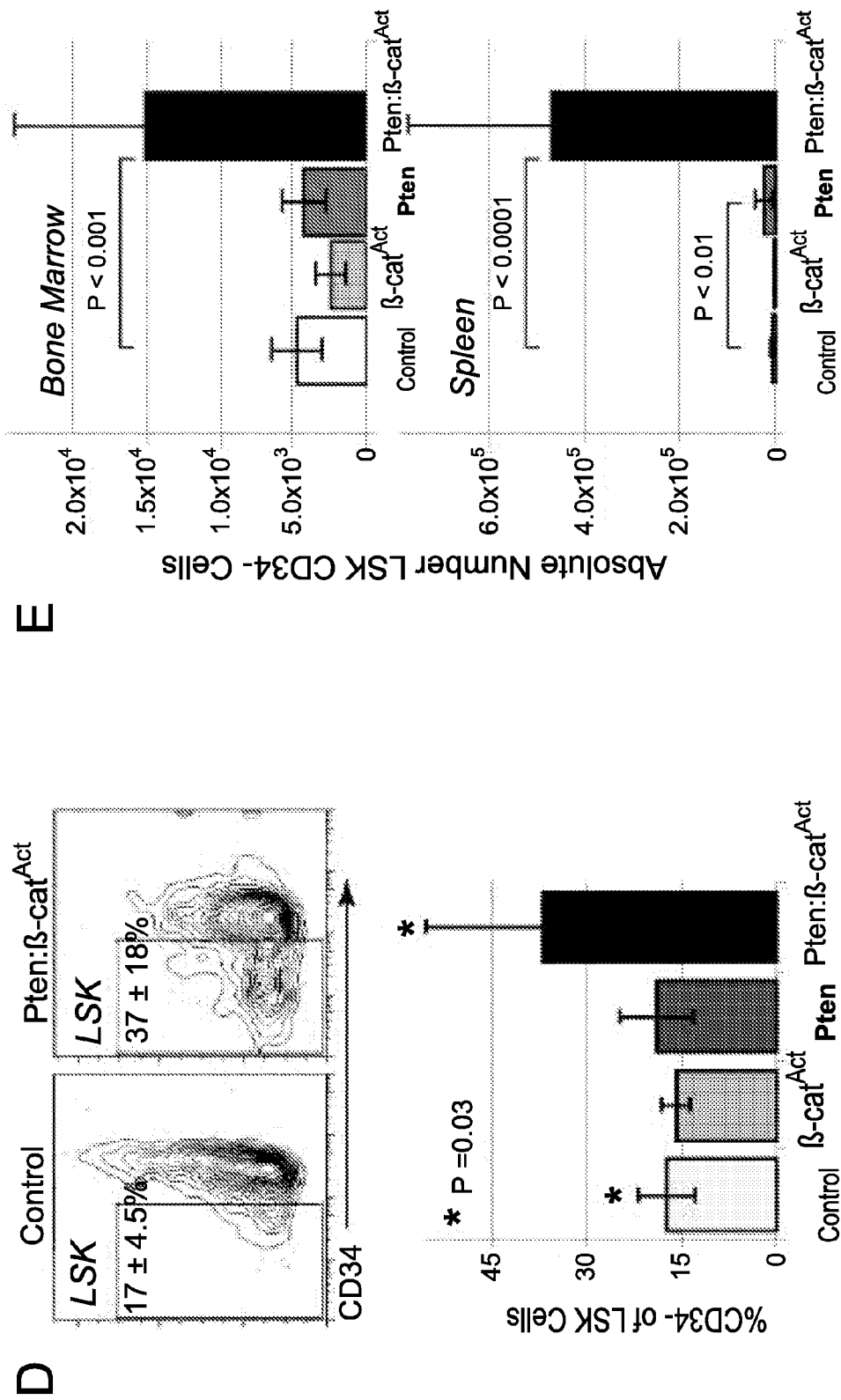
Figure 1:
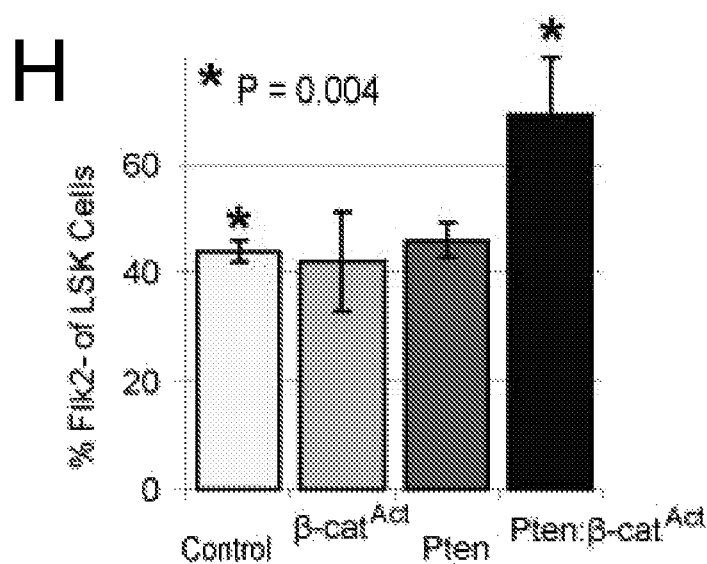
Figure 1:
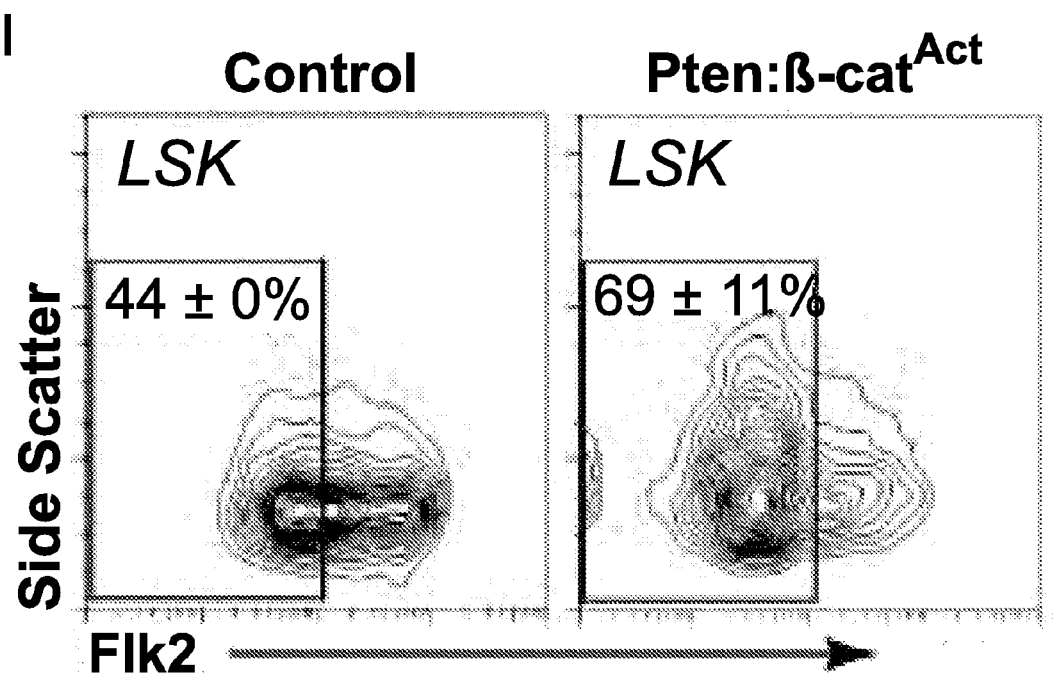
Figure 1:
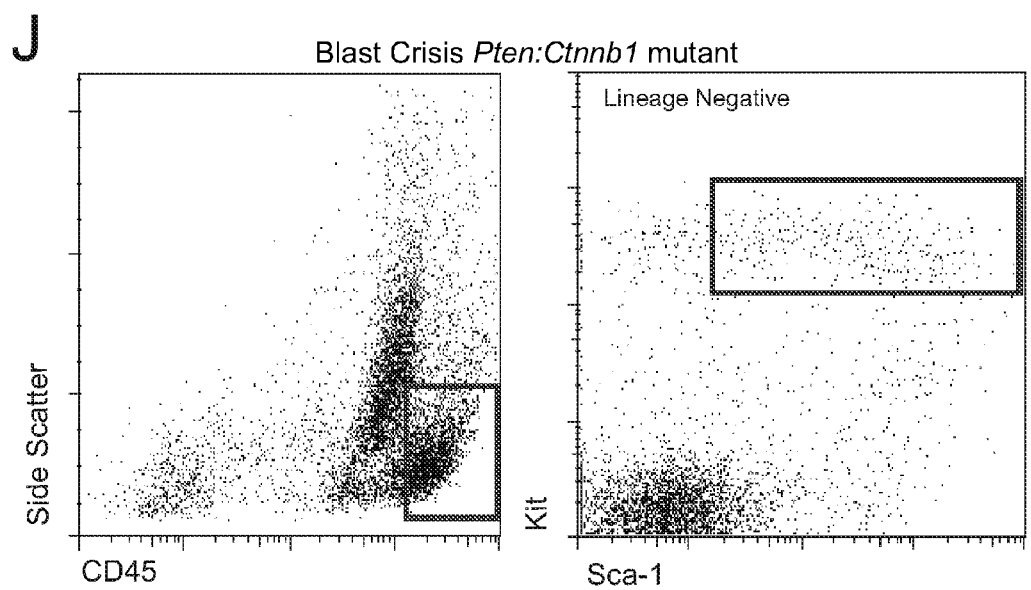
Figure 1:
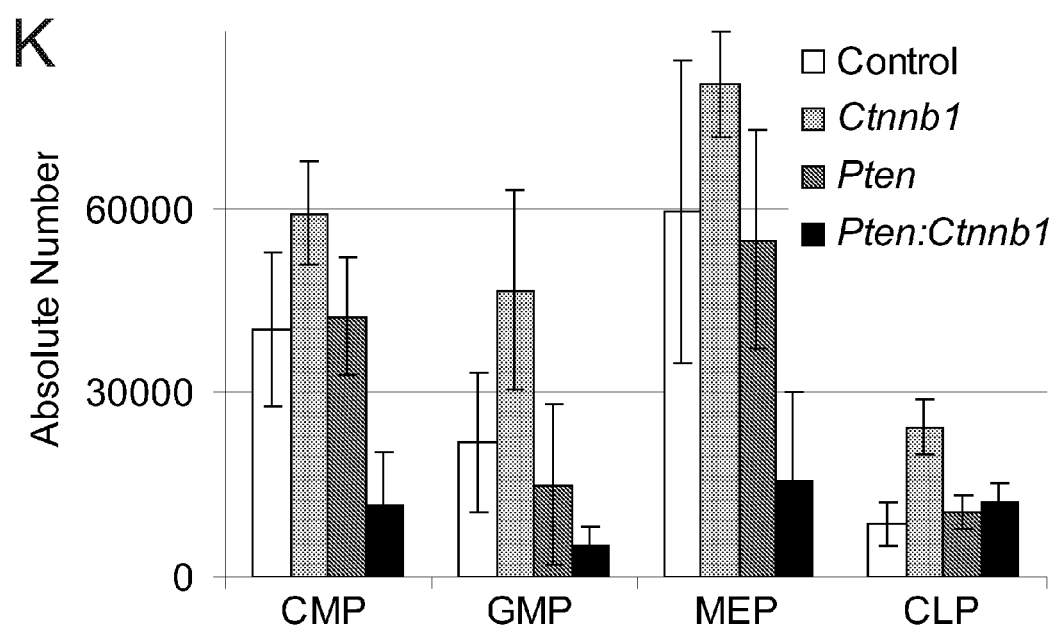

By 6 wpi, about 50% of double mutants began to develop leukemia with substantial blast cell (CD45$^{High}$) populations (FIG. 1J and data not shown) (Borowitz, M. J., Guenther, K. L., Shults, K. E., Stelzer, G. T. Immunophenotyping of acute leukemia by flow cytometric analysis. *Am. J. Clin. Pathol.* 100, 534-540 (1993)). As shown in FIG. 1J, CD45 (high) blast crisis cells are indicated in the blue box of the left panel. LSK analysis of leukemic Pten:Ctnnb1 mutant mouse bone marrow was also performed (FIG. 1J, right panel). Note the conversion to blast cells (lower left) with only a remnant LSK population (compare to FIG. 1C). These leukemic mice were excluded from the analyses presented in the rest of FIG. 1 and FIG. 24 because their LSK population was reduced when blast cells increased and out-competed other cells, which was accompanied by stromal/niche disruption (see below). By 10-11 wpi, all double mutants had to be euthanized due to severe leukemia comprised of early T-lymphoid precursors. In comparison, no blast cell population is observed in control or Ctnnb1 single mutants while a minor one was observed in 1 of 8 Pten single mutant mice at 6 weeks post-induction (data not shown). The long-term phenotype of double as well as single mutants is detailed in FIGS. 10, 12, 16, 17, 20, and 28. Overall, double mutants ultimately exhibited reductions in most major hematopoietic lineages except for early T-cell precursors, which predominated. Interestingly, double mutants at 9 wpi frequently exhibited a unique population of lineage negative, Sca-1$^{Low}$, Kit$^{Low}$ or LSK-like cells prior to the complete dominance of leukemic blast cells. Preliminary evidence indicates that this population is particularly enhanced in leukemia-initiating or cancer stem cell activity (FIG. 10A and data not shown).

Together, this data demonstrates the phenotypic effect of the genetic loss of PTEN coupled with constitutive activation of β-catenin in HSCs. While loss of PTEN alone results in a slight but significant expansion in splenic HSCs due to mobilization from the bone marrow, double mutant HSCs exhibit the greatest mobilization at 10 days post-induction. By six weeks post-induction, only double mutant splenic HSCs are dramatically increased while single mutants are not significantly different from controls. In addition, this dramatic increase in HSCs is not accompanied by an increase in early hematopoietic progenitors; rather these early progenitors are all reduced with the exception of CLPs which are not significantly different from control. HSCs accumulate dramatically in the spleen of double, but not single, mutants by proliferation with reduced differentiation. Thus, surprisingly and unexpectedly, loss of PTEN coupled with the constitutive activation of β-catenin drives stem cell self-renewal while neither pathway individually is capable of driving long-term self-renewal.

Example 2

In Vitro Culture of Control and Mutant LSK Cells

Cell Culture

LSK or LSK Flk2$^-$ cells were sorted into 96-well U-bottom tissue culture plates at 100 cells/well with 200 μl media/well. Cells were incubated at 37° C., 5% O$_2$, 5% CO$_2$ (balance N$_2$) for the indicated number of days. One-half total volume of media (see Table 1, below for the base media) was carefully pipetted from the top and replaced with fresh media every other day.

TABLE 1

Base Media

| Components | Source |
|---|---|
| StemSpan Media: (Iscove's-modified Dulbecco's medium (IMDM) supplemented with 1% bovine serum albumin, 10 µg ml$^{-1}$ recombinant human insulin, 200 µg ml$^{-1}$ iron-saturated transferrin, 0.1 mM 2-mercaptoethanol and 2 mM glutamine.) | Stem Cell Technologies; Cat. No. 09600 |
| 1 µg/ml Heparin | Sigma, Cat. No. H-3149 |
| 0.5X Penicillin/Streptomycin | Sigma, Cat. No. P4333 |
| 10 ng/ml recombinant mouse (rm) Stem Cell Factor | Biovision, Cat. No. 4328-10 |
| 20 ng/ml rm-Thrombopoietin | Cell Sciences, Inc, Cat. No. CRT401B |

Double Mutant HSCs Expand Dramatically In Vitro and In Vivo but Fail to Differentiate.

For the following experiments, the base media from Table 1 was further supplemented with 20 ng/ml rm-IGF-2 (R&D Systems, Cat. No. 792-MG) and 10 ng/ml recombinant human FGF-1 (Affinity BioReagents, Cat. No. ORP16010).

The ability of HSCs isolated from Mx1-Cre$^+$ single and double mutants to expand in vitro was examined. Lineage negative, Sca-1$^+$, Kit$^+$ (LSK) cells (a population highly enriched in HSCs) were sorted from wild-type (control), single, and double mutant Mx1-Cre$^+$ bone marrow and cultured in defined media based on a previous report regarding ex vivo HSC expansion (Zhang, C. C. & Lodish, H. F. Murine hematopoietic stem cells change their surface phenotype during ex vivo expansion. *Blood* 105, 4314-4320 (2005)). After 10 days culture, control LSK cells had undergone a modest expansion; however, Ctnnb1 LSK cells did not survive, suggesting they had undergone apoptosis. In contrast, Pten LSK cultures expanded to a greater degree than control, while the best expansion was observed from double mutant cultures (FIG. 2A). Pten and Pten:Ctnnb1 cultures continued to expand up to 5 weeks in vitro (FIG. 2B); however, control cultures began to decline after 4 weeks (data not shown). Unlike control, both Pten and Pten:Ctnnb1 cultures remained robust after 5 weeks, but Pten:Ctnnb1 cultures contained far more cells and their appearance was more homogenous than Pten cultures (FIG. 2B). At 7 weeks, a portion of the remaining Pten and Pten:Ctnnb1 cultures was re-analyzed by fluorescence-activated cell scanning (FACS) analysis to determine how many cells had maintained their LSK phenotype (FIG. 2E). Due to long-term culture, these cells expressed unusually high levels of Kit and Sca-1. While LSK cells from Pten cultures had expanded 50-fold, Pten:Ctnnb1 cultures expanded more than 1,200-fold (FIG. 2C). In addition, the purity of LSK cells % of total cells maintaining the LSK phenotype) was significantly higher in Pten:Ctnnb1 cultures compared to Pten only (84% vs. 52%, respectively, FIG. 2D).

Example 3

Transplantation Analysis of Pten and Pten:Ctnnb1 LSK Cells after 5 Weeks of Culture For the following experiments, cells were cultured in the same manner as described in Example 2. As in Example 2, the base media of Table 1 was supplemented with 20 ng/ml rm-IGF-2 (R&D Systems, 792-MG) and 10 ng/ml recombinant human FGF-1 (Affinity BioReagents, ORP16010).

While Pten and especially Pten:Ctnnb1 cultures exhibited significant expansion in LSK cells, whether these cells were functional in vivo was determined.

At 5 weeks culture, Pten and Pten:Ctnnb1 LSK cultures were re-sorted and 1000 LSK cells (CD45.2$^+$) from each were transplanted into lethally irradiated (10 Gy) CD45.1$^+$ recipient mice along with 2×10$^5$ congenic whole bone marrow competitor cells. Because wild-type cells did not survive 5 weeks culture, 1000 fresh wild-type LSK cells were also transplanted as a separate control group. Peripheral blood analysis at 4 weeks post-transplantation revealed robust repopulation in mice transplanted with fresh/uncultured control cells as expected; however, mice transplanted with either Pten or Pten:Ctnnb1 cultured cells did not exhibit repopulation (data not shown). At 5 weeks post-transplant, bone marrow from recipient mice was analyzed for donor engraftment (CD45.2$^+$ cells) and donor LSK cells (CD45.2$^+$ LSKs).

To determine whether LSK or other donor-derived (CD45.2+) cells remained in the bone marrow of mice transplanted with cultured cells, bone marrow was analyzed for donor (CD45.2+) and LSK cells. While the control group exhibited robust repopulation of CD45.2+ bone marrow cells, few CD45.2+ cells were maintained as LSK cells as expected (FIGS. 2C-D and 2F). In contrast, recipients transplanted with in vitro expanded Pten or Pten:Ctnnb1 mutant LSK cells exhibited few donor-derived total bone marrow cells (FIGS. 2G-H). However, a large portion of Pten:Ctnnb1 donor-derived cells were maintained as LSK cells in recipients, whereas those from Pten only cultures were similar in number to control (FIGS. 2G-I). In order to determine whether ex vivo expanded donor cells had further expanded in vivo following transplantation, the total number of donor LSK cells in total bone marrow per mouse were estimated (Smith, L. H. & Clayton, M. L. Distribution of injected 59Fe in mice. *Exp. Hematol.* 20, 82-86 (1970)). As shown in FIG. 2J, the expansion of total donor-derived LSK cells in transplant recipients was modest and similar between control and Pten (8.6±1.4 and 13±6.3, respectively), but significantly greater in recipients transplanted with cultured Pten:Ctnnb1 LSK cells (43±3.4).

Collectively, these data demonstrate that double mutant HSCs can be cultured longer and with far greater expansion than either single mutant or control HSCs. However, permanent genetic alteration of both pathways leads to an increased ability to self-renew both in vitro as well as in vivo following long-term culture but a failure to differentiate and thus repopulate the hematopoietic system of transplant recipients. This further demonstrates the ability of the PTEN and β-catenin signaling pathways to cooperatively drive stem cell expansion by proliferation without differentiation.

Example 4

Transplanted Double Mutant LSK Flk2$^-$ Cells are Maintained as Phenotypic HSCs In Vivo Initially, primary (non-transplanted) animals were used for phenotypic analysis. These mice eventually exhibited severe non-hematopoietic defects, including reduction of the marrow cavity and splenic fibrosis resulting in disruption of splenic niches (FIG. 16). Consequently, LT-HSC transplantations were used to verify Scl-Cre specificity (FIG. 10). Comparing these transplant groups with the initial data from primary mutants revealed an essentially identical phenotypic manifestation of defects between transplant and non-transplant groups, demonstrating that non-hematopoietic effects are due to interaction between the hematopoietic system and stroma rather than from defects arising from the stroma (FIG. 17 and data not shown).

The health of double mutants typically declined by 9 wpi (see below). LSK cells and early progenitors from control, single, and double mutant bone marrow and spleen at 9-10 wpi were analyzed by FACS (FIGS. 10A-B). Absolute number of LSK cells were reduced in bone marrow and spleen of Ctnnb1 single mutants but increased in the spleens of Pten single mutants (FIGS. 10A and 10C-D). CMPs and MEPs were increased in Pten bone marrow and spleen (FIG. 10B-D). In contrast, LSK cells and all early progenitors including CMPs, MEPs, GMPs and CLPs (Akashi, K., Traver, D., Miyamoto, T. & Weissman, I. L. A clonogenic common myeloid progenitor that gives rise to all myeloid lineages. *Nature* 404, 193-197 (2000); Kondo, M., Weissman, I. L. & Akashi, K. Identification of clonogenic common lymphoid progenitors in mouse bone marrow. *Cell* 91, 661-672 (1997)) were severely depleted in Pten:Ctnnb1 bone marrow. Interestingly, when leukemic cells predominated but health had not yet severely declined, Pten:Ctnnb1 mutants exhibited a distinct population of Lin– Sca-1$^{Low}$ Kit$^{Mid}$ (LS$^{Low}$K$^{Mid}$) cells at 9 wpi (FIG. 10A, panels IV and IX). At 10 wpi when health had severely declined, this population was typically absent and only leukemic blast cells remained (FIG. 10A, panels V and X).

CD45.1 (recipient) and CD45.2 (donor) markers were used to measure engraftment levels in recipients at 9-10 wpi. 1,000 sorted LSK Flk2$^-$ cells from control, single, and double mutant mice (CD45.2$^+$) were transplanted along with $2 \times 10^5$ competitor (CD45.1$^+$) bone marrow cells into lethally-irradiated CD45.1$^+$ recipients. As expected, robust engraftment was observed in recipients of 1,000 control LSK Flk2– cells (77±6%) (FIG. 10E). Pten mutants exhibited somewhat higher average engraftment of 88±4%. The highest and most consistent engraftment of 97±1.5% was exhibited in Pten:Ctnnb1 mice. In contrast, average engraftment was only 32±36% in Ctnnb1 mutants, with half the recipients exhibiting little to no engraftment. The relatively poor and variable engraftment observed in the Ctnnb1 transplant group may be due to a minor portion of HSCs that escaped knockout of the floxed Ctnnb1 allele. Indeed, previous reports have shown that phenotypically defined HSCs in Ctnnb1 mutants are no longer functional (Kirstetter, P., Anderson, K., Porse, B. T., Jacobsen, S. E. & Nerlov, C. Activation of the canonical Wnt pathway leads to loss of hematopoietic stem cell repopulation and multilineage differentiation block. *Nat Immunol* 7, 1048-1056 (2006); Scheller, M. et al. Hematopoietic stem cell and multilineage defects generated by constitutive [beta]-catenin activation. *Nature Immunology* 7, 1037-1047 (2006)). In order to test this, LSK Flk2– cells from Scl-Cre negative (control) as well as Ctnnb1 mutants at 2 and 16 wpi were sorted and genotyped for presence of the knockout allele. At 2 wpi, the mutant Ctnnb1 allele was present; however, by 16 wpi no cells containing mutant Ctnnb1 allele remained, demonstrating that Ctnnb1 mutant HSCs are not maintained long-term (FIG. 18). In contrast, Pten:Ctnnb1 HSCs were highly dominant and almost wholly out-competed all HSCs found within the competitor bone marrow cells.

To verify this, the Z/EG reporter system was included to determine which cells had undergone Cre-mediated excision of their floxed alleles (Novak, A., Guo, C., Yang, W., Nagy, A. & Lobe, C. G. Z/EG, a double reporter mouse line that expresses enhanced green fluorescent protein upon Cre-mediated excision. *Genesis* 28, 147-155 (2000)). The Z/EG reporter system activates expression of enhanced green fluorescent protein (EGFP) upon Cre-mediated excision.

Given the impaired myeloid differentiation and accumulation of phenotypic HSCs in double mutants, whether mutant LSK Flk2$^-$ cells were maintained in recipient mice was tested. LSK Flk2$^-$ cells was gated in each recipient group, and GFP expression in this subpopulation was observed. As expected, mice transplanted with Scl-Cre negative (control)-Z/EG donor LSK Flk2– cells exhibited no EGFP$^+$ LSK Flk2$^-$ cells (0.8±0.8%) (FIG. 10F). Similarly, recipients of Ctnnb1-Z/EG LSK Flk2$^-$ cells also had very few EGFP+ LSK Flk2– (1.6±0.9%) cells, further demonstrating that essentially only those LSK Flk2– cells escaping knockout induction remained. LSK Flk2$^-$ cells from Pten-Z/EG transplant recipients exhibited a minor GFP$^+$ population (8.6±2.1%), demonstrating that some mutant LSK Flk2$^-$ cells remained even after 9-10 wpi, although most had differentiated or had been otherwise lost. In contrast, LSK Flk2– cells from Pten:Ctnnb1-Z/EG transplant recipients were 90.0±4.0% EGFP+. These data demonstrate that, while Ctnnb1 mutant phenotypic HSCs are not maintained and Pten mutant phenotypic HSCs differentiate, double mutant phenotypic HSCs are maintained in vivo.

Example 5

Differentiation Block and Dominant Phenotype of Pten:Ctnnb1 Mutant HSCs

Colony Forming Unit (CFU) Assays

CFU Assays were performed according to manufacturer's instructions using complete methylcellulose media with Epo (Cat. No. M3434, Stem Cell Technologies, Inc., Vancouver, Canada).

Lentiviral Production/HSC Transduction

To knockdown mouse β-catenin in HSCs and their progeny, lentiviruses in which mouse β-catenin short-hairpin RNAs (shRNAs) and an IRES GFP label are driven by a MSCV (murine stem cell virus) LTR promoter were generated. Lentiviral constructs were produced by directionally cloning DNA oligonucleotides corresponding to two Ctnnb1 shRNAs (sequences HP_224742 and HP_240000; SEQ ID NOs: 3-4, RNAicodex, Cold Spring, N.Y.) into the Gateway® entry vector pEN-LmiRc3 (Invitrogen), then recombining with the destination vector pDSL-hpIG (Zhu, X. et al. A versatile approach to multiple gene RNA interference using microRNA-based short hairpin RNAs. *BMC molecular biology* 8, 98 (2007)). The control viral construct drives a luciferase shRNA (Id.) from the same vector backbone. Virus was produced in 293T cells by co-transfection of the virus plasmid with packaging plasmids (pRC-CMV-RaII, HDM-Tat16, HDM-HGPM2 and HDM-VSVG, a gift from Dr. Jeffrey M. Rosen, Baylor College of Medicine), and was purified by poly-ethylene-glycol (PEG) precipitation (0.45 μm-filtered supernatant was precipitated with 10% PEG-8000, 1.5% fetal bovine serum for 72 hours at 4° C., then pelleted at 1,500 g for 10 minutes), followed by ultracentrifugation through a sucrose cushion (al Yacoub, N., Romanowska, M., Haritonova, N. & Foerster, J. Optimized production and concentration of lentiviral vectors containing large inserts. *The journal of gene medicine* 9, 579-584 (2007)). Titres were established using 293T cells due to the limited numbers of HSCs available. Viral transduction of HSCs was performed overnight in ST media with 8 μM final polybrene at a multiplicity of infection of 20-50 relative to the initial cell HSC number (500 cells).

Experimental Results

Although putative HSCs can be highly enriched by cell surface marker phenotype, bona fide HSCs are functionally defined. When genetic mutation compromises function, formal proof that a putative HSC population represents true HSCs can be precluded. This is the case for mutants with constitutively active β-catenin because differentiation is blocked. Whether LSK Flk2$^-$ cells isolated from double mutants could recover multilineage differentiation capacity if β-catenin transcripts were degraded by RNA interference (RNAi) were determined. LSK Flk2$^-$ cells from uninduced control, Pten, and Pten:Ctnnb1 mice were sorted and induced knockout in vitro with 4-hydroxy-tamoxifen (OHT) added for 3 days in culture. At day 3, HSC cultures were transduced using lentiviral vectors targeting β-catenin transcripts by RNAi as set forth below.

At day 6, myeoloid-specific colony forming unit (CFU) assays were performed on these HSC cultures. While knockdown of β-catenin in control and Pten HSC cultures did not significantly affect colony formation, knockdown of β-catenin in double mutant cultures resulted in reversal from a novel CFU phenotype to a CFU phenotype similar to Pten single mutants (FIGS. 19A-B). Specifically, double mutant HSC cultures transduced with control vector formed large CFU (>0.5 mm) which were not produced in control or Pten cultures. Interestingly, these primitive CFU were mostly CD3$^+$ (T lymphoid) cells not found in control colonies or Pten colonies (FIG. 19C). These novel CFUs are apparently the result of myeloid differentiation blockage and leukemic transformation in double mutants. In contrast, double mutant cultures transduced with short-hairpin (sh) RNA targeting β-catenin produced only small CFU morphologically and quantitatively similar to Pten CFU. These smaller colonies further contained only minor proportions of CD3$^+$ cells. In addition, the number of colonies was shifted toward a predominance of granulocyte/monocyte progenitors (CFU-GM) similar to Pten single mutants (FIGS. 19A-C). These data demonstrate that the differentiation blockage exhibited by double mutant LSK Flk2$^-$ cells is functionally reversible via knockdown of β-catenin, supporting the idea that the phenotypically defined HSCs expanding in double mutants are, indeed, bona fide, though functionally compromised, HSCs.

Example 6

Pten Single Mutants Exhibit Increased Myeloid Differentiation

Though not nearly as large as the increase observed in double mutants, Pten single mutants exhibited increased frequency and absolute number of LSK CD34$^-$ cells in spleen at 6 wpi (FIGS. 1C and 1E). At 9-10 wpi, early myeloid progenitors were substantially increased in bone marrow and especially spleen of Pten single mutants (FIG. 25), as were more mature myeloid cells (FIG. 28). Indeed, the trend of moderate but variable LSK cell expansion in spleen, coupled with increased myeloid differentiation, was sustained for at least 15 wpi (FIG. 29).

In order to more comprehensively study the role of β-catenin interaction with the PTEN/Akt signaling pathway, mice with floxed null alleles of β-catenin (Ctnnb1$^{tm2Kem}$) (Cobas, M. et al. Beta-catenin is dispensable for hematopoiesis and lymphopoiesis. *The Journal of experimental medicine* 199, 221-229 (2004)) were obtained and crossed to Mx1-Cre and Mx1-Cre Pten mutants, allowing for the combination of conditional deletion of β-catenin (β-cat$^{-/-}$), Pten, and Pten:β-cat$^{-/-}$. As with the Pten:Ctnnb1 compound mutant, primary animals were studied; however, this was difficult to pursue because β-cat$^{-/-}$ mice typically had to be sacrificed by 15 dpi, while Pten:β-cat$^{-/-}$ double mutants rarely maintained adequate health beyond 7 dpi (data not shown).

In order to study long-term and hematopoietic-specific defects in single and double knockout mutants, whole bone marrow transplantations were performed. Bone marrow from control (Cre$^-$), Mx1-Cre$^+$ single and double mutant donors into lethally irradiated Ptprc recipients using 1×10$^6$ cells/recipient prior to induction. At 10 wpi of transplant recipients, 5 mice from each group were sacrificed, and LSK cells as well as early progenitors were analyzed by FACS. Unlike Pten:β-cat$^{Act}$ double mutants, none of the Pten:β-cat$^{-/-}$ double mutants exhibited signs of leukemia by 10 wpi (data not shown). Consistent with previous reports, β-cat$^{-/-}$ single mutants did not exhibit any defects in absolute numbers of LSK or early progenitors (Cobas, M. et al. Beta-catenin is dispensable for hematopoiesis and lymphopoiesis. *The Journal of experimental medicine* 199, 221-229 (2004)); however Pten single mutants exhibited an expansion of LSK cells as well as CMPs and MEPs in the spleen (FIG. 11D). Interestingly, Pten:β-cat$^{-/-}$ double knockout transplant recipients did not exhibit an expansion of LSK cells in the spleen, while CMPs and MEPs were increased compared to control but less than Pten only mutants (FIG. 11D). In contrast, analysis of more mature hematopoietic lineages revealed similar increases in Mac-1$^+$ Gr1$^+$ cells between Pten single and Pten:β-cat$^{-/-}$ double knockouts, indicative of MPD, while lymphoid lineages were similarly reduced in both Pten and Pten:β-cat$^{-/-}$ transplant recipients (FIGS. 11E-G). These results demonstrate that loss of β-catenin rescues the LSK cell expansion observed in Pten mutant spleen and partially rescues the early myeloid progenitor cell expansion, although MPD development still occurs. Relative to the number of LSK cells, Pten:β-cat$^{-/-}$ mutants expanded early myeloid progenitors as well as or greater than Pten single mutants (FIG. 11D). Thus, loss of β-catenin appears to primarily rescue HSC-specific effects, with the downstream events that lead to MPD being separable, β-catenin-independent phenomena. These data also further confirm that the Wnt/β-catenin and PTEN/Akt pathways cooperatively interact in driving HSC expansion.

Example 7

β-Cat$^{Act}$ Single Mutant HSCs Rapidly Undergo Apoptosis In Vitro

β-cat$^{Act}$ single mutants exhibited a reduced frequency of LSK CD34$^-$ cells in bone marrow at 6 wpi (FIG. 1B); however, long-term defects in β-cat$^{Act}$ single mutants was not observed. Indeed, although efficient knockout in sorted β-cat$^{Act}$ HSCs at 2 wpi was detected, at 16 wpi HSCs with the mutant β-cat$^{Act}$ allele were not present in induced β-cat$^{Act}$ mice (FIG. 18). Similarly, the transplantation experiments demonstrated that β-cat$^{Act}$ single mutant HSCs were not maintained in vivo (FIG. 10F).

Because the exact time point when β-cat$^{Act}$ HSCs were lost in vivo is not known, whether β-cat$^{Act}$ HSCs undergo apoptosis was tested. LSK Flk2$^-$ cells were isolated from uninduced mice, genetic deletion was induced in vitro, and the resulting cultures were then visually monitored. These experiments revealed that, by 4 days post-induction, no β-cat$^{Act}$ LSK Flk2$^-$ cells survived; whereas control, Pten, and particularly double mutant LSK Flk2⁻ cells survived and expanded (FIG. 11A). At 48 hours post-induction, although some β-cat$^{Act}$ LSK Flk2⁻ cells remained, their numbers were reduced relative to control (FIG. 11B). Whether these cells were undergoing apoptosis was tested by Annexin V staining. Unlike control, the majority of β-cat$^{Act}$ LSK Flk2⁻ cells at 48 hours post-induction were either undergoing apoptosis or already dead, demonstrating that constitutive activation of β-catenin in LSK Flk2⁻ cells in vitro results in rapid apoptosis (FIG. 11C). These data demonstrate that while most Pten mutant HSCs differentiate, β-cat$^{Act}$ mutant HSCs undergo rapid apoptosis in vitro, exhibit functional failure in vivo, and are not maintained in recipients. In contrast, double mutant LT-HCSs were phenotypically maintained 9-10 wpi, becoming the dominant HSC population in transplant recipients. These data demonstrate that β-cat$^{Act}$ mutant HSCs have a survival defect and that this survival defect can be rescued by additional loss of Pten.

Example 8

Unlike Single Mutants, Double Mutants Rapidly and Consistently Develop Leukemia

Control animals (Scl-Cre negative littermates) remained healthy as expected, and Ctnnb1 mutants also remained healthy through at least 20 wpi. In contrast, about 30% of Pten single mutants had to be sacrificed by 20 wpi, but the majority survived through at least 28 wpi. Pten:Ctnnb1 double mutants exhibited a far more rapid decline in health than Pten single mutants. Double mutants typically survived until at least 8 wpi when a minority had to be sacrificed due to poor condition (FIG. 12A). By 11 wpi, however, all double mutants had to be sacrificed. Histological examination of Pten:Ctnnb1 bone marrow at 9-10 wpi revealed that the bone shaft (diaphysis) became substantially filled with bone, while trabecular bone regions (metaphysis), reported to be enriched in sites containing the HSC niche (Xie, Y. et al. Detection of functional haematopoietic stem cell niche using real-time imaging. *Nature* 457, 97-101 (2009); Arai, F. et al. Tie2/angiopoietin-1 signaling regulates hematopoietic stem cell quiescence in the bone marrow niche. *Cell* 118, 149-161 (2004); Calvi, L. M. et al. Osteoblastic cells regulate the haematopoietic stem cell niche. *Nature* 425, 841-846 (2003); Zhang, J. et al. Identification of the haematopoietic stem cell niche and control of the niche size. *Nature* 425, 836-841 (2003)), were largely hypo-cellular with areas that appeared grossly normal (FIG. 11B). In contrast, no obvious defects were apparent in either single mutant bone marrow (data not shown). Splenomegaly in Pten:Ctnnb1 mutants at 9-10 wpi was observed, with the spleen exhibiting severe hypo-cellularity and fibrosis (FIG. 16). In contrast, gross appearance of single mutant spleen was normal at 9-10 wpi. Furthermore, the hypo-cellularity and fibrosis observed in double mutant spleen was present even in wild-type mice transplanted with LSK Flk2− cells from Pten:Ctnnb1 donors. The stromal abnormalities observed were most likely a consequence of loss of negative inhibition from hematopoietic cells to normal stroma rather than of defects originating in the stroma.

Suspecting that acute leukemia/lymphoma caused the rapid decline in health of Pten:Ctnnb1 mutants between 8-11 wpi, FACS analysis was used to examine the abundance of CD45$^{High}$ primitive blast cells in control, single, and double mutants (Borowitz, M. J., Guenther, K. L., Shults, K. E., Stelzer, G. T. Immunophenotyping of acute leukemia by flow cytometric analysis. *Am. J. Clin. Pathol.* 100, 534-540 (1993)). As shown in FIG. 5C, Pten:Ctnnb1 mutants exhibited a conversion to predominantly leukemic blast cells in the bone marrow by 9-10 wpi. This was observed in all double mutants examined (n>20). In contrast, control and Ctnnb1 mice never exhibited a significant blast population. Typically, Pten mutants were also similar to control regarding bone marrow CD45 expression level at 9-10 wpi, although 2/16 exhibited a minor blast population (data not shown). These data demonstrate that all Pten:Ctnnb1 mutants develop a severe acute leukemia by 9-10 wpi while single mutants do not. Lineage marker analysis further characterized the leukemic cells to express the T-cell specific marker CD3, revealing the leukemia to be T-cell acute lymphocytic leukemia or T-ALL (FIG. 5C).

To further investigate hematopoietic lineage defects in Pten:Ctnnb1 mutants and to characterize the type of leukemia, the major hematopoietic lineages was examined in bone marrow at 8-9 wpi (FIGS. 20A-G). Most prominently, CD3⁺ cells in double mutants did not express more differentiated T-cell markers, CD4 or CD8. Overall, more than 75% of total bone marrow cells in double mutants were CD3⁺ but CD4 and CD8 negative, compared with less than 5% in control (FIGS. 20B-C). To further define the origin and nature of the T-ALL observed in double mutants, T-cell development in thymus was also examined. Double negative (DN) early T-cell precursors lack CD3, 4 and 8 expression, and their stage of maturation can be distinguished by CD25 and/or CD44 expression. While less than 5% of thymocytes were within the DN subset in control and single mutants, the majority of thymocytes were within this subset in double mutants (FIGS. 20D-E). Although both single mutants were similar to control, Pten:Ctnnb1 mice exhibited a large increase in DN CD25− CD44− cells (FIGS. 20D-E). Also, while the majority of thymocytes were double positive precursors in control and single mutants as expected, this population was essentially absent from Pten:Ctnnb1 mice (FIGS. 20E-G). These data demonstrate that the T-ALL observed in double mutants involves expansion of an early thymic progenitor, resulting in the accumulation of immature T-lineage precursors.

Self-renewal has been proposed to require the concurrence of three events, proliferation while preventing apoptosis and blocking differentiation (Zhang, J. & Li, L. BMP signaling and stem cell regulation. Dev Biol 284, 1-11 (2005)). However, the imposition of differentiation on proliferating stem cells—or apoptosis for stem cells that fail to properly differentiate—is critical to HSC homeostasis and cancer prevention. By studying the individual and combined effects of PTEN and β-cat mutants, the inventors have discovered that HSC self-renewal is cooperatively controlled by the PTEN/Akt and Wnt/β-catenin pathways acting in a manner consistent with this tripartite view of self-renewal. Switching from a non-tissue specific method of gene disruption to generating HSC-specific conditional mutants using the Scl-Cre system allowed for the study of defects arising primarily from HSCs and for the long-term, controlled study of double mutants. With this more refined model, it was found that Pten deletion results in relatively moderate HSC proliferation but sustained phenotypic HSC expansion. However, this is coupled with increased myeloid differentiation. Pten deletion also results in Akt activation, a potent cell survival factor which prevents apoptosis (Datta, S. R. et al. Akt phosphorylation of BAD couples survival signals to the cell-intrinsic death machinery. *Cell* 91, 231-241 (1997); Salmena, L., Carracedo, A. & Pandolfi, P. P. Tenets of PTEN Tumor Suppression. *Cell* 133, 403-414 (2008)). In contrast, Wnt/β-catenin signaling blocks differentiation, but additional signals are needed for HSC expansion. Similarly, all β-catenin and most Pten single mutants fail to develop leukemia, which requires aberrant self-renewal. However, these experiments demonstrates that only in cooperation can Wnt/β-catenin and PTEN/Akt signaling drive self-renewal and expansion without extensive differentiation. Although permanent mutation in both these pathways ultimately leads to T-ALL, transient, pharmacological manipulation allows for the expansion of functional HSCs. Thus, at the stem cell level, the interaction between these two pathways coordinates the necessary components of self-renewal, with each pathway making unique as well as joint contributions to HSC expansion.

These findings that Pten:Ctnnb1 double mutants expand HSCs to a greater degree than single mutants and that compound loss of both β-catenin and Pten rescues Pten-deficiency-induced HSC expansion demonstrate that the effects of Pten loss on HSCs are partially mediated through β-catenin. Rapamycin treatment has been reported to prevent the formation of leukemia-initiating cells in Pten mutants and to restore normal HSC function, indicating that mammalian target of rapamycin (mTor) is also an important mediator of the effects of Pten-deficiency (Yilmaz, O. H. et al. Pten dependence distinguishes haematopoietic stem cells from leukaemia-initiating cells. *Nature* 441, 475-482 (2006)).

A recent study using VE-cadherin-Cre mediated deletion of Pten has demonstrated that leukemic stem cells are highly enriched in a relatively rare population of $Kit^{Mid}$ CD3+Lin– cells, which appear to be driven by increased β-catenin activation (Guo, W. et al. Multi-genetic events collaboratively contribute to Pten-null leukaemia stem-cell formation. *Nature* 453, 529-533 (2008)). Thus, excessive self-renewal driven by Wnt/β-catenin and PTEN/Akt interaction may be important in cancer stem cell development as well as normal HSC self-renewal. Defining the origins and characteristics of cancer stem cells is critical if they are to be detected, if their formation is to be prevented, or if they are to be selectively eliminated. In the instant application, the HSC-like $LS^{Low}K^{Mid}$ population frequently observed in double mutants prior to being out-competed by leukemic blast cells (FIG. 10A) may be of particular interest. As a primitive population these could be cancer stem cells or they could be the ultimate source of a more mature population of CD3+ cancer stem cells, possibilities that require further testing.

Example 9

Ex Vivo Pharmacological Manipulation of the PTEN/Akt and Wnt/β-Catenin Signaling Pathways Cooperatively Drive Functional HSC Expansion In double mutants, permanent genetic alteration leads to enhanced self-renewal, while differentiation is blocked except toward early T-cell commitment, ultimately resulting in T-ALL. The conversion of essentially all bone marrow cells to competitive leukemic blast cells along with the niche disruption prevents sustained HSC expansion in double mutants. However, reversible, pharmacological manipulation of the PTEN/Akt and/or Wnt/β-catenin pathways may allow for the transient enhancement of self-renewal in vitro with the capacity to function as normal HSCs following removal of these agents and in vivo transplantation.

This concept was tested by utilizing a small molecule inhibitor of GSK3β (CHIR99021) (Ring, D. B. et al. Selective glycogen synthase kinase 3 inhibitors potentiate insulin activation of glucose transport and utilization in vitro and in vivo. *Diabetes* 52, 588-595 (2003); Schmid, A. C., Byrne, R. D., Vilar, R. & Woscholski, R. Bisperoxovanadium compounds are potent PTEN inhibitors. *FEBS Lett* 566, 35-3β (2004)). GSK3β inhibits β-catenin by targeting β-catenin for proteosomal degradation and acts in the Wnt/β-catenin pathway. Indeed, CHIR99021, which is the most specific and potent small molecule inhibitor of the Wnt/β-catenin pathway reported (Ring, D. B. et al. Selective glycogen synthase kinase 3 inhibitors potentiate insulin activation of glucose transport and utilization in vitro and in vivo. *Diabetes* 52, 588-595 (2003)), has been shown to promote embryonic stem (ES) cell self-renewal and expansion (Ying, Q.-L. et al. The ground state of embryonic stem cell self-renewal. *Nature* 453, 519-523 (2008)).

The inventors have developed a defined culture system utilizing only two cytokines, stem cell factor (SCF) and thrombopoietin (Tpo) (ST media), which have been shown previously to support HSC expansion in vitro (Zhang, C. C. & Lodish, H. F. Murine hematopoietic stem cells change their surface phenotype during ex vivo expansion. *Blood* 105, 4314-4320 (2005)). While addition of CHIR99021 increased the expansion of LSK Flk2⁻ cells, addition of a small molecule inhibitor of PI3K (NVP-BEZ235) (Maira, S. M. et al. Identification and characterization of NVP-BEZ235, a new orally available dual phosphatidylinositol 3-kinase/mammalian target of rapamycin inhibitor with potent in vivo antitumor activity. *Molecular cancer therapeutics* 7, 1851-1863 (2008)) decreased the ability of LSK Flk2⁻ cells to expand in a dose-dependent manner (FIG. 21). Also, the ability of CHIR99021 to enhance expansion was negated by PI3K inhibition (FIG. 21). Together, these data demonstrate that stimulation of PI3K signaling is required for substantial HSC expansion in our culture system. Indeed, a recent study reports that the growth factor pleiotrophin expands HSCs, in part, by activating PI3K signaling (Himburg, H. A. et al. "Pleiotrophin regulates the expansion and regeneration of hematopoietic stem cells" *Nat Med* Vol 16, pages 475-482 (2010)).

One hundred LSK Flk2⁻ cells were sorted from wild-type (C57Bl/6) mice and cultured in (1) media, (2) media+1 μM CHIR99021 (a GSK-3β inhibitor, a gift from Dr. Sheng Ding), (3) media+200 nM Dipotassium Bis-peroxo(picolinato)oxovanadate (BpV(pic), a PTEN inhibitor, available from Calbiochem, Cat. No. 203705), (4) media+1 μM CHIR99021+200 nM BpV(pic), (5) media+200 nM Shikonin (also a PTEN inhibitor, available from Calbiochem, Cat. No. 565850), and (6) media+200 nM Shikonin+1 μM CHIR99021. (FIGS. 3B-C). Cells were cultured as described above. Cells were examined at 17 days of culture (FIG. 3B, original magnification 100×) and 23 days (FIG. 3C, original magnification 40×). Compared to control, both inhibitors applied individually exhibited greater expansion of LSK cells indicating that GSK-3β inhibition is not strictly equivalent to constitutive activation of β-catenin shown in Ctnnb1 mutant LSKs, while BpV(pic) exhibited similar results compared to Pten mutant LSKs (see FIG. 2). Similar to double mutant LSKs (FIG. 2), the greatest expansion occurred with both inhibitors present (FIG. 3B/C panel 4).

LSK Flk2⁻ cells at 28 days culture in the indicated media conditions were examined (FIG. 3D, original magnification 200×). Here, significant expansion relative to control was observed with both inhibitors present individually; however, significant differentiation/heterogeneity of cell morphology was observed in both cases, including more variable cell size/morphology and/or differentiation to adherent, spindle-shaped cells (middle panels). In contrast, expansion with homogeneity was achieved when both inhibitors were present (last panel).

FACS analysis of 28 day LSK Flk2$^-$ cells cultured in media+BpV(pic)+CHIR99021 (FIG. 3E) was performed. Cells were pre-gated on live, lineage negative cells. Greater than 90% of LSKs retained Flk2 negativity (data not shown). Thus, the LSK Flk2$^-$ phenotype was maintained with high purity in cultures containing both inhibitors.

Fold expansion of LSK Flk2$^-$ cells after 28 days culture in (1) media, (2) media+BpV(pic), (3) media+CHIR99021, and (4) media+CHIR99021+BpV(pic) were analyzed. While each inhibitor added individually led to significant expansion compared to media without either inhibitor, the greatest expansion (~270 fold) was observed when both inhibitors were added together.

Example 10

Transplantation Analysis of Cultured Sorted LSK Cells after Ex Vivo Pharmacological Manipulation Cell Harvest and Repopulation Cells were harvested from the wells prior to transplantation by pipetting up and down several times before transferring to a fresh tube. Residual was then collected by adding more media and repeating. Cells were washed in DMEM (Invitrogen, Cat. No. 31053) without phenol red and added to the appropriate number of whole bone marrow rescue cells from a congenic donor (for 200,000 rescue cells+1,000 re-sorted LSK Flk2$^-$ cells (FIGS. 3F-H) or the non-adherent product of 10 days culture of 100 LSK Flk2$^-$ cultured cells (FIGS. 3I-K) per mouse as indicated). Cells were injected into lethally irradiated (10 Grays, single dose) Ptprc (CD45.1$^+$) recipient mice through the tail vein using an insulin syringe.

Repopulation was measured at 4 weeks post-transplant by collection of peripheral blood, red blood cell lysis, and staining of CD45.1 (recipient) compared to CD45.2 (donor) engraftment using antibodies purchased from eBiosciences (FITC conjugated CD45.2 (Cat. No. 11-0454-85) and PE-Cy5 conjugated CD45.1 (Cat. No. 15-0453-82)). Mice transplanted with rescue/competitor cells only were used as a control to determine the limits of repopulation detection. Multi-lineage reconstitution was determined by CD3, B220 (for lymphoid) and Gr1, Mac-1 (for myeloid), as described above.

Transplantation Analysis of 28 Day Cultures.

Cells cultured for 28 days in (1) media, (2) media+BpV (pic), (3) media+CHIR99021 and (4) media+CHIR99021 (1 μM)+BpV(pic) (200 nM) were re-sorted for LSK Flk2$^-$ cells. One thousand LSK Flk2$^-$ cells (CD45.2$^+$) from each media condition were transplanted into lethally irradiated (10 Gy) CD45.1$^+$ recipient mice along with 2×10$^5$ congenic whole bone marrow competitor cells. At 4 weeks post-transplant, peripheral blood was analyzed for donor (FIG. 3G) and multi-lineage (FIG. 3H) engraftment. In FIG. 3G, each bar represents an individual mouse. The horizontal-dashed line represents the average 'engraftment' of mice transplanted with competitor cells only and, thus, the limit of detectability for true engraftment. Long-term (4 month) engraftment has not been observed from 28-day cultures (data not shown). Six of 8 mice show >1% engraftment when transplanted with LSK Flk2$^-$ cells cultured with both inhibitors present compared to 4/8 with only CHIR99021 present, 0/10 with only BpV(pic) present, and 2/6 with media only. One percent or greater engraftment is a standard limit for substantial engraftment. (Zhang, C. C., et al., *Nat Med*, 12(2): 240-5, 2006. Zhang, C. C. and H. F. Lodish, *Blood*, 105(11): 4314-20, 2005). Thus, while both inhibitors together leads to greatest expansion in LSKs (FIG. 2F), transplantation of equivalent numbers of these cultured LSK Flk2$^-$ cells also leads to increased short-term engraftment/functionality when cultured with both inhibitors compared to no or either single inhibitor only.

While all mice with genetic alterations resulting in constitutively active β-catenin and loss of PTEN will develop leukemia and must be sacrificed due to poor health within 8-10 weeks post-mutation induction (FIG. 1I and data not shown), no mice transplanted with LSK Flk2$^-$ cells cultured in either inhibitor singly or in combination has shown any sign of leukogenesis up to 16 weeks post-transplantation. All such mice appeared healthy unlike 8-10 weeks post-induction genetically double mutant mice, exhibiting no loss of body weight, anemia, loss of appetite, lethargy, hunched posture, etc. Thus, the effects of the inhibition of both pathways using, e.g., BpV(pic) and CHIR99021, is reversible.

Transplantation Analysis of 10 Day Cultures.

Cells cultured for 9 days in (1) media, (2) media+BpV (pic) (200 nM), (3) media+CHIR99021 (100 nM), and (4) media+CHIR99021 (100 nM)+BpV(pic) (200 nM) were re-sorted for LSK Flk2$^-$ cells, and fold expansion of LSK Flk2$^-$ cells after 9 days culture in the indicated conditions was determined (FIG. 3I). Because long-term engraftment was not observed from 28 day cultures (FIGS. 3D-H and data not shown), LSK Flk2$^-$ cells were cultured for only 9 days to test if both expansion and long-term repopulation could be achieved. Similar trends were observed here when compare to the 28 day cultures (compare to FIG. 9F) although the extent of expansion was substantially reduced at only 9 days versus 28 days culture.

FACS analysis was performed on 9 day LSK Flk2$^-$ cells cultured in media+BpV(pic) (200 nM)+CHIR99021 (100 nM) (FIG. 3J). Cells were pre-gated on live, lineage negative cells. Greater than 90% of LSKs retain Flk2 negativity (data not shown). Here, the levels of Sca-1 and Kit appear normal compared to the Sca-1$^{(high)}$Kit$^{(high)}$ population shown from 28 day cultures (FIG. 1E).

Ten day cultures were transplanted into lethally irradiated (10 Gy) CD45.1$^+$ recipient mice along with 2×10$^5$ congenic whole bone marrow competitor cells. The total, non-adherent cell product after 10 days culture of 100 initial LSK Flk-2 cells was transplanted per mouse. At 8 weeks post-transplant, peripheral blood was analyzed for donor (FIG. 3G) and multi-lineage (FIG. 3H) engraftment. As shown, multi-lineage reconstitution was observed from all mice exhibiting true engraftment (data not shown). In FIG. 3G, each bar represents an individual mouse; the horizontal-dashed line represents the average 'engraftment' of mice transplanted with competitor cells only and thus the limit of detectability for true engraftment. Here, 3/7 mice transplanted with LSK Flk2$^-$ cells cultured in the presence of both inhibitors exhibited 1% or greater donor engraftment compared to no mice reaching this threshold in the single or no inhibitor groups.

Figure 2:
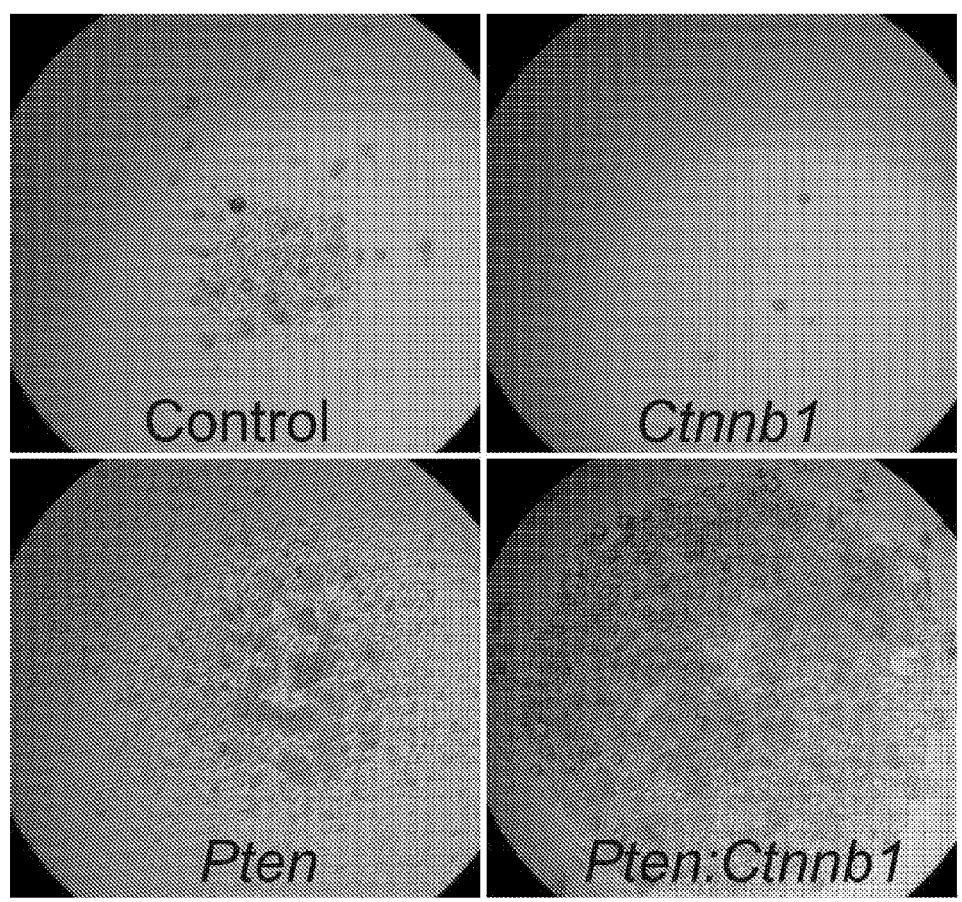
FIGS. 2A-J are a series of photographs, bar graphs, and FACS analyses that collectively show that double mutant HSCs expand dramatically in vitro and in vivo but fail to differentiate.
Figure 2:
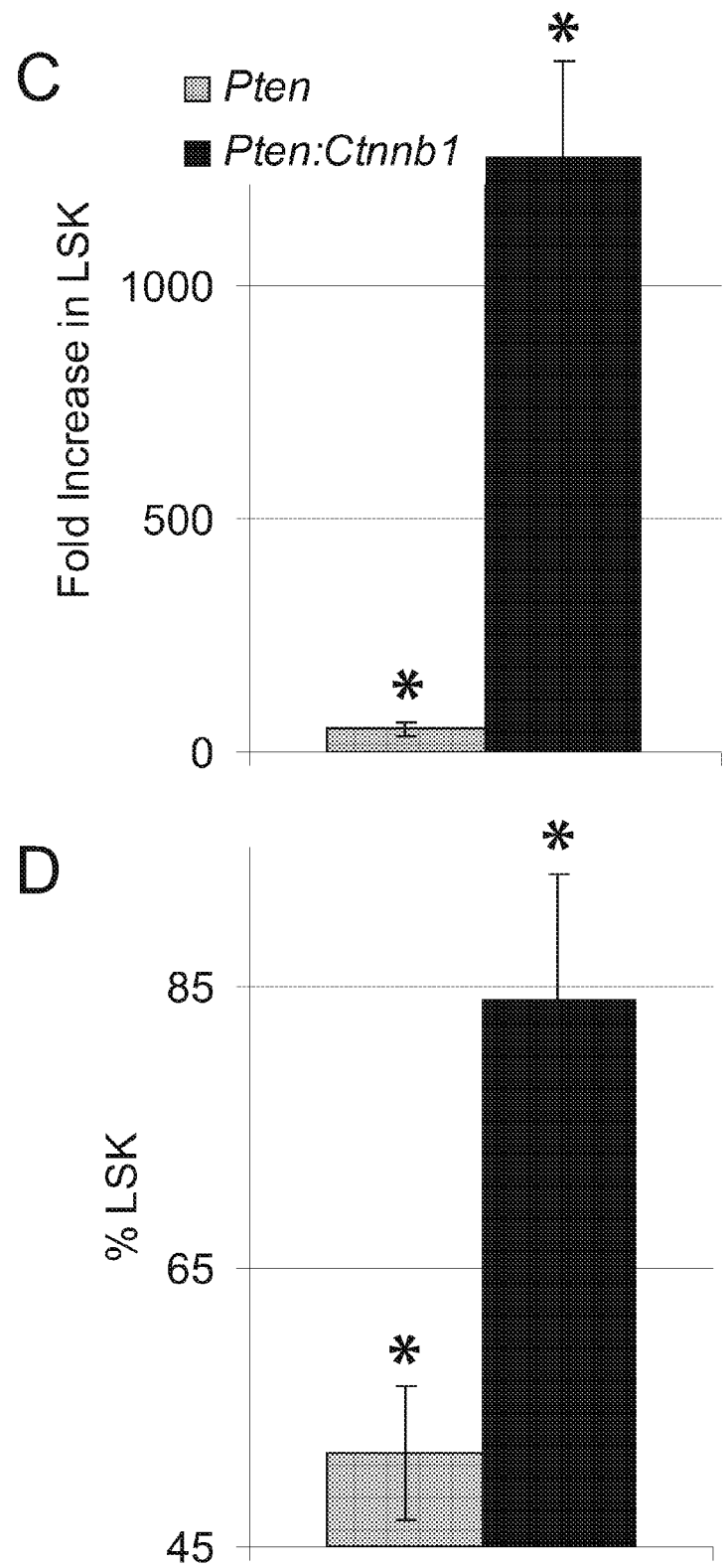
Figure 2:
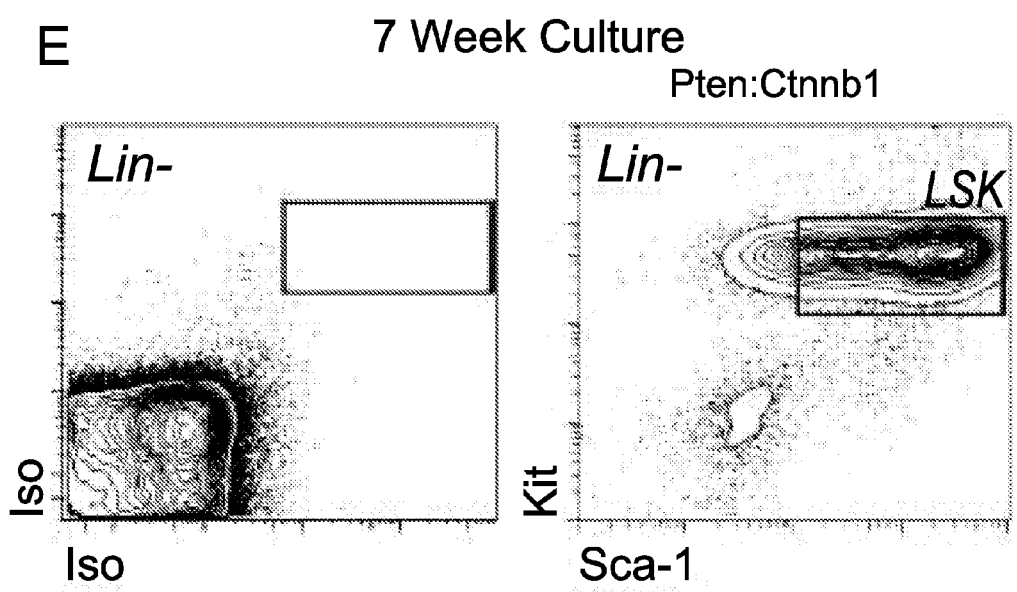
Figure 2:
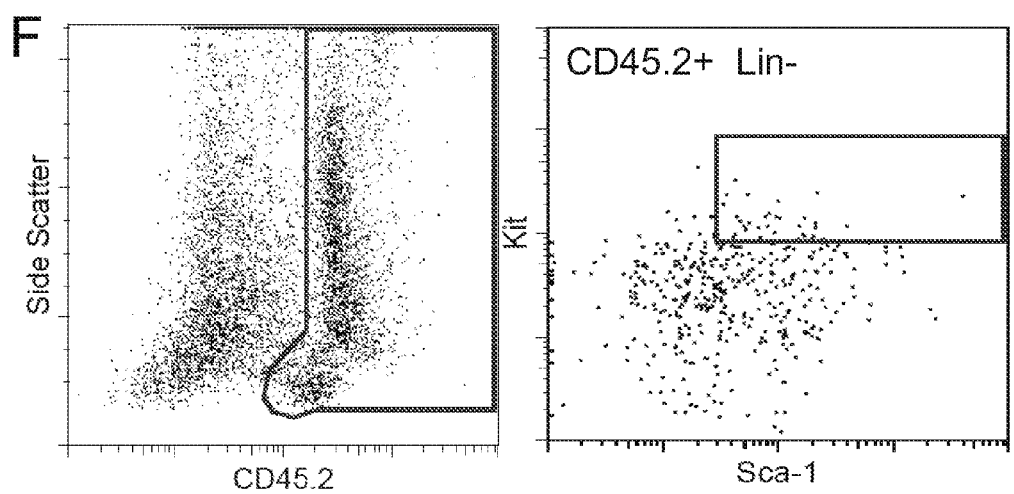
Figure 2:
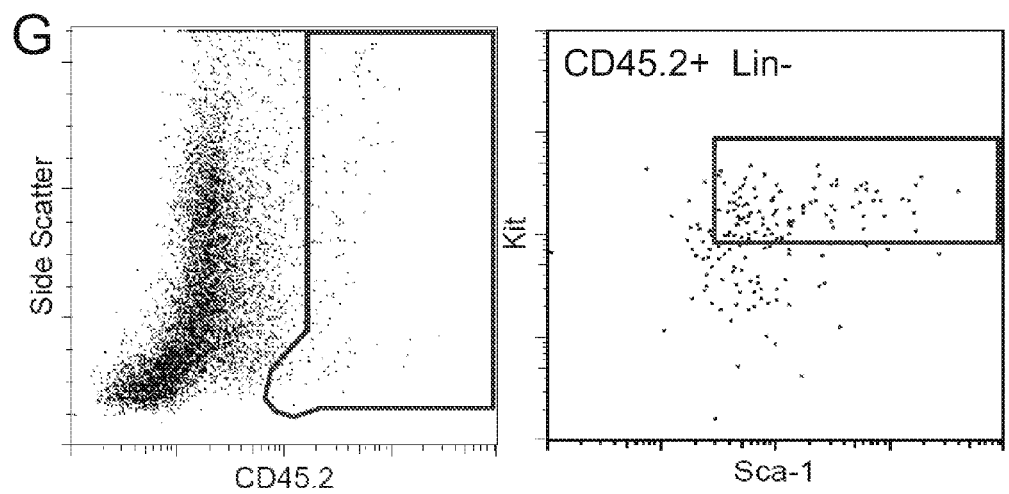

Collectively, these data demonstrate that the PTEN/Akt and Wnt/β-catenin signaling pathways can be manipulated pharmacologically to drive HSC expansion. Functional, short-term HSCs show highest reconstitution ability when cultured in the presence of both inhibitors. Substantial longer-term reconstitution (8 weeks) occurs only when HSCs are cultured in the presence of both inhibitors but not when cultured with either single inhibitor or in the absence of either inhibitor. Thus, the pharmacological manipulation of both pathways simultaneously results in the greatest expansion of functional HSCs. This effect is reversible because recipient animals did not develop leukemia as genetic mutants did (FIG. 1) and cultured HSCs were able to differentiate unlike cultured HSCs from genetic mutants (FIG. 2).

Example 11

Transplantation Analysis of HSCs in a Population of Bone Marrow Mononuclear Cells Materials and Methods For the experiments set forth in this Example, a particular HSC expansion media was used. This HSC expansion media consists of the following ingredients: (1) StemSpan Media (Stem Cell Technologies; Cat. No. 09600) (StemSpan Media consists of Iscove's-modified Dulbecco's medium (IMDM) supplemented with 1% bovine serum albumin, 10 µg/ml recombinant human insulin, 200 µg/ml iron-saturated transferrin, 0.1 mM 2-mercaptoethanol and 2 mM glutamine.); (2)10 µg/ml Heparin (Sigma; Cat. No. H-3149); (3) 0.5× Penicillin/Streptomycin (Sigma; Cat. No. P4333); (4) 10 ng/ml recombinant mouse (rm) or recombinant human (rh) Stem Cell Factor (SCF) (Biovision; Cat. No. 4328-10 or 4327-10, respectively); (5) 20 ng/ml rm or rh Thrombopoietin (Tpo) (Cell Sciences, Inc; Cat. No. CRT401B or CRT400B, respectively). CHIR99021 (250 nM) (Stemgent, Inc; Cat. No. 04-0004) may be added to this HSC expansion media as indicated.

Note that the optimal base media for expanding phenotypic HSCs (StemSpan SFEM, Stem Cell Technologies, Inc.) contained a high concentration of insulin, a major stimulator of the PI3K/Akt pathway. Because the same media without insulin was unable to substantially expand HSCs, expansion of phenotypic HSCs is dependent on insulin in our culture system (FIG. 30). Similarly, SCF, a typical cytokine utilized for ex vivo HSC expansion, also activates the PI3K pathway. It was found that Tpo or SCF alone could not expand HSCs in culture, both Tpo and SCF were necessary for substantial expansion (data not shown).

Cells were cultured in 96-well U-bottom tissue culture plates (Becton, Dickinson and Company; Cat. No. 353077).

Antibodies used are listed below and as set forth in Example 1. The following antibodies were obtained from eBiosciences: FITC conjugated CD45.2 (Cat. No. 11-0454-85), PE-Cy5 conjugated CD45.1 (Cat. No. 15-0453-82), PE conjugated CD34 (Cat. No. 12-0349-73), and APC conjugated CD38 (Cat. No. 17-0389-73).

Cell counts were obtained using a Quanta cell counter/cytometer (Beckman-Coulter). Cell sorting and analysis were performed using a MoFlo (Dako, Ft. Collins, Colo.) flow cytometer and/or a CyAn ADP (Dako, Ft. Collins, Colo.). Frequency of LSK Flk$^-$ cells was determined by analyzing >3×10$^5$ cells per sample independently in triplicate.

Bone marrow cells were harvested from C57Bl/6 (CD45.2) mice and made into a single cell suspension by gently drawing through a 22 g needle several times. Mobilized peripheral blood or bone marrow from human patients was harvested at the University of Kansas Medical Center (Kansas City, Mo. USA). Because red blood cell (RBC) lysis was determined to severely inhibit functional HSC expansion, cells were not exposed to any RBC lysis procedure. Mononuclear cells were isolated from mouse bone marrow using Histopaque 1077 (Sigma; Cat. No. 10771) and human blood or bone marrow using Ficoll-Paque PLUS (Stem Cell Technologies; Cat. No. 07917) according to the manufacturers' instructions. Cells were washed and resuspended in HSC expansion media. Cells were counted and a fraction of mononuclear cells (MNCs) were stained for lineage markers using CD3, CD4, CD8, B220, IgM, Mac-1, Gr1, and Ter119 antibodies along with Kit, Sca-1, and Flk2 for mouse HSC analysis or CD34 and CD38 for human HSC analysis. 1×10$^6$ cells/0.1 ml were stained at 4° C. for 30 minutes using 0.05 µg of antibody for each lineage marker and 0.2 µg for remaining antibodies. Cells were washed twice in staining buffer (1× Phosphate buffered saline (PBS) (Mediatech, Inc, Cat. No. 20-031-CV)+2% fetal bovine serum (FBS) (Gibco-BRL, Cat. No. 16140-071)). Frequency of putative HSCs (lineage negative, Sca-1$^+$, Kit$^+$, Flk-1$^-$ for mouse or CD34$^+$, CD38$^-$ cells for human) was determined by analyzing >3×10$^6$ cells per sample independently in triplicate. MNCs were then plated at 100 putative HSCs (along with 2.5-5.0× 10$^4$ MNCs depending on frequency of putative HSCs in the particular sample—typically 0.2-0.4%) in 200 µl of HSC expansion media per well in a 96-well U bottom plate (Becton, Dickinson and Company; Cat. No. 353077). MNCs were also plated at 50 LSK Flk2$^-$ cells (along with 1.7-5.0× 10$^4$ MNC cells depending on frequency of putative HSC in the particular sample—typically 0.1-0.3%) in 200 µl of HSC expansion media per well in a 96-well U-bottom plate.

Cells were incubated at 37° C. with 5% CO$_2$ and 5% O$_2$ (balance N$_2$) for 14 days. Cultures were checked daily and cell pellets accumulating at the bottom of each well which exceeded 2 mm in diameter were split into new wells at a 1:1 ratio (splitting involved resuspension of the culture cell pellet by gently pipetting up and down 5-7 times and removing ½ of the volume of the original well and placing it into a fresh well. That volume of fresh media was then replaced in each "old" and "new" well). It is critical for optimal HSC expansion that cell pellets are maintained at a density of 1-2 mm in size. Splitting is typically required at day 1 and every 2-3 days thereafter. In parallel, putative HSCs were sorted into 96-well U bottom plates at 100 putative HSCs per well. Sorted putative HSCs were handled equivalently to unsorted cultures. After 14 days culture, the total culture product was harvested by pipetting up and down 10 times and combining into a test tube. Cells were washed and resuspended in DMEM (Invitrogen; Cat. No. 31053) in a volume equivalent to 5 original input putative HSCs per 100 µl for unsorted HSC cultures (for example, a well containing MNCs with 100 putative HSCs along with its descendant wells resulting from splitting would be resuspended in 2,000 µl) or 100 original input putative HSCs per 100 µl for sorted HSC cultures.

For competitive repopulation assays, 1×10$^5$ bone marrow cells congenic with the host (CD45.1$^+$) were included per mouse. 100 µl of cultured cells or cells freshly isolated and quantified in the same manner were transplanted into lethally irradiated (10 Grays, single dose) Protein tyrosine phosphatase, receptor type, C (Ptprc or CD45.1) recipient mice through the tail vein using an insulin syringe (29 gauge). Mice were placed on Batril® water (Bayer Healthcare, LLC, Shawnee Mission, Kans.) 3 days prior to irradiation which continued for 2 weeks post-irradiation. Repopulation was measured every 4 weeks post-transplant by collection of peripheral blood, red blood cell lysis and staining of CD45.1 (recipient) vs. CD45.2 (donor) engraftment. Mice transplanted with rescue/competitor cells only were used as a control to determine the limits of detectable repopulation (typically 0.2%). Multi-lineage reconstitution was determined by CD3, B220 (for T and B lymphoid, respectively) and Gr1, Mac-1 (for myeloid) gating on donor (CD45.2+) cells. For secondary transplantation, the original, primary transplant recipients were sacrificed and bone marrow was harvested from the femur, made into a single-cell suspension, and strained through a 70 μM cell strainer (BD Biosciences; Cat. No. 21008-952). Bone marrow cells were counted and transplanted as above at a dosage of 1×10$^6$ per mouse.

Experimental Results

The effect of GSK3β inhibition (using lithium or the small molecule inhibitor CHIR99021) in the HSC culture system was tested. It was found that increasing concentrations of GSK3β inhibitor resulted in increasing proportions of LSK cells relative to early myeloid progenitors. Specifically, without GSK3β inhibition, the frequency of early myeloid progenitors was more than twice as high as that of LSK cells. However, addition of GSK3β inhibitor decreased the frequency of myeloid progenitors but increased the frequency of LSK cells, yielding equivalent frequencies of early myeloid and LSK cells (FIG. 26A). Although the pre-culture frequency of LSK cells was only 0.14±0.08% in bone marrow MNCs, this increased to 9.5±0.9% after 14 day culture in ST media and further increased to 15.1±1.1% with GSK3β inhibitor addition. Although the total number of cells after culture was not increased, the total number of LSK Flk2$^-$ cells increased 78-fold on average which further increased to 93-fold with GSK3β inhibitor addition (FIG. 26B). Interestingly, these data partially mimic the genetic mutant animal models disclosed above.

To determine whether the culture method expands not only phenotypic but also functional HSCs, in vivo transplantation assays were performed. The results show that ex vivo expansion of unsorted bone marrow mononuclear cells enhances functional long-term hematopoietic reconstitution in vivo relative to sorted, ex vivo expanded HSCs (FIG. 4). These data demonstrate that the culture methodology set forth above results in substantial expansion of functional HSCs with long-term, multi-lineage repopulating potential. The presence of non-stem cells is critical to this expansion, demonstrating that the typical practice of purifying specific putative HSC populations is not ideal for the ex vivo expansion of HSCs. Indeed, the cultured product of MNCs containing only 5 putative HSCs exhibits increased repopulation potential compared to 100 sorted putative HSCs which are either freshly isolated or also cultured. Secondary transplant experiments further demonstrate that functional, long-term repopulating HSCs have been expanded with all recipients exhibiting >25% donor repopulation with the average being >60%. In contrast, an equivalent sample of unexpanded MNCs yields long-term (16+ weeks) donor repopulation of <1% in all recipients, with 2/5 recipients being at or below levels of detectable engraftment. This culture expansion protocol meets rigorous functional tests, including the ability to yield high levels of repopulation even in the presence of 10$^5$ fresh, uncompromised competitor cells and in serial transplantation experiments, conditions that are generally more rigorous than those encountered clinically.

The results further showed that culture with the small-molecule inhibitor of GSK-3β, CHIR99021, enhances long-term engraftment of ex vivo expanded HSCs (FIGS. 5 and 13). While 100 sorted, putative HSCs cultured without CHIR99021 yield average repopulation of 1.1%, culturing with CHIR99021 yields average repopulation of 12.3%. Similarly, unsorted MNC cultures in the absence and presence of CHIR99021 yields average repopulation of 37.4 and 64.8%, respectively. These data demonstrate that ex vivo expansion in the presence of a small molecule inhibitor of GSK-3β, CHIR99021, substantially increases the level of long-term, multi-lineage engraftment.

Similarly, culture with another small-molecule inhibitor of GSK-3β, lithium, also enhanced long-term engraftment of ex vivo expanded HSCs, as shown in FIGS. 22 and 23.

To quantify the number of functional HSC resulting from the culture system, limiting-dilution, competitive repopulating unit (CRU) assays were performed (Delaney, C. et al. Notch-mediated expansion of human cord blood progenitor cells capable of rapid myeloid reconstitution. *Nat Med* Vol. 16, pages 232-236 (2010); Zhu, X. et al. A versatile approach to multiple gene RNA interference using microRNA-based short hairpin RNAs. *BMC molecular biology* Vol. 8, page 98 (2007)). Poisson statistical analysis of n=60 total recipient mice showed that, based on pre-culture number of LSK Flk2$^-$ cells, the cultured progeny contained a frequency of 1/2 CRU (95% confidence interval: 1/1 to 1/5) for ST media conditions, but when CHIR99021 was added, the frequency was 1/0.4 (95% confidence interval: 1/0.2 to 1/0.8) (FIG. 27A). Thus, addition of CHIR99021 increases the CRU frequency by an average of 5-fold (2/0.4).

More mature, radioprotective cells are necessary for short-term survival of recipients transplanted with purified HSCs, and early myeloid progenitors have been found to confer this radioprotective effect (Na Nakorn, T., Traver, D., Weissman, I. L. & Akashi, K. Myeloerythroid-restricted progenitors are sufficient to confer radioprotection and provide the majority of day 8 CFU-S. *The Journal of clinical investigation* 109, 1579-1585 (2002)). Considering the high frequency of progenitor cells present in the culture system (FIG. 26A), the inventors hypothesized that the culture system might allow for the transplantation of only ex vivo expanded cells without the necessity of any fresh competitor/radioprotective bone marrow cells. Eliminating the need for fresh, whole bone marrow cells would make the culture system more relevant to and useful in a potential clinical setting—indeed, short-term repopulation is equally critical to survival. To test this, after 14 days culture in ST media with and without CHIR99021, only the cultured product of MNCs containing 5 LSK Flk2$^-$ cells were transplanted into lethally irradiated recipients. For comparison, fresh, uncultured MNCs containing 5 LSK Flk2$^-$ cells per mouse were also transplanted. In addition, because the average 14-day expansion of LSK Flk2$^-$ cells in the unsorted cultures was approximately 100-fold (FIG. 26B), fresh, uncultured MNCs containing 500 LSK Flk2$^-$ cells (100× uncultured cells) were also transplanted into lethally irradiated recipients for comparison. No rescue/competitor cells were added in these groups. While recipients of uncultured MNCs containing 5 LSK Flk2$^-$ cells had to be sacrificed due to bone marrow failure between 2-3 weeks post-irradiation, mice transplanted with only cultured cells containing 5 LSK Flk2$^-$ cells or fresh MNCs containing 500 LSK Flk2$^-$ cells recovered. In these surviving groups, all primary recipients exhibited robust donor engraftment (>90%) with no significant difference between groups (FIG. 27B).

To determine if CHIR99021 was affecting the long-term potential of HSCs, the primary recipients were euthanized, and serial bone marrow transplantation into secondary, lethally-irradiated recipients was performed. At 16 weeks post-secondary transplant, donor reconstitution was 67.3±20.6% for ex vivo expansion in ST media and 90.6±4.8% in ST media with CHIR99021 (FIGS. 6G and 6H). Notably, there was no significant difference in long-term, multi-lineage donor reconstitution between mice receiving ex vivo expanded HSCs in the presence of CHIR99021 and mice receiving a 100-fold greater dosage of fresh LSK Flk2⁻ cells (90.6±4.8% vs. 90.1±3.1, respectively; p=0.88). Thus, at 16 weeks, secondary transplant recipients of cells cultured in ST media exhibited reduced average repopulation compared to secondary recipients of cells cultured in ST+CHIR99021 or 100× uncultured cells.

Bone marrow cells from these secondary recipients were then transplanted into tertiary recipients. At 16 weeks, average repopulation of tertiary recipients of cells cultured in ST media was again further reduced relative to recipients of cells cultured with CHIR99021 or 100× uncultured cells. Notably, tertiary recipients of cells cultured with CHIR99021 or 100× uncultured cells exhibited equivalent levels of repopulation with no statistical difference between the two groups (P=0.9) (FIG. 27B).

While tertiary recipients of cells cultured without CHIR99021 all succumbed to bone marrow failure by 6 months post-transplantation, recipients of cells cultured with CHIR99021 exhibited survival rates similar to tertiary recipients of 100× uncultured cells (FIG. 27C). Importantly, even those mice euthanized due to poor health did not exhibit signs of leukemia but rather succumbed to bone marrow failure, exhibiting low overall blood cell counts (data not shown). Thus, unlike the results of permanent genetic manipulation in vivo, the transient ex vivo manipulation of the PI3K/Akt and/or Wnt/β-catenin pathways does not result in leukemic transformation. These data demonstrate that functional LT-HSCs can be expanded ex vivo to a significantly greater degree when they are not fractionated from more mature cells. Furthermore, by manipulating the Wnt/β-catenin pathways, inhibition of GSK3β, e.g. with CHIR99021 or with lithium, during ex vivo HSC expansion substantially enhances long-term donor reconstitution.

These data demonstrate that the ex vivo expansion protocol allows for transplantation of only the cultured product of MNCs containing 5 putative HSCs, resulting in long-term survival of recipients. No fresh, rescue bone marrow cells are required. In contrast, transplantation of fresh, unexpanded MNCs containing 5 putative HSCs does not allow any of the recipients to survive beyond 2-3 weeks, the typical survival time of mice receiving lethal irradiation without transplantation (Na Nakorn, T., Traver, D., Weissman, I. L. & Akashi, K. Myeloerythroid-restricted progenitors are sufficient to confer radioprotection and provide the majority of day 8 CFU-S. *The Journal of clinical investigation*, Vol. 109, 1579-1585 (2002)). Thus, in addition to the expansion of long-term repopulating HSCs, short-term radioprotective cells are also expanded utilizing the ex vivo expansion protocol. With the inclusion of CHIR99021 during ex vivo expansion, the level of repopulation of recipients of ex vivo expanded MNCs containing 5 putative HSCs is equivalent to fresh, unexpanded MNCs containing 500 putative HSCs at 16 weeks post-secondary transplantation. This data demonstrates that the ex vivo expansion protocol allows for long-term repopulation equivalent to a 100-fold greater dose of fresh, unexpanded cells.

The data obtained from experiments involving ex vivo expansion of human HSCs (FIG. 7) indicate that the culture methodology developed in the mouse system should translate into the human system, allowing for substantial expansion of HSCs in culture. This should allow for currently limited sources of HSCs, such as umbilical cord blood, which is widely available but is low in cell number, to be utilized with greater efficacy.

HSCs are known to be able to undergo considerable expansion in vivo and are the most extensively studied stem cell system. It is somewhat paradoxical, therefore, that they remain difficult to expand in culture, although progress has been recently achieved, particularly by activation of the Notch pathway (Himburg, H. A. et al. Pleiotrophin regulates the expansion and regeneration of hematopoietic stem cells. *Nat Med* 16, 475-482 (2010); Antonchuk et al., HOXB4-induced expansion of adult hematopoietic stem cells ex vivo. *Cell* 109, 39-45 (2002); Butler, J. M. et al. Endothelial cells are essential for the self-renewal and repopulation of Notch-dependent hematopoietic stem cells. *Cell stem cell* 6, 251-264 (2010); Delaney, C. et al. Notch-mediated expansion of human cord blood progenitor cells capable of rapid myeloid reconstitution. *Nat Med* 16, 232-236 (2010)). Typically, only modest expansion being consistently achieved, while more significant expansion is usually coupled with substantial differentiation (North, T. E. et al. Prostaglandin E2 regulates vertebrate haematopoietic stem cell homeostasis. *Nature* 447, 1007-1011 (2007).; Kobayashi, M., Laver, J. H., Kato, T., Miyazaki, H. & Ogawa, M. Thrombopoietin supports proliferation of human primitive hematopoietic cells in synergy with steel factor and/or interleukin-3. *Blood* 88, 429-436 (1996); Antonchuk, J., Sauvageau, G. & Humphries, R. K. HOXB4-induced expansion of adult hematopoietic stem cells ex vivo. *Cell* 109, 39-45 (2002); Varnum-Finney, B. et al. Pluripotent, cytokine-dependent, hematopoietic stem cells are immortalized by constitutive Notch1 signaling. *Nat Med* 6, 1278-1281 (2000)). In addition, ex vivo expansion protocols often use genetically modified cells or feeder layers which may present difficulties in translating to a clinical setting.

Driving self-renewal appears to require activation of certain proto-oncogenes along with simultaneous inhibition of certain tumor suppressors, a combination that limits regenerative capacity and makes substantial expansion difficult without risking oncogenesis or stem cell exhaustion (Reya, T. et al. A role for Wnt signaling in self-renewal of haematopoietic stem cells. *Nature* 423, 409-414 (2003); Yilmaz, O. H. et al. Pten dependence distinguishes haematopoietic stem cells from leukaemia-initiating cells. *Nature* 441, 475-482 (2006); Zhang, J. et al. PTEN maintains haematopoietic stem cells and acts in lineage choice and leukaemia prevention. *Nature* 441, 518-522 (2006); Varnum-Finney, B. et al. Pluripotent, cytokine-dependent, hematopoietic stem cells are immortalized by constitutive Notch1 signaling. *Nat Med* 6, 1278-1281 (2000); Matsuoka, S. et al. Fbxw7 acts as a critical fail-safe against premature loss of hematopoietic stem cells and development of T-ALL. *Genes Dev* 22, 986-991 (2008); Park, I. K. et al. Bmi-1 is required for maintenance of adult self-renewing haematopoietic stem cells. *Nature* 423, 302-305 (2003); Perry, J. M. & Li, L. Self-renewal versus transformation: Fbxw7 deletion leads to stem cell activation and leukemogenesis. *Genes Dev.* 22, 1107-1109 (2008)). Simultaneous manipulation of proto-oncogene and tumor suppressor activity can achieve substantial stem cell expansion in vitro; however, it is critical to balance this transient expansion with return to conditions that mimic the in vivo situation where relative quiescence is recovered and tumor suppressors are reactivated.

Although sorting specific populations enriched in HSCs has been the typical methodology utilized for culturing HSCs, the inventors found ex vivo HSC expansion to be best supported when cultured in the presence of more mature cells. It was observed that sorted LSK Flk2⁻ cells typically declined in number within the first 48 hours in culture. Indeed, when LSK Flk2⁻ cells were sorted, substantial HSC expansion was achieved only after some differentiation had occurred, yielding HSCs in an environment surrounded by mature cells, a situation similar to that encountered by HSCs in vivo. It may be that HSCs negatively inhibit self-renewal and even survival of other HSCs in close proximity, helping to maintain stem cells as a rare population in vivo. Culturing unsorted HSCs combined with other technical procedures results in robust functional HSC expansion. While the ex vivo HSC expansion protocol yielded robust long-term reconstitution, even in competitive repopulation assays, competitor or rescue bone marrow cells were not necessary following ex vivo expansion, demonstrating that radioprotective cells also expanded in the culture system. Utilizing a small molecule inhibitor of GSK3β, the ex vivo HSC expansion protocol allowed for expansion of LT-HSCs which performed equivalently to a 100-fold greater dosage of uncultured cells even in long-term, serial transplant recipients. Beyond this expansion, there is a distinct practical advantage with the disclosed culture system. By employing a serum-free with relatively low concentrations of only two cytokines, but without the necessity of feeder layers, cell sorting, or the use of fresh bone marrow for radioprotection, this culture system may have clinical value if developed for humans.

In summary, this process for the ex vivo expansion of hematopoietic stem cells utilizes defined culture media supplemented with low concentrations of only two specific cytokines and does not require complicated schemes such as cell sorting or contaminating cellular feeder layers. Therefore, it allows for fast, simple and relatively inexpensive expansion of functional HSCs. In addition, HSC transplantation following myeloablative therapy requires the transplantation of radioprotective cells, typically whole bone marrow cells, for short-term survival prior to the establishment of long-term hematopoiesis by HSCs (Paquette, R. & Dorshkind, K. Optimizing hematopoietic recovery following bone marrow transplantation. The Journal of clinical investigation 109, 1527-1528 (2002)). This HSC expansion protocol also expands these radioprotective cells, allowing for the transplantation of the cultured product alone. When cultured with the small molecule CHIR99021, an inhibitor of GSK-3β, this ex vivo expansion protocol allows for long-term repopulation equivalent to a 100-fold greater dose of fresh, unexpanded cells.

Example 12

Culturing of HSC in Media Containing Biologics

Anti-GSK-3β and anti-PTEN antibodies may be made in accordance with procedures known in the art (or purchased, e.g., from Sigma, ExactAntigene, and Biocompare).

One hundred LSK Flk2⁻ cells are sorted from wild-type (C57Bl/6) mice and are cultured in (1) media, (2) media+an GSK-3β antibody, (3) media+an anti-PTEN antibody, and (4) media+anti-GSK-3β and anti-PTEN antibodies. Cells are cultured as described above. Cells are examined at 9 days, 17 days and 23 days of culture. The greatest expansion of HSCs is expected to occur when both antibodies are present.

Example 13

Culturing of HSC in Media Containing siRNA or RNAi

PTEN siRNA and GSK-3b siRNA may be made in accordance with procedures known in the art. (See, e.g., Mise-Omata S et al. *Biochem Biophys Res Commun.* 328 (4):1034-42 2005, or may be purchased from Biocompare).

One hundred LSK Flk2⁻ cells are sorted from wild-type (C57Bl/6) mice and are cultured in (1) media, (2) media+ GSK-3β siRNA, (3) media+PTEN siRNA, and (4) media+ GSK-3β siRNA and PTEN siRNA. Cells are cultured as described above. Cells are examined at 9 days, 17 days and 23 days of culture. The greatest expansion of HSC is expected to occur when both siRNAs are present.

Example 14

Expansion of Human Long-Term Reconstituting Hematopoietic Stem Cells

HSC expansion media (ST media) consists of StemSpan SFEM media (Stem Cell Technologies, Vancouver, Canada) supplemented with 10 µg/ml heparin (Sigma, St. Louis, Mo.), 0.5× Penicillin/Streptomycin (Sigma, St. Louis, Mo.), 10 ng/ml recombinant human (rh) SCF and 20 ng/ml rh-Tpo (Biovision, Inc., Mountain View, Calif.). 2 mM lithium chloride (LiCl) and/or 1 µM StemRegenin 1 (SR1, Cellagen Technologies, San Diego, Calif.) were added as indicated in FIG. 31. Human umbilical cord blood (UCB) cells were obtained from healthy donors at the University of Kansas Medical Center (Kansas City, Kans.) or the St. Louis Cord Blood Bank (St. Louis, Mo.). MNCs were isolated using Ficoll-Paque™ PLUS (GE Healthcare) according to manufacturer's instructions. Cells were washed and resuspended in HSC expansion media. Total nucleated cell counts were obtained using a Quanta cell counter (Beckman-Coulter, Inc., Fullerton, Calif.). $1 \times 10^5$ MNCs were then plated in 200 µl of HSC expansion media per well in a 96-well U-bottom plate (Becton, Dickinson and Company; Cat. No. 353077). Cells were incubated at 37° C. with 5% $CO_2$ and 5% $O_2$ (balance $N_2$) for 14 days. Cultures were checked daily, and cell pellets accumulating at the bottom of each U-shaped well that exceeded 2 mm in diameter were split by transferring ½ of the culture into a fresh well. It is critical for optimal HSC expansion that cell pellets are maintained at a density of 1-2 mm in size. At least ½ volume of media was replaced every 2-3 days. After 14 days culture, the total culture product was harvested, and cells were washed and resuspended in DMEM (Invitrogen; Cat. No. 31053). The cultured product of $2 \times 10^5$ MNCs per mouse were transplanted by IV (tail vein) injection into irradiated (325 cGy) NOD/SKID/IL2Rγ (NSG) recipient mice. Mice were placed on Baytril water 3 days prior to irradiation and continued for 2 weeks post-irradiation. Repopulation was measured at 13 weeks post-transplant (primary recipients) by collection of bone marrow and staining for anti-human CD45 vs. anti-mouse CD45. Multilineage reconstitution was determined by anti-human CD19 (lymphoid), CD13, and anti-human CD33 (Myeloid). For secondary transplantation, the original primary transplant recipients were sacrificed, and bone marrow was harvested from the femurs and tibias, made into a single-cell suspension, and strained through a 70 µM cell strainer. Bone marrow cells were counted and transplanted as above at a dosage of $5 \times 10^6$ per irradiated (325 cGy) NSG recipient. Repopulation analysis of recipient bone marrow was performed on secondary recipients at 19 weeks post-transplant.

The results of the experiment are shown in FIG. 31, which shows that the activation of both Wnt/β-catenin and PI3K/Akt signaling during ex vivo expansion preferentially expands human, long-term reconstituting hematopoietic stem cells (LT-HSC). These data demonstrate that simultaneous activation of both the Wnt/β-catenin and PI3K/Akt signaling pathways preferentially expands human UCB-derived LT-HSC compared to SR1 using the culture method disclosed herein (see also Perry et al., Cooperation between both Wnt/β-catenin and PTEN/PI3K/Akt signaling promotes primitive hematopoietic stem cell self-renewal and expansion. Genes & Development. 25: 1928-1942 (2011)). All recipients with human engraftment showed both lymphoid and myeloid (multi-lineage) repopulation (data not shown).

Example 15

Hypomethylated State in the Maternal DMR of the H19 Gene is Required for Long Term Maintaining Quiescent, Long-Term Hematopoietic Stem Cells In Vivo Bone marrow cells isolated from the maternally deleted hypomethylated region of imprinting gene H19 (H19DMR) were analyzed by flow cytometry. Representative FACS analysis of gated on Lineage negative$^-$Sca-1$^+$, CD34 and Flk2 expression after conditional deletion of H19 DMR are shown in FIG. 32. FIG. 32A shows a FACS plot of a control littermate. FIGS. 32B and 32C are FACS plots at different time points. FIG. 32D shows the absolute number of stem cells at different time points from a mutant and its control littermate. FIG. 32E shows a competitive repopulation unit plot for different doses of bone marrow cells transplanted from a mutant and its control littermate to the recipient mice. FIG. 32G shows analysis of % donor engraftment 16 weeks after secondary transplant using the competitive repopulation assay. FIG. 32F shows a representative DNA sequencing after bisulphite conversion in a mutant and its control littermate. These data indicate that the hypomethylated state in the differentiation methylation region (DMR) in the H19-Igf2 locus in vivo is required for long-term HSC maintenance in mouse. With increased methylation, there is an increase in differentiation.

Example 16

Inhibition of DNA Methyltransferase (DNMT) Activity Enhances Phenotypic HSC Expansion in Long-Term, Ex Vivo Cultures Cells were cultured in STL media, which consists of the following: StemSpan SFEM media (Stem Cell Technologies, Vancouver, Canada) supplemented with 10 µg/ml heparin (Sigma, St. Louis, Mo.), 0.5× Penicillin/Streptomycin (Sigma, St. Louis, Mo.), 10 ng/ml recombinant human (rh) SCF, 20 ng/ml rh-Tpo (Biovision, Inc., Mountain View, Calif.), and 2 mM lithium chloride (LiCl).

Mononuclear cells (MNCs) were isolated from human umbilical cord blood (UCB) and cultured in STL media (activating both Wnt/β-catenin and PI3K/Akt signaling), STL+StemRegenin1 (SR1), or STL+DNMT inhibitor (DNMTi) and analyzed by flow cytometry. FIG. 33A shows representative FACS analysis of Lineage negative (Lin$^-$), CD34 and CD38 expression on UCB prior to culture and in the indicated culture conditions at 41 days post-culture. FIG. 33B shows the frequency of Lin$^-$, CD34$^+$, CD38$^-$ cells before and after culture. FIG. 33C shows the fold-increase in Lin$^-$, CD34$^+$, CD38$^-$ cells for the indicated culture conditions following 6 weeks culture. 1 µM SR1 (Cellagen Technologies, San Diego, Calif.) or 500 nM of DNMTi (5-Aza-2'-deoxycytidine, A3656, Sigma, St. Louis, Mo.) was added where indicated. DNMTi was prepared fresh in DMSO and added from the start of the culture. 24 hours later, about 75% of media was changed using fresh DNMT inhibitor. 60 hours after culture began, no additional DNMT inhibitor was added during media changes. These data indicate that human UCB-derived HSC expansion is enhanced by addition of DNMT inhibitor in long-term ex vivo culture. Unlike DNMT inhibition, SR1 did not enhance overall HSC expansion in long-term cultures relative to the base media (STL media activating both Wnt/β-catenin and PI3K/Akt signaling).

Example 17

Transplantation of Cells Obtained from Human Umbilical Cord Blood Cultured in Media Activating Both the PI3K/Akt and Wnt/β-Catenin Pathways Improves Survival of Xenograft Recipient Mice Mononuclear cells (MNCs) were isolated from human umbilical cord blood (UCB) and cultured in STL media (activating both Wnt/β-catenin and PI3K/Akt signaling), STL+1 µM StemRegenin1 (SR1) (Cellagen Technologies, San Diego, Calif.), or STL+DNMT inhibitor (DNMTi) (15 nM of Decitabine, cat# S1200, SelleckChem, Houston, Tex.). The contents of the STL media is as set forth above.

CD34$^+$ cells were enriched using magnetic MicroBead separation kits (cat. #130-046-703; Miltenyi Biotec, Inc., Auburn, Calif., USA) according to manufacturer's instructions. Two rounds of enrichment were performed.

For human HSC isolation, CD34$^+$ enriched wells were stained for lineage (mature) cells, CD34 and CD38. Lineage negative CD34$^+$ CD38$^-$ phenotypic HSCs were sorted by FACS (fluorescence activated cell sorting).

Mononuclear cells (MNCs) from human umbilical cord blood (UCB) were divided into four equal portions and either 1) transplanted into sub-lethally irradiated (3.25 Gy) NOD SKID IL2Rγ (NSG) recipients or, 2) cultured for 2 weeks in STL media prior to transplantation, 3) enriched for CD34$^+$ cells prior to transplant, or 4) enriched for CD34$^+$ cells, cultured for 2 weeks and then transplanted. Survival of recipients was monitored for more than 45 days. The results are shown in FIG. 34. Transplantation of the cultured product of either MNCs or CD34$^+$ cells resulted in survival of all recipient mice. In contrast, all mice transplanted with uncultured MNCs succumbed within the first 4 weeks after transplant. Transplantation of uncultured CD34$^+$ enriched cells resulted in survival of one-half of recipient mice.

These data indicate that ex vivo expansion of cells in media activating both the PI3K/Akt and Wnt/β-catenin pathways enhances survival of xenograft recipients. Transplantation of uncultured MNCs results in morbidity of all transplant recipients. Preliminary evidence suggests this morbidity is due to acute graft vs. host disease (GvHD). This effect is eliminated by the ex vivo HSC expansion protocol.

Example 18

Using MNCs Rather than Sorted HSCs as the Original Culture Input Results in Further HSC Expansion in Media Activating Both the PI3K/Akt and Wnt/β-Catenin Pathways 600 HSCs (lineage negative, CD34$^+$, CD38$^-$ cells) were sorted from human UCB and transplanted into sub-lethally irradiated (3.25 Gy) NSG recipients or cultured for 2 weeks in STL media prior to transplantation. MNCs containing 600 HSCs were also cultured equivalently and transplanted. The results are shown in FIG. 35. The uncultured MNC group is not shown due to morbidity of transplant recipients.

These data demonstrate that ex vivo expansion using media activating both the PI3K/Akt and Wnt/β-catenin pathways expands functional human HSCs. Furthermore, use of MNCs rather than purified HSCs enhances this expansion. In either culture condition, relatively normal proportions of lymphocytes and myeloid cells are obtained whereas uncultured HSCs yield abnormally high levels of lymphocytes.

Example 19

Brief Exposure to Low Levels of the Epigenetic Modulator, Decitabine, Enhances the Expansion of Functional, Primitive Human HSCs MNCs were isolated from human UCB and cultured in STL media or STL media with the DNA methyltransferase inhibitor (DNMTi), Decitabine, added at the concentration of 15 nM. DNMTi was prepared fresh in DMSO and added 12 hours after the start of the culture. Media containing Decitabine was replaced with freshly prepared media every 24 hours two more times. 72 hours after adding Decitabine initially, Decitabine was removed from the culture.

HSC expansion was determined by FACS analysis 6 weeks post-culture. The results are shown in FIG. 36A. It was observed that no significant HSC expansion was observed at 2 or 4 weeks post-culture (data not shown).

For the transplant experiments, MNCs isolated from human UCB were cultured in media activating the PI3K/Akt pathway (ST media), ST media with StemRegenin1 (SR1), media activating both the PI3K/Akt and Wnt/β-catenin pathways (STL media), or STL media+DNMTi for 14 days. The cultured progeny of $2 \times 10^5$ MNCs per recipient were transplanted into sub-lethally irradiated (3.25 Gy) NSG recipients. 12 weeks post-transplant, bone marrow was harvested and transplanted into secondary recipients ($2 \times 10^6$ whole bone marrow cells from a primary mouse per secondary recipients). 12 weeks post-secondary transplant, human donor cells repopulation was determined (FIG. 36B).

These data demonstrate that media activating both the PI3K/Akt and Wnt/β-catenin pathways expands functional, primitive human HSCs. This expansion is further enhanced by the inhibition of DNMT.

Example 19

Long-Term Ex Vivo Expansion of Human CD34$^+$ Cells in Media Activating Both the PI3K/Akt and Wnt/β-Catenin Pathways Yields Normal Karyotypes CD34$^+$ cells were enriched from human UCB. One portion of these cells was submitted to the University of Kansas Medical Center's Cytogenetics Laboratory for karyotype analysis, while the other portion was cultured for 4 weeks in STL media. In both cases, 10% fetal bovine serum (FBS) was added 2 hours prior to harvesting in order to stimulate cell cycling and increase the frequency of cells in metaphase.

Enriched CD34$^+$ cells were submitted for karyotype analysis (Pre-culture) or cultured in STL media for 4 weeks prior to submission (Post-culture). No gross changes in karyotypes were observed in cultured cells. At least 10 metaphase spreads from 2 different samples were observed for each group. One typical example is shown in FIG. 37.

These data indicate that the ex vivo expansion using media activating both the PI3K/Akt and Wnt/β-catenin pathways does not result in transformation-inducing chromosomal abnormalities, at least at the level observed from gross karyotype analysis. Furthermore, no donor cell-derived leukemias or other malignancies were observed in any transplant recipients to-date.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. An ex vivo method for expanding the number of hematopoietic stem cells (HSC) in a population of mononuclear cells (MNC) comprising:
culturing the population of MNCs comprising at least one HSC in an HSC expansion media comprising a modulator of DNA methyltransferase (DNMT) and a modulator of the Wnt pathway for a period of time sufficient to expand the number of HSCs in the MNC population, wherein the combination of MNCs, DNMT, and modulator of Wnt pathway is effective to enhance ex vivo expansion and repopulation potential of the HSCs.

2. The method according to claim 1, wherein the modulator of DNMT is a DNA methyltransferase inhibitor (DNMTi).

3. The method according to claim 2, wherein the DNMTi is selected from the group consisting of a small molecule, a biologic, an antisense RNA, a small interfering RNA (siRNA), and combinations thereof.

4. The method according to claim 3, wherein the DNMTi is a nucleoside analog.

5. The method according to claim 4, wherein the DNMTi is selected from the group consisting of azacitidine (5-azacytidine), decitabine (5-aza-2'-deoxycytidine), 5-fluoro-2'-deoxycitidine, 5,6-dihydro-5-azacytidine (DHAC), zebularine (1-β-D-ribofuranosyl-2(1H)-pyrimidinone), fazarabine (1-β-D-arabinofuranosyl-5-azacytosine), RX-3117 (Rexahn Pharmaceuticals Inc., Rockville, Md.), SGI-110 (Astex Pharmaceuticals, Dublin, Calif.), DNA methyltransferase inhibitors (IkerChem, San Sebastian, Spain), EGX-30P (EpiGenX Pharmaceuticals, Santa Barbara, Calif.), MeTase inhibitor (MethylGene, Montreal, Canada), prodrugs thereof, pharmaceutically acceptable salts thereof, and combinations thereof.

6. The method according to claim 5, wherein the DNMTi is 5-aza-2'-deoxycytidine, pharmaceutically acceptable salts thereof, or combinations thereof.

7. The method according to claim 3, wherein the DNMTi is a non-nucleoside analog.

8. The method according to claim 7, wherein the DNMTi is selected from the group consisting of hydralizine, disulfiram, procaine, procainamide, epigallocatechin gallate, psammaplins, RG108 ((S)-2-(1,3-dioxo-1,3-dihydro-isoindol-2-yl)-3-(1H-indol-3-yl)-propionic acid), antineoplaston AS2-1 (Burzynski Research Institute, Houston, Tex.), prodrugs thereof, pharmaceutically acceptable salts thereof, and combinations thereof.

9. The method according to claim 3, wherein the DNMTi is selected from the group consisting of MG-98 (MethylGene, Montreal, Canada), CC-014 (CellCentric, Cambridge, UK), CC-034 (CellCentric), and combinations thereof.

10. The method according to claim 1, wherein the modulator of the Wnt pathway down-regulates GSK-3β.

11. The method according to claim 1, wherein the modulator of the Wnt pathway is a reversible GSK-3β inhibitor selected from the group consisting of a small molecule, a biologic, an antisense RNA, a small interfering RNA (siRNA), and combinations thereof.

12. The method according to claim 11, wherein the reversible GSK-3β inhibitor is a small molecule.

13. The method according to claim 11, wherein the reversible GSK-3β inhibitor is selected from the group consisting of Hymenialdisine, Flavopiridol, Kenpaullone, Alsterpaullone, Azakenpaullone, Indirubin-30-oxime, 6-Bromoindirubin-30-oxime (B10), 6-Bromoindirubin-30-acetoxime, Aloisine A, Aloisine B, TDZD8, Compound 12, CHIR98014, CHIR99021 (CT99021), CT20026, Compound 1, SU9516, ARA014418, Staurosporine, Compound 5a, Compound 29, Compound 46, GF109203x (bisindolylmaleimide I), Ro318220 (bisindolylmaleimide IX), SB216763, SB415286, 15, CGP60474, Compound 8b, TWS119, Compound 1A, Compound 17, Lithium, Beryllium, Zinc, small molecule GSK-3β inhibitors (Vertex Pharmaceuticals), NP-12 (Neuropharma), GSK-3β inhibitors (Amphora), GSK-3β inhibitors (CrystalGenomics), SAR-502250 (Sanofi-Aventis), 3544 (Hoffmann-La Roche), GSK-3β inhibitors (Lundbeck), TDZD-8 (Cancer Center, University of Rochester), pharmaceutically acceptable salts thereof, and combinations thereof.

14. The method according to claim 13, wherein the GSK-3β inhibitor is lithium.

15. The method according to claim 1, wherein the HSC is obtained from a mammalian tissue selected from the group consisting of cord blood, peripheral blood, and bone marrow.

16. The method according to claim 15, wherein HSC is obtained from mammalian cord blood.

17. The method according to claim 1, wherein the HSC is human.

18. The method according to claim 1, wherein the HSC expansion is 3-fold more compared to a method in which the HSC expansion media does not contain a DNMT modulator.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Synthetic Construct

<400> SEQUENCE: 1
cgtggacaat ggctactcaa                                            20

<210> SEQ ID NO 2
<211> LENGTH: 20
<212> TYPE: DNA
<213> ORGANISM: Artificial
<220> FEATURE:
<223> OTHER INFORMATION: Synthetic Construct

<400> SEQUENCE: 2
tgtcagctca ggaattgcac                                            20

```
<210> SEQ ID NO 3
<211> LENGTH: 97
<212> TYPE: DNA
<213> ORGANISM: Artificial
<220> FEATURE:
<223> OTHER INFORMATION: Synthetic Construct; HP_224742

<400> SEQUENCE: 3
tgctgttgac agtgagcgac cagtgtgggt gaatacttta tagtgaagcc acagatgtat      60
aaagtattca cccacactgg ctgcctactg cctcgga                              97

<210> SEQ ID NO 4
<211> LENGTH: 97
<212> TYPE: DNA
<213> ORGANISM: Artificial
<220> FEATURE:
<223> OTHER INFORMATION: Synthetic Construct; HP_240000

<400> SEQUENCE: 4
tgctgttgac agtgagcgcg gaccaggtgg tagttaataa tagtgaagcc acagatgtat      60
tattaactac cacctggtcc ttgcctactg cctcgga                              97
```